United States Patent
Oohashi et al.

(10) Patent No.: US 8,167,826 B2
(45) Date of Patent: May 1, 2012

(54) VIBRATION GENERATING APPARATUS AND METHOD INTRODUCING HYPERSONIC EFFECT TO ACTIVATE FUNDAMENTAL BRAIN NETWORK AND HEIGHTEN AESTHETIC SENSIBILITY

(75) Inventors: Tsutomu Oohashi, Tokyo (JP); Norie Kawai, Tokyo (JP); Emi Nishina, Tokyo (JP); Manabu Honda, Tokyo (JP); Tadao Maekawa, Tokyo (JP); Masako Morimoto, Tokyo (JP); Reiko Yagi, Tokyo (JP); Osamu Ueno, Tokyo (JP)

(73) Assignee: Action Research Co., Ltd., Tokyo (JP)

( * ) Notice: Subject to any disclaimer, the term of this patent is extended or adjusted under 35 U.S.C. 154(b) by 115 days.

(21) Appl. No.: 12/742,343

(22) PCT Filed: Aug. 5, 2009

(86) PCT No.: PCT/JP2009/063880
§ 371 (c)(1),
(2), (4) Date: May 11, 2010

(87) PCT Pub. No.: WO2010/089911
PCT Pub. Date: Aug. 12, 2010

(65) Prior Publication Data
US 2011/0152729 A1 Jun. 23, 2011

(30) Foreign Application Priority Data
Feb. 3, 2009 (JP) .................................. 2009-022635

(51) Int. Cl.
*A61H 1/00* (2006.01)

(52) U.S. Cl. .......................................................... 601/2
(58) Field of Classification Search .................... 601/2
See application file for complete search history.

(56) References Cited

U.S. PATENT DOCUMENTS
6,104,822 A * 8/2000 Melanson et al. ............ 381/320
(Continued)

FOREIGN PATENT DOCUMENTS
JP 9-313610 12/1997
(Continued)

OTHER PUBLICATIONS
International Preliminary Report on Patentability issued Aug. 18, 2011 in International (PCT) Application No. PCT/JP2009/063880.
(Continued)

*Primary Examiner* — Tse Chen
*Assistant Examiner* — Hien Nguyen
(74) *Attorney, Agent, or Firm* — Wenderoth, Lind & Ponack, L.L.P.

(57) ABSTRACT

A means is provided for generating a vibration or a vibration signal, which contains audible range components that are vibration components in the audible frequency range and super-high-frequency components within a range exceeding the audible frequency range up to a predetermined maximum frequency, and which has an autocorrelation order represented by at least either one of a first property and a second property. By applying the vibration or an actual vibration generated from the vibration signal to a human being, a fundamental brain activation effect activating the fundamental brain network system constituted of a fundamental brain including the brain stem, thalamus and hypothalamus that are regions to bear the fundamental function of the human being and the fundamental brain network of neuronal projection from the fundamental brain to various brain regions is introduced.

24 Claims, 90 Drawing Sheets

U.S. PATENT DOCUMENTS

| | | |
|---|---|---|
| 7,079,659 B1 | 7/2006 | Oohashi et al. |
| 7,676,043 B1 * | 3/2010 | Tsutsui et al. .................... 381/1 |
| 2007/0280051 A1 * | 12/2007 | Novick et al. ................. 367/118 |
| 2008/0071136 A1 | 3/2008 | Oohashi et al. |
| 2008/0281238 A1 | 11/2008 | Oohashi et al. |

FOREIGN PATENT DOCUMENTS

| | | |
|---|---|---|
| JP | 2002-15522 | 1/2002 |
| JP | 2005-111261 | 4/2005 |
| JP | 2006-132054 | 5/2006 |
| JP | 3933565 | 3/2007 |
| JP | 4009660 | 9/2007 |
| JP | 4009661 | 9/2007 |
| JP | 2008-278999 | 11/2008 |
| WO | 2008/056673 | 5/2008 |

OTHER PUBLICATIONS

International Search Report issued Nov. 2, 2009 in International (PCT) Application No. PCT/JP2009/063880.

Oohashi, T. et al., "Inaudible high-frequency sounds affect brain activity: hypersonic effect", Journal of Neurophysiology, vol. 83, pp. 3548-3558, Jun. 2000.

Oohashi T. et al., "High-Frequency Sound above the Audible Range Affects Brain Electric Activity and Sound Perception", An Audio Engineering Society Preprint, 3207, Oct. 1991.

Tsutomu Oohashi, "Sound and Civilization", Iwanami Shoten, pp. 53-113, Oct. 2003 along with partial English translation.

Emi Nishina, "Progress in Researches on Development Mechanism of Hypersonic Effect", Journal of Acoustical Society of Japan, vol. 65, pp. 40-45, Jan. 2009 along with partial English translation.

Kaoru Ashihara, "Factual survey of Super-highfrequency Sounds Existing in Surroundings", Journal of Acoustical Society of Japan, vol. 65, pp. 23-28, Jan. 2009 along with partial English translation.

Tomomi Yamada, "Super-highfrequency Sounds Generated from Dental Instruments", Journal of Acoustical Society of Japan, vol. 65, pp. 52-57, Jan. 2009 along with partial English translation.

Mikio Hino, "Spectrum Analysis", Asakura Shoten, pp. 210-217, Oct. 1977 along with partial English translation.

* cited by examiner

Fig.5

| VIBRATION SATISFYING FIRST PROPERTY ON PREDETERMINED AUTOCORRELATION ORDER | LOCAL EXPONENT OF FRACTAL DIMENSION | | |
|---|---|---|---|
| | MAXIMUM VALUE | MINIMUM VALUE | FLUCTUATION RANGE |
| CEMBALO | 2.709 | 2.518 | 0.191 |
| BLU-RAY DISC VERSION AKIRA SOUNDTRACK | 2.668 | 2.338 | 0.330 |
| JAPANESE BAMBOO FLUTE | 2.645 | 2.380 | 0.265 |
| VIOLIN | 2.635 | 2.482 | 0.153 |
| TROPICAL RAIN FOREST ENVIRONMENTAL SOUND | 2.560 | 2.452 | 0.108 |
| GAMELAN | 2.548 | 2.526 | 0.022 |
| RUNNING WATER SOUND | 2.411 | 2.319 | 0.091 |
| GEORGIAN MALE CHORUS | 2.372 | 2.202 | 0.170 |

REGIONS 101 AND 102 WHERE REGIONAL CEREBRAL BLOOD FLOW
SIGNIFICANTLY INCREASES IN FRS CONDITION AGAINST LFC ALONE CONDITION
*Fig. 16A*
SAGITTAL PROJECTION CHART
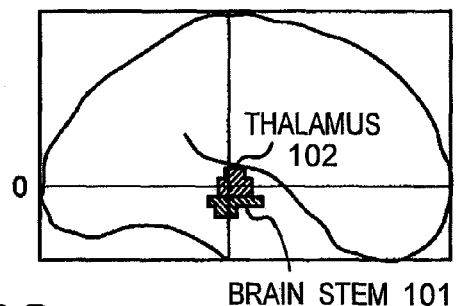
*Fig. 16B*
CORONAL PROJECTION CHART
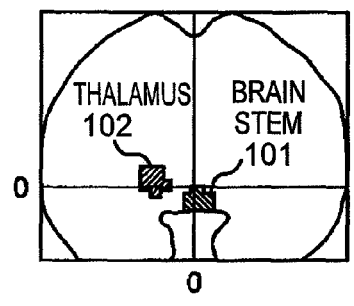
*Fig. 16C* HORIZONTAL PLANE PROJECTION CHART
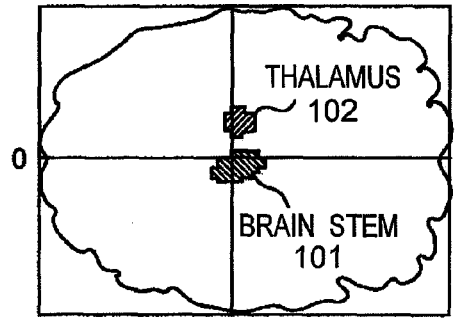

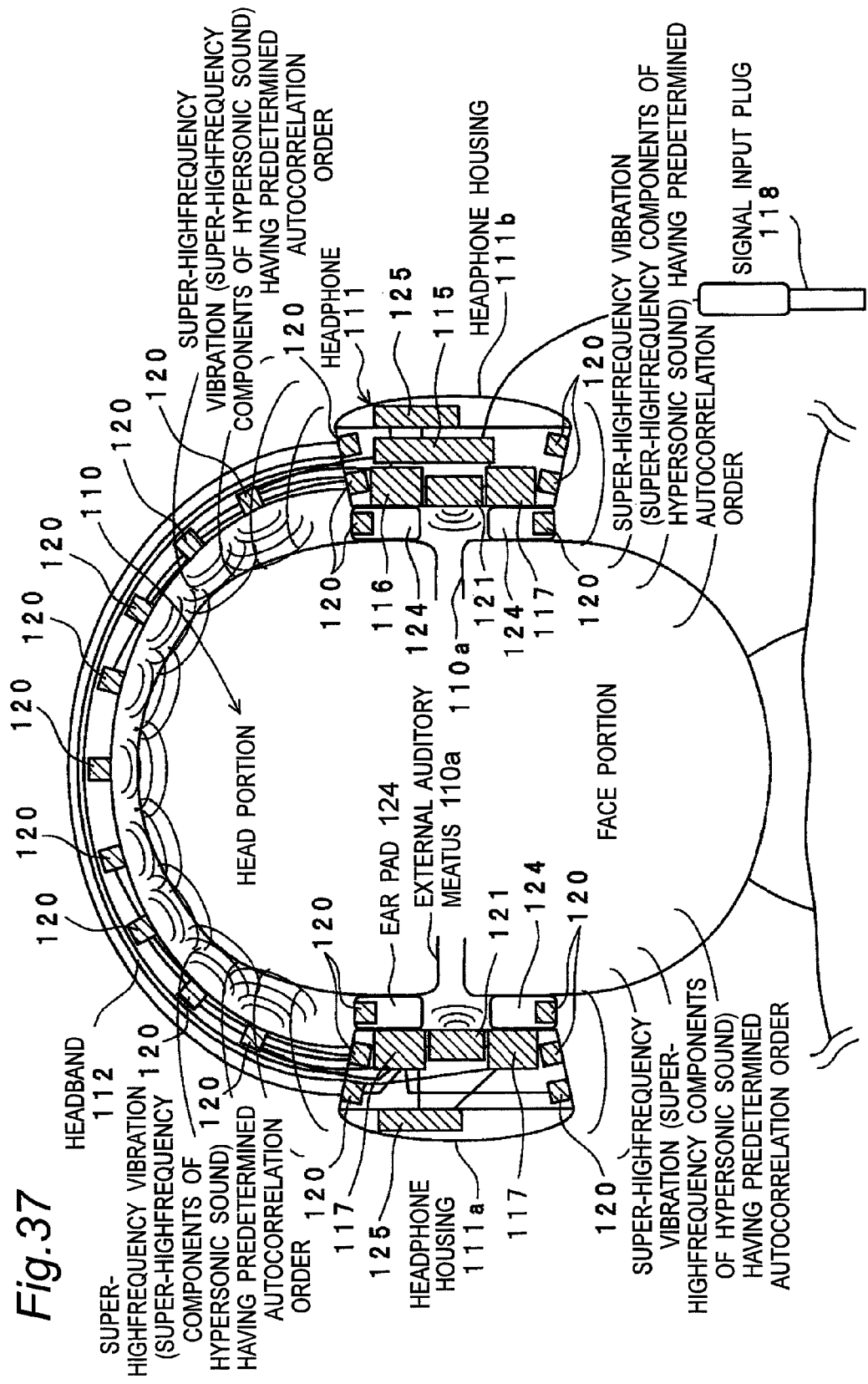

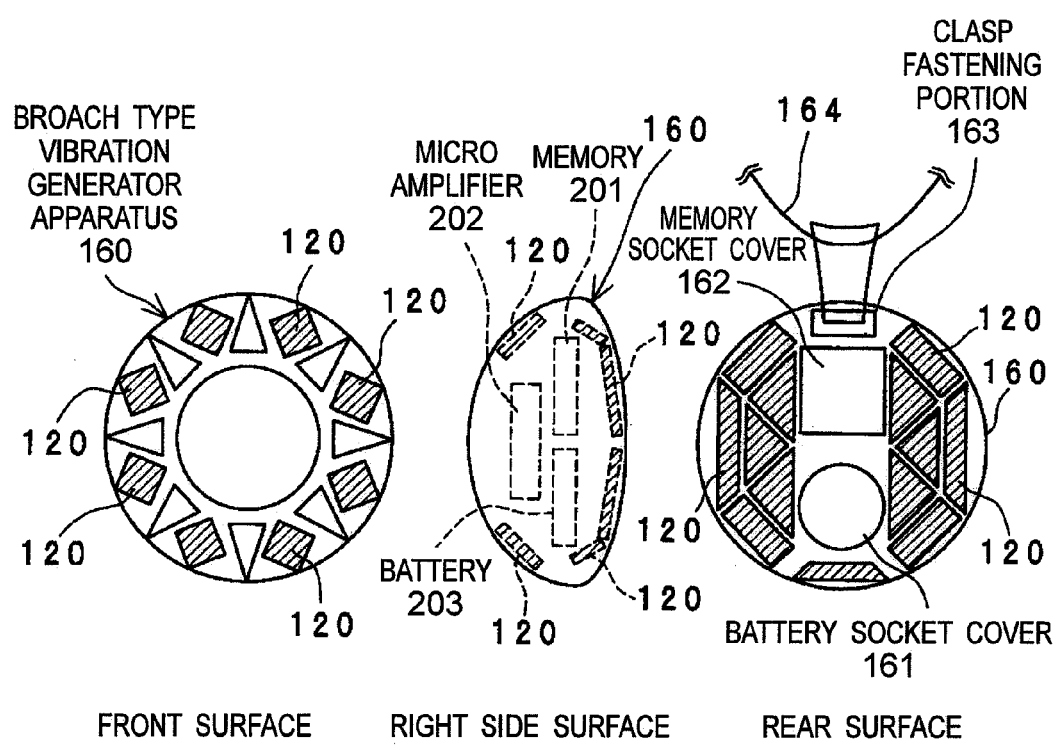

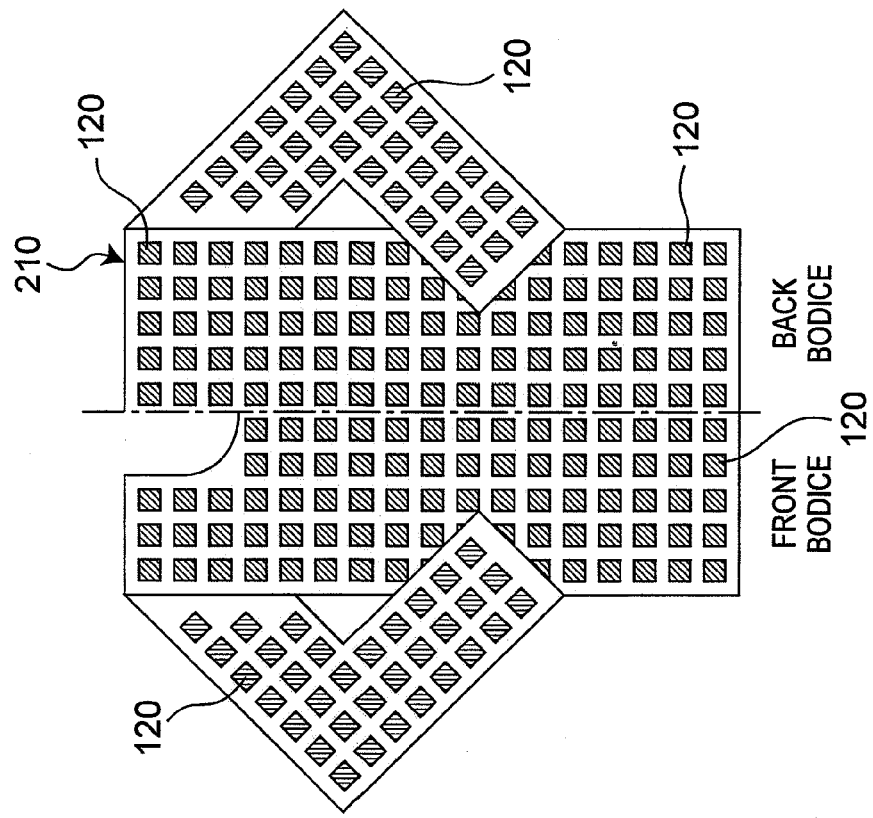
Fig.39B INNER SURFACE
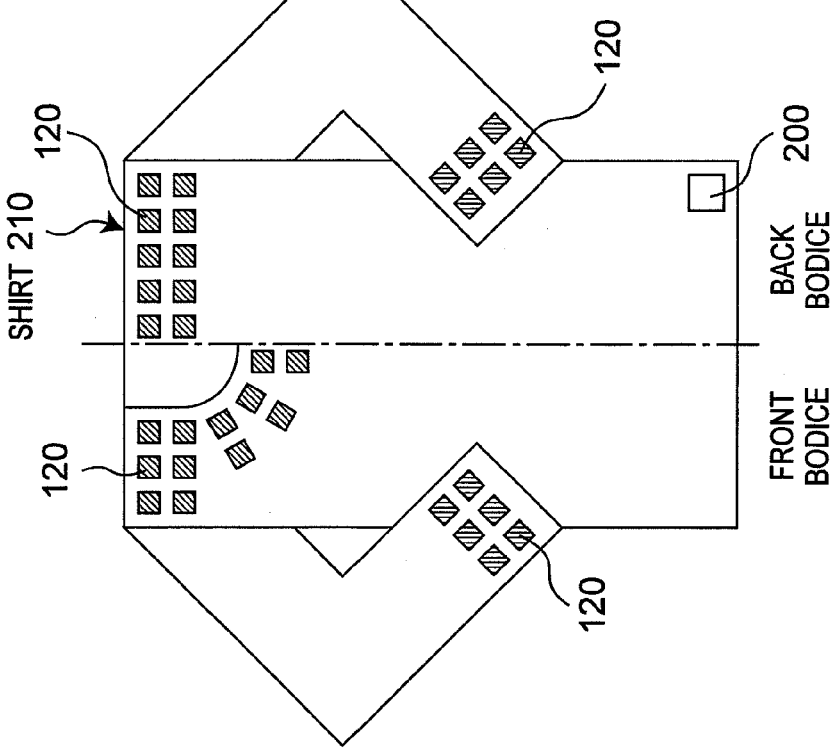
Fig.39A OUTER SURFACE

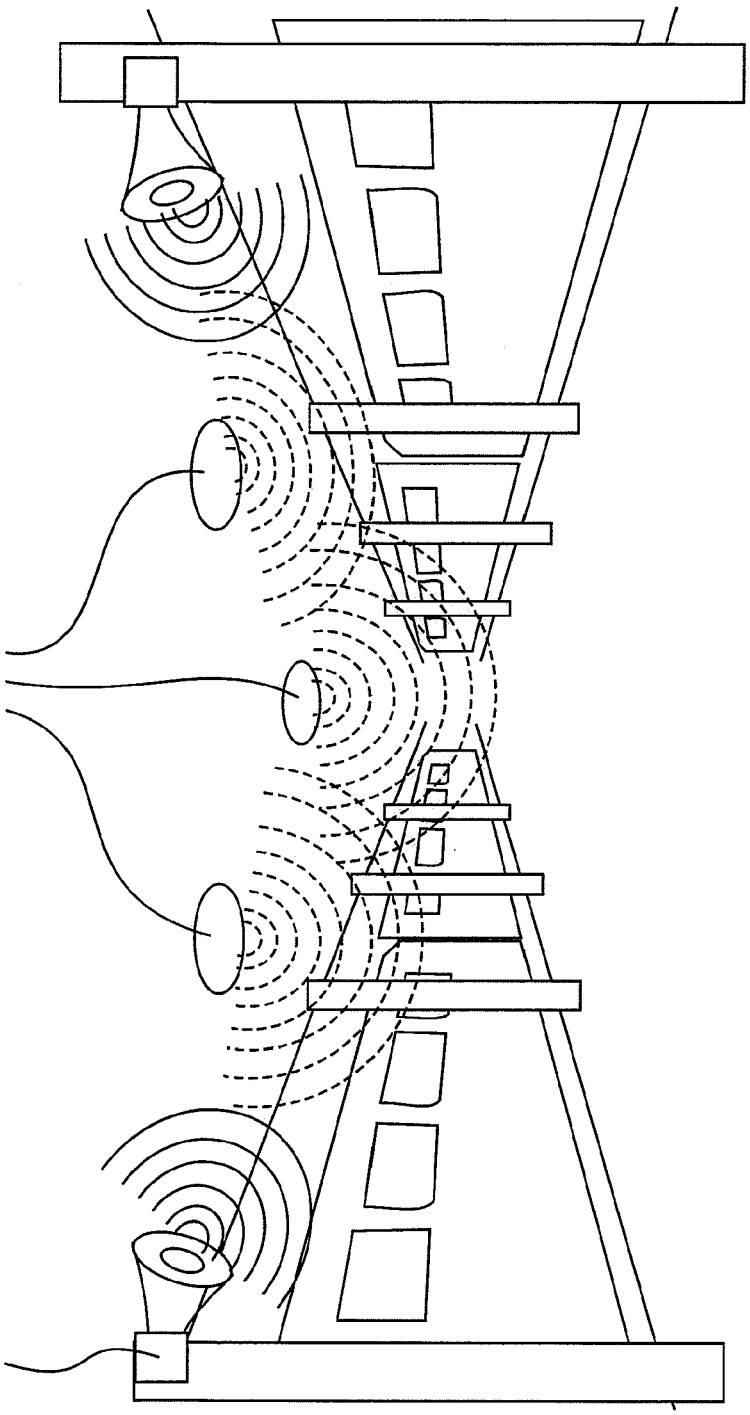

POSITION OF BRAIN STEM

POSITION OF LEFT THALAMUS

Fig.102

HYPERSONIC THERAPY TABLE

| | MUSICOTHERAPY (PASSIVE MUSICOTHERAPY) | HYPERSONIC THERAPY |
|---|---|---|
| OPERATIVE MECHANISM | CONSCIOUSNESS = PERCEIVABLE RECOGNIZED MUSIC EFFECT - SUBJECTIVE | UNCONSCIOUSNESS = UNPERCEIVABLE UNRECOGNIZED HIGH-FREQUENCY EFFECT - OBJECTIVE |
| DISTRIBUTION OF EFFECTS | INDIVIDUAL AND SITUATION-DEPENDENT (DETERMINED BY INDIVIDUAL TASTE DIFFERENCE AND INFLUENCED BY SITUATION) | UNIVERSAL (INDIVIDUAL TASTE CAN BE TRANSCENDED SO LONG AS NATURAL ENVIRONMENTAL SOUND IS USED) |
| DIAGNOSIS (ASSESSMENT) AND PRESCRIPTION | SUITABLE MUSIC NEEDS TO BE INDIVIDUALLY EXAMINED AND USED | UNNECESSARY |
| SPATIAL STRUCTURING | SOUND SPACE SEPARATED FROM OTHERS IS STRUCTURED EVERY INDIVIDUAL OR COEXISTABLE SMALL GROUPS | UNRESTRAINT |
| TEMPORAL STRUCTURING | DISPOSED IN SPECIFIED TIME EVERY INDIVIDUAL OR COEXISTABLE SMALL GROUPS | UNRESTRAINT |
| DISPOSAL AND NEEDED PERSONNEL | INDIVIDUAL DISPOSALS ARE RESPECTIVELY MANAGED AND EXECUTED BY THERAPIST | UNMANNED AUTOMATIC REPRODUCING SYSTEM IS ACCEPTABLE |
| EVALUATION OF EFFECTS | COMPREHENSIVE (OFTEN SUBJECTIVE AND OBSCURE) | PHYSIOLOGICAL INDEX (BRAIN WAVE, TOMOGRAPHIC IMAGING, IMMUNE ACTIVITY, ENDOCRINE SUBSTANCES, ETC.) + STATISTIC PROCESSING (OBJECTIVE AND HIGHLY RELIABLE) |

Fig.103

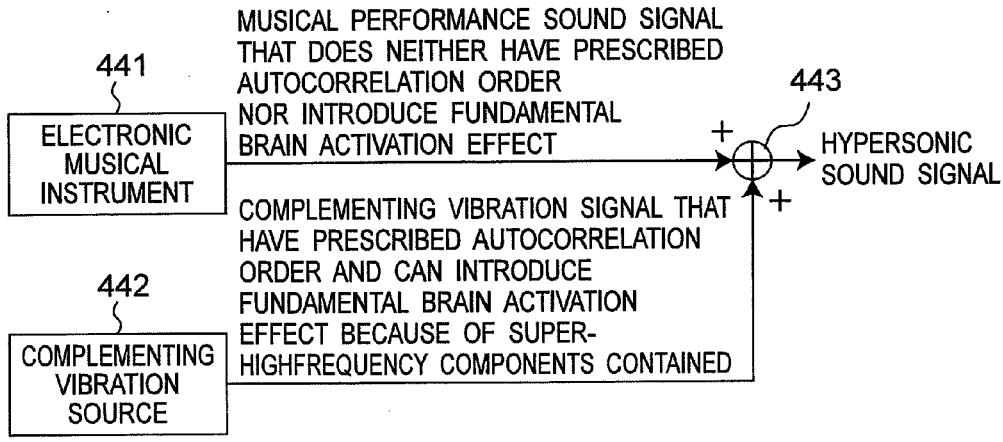

VIBRATION GENERATING APPARATUS AND METHOD INTRODUCING HYPERSONIC EFFECT TO ACTIVATE FUNDAMENTAL BRAIN NETWORK AND HEIGHTEN AESTHETIC SENSIBILITY

TECHNICAL FIELD

The present invention relates to a vibration generating apparatus and method for generating a vibration that can introduce an effect (hereinafter referred to as a hypersonic effect) of comprehensively enhancing mental activity and physical activity by increasing the regional cerebral blood flow of the fundamental brain including the brain stem, thalamus and hypothalamus, which are the regions that bear the fundamental functions of the brain, and the neuronal projection from the fundamental brain to various areas in the brain (these are hereinafter collectively referred to as a fundamental brain network system) and by activating these regions with a hypersonic sound, which is a sound having a non-stationary structure that abundantly contains super-high-frequency components exceeding the human audible frequency upper limit, and relates also to a vibration discriminating apparatus and method for discriminating the vibration. That is, the present invention relates, in concrete, to a vibration generating apparatus and method for generating a vibration that can introduce the effects of increasing α rhythm power of the brain wave, heightening the aesthetic sensibility to general sensory inputs inclusive of receiving of sounds pleasantly, beautifully and movingly, thereby heightening the sensibility effects of composite sensory information including sounds, intensifying a sound listening behavior, and adjusting the activities of the emotional system, the behavior control system, the autonomic nervous system, the endocrine system and the immune system located in the fundamental brain network system, thereby reducing stress and comprehensively improving lifestyle-related diseases of metabolic syndromes such as hypertension, hyperlipidemia and diabetes, cancer, cerebrovascular disorder and cardiopathy, immune abnormalities including pollinosis and atopic dermatitis, various mental disorders such as depression, schizophrenia, dementia, chronic fatigue syndrome and attention-deficit hyperactivity disorder, behavioral abnormalities such as suicide and self-injurious behaviors, abnormal exaltation of aggressiveness and so on, which are caused by the abnormality of the fundamental brain activity and pose serious problems, in the modern society, and relates to a vibration discriminating apparatus and method for discriminating the vibration.

BACKGROUND ART

The present inventor and others discovered that a hypersonic sound, which was a non-stationary sound abundantly containing super-high-frequency components exceeding the audible frequency upper limit, introduced a fundamental brain activation effect of increasing the regional cerebral blood flow of the fundamental brain, including the brain stem, thalamus and hypothalamus, and the fundamental brain network (fundamental brain network system) of a human being listening to the sound and boosting α rhythm of the brain wave power of an index of the fundamental brain activation, and had the effects of heightening the aesthetic sensibility inclusive of receiving of sounds pleasantly, beautifully and movingly, reducing stress, rationalizing the activities of the autonomic nerve system, the endocrine system and the immune system, and comprehensively improving the mental and physical states, i.e., a hypersonic effect, by contrast to which the fundamental brain activity was more deteriorated than in a background noise state when he or she was listening to a sound containing no super-high-frequency component (See, for example, the Patent Documents 1 to 4 and the Non-Patent Documents 1 and 2).

In addition, the present inventor and others have revealed that, by contrast to the fact that the natural environmental sounds of the tropical rain forests, which are the most powerful candidate of the environments where the human genes had been formed through evolution, abundantly contained super-high-frequency components that largely exceeded 20 kHz at the human audible frequency upper limit and had a complicatedly changing structure capable of introducing the fundamental brain activation effect, environmental sounds in cities where the modern people lived contained almost no such super-high-frequency components and deteriorated the fundamental brain activity (See, for example, the Patent Document 5 and the Non-Patent Documents 3 and 4).

The fundamental brain activated by the hypersonic sound serves as an important base of the neural circuit inclusive of the monoamine nerve system and the opioid nerve system closely related to the control of human emotions and behaviors. Therefore, it has been discovered that the activity disorder of the fundamental brain and the neural network projected on the entire brain from there leads to various mental and behavioral disorders. Further, the fundamental brain, which is the ultimate center of the autonomic nerve system and the endocrine system, controls the immune system via them and bears a function to maintain the homeostasis of the whole body through these and a biophylactic function. Therefore, the disorder of the fundamental brain activity has a close relation to the induction of the lifestyle-related diseases that are rapidly increasing in the modern society by incurring breakdown of the homeostatic function and the biophylactic function.

Therefore, paying attention to the fact that the aforementioned mental and behavioral disorders and the lifestyle-related diseases and the like are increasing specifically and rapidly in the modern society, it is highly possible that a cause is ascribed to the fact that the sound environments surrounding the modern people largely deviate from the specific sound structure characterizing the environmental sounds of the tropical rain forests, which are the most powerful candidate of the environments where the human genes have been evolutionally formed, and particularly the complicatedly changing super-high-frequency components drop out, consequently causing the disorder of the fundamental brain activity.

On the other hand, reproducing the tropical rain forest natural environment as it is in the modern cities does not become a realistic solution method counterbalancing the urgency of the aforementioned problems that the modern societies confront in terms of climate and biological conditions and also in the aspect of the needed time and the amount of a social investment cost. Accordingly, a method for solving the aforementioned problems in the aspects of psychosomatic health that the modern people confront is proposed by using a vibration signal having a specific structure to introduce the fundamental brain activation effect and a vibration generating apparatus capable of generating it, generating a vibration to introduce the fundamental brain activation effect in a manner similar to that of the tropical rain forest environmental sounds suited to the design of the human genes and applying the same to the modern people, thereby introducing the fundamental brain activation effect (See, for example, the Patent Document 5).

However, almost all of the audio signals in the digital formats outputted from compact discs (CD), mini discs (MD) and those recorded in solid memories of portable players, which are audio information media widely popularized in the modern society, and the audio signals in the digital formats distributed and delivered via broadcastings and telecommunications can neither record nor reproduce super-high-frequency components, and therefore, they are unable to generate a hypersonic sound and to activate the fundamental brain.

On the other hand, it is recently becoming possible to use digital media, which have formats capable of recording, transmitting and reproducing to a range that largely exceeds the audible range upper limit, such as super audio CD (SACD), DVD audio, soundtracks of blu-ray disc (BD) and network distribution by high-speed optical communications or the like. However, the vibration signals recorded in the recording media, i.e., the contents contain no super-high-frequency component in these due to limitations in the vibration generating function owned by the sound sources and limitations in the capability of the recording and editing apparatuses and the like, and therefore, it is customary that the hypersonic sound cannot be generated and the fundamental brain activation effect cannot be introduced.

Further, the present inventor and others revealed that, when an artificial signal of a white noise or the like was applied as super-high-frequency components to a listener with the audible range components, or the vibration components in the audible frequency range, the hypersonic effect was not induced even if sufficient super-high-frequency components are contained (See, for example, the Non-Patent Document 2). Moreover, none of a sine-wave-like signal having a peak at a specific frequency, its harmonic sound and super-high-frequency components of a quantization noise entailed by a high-speed sampling 1-bit quantization system or the like similarly produce the hypersonic effect. Further, it is recently revealed that super-high-frequency components, which are composed of a sine-wave-like signal having a peak at a specific frequency and are generated from artificial objects of electronic equipment and the like, introduce negative effects of unpleasant sensation, escape behavior and so on in human beings and animals to which they are applied, and they are used as an apparatus for rejecting young people and an apparatus for repulsing mice (See, for example, the Non-Patent Documents 5 and 6).

These findings suggest that, in order to introduce the fundamental brain activation effect by the hypersonic effect, it is not proper to merely apply super-high-frequency components exceeding the audible range upper limit, but it is necessary that those super-high-frequency components have a certain specific structural feature, whereas the vibration of the super-high-frequency components having a certain peculiar structure different from it has a risk of possibly exerting a negative influence on the physiological states of human beings and animals. However, such a structural feature that the super-high-frequency components of the vibration that can introduce the fundamental brain activation effect should have has not been clarified thus far. Therefore, even if the digital formats capable of recording, transmitting and reproducing super-high-frequency components in a manner similar to that of the super audio CD (SACD), soundtracks of blu-ray disc (BD) and network distribution utilizing high-speed optical communications and the like are made usable, it is unclear what sort of structural feature should be owned by the vibration signals recorded and transmitted there in order to introduce the fundamental brain activation effect.

PRIOR ART DOCUMENTS

Patent Documents

Patent Document 1: Japanese patent laid-open publication No. JP H09-313610 A;
Patent Document 2: Japanese patent No. JP 3933565;
Patent Document 3: Japanese patent No. JP 4009660;
Patent Document 4: Japanese patent No. JP 4009661;
Patent Document 5: Japanese patent laid-open publication No. JP 2005-111261 A;
Patent Document 6: Japanese patent laid-open publication No. JP 2002-015522 A; and
Patent Document 7: Japanese patent laid-open publication No. JP 2006-132054 A.

Non-Patent Documents

Non-Patent Document 1: Oohashi, T. et al., "Inaudible high-frequency sounds affect brain activity: hypersonic effect", Journal of Neurophysiology, Vol. 83, pp. 3548-3558, June 2000;
Non-Patent Document 2: Oohashi T. et al., "High-Frequency Sound above the Audible Range Affects Brain Electric Activity and Sound Perception", An Audio Engineering Society Preprint, 3207, October 1991;
Non-Patent Document 3: Tsutomu Oohashi, "Sound and Civilization", Iwanami Shoten, pp. 53-113, October, 2003.
Non-Patent Document 4: Emi Nishina, "Progress in Researches on Development Mechanism of Hypersonic Effect", Journal of Acoustical Society of Japan, Vol. 65, pp. 40-45, January, 2009.;
Non-Patent Document 5: Kaoru Ashihara, "Factual survey of Super-high-frequency Sounds Existing in Surroundings", Journal of Acoustical Society of Japan, Vol. 65, pp. 23-28, January, 2009;
Non-Patent Document 6: Tomomi Yamada, "Super-high-frequency Sounds Generated from Dental Instruments", Journal of Acoustical Society of Japan, Vol. 65, pp. 52-57, January, 2009; and
Non-Patent Document 7: Mikio Hino, "Spectrum Analysis", Asakura Shoten, pp. 210-217, October, 1977.

DISCLOSURE OF INVENTION

Problems to be Solved

First of all, there is such a problem that, since the structural feature of super-high-frequency components that can introduce the fundamental brain activation effect has not been conventionally identified, it is impossible to estimate whether a sound applied to a listener can actually introduce the fundamental brain activation effect from the structure itself of the vibration signal even if it contains super-high-frequency components as observed in an example in which super-high-frequency components artificially synthesized from, for example, a white noise or the like do not introduce the hypersonic effect. That is, as to whether a certain vibration introduces the fundamental brain activation effect, it is necessary to actually observe whether the fundamental brain is activated by applying the vibration to the listener in each case and measuring the activation of the fundamental brain of the listener by a strict physiological experiment using advanced functional brain measuring means such as a positron emission tomography or an electroencephalograph. It is unreal to carry out such a physiological experiment for every vibration, measure the fundamental brain activation and thereafter link them to practical use. Therefore, it is necessary to specify the structural features of the vibration signal that can introduce the fundamental brain activation effect in order to estimate whether a specified vibration can introduce the fundamental brain activation effect without carrying out a physiological experiment.

Secondly, there is such a problem that a vibration containing super-high-frequency components that can introduce the fundamental brain activation effect cannot be artificially synthesized since the structural feature of the super-high-frequency components that can introduce the fundamental brain activation effect has not been conventionally identified. In particular, considering the uncovered existence of a problem in the safety aspect such that a definite kind of artificial super-high-frequency components produces a negative effect in the physiological states of human beings and animals, a vibration generated from a specific inartificial natural vibration generating source of which the effectiveness and safety have been proven by the past results, such as the environmental sounds of tropical rain forests and a definite kind of native musical instrument sound are to be recorded and used as the vibration that can introduce the fundamental brain activation effect. However, the kinds and the amount of inartificial natural vibration generating sources that can introduce such a fundamental brain activation effect are limited, and collection and recording of them are frequently accompanied by immense difficulties and sometimes even risks. Therefore, in order to artificially abundantly synthesize various kinds of vibrations that can introduce the fundamental brain activation effect without relying on the limited inartificial natural vibration generating sources, it is necessary to identify the structural feature of the vibration that can introduce the fundamental brain activation effect.

Thirdly, there is such a problem that, since the structural feature of the super-high-frequency components that can introduce the fundamental brain activation effect has not been conventionally identified in spite of a variety of past proposals of band expanding methods as one method for complementing a vibration signal from which the super-high-frequency components drop out with super-high-frequency components, it is necessary to carry out a physiologic experiment in each case and confirm every vibration whether the super-high-frequency components artificially expanded by such a conventional band expanding method introduce the fundamental brain activation effect. In particular, considering the reported examples in which the hypersonic effect does not occur or conversely produce a negative effect in the case of a definite kind of artificially synthesized super-high-frequency components as described above, it is very important to discriminate whether the structure of the super-high-frequency components artificially expanded by the band expanding method is able to introduce the fundamental brain activation effect, i.e., whether it is effective and safe for human beings.

Fourthly, due to the existence of such wide variety of problems, there is such a problem that the vibration generated by the vibration sources of the existent vast amount of record library and the vibration generating apparatus not only significantly impair the sensuous artistic value but also rather invite various modern diseases due to a deterioration in the fundamental brain activity failing in introducing the fundamental brain activation effect, and this leads to a high possibility of significantly threatening the comfort and safety of modern people. There is a growing demand for a technique to overcome such limitations and prevent the risks.

Fifthly, there is such a problem that, in contents comprehensively working on multiple sensory systems of visual sensation, auditory sensation and so on, such as video and audio contents recorded in a large-capacity package media of DVD, Blu-ray Disc and the like popularized recently rapidly and video and audio distributed and delivered by using high-speed large-capacity communication lines such as high-definition television and high-speed optical communications, the recording media have restrictions in the recordable information capacity and restrictions in the information transfer rate (transmittable information capacity per unit time) in the case of reading the recorded information from the recording media and transmitting through communication lines, which therefore leads to a trade-off relation between the information capacity usable for video and the information capacity usable for audio, resulting in an antinomy between the image quality and the sound quality of the contents. That is, data volume assigned to audio data is reduced when a large information capacity is assigned to video giving priority to the image quality, and therefore, it is necessary to perform processing such as limitation or compression of the sound frequency domain, reducing the sensuous artistic value like impairment of an expressive effect as a consequence of a deterioration in the sound quality. Conversely, data volume assigned to image data is reduced when a large information capacity is assigned to sound information giving priority to the sound quality, and therefore, it is necessary to perform processing such as a reduction in resolution by saving or compressing images, reducing the sensuous artistic value like impairment of an expressive effect as a consequence of a deterioration in the image quality.

Sixthly, there is a problem of the phenomenon of an antinomy between the fact that "necessary information cannot be caught unless sound volume is increased" and the fact that "the sound becomes bothersome and unpleasant when the sound volume is increased" on the other hand when a sound aimed at information transmission such as sound-reinforcement broadcasting coexists with another sound that disturbs the transmission such as a significant background noise. Problems resembling this exist under various situations, and, for example, sound effects of audio and video contents and sound effects of theatrical performance have the problem of an antinomy between the fact that "the intended artistic effect cannot be obtained unless sound volume is increased" and "sound becomes unpleasant when the sound volume is increased" on the other hand.

It is an object of the present invention to solve the aforementioned problems by clarifying the detailed structural feature of a vibration that can introduce the fundamental brain activation effect and thereby provide an apparatus and method for generating a vibration that can introduce hypersonic effect and an apparatus and method for discriminating the vibration. It is a further object to provide an apparatus and method capable of enhancing the aesthetic sensibility to sensory inputs other than sounds and heightening the expressive effect in the entire sensory system by generating a vibration that can introduce the hypersonic effect in complex sensory information generating means for comprehensively working on multiple sensory systems and activating the fundamental brain including the reward system (fundamental brain network system) as its application. It is a further object to provide an apparatus and method for developing or intensifying both sensitization and comforting of sound perception in a coexistent state by applying the effect of enhancing the activity of the entire fundamental brain network system.

Means for Solving the Problems

A vibration generating apparatus according to a first aspect of the present invention includes means for generating a vibration or a vibration signal, which contains audible range components that are vibration components in an audible frequency range and super-high-frequency components within a range exceeding the audible frequency range up to a predetermined maximum frequency and has an autocorrelation order, which is the internal correlation property which is widely contained in natural conformation, represented by at least either one of a first property and a second property. The vibration generating apparatus is able to introduce a fundamental brain activation effect for activating a fundamental brain network system of a human being into a fundamental brain including brain stem, thalamus and hypothalamus that are regions to bear the fundamental brain function and a fundamental brain network of neuronal projection from the fundamental brain to various brain regions by applying the vibration or an actual vibration generated from the vibration signal to the human being.

The first property has a fractal nature such that a shape of a three-dimensional power spectrum array of time, frequency and power of the components exceeding the audible frequency range is a complexity having a self-similarity. A local exponent of fractal dimension is a value obtained, upon calculating the fractal dimension of a curved surface of the three-dimensional power spectrum array by using a box-counting method, by inverting the sign of an inclination of a straight line that interconnects two mutually adjacent points when logarithms of a necessary minimum number of reference boxes for covering the curved surface are plotted with respect to a logarithm of a size of each one side of the reference boxes. The local exponent of fractal dimension is a value that represents a self-similarity of the shape, and the local exponent of fractal dimension has a value of not smaller than 2.2 and not greater than 2.8 in a range in which a spectro-temporal index defined by normalizing one side of the reference box is $2^{-1}$ to $2^{-5}$ and a fluctuation range of the local exponent of fractal dimension within 0.4 when the spectro-temporal index changes in a range of $2^{-1}$ to $2^{-5}$.

The second property is defined such that a degree of one of predictability and irregularity of time series of the vibration signal changes with time except for the time series of the vibration signal that are completely predictable and regular and for the time series of the vibration signal that are completely unpredictable and random. An information entropy density representing the irregularity of time series data has a value in a range of not smaller than −5 and smaller than zero, and an entropy variation index (Entropy Variation Index; EV-index), which is a variance of the information entropy density and represents a degree of time variance, has a value of not smaller than 0.001 for 51.2 seconds.

A vibration generating space apparatus according to a second aspect of the present invention generates a vibration having the autocorrelation order by radiating the vibration generated by at least one vibration generating apparatus installed in a space into the space or by making the vibrations become added together or mutually interfere in the space or by making things constituting the space resonate with the vibrations.

A vibrating object or body according to a third aspect of the present invention is a vibrating object in a vibrational state generated by at least one vibration generating apparatus.

A vibration generating method according to a fourth aspect of the present invention includes a step of generating a vibration or a vibration signal, which contains audible range components that are vibration components in an audible frequency range and super-high-frequency components within a range exceeding the audible frequency range up to a predetermined maximum frequency and has an autocorrelation order represented by at least either one of a first property and a second property. The vibration generating method is able to introduce a fundamental brain activation effect for activating a fundamental brain network system including a fundamental brain including brain stem, thalamus and hypothalamus that are regions to bear the fundamental brain function of a human being and a fundamental brain network of neuronal projection from the fundamental brain to various brain regions by applying the vibration or an actual vibration generated from the vibration signal to the human being.

The first property has a fractal nature such that a shape of a three-dimensional power spectrum array of time, frequency and power of the components exceeding the audible frequency range is a complexity having a self-similarity. A local exponent of fractal dimension is a value obtained, upon calculating the fractal dimension of a curved surface of the three-dimensional power spectrum array by using a box-counting method, by inverting the sign of an inclination of a straight line that interconnects two mutually adjacent points when logarithms of a necessary minimum number of reference boxes for covering the curved surface are plotted with respect to a logarithm of a size of each one side of the reference boxes. The local exponent of fractal dimension is a value that represents a self-similarity of the shape, and the local exponent of fractal dimension has a value of not smaller than 2.2 and not greater than 2.8 in a range in which a spectro-temporal index defined by normalizing one side of the reference box is $2^{-1}$ to $2^{-5}$ and a fluctuation range of the local exponent of fractal dimension within 0.4 when the spectro-temporal index changes in a range of $2^{-1}$ to $2^{-5}$.

The second property is defined such that a degree of one of predictability and irregularity of time series of the vibration signal changes with time except for the time series of the vibration signal that are completely predictable and regular and for the time series of the vibration signal that are completely unpredictable and random. An information entropy density representing the irregularity of time series data has a value in a range of not smaller than −5 and smaller than zero, and an entropy variation index (Entropy Variation Index; EV-index), which is a variance of the information entropy density and represents a degree of time variance, has a value of not smaller than 0.001 for 51.2 seconds.

The vibration generating apparatus of the first aspect of the present invention further includes addition means for adding a complementing vibration signal that has the autocorrelation order and is generated by the vibration generating apparatus, to an original vibration signal not having the autocorrelation order, and outputting a vibration signal of an addition result is included.

Moreover, the vibration generating apparatus further including band expanding means and addition means. The band expanding means performs band expanding so that a band of the original signal exceeds the audible frequency range with respect to the original vibration signal not having the autocorrelation order, and outputting a band-expanded vibration signal that contains the band exceeding the audible frequency range and the band of the original vibration signal. The addition means adds a complementing vibration signal that has the autocorrelation order and is generated by the vibration generating apparatus, to the band-expanded vibration signal, and outputting a vibration signal of an addition result.

Further, the vibration generating apparatus further includes high-pass filter means, which is provided between the vibration generating apparatus and the addition means, for performing high-pass filtering of the complementing vibration signal having the autocorrelation order.

Furthermore, the vibration generating apparatus further includes attenuation means for comparing the signal level of the original vibration signal or the band-expanded vibration signal with a predetermined threshold value, and attenuating by a predetermined attenuation amount the complementing vibration signal that has the autocorrelation order and is inputted to the addition means or its high-pass filtered signal, when the signal level is smaller than the threshold value.

Further, the vibration generating apparatus further includes level changing means for detecting the absolute value of the signal level of the original vibration signal or the band-expanded vibration signal and performing amplification or attenuation of the signal level of the complementing vibration signal that has the autocorrelation order and is inputted to the addition means or its high-pass filtered signal, in accordance with the magnitude of the absolute value of the signal level.

Further, in the vibration generating apparatus, the complementing vibration signal, that has the autocorrelation order and is inputted to the addition means, contains a plurality of kinds of vibration signals each having the autocorrelation order. The vibration generating apparatus further includes control means for selecting at least one kind of complementing vibration signal from among the plurality of kinds of complementing vibration signals in correspondence with at least one of the original vibration signal and the band-expanded vibration signal, and outputting the signal to the addition means.

Furthermore, the vibration generating apparatus further includes first processing means for calculating an autocorrelation coefficient of a reference vibration signal having the autocorrelation order, and performing convolution calculation of the original vibration signal not having the autocorrelation order with the calculated autocorrelation coefficient, thereby generating a vibration signal having the autocorrelation order.

Furthermore, the vibration generating apparatus further includes second processing means for calculating a transfer function of the reference vibration signal having the autocorrelation order, and multiplying the original vibration signal not having the autocorrelation order by the calculated transfer function, thereby generating a vibration signal having the autocorrelation order.

Further, the vibration generating apparatus includes an elastic vibrating object, first transducing means, and second transducing means. The first transducing means transduces the vibration signal having the autocorrelation order or a vibration signal not having the autocorrelation order, into a vibration and applying the vibration to the elastic vibrating object. The second transducing means transduces the vibration of the elastic vibrating object into an electric signal. At least either one of the first property and the second property on the autocorrelation order in the vibration signal is enhanced or imparted by processing the applied vibration using a vibration characteristic owned by the elastic vibrating object, and vibration components not introducing the fundamental brain activation effect and being existable as an electric signal but not existable in the natural elastic vibrating object are attenuated or removed, thereby emphasizing or imparting the effect of a vibration that can introduce the fundamental brain activation effect.

Furthermore, in the vibration generating apparatus, the elastic vibrating object is installed in a container filled with a predetermined vibration transmission medium.

Furthermore, in the vibration generating apparatus activates a fundamental brain network system including a fundamental brain including a reward system neural circuit that is a brain function region being unitarily comprehensively responsible for the generation of all reactions of pleasure, beauty and emotion and a fundamental brain network in a human being by applying a vibration generated by the vibration generating apparatus to the human being while applying predetermined information to the human through at least one of visual sensation, gustatory sensation, somatic sensation and olfactory sensation other than auditory sensation, thereby enhancing also an aesthetic sensibility to sensory inputs from other than auditory sensation and heightening expressive effects of sensory information other than auditory sensation.

Furthermore, the vibration generating method activates a fundamental brain network system including a fundamental brain including a reward system neural circuit that is a brain function region being unitarily comprehensively responsible for the generation of all reactions of pleasure, beauty and emotion and a fundamental brain network in a human being by applying a vibration generated by the vibration generating apparatus to the human being while applying predetermined information to the human through at least one of visual sensation, gustatory sensation, somatic sensation and olfactory sensation other than auditory sensation, thereby enhancing also an aesthetic sensibility to sensory inputs from other than auditory sensation and heightening expressive effects of sensory information other than auditory sensation.

A computer-readable recording medium according to a fifth aspect of the present invention records the vibration signal generated by the vibration generating apparatus.

A communication apparatus according to a sixth aspect of the present invention includes communication means for transmitting the vibration signal generated by the vibration generating apparatus via a communication medium.

A vibration discriminating apparatus according to a seventh aspect of the present invention includes discrimination means for discriminating whether or not an inputted vibration signal contains audible range components that are vibration components in an audible frequency range and super-high-frequency components within a range exceeding the audible frequency range up to a predetermined maximum frequency and has an autocorrelation order represented by at least either one of a first property and a second property. The discrimination means discriminates whether or not a fundamental brain network system of a human being can be introduced into a fundamental brain including the brain stem, thalamus and hypothalamus that are regions to bear the fundamental brain function and a fundamental brain network of neuronal projection from the fundamental brain to various brain regions, by applying an actual vibration generated from the vibration signal to the human being.

The first property has a fractal nature such that a shape of a three-dimensional power spectrum array of time, frequency and power of the components exceeding the audible frequency range is a complexity having a self-similarity. A local exponent of fractal dimension is a value obtained, upon calculating the fractal dimension of a curved surface of the three-dimensional power spectrum array by using a box-counting method, by inverting the sign of an inclination of a straight line that interconnects two mutually adjacent points when logarithms of a necessary minimum number of reference boxes for covering the curved surface are plotted with respect to a logarithm of a size of each one side of the reference boxes. The local exponent of fractal dimension is a value that represents a self-similarity of the shape, and the local exponent of fractal dimension has a value of not smaller than 2.2 and not greater than 2.8 in a range in which a spectro-temporal index defined by normalizing one side of the reference box is $2^{-1}$ to $2^{-5}$ and a fluctuation range of the local exponent of fractal dimension within 0.4 when the spectro-temporal index changes in a range of $2^{-1}$ to $2^{-5}$.

The second property is defined such that a degree of one of predictability and irregularity of time series of the vibration signal changes with time except for the time series of the vibration signal that are completely predictable and regular and for the time series of the vibration signal that are completely unpredictable and random. An information entropy density representing the irregularity of time series data has a value in a range of not smaller than −5 and smaller than zero, and an entropy variation index (Entropy Variation Index; EV-index), which is a variance of the information entropy density and represents a degree of time variance, has a value of not smaller than 0.001 for 51.2 seconds.

In the above-mentioned vibration discriminating apparatus, the discrimination means includes first, second and third partial discrimination means, and final discrimination means. The first partial discrimination means discriminates whether or not the inputted vibration signal is a vibration signal containing audible range components that are vibration components in the audible frequency range and whether or not the signal contains super-high-frequency components within a range exceeding the audible frequency range up to the maximum frequency. The second partial discrimination means discriminates whether or not the inputted vibration signal has the autocorrelation order represented by the first property. The third partial discrimination means discriminates whether or not the inputted vibration signal has the autocorrelation order represented by the second property. The final discrimination means discriminates whether or not the inputted vibration signal has the feature of a hypersonic sound based on the discrimination results of the first to third discrimination means.

A vibration monitoring system according to an eighth aspect of the present invention includes the vibration discriminating apparatus. The vibration monitoring system includes at least one of alarm generating means, and addition means. The alarm generating means outputs an alarm when the discrimination result of the discrimination means indicates that the inputted vibration signal cannot introduce the fundamental brain activation effect. The addition means adds the complementing vibration signal, that has the autocorrelation order and is generated by the vibration generating apparatus, to the inputted vibration signal when the discrimination result of the discrimination means indicates that the inputted vibration signal cannot introduce the fundamental brain activation effect.

A vibration discriminating method according to a ninth aspect of the present invention includes a discrimination step of discriminating whether or not an inputted vibration signal contains audible range components that are vibration components in an audible frequency range and super-high-frequency components within a range exceeding the audible frequency range up to a predetermined maximum frequency and has an autocorrelation order represented by at least either one of a first property and a second property. The discrimination step discriminating whether or not a fundamental brain network system of a human being can be introduced into a fundamental brain including the brain stem, thalamus and hypothalamus that are regions to bear the fundamental brain function and a fundamental brain network of neuronal projection from the fundamental brain to various brain regions, by applying an actual vibration generated from the vibration signal to the human being.

The first property has a fractal nature such that a shape of a three-dimensional power spectrum array of time, frequency and power of the components exceeding the audible frequency range is a complexity having a self-similarity. A local exponent of fractal dimension is a value obtained, upon calculating the fractal dimension of a curved surface of the three-dimensional power spectrum array by using a box-counting method, by inverting the sign of an inclination of a straight line that interconnects two mutually adjacent points when logarithms of a necessary minimum number of reference boxes for covering the curved surface are plotted with respect to a logarithm of a size of each one side of the reference boxes. The local exponent of fractal dimension is a value that represents a self-similarity of the shape, and the local exponent of fractal dimension has a value of not smaller than 2.2 and not greater than 2.8 in a range in which a spectro-temporal index defined by normalizing one side of the reference box is $2^{-1}$ to $2^{-5}$ and a fluctuation range of the local exponent of fractal dimension within 0.4 when the spectro-temporal index changes in a range of $2^{-1}$ to $2^{-5}$.

The second property is defined such that a degree of one of predictability and irregularity of time series of the vibration signal changes with time except for the time series of the vibration signal that are completely predictable and regular and for the time series of the vibration signal that are completely unpredictable and random. An information entropy density representing the irregularity of time series data has a value in a range of not smaller than −5 and smaller than zero, and an entropy variation index (Entropy Variation Index; EV-index), which is a variance of the information entropy density and represents a degree of time variance, has a value of not smaller than 0.001 for 51.2 seconds.

In the above-mentioned vibration discriminating method, the discrimination step includes first, second and third partial discrimination steps and a final discrimination step. The first partial discrimination step discriminates whether or not the inputted vibration signal is a vibration signal containing audible range components that are vibration components in the audible frequency range and whether or not the signal contains super-high-frequency components within a range exceeding the audible frequency range up to the maximum frequency. The second partial discrimination step discriminates whether or not the inputted vibration signal has the autocorrelation order represented by the first property. The third partial discrimination step discriminates whether or not the inputted vibration signal has the autocorrelation order represented by the second property. The final discrimination step discriminates whether or not the inputted vibration signal has the feature of a hypersonic sound based on the discrimination results of the first to third discrimination steps.

A computer-executable program according to a tenth aspect of the present invention includes the steps of the above-mentioned vibration discriminating method.

A computer-readable medium according to an eleventh aspect of the present invention stores the above-mentioned program.

Effects of the Invention

According to the present invention, by clarifying the detailed structural feature of the vibration that can introduce the fundamental brain activation effect, the apparatus and method for generating a vibration that can introduce a hypersonic effect, i.e., a hypersonic sound, and the apparatus and method for discriminating the vibration can be provided.

As an advantageous effect, in order to first know whether a certain vibration introduces the fundamental brain activation effect, it is not necessary to apply the vibration to a listener in each case and to examine the activation of the listener's fundamental brain by a strict physiological experiment as conventionally performed, and it becomes possible to know whether the vibration introduces the fundamental brain activation effect by only examining the structural feature of the super-high-frequency components of the vibration.

Secondly, it becomes possible to artificially synthesize various kinds of vibrations that can introduce the fundamental brain activation effect without relying on the inartificial natural vibration generating sources, of which the effectiveness and safety have been proven by the past results, in order to generate a vibration that can introduce the fundamental brain activation effect.

Thirdly, in order to know whether the super-high-frequency components, which are artificially expanded by the conventional band expanding method that hardly expects prevention of the deterioration in the fundamental brain activity and cannot deny the possibility of causing a safety problem depending on circumstances, are safe and possible to introduce the fundamental brain activation effect, it is not necessary to apply the vibration to a listener in each case as conventionally performed and examine the activation of the listener's fundamental brain by a strict physiologic experiment, and it becomes possible to know whether the vibration is safe and able to introduce the fundamental brain activation effect by only examining the structural feature of the super-high-frequency components of the vibration.

Fourthly, by activating the fundamental brain network system responsible for the generation of all reactions of pleasure, beauty and emotion by generating a vibration to which the super-high-frequency components having the feature of the autocorrelation order are added or enhanced, it becomes possible to increase the expressive effects, heighten the sensuous artistic value and concurrently promote the safety of the already accumulated record library of sound sources, which are currently voluminously accumulated in terms of both quality and quantity and are unable to introduce the fundamental brain activation effect because they contain utterly or almost no super-high-frequency component having the feature of the autocorrelation order.

Fifthly, in the contents comprehensively working on multiple sensory systems such as video and audio contents recorded in large-capacity package media that are rapidly popularized in recent years and video and audio that are distributed and delivered by using Internet and the like, there is the problem of a trade-off relation between the information capacity usable for video and the information capacity usable for audio, and consequently, this leads to the problem of an antinomy between image quality and sound quality. Against the problems, by heightening the activity of the fundamental brain network system being unitarily responsible for the generation of all reactions of pleasure, beauty and emotion by generating a vibration to which the super-high-frequency components having the feature of the autocorrelation order are added or enhanced, it becomes possible to enhance also the aesthetic sensibility to sensory inputs other than sounds in parallel and heighten the expressive effects in the entire sensory system.

Sixthly, in order to solve the problem of the antinomy occurring in information transmitting sounds in spaces having significant background noises, the sound effects of artistic productions and so on, i.e., such a problem that "necessary information cannot be caught unless sound volume is increased" whereas "the sound becomes bothersome and unpleasant when the sound volume is increased" on the other hand without contradiction, by complementing a vibration containing super-high-frequency components having the feature of the autocorrelation order, it becomes possible to heighten the activity of the entire fundamental brain network system and activate the thalamus and the brain stem that is included in this system and have operation to sensitize the sensibility to general sensory information inputs (excluding olfactory sensation) and concurrently activate the reward system neural circuit that is included in the same system and has operation to generate pleasant sensation and alleviate the unpleasant sensation in parallel, thereby allowing both the sensitization and comforting of sound perception to be developed or reinforced in a coexistent state.

If the above is generalized, it becomes possible to generate vibrations that can introduce the fundamental brain activation effect voluminously and easily in terms of both quality and quantity, and by applying them to a human being, activation of the fundamental brain network system constituted of the fundamental brain and the fundamental brain network including the reward system neural circuit of the brain being unitarily comprehensively responsible for the generation of reactions of pleasure, beauty and emotion in the human being is induced, consequently making it possible to enhance the aesthetic sensitivity to various general sensory inputs inclusive of sounds and heighten the sensuous artistic value of input information. In addition, an effect of heightening the physical activation such as homeostatic maintenance and biophylaxis of the whole body managed by the fundamental brain network system is introduced, and it consequently becomes possible to introduce the effects of comprehensively remedying lifestyle-related diseases of metabolic syndromes such as hypertension, hyperlipemia and diabetes, cancer, cerebrovascular disorder and cardiopathy, immune abnormalities including pollinosis and atopic dermatitis, various mental disorders such as dementia, depression, schizophrenia, chronic fatigue syndrome and attention-deficit hyperactivity disorder, behavioral abnormalities such as suicide and self-injurious behaviors, abnormal exaltation of aggressiveness and so on, which are caused by the abnormality of the fundamental brain activity and pose serious problems in the modern society.

BRIEF DESCRIPTION OF DRAWINGS

FIG. 5 is a table showing a local exponent of fractal dimension of a vibration that satisfies the first property on the autocorrelation order of the present invention within a range in which the spectro-temporal index (ST-index) is $2^{-1}$ to $2^{-5}$;

FIG. 16 is a projection chart showing brain regions where the regional cerebral blood flow in an FRS condition is significantly increased by contrast to an LFC alone condition, in which (a) is a projection chart (sagittal projection chart) along the sagittal suture of a human cranium, (b) is a projection chart (coronal projection chart) along the coronal suture, and (c) is a horizontal plane projection chart of them, or experimental results measured by the apparatus of FIG. 15;

FIG. 37 is a front view of a headphone type vibration generating apparatus according to the first preferred embodiment;

FIG. 38 is a diagram of an accessory type vibration generating apparatus according to the first preferred embodiment, in which (a) is its front view, (b) is its right side view, and (c) is its rear view;

FIG. 39 is a diagram of a clothes embedded type vibration generating apparatus according to the first preferred embodiment, in which (a) is its external view, and (b) is its internal view;

Figure 15:
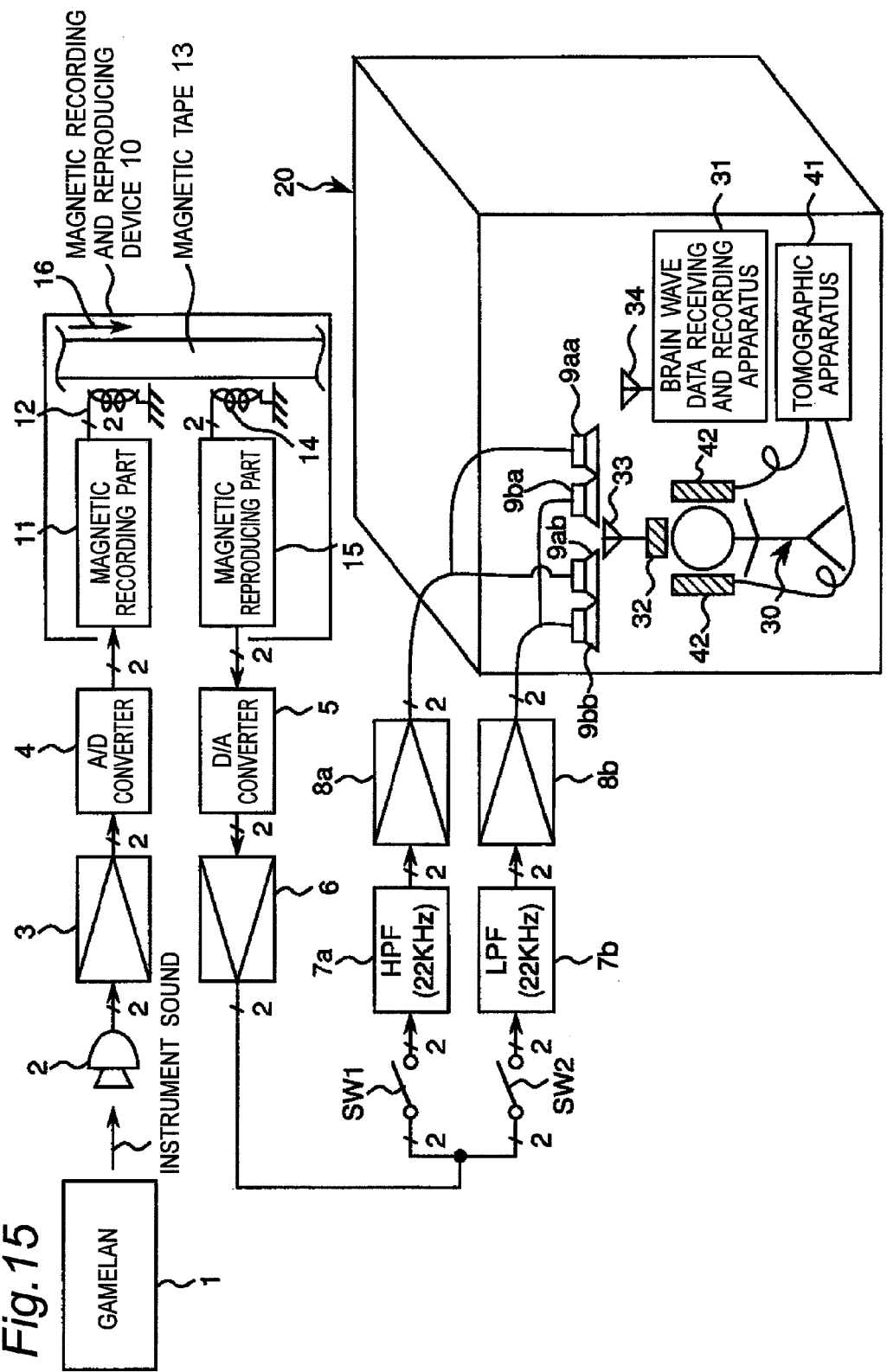
FIG. 15 is a block diagram of a vibration generating apparatus including a configuration of a positron emission tomography (PET) and a brain wave measurement apparatus used in the first preferred embodiment of the present invention and a perspective view showing a room for generating a vibration by the vibration generating apparatus.
Figure 71:
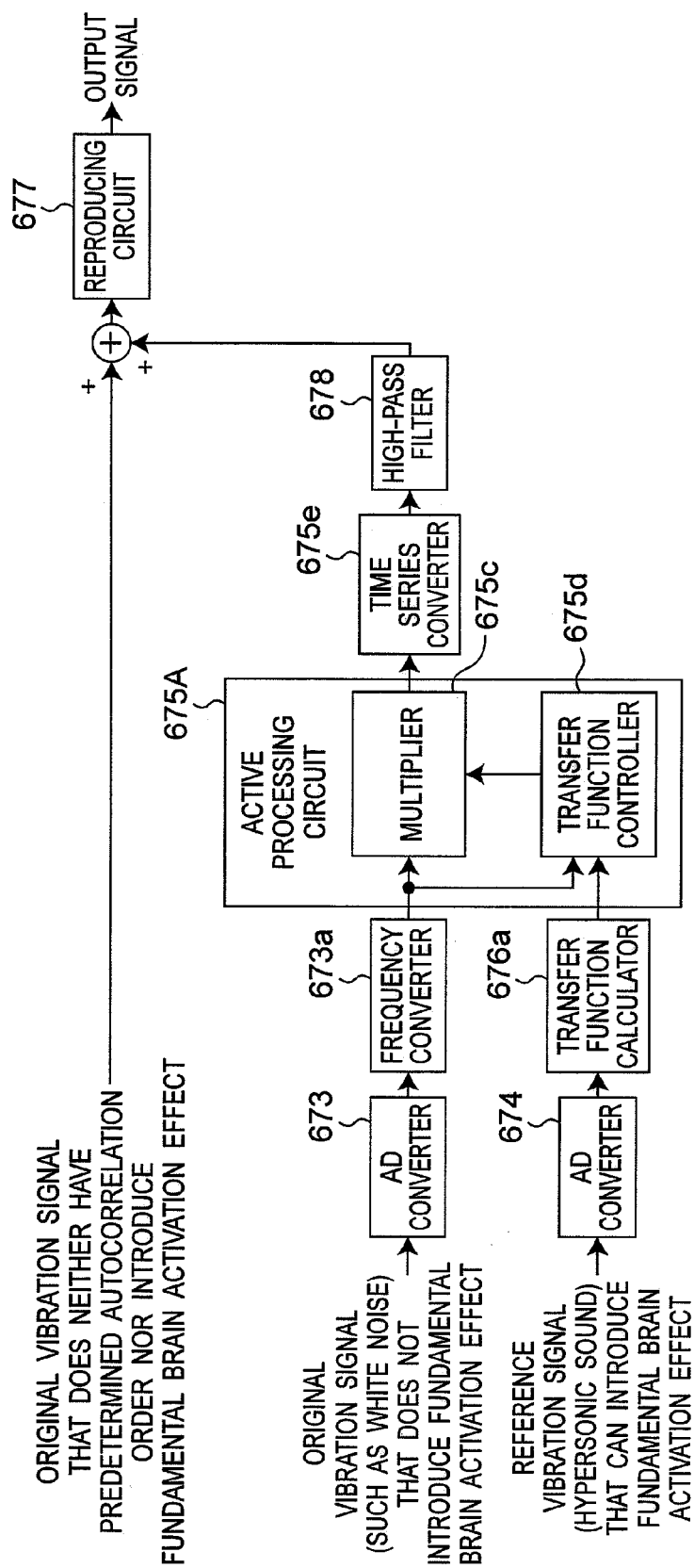
Figure 72:
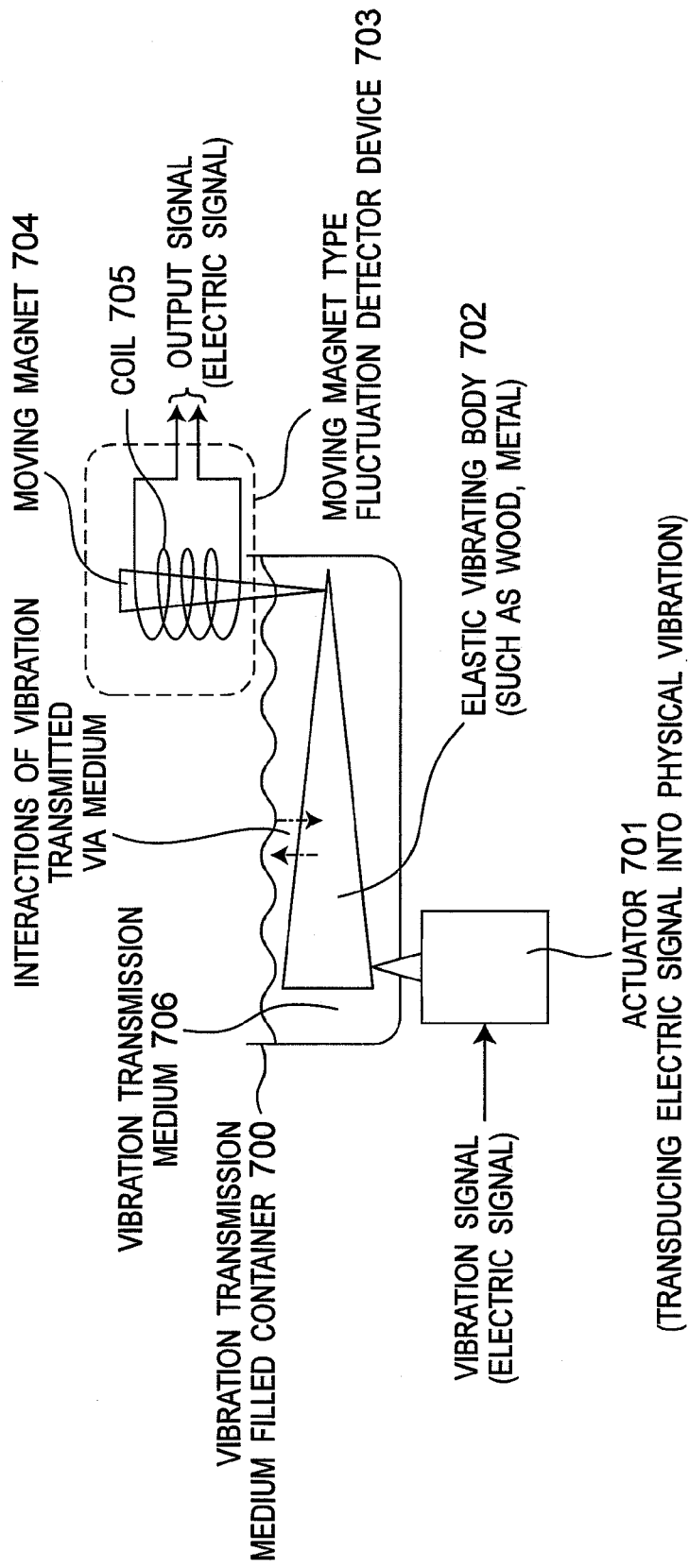
Figure 73:
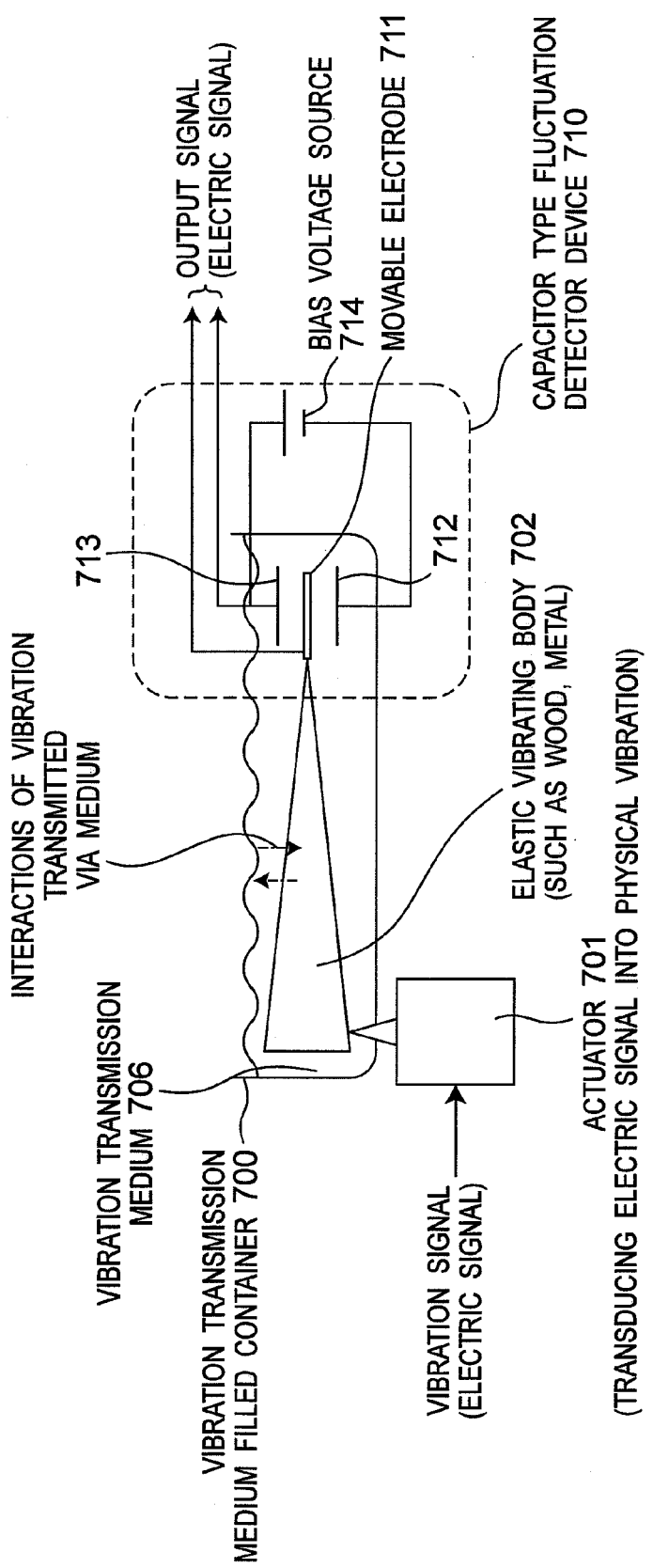
Figure 74:
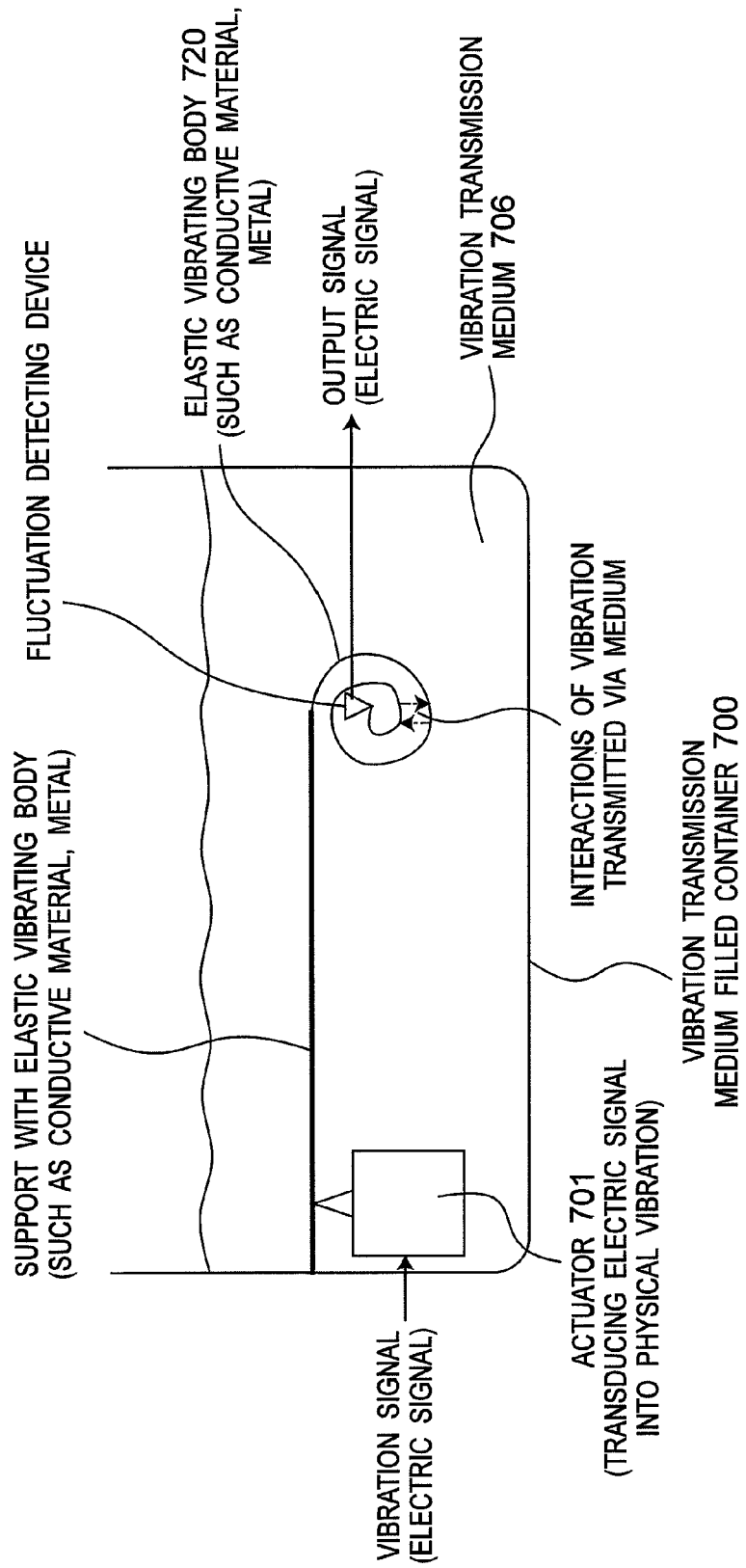
Figure 75:
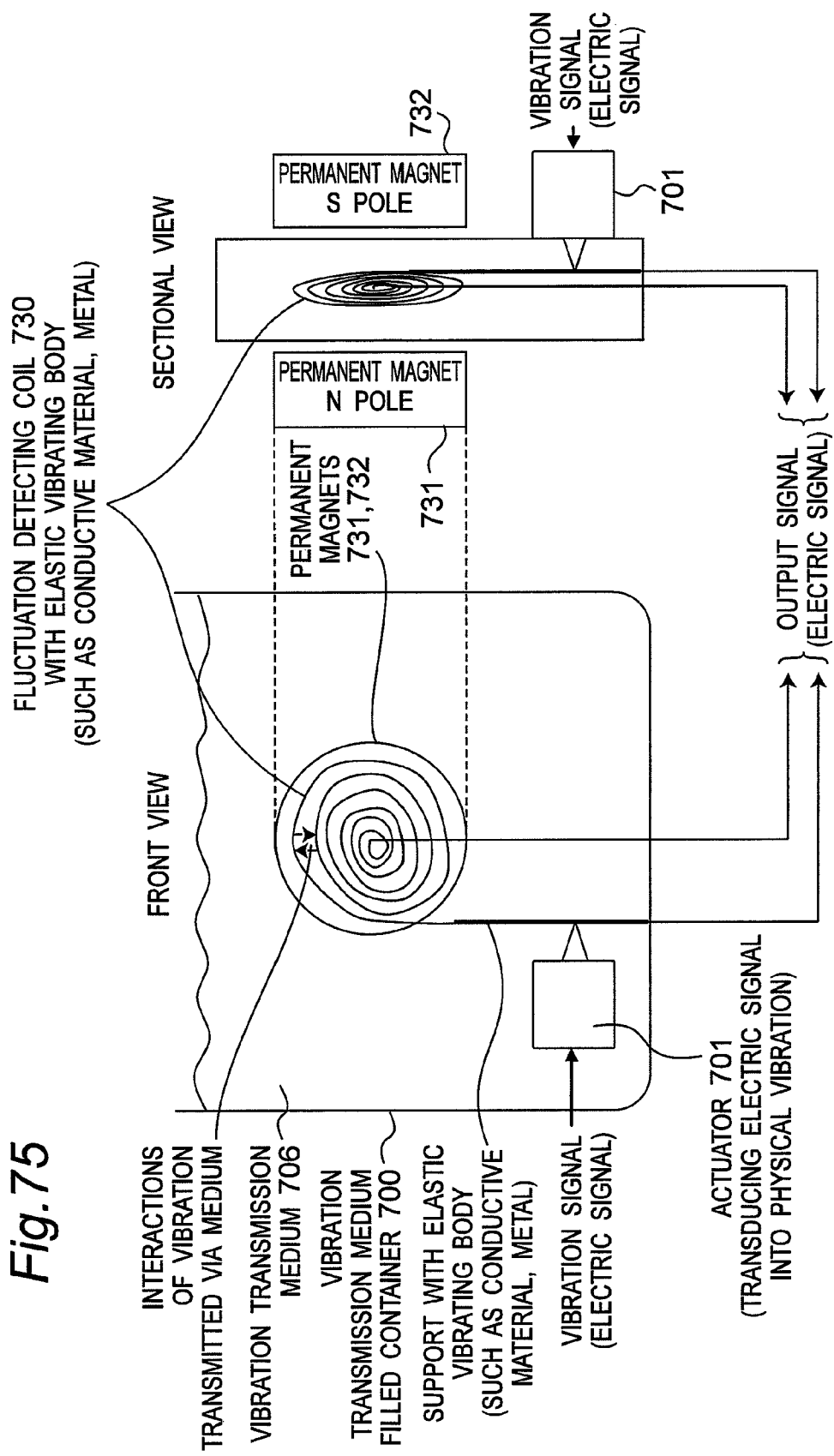
Figure 76:
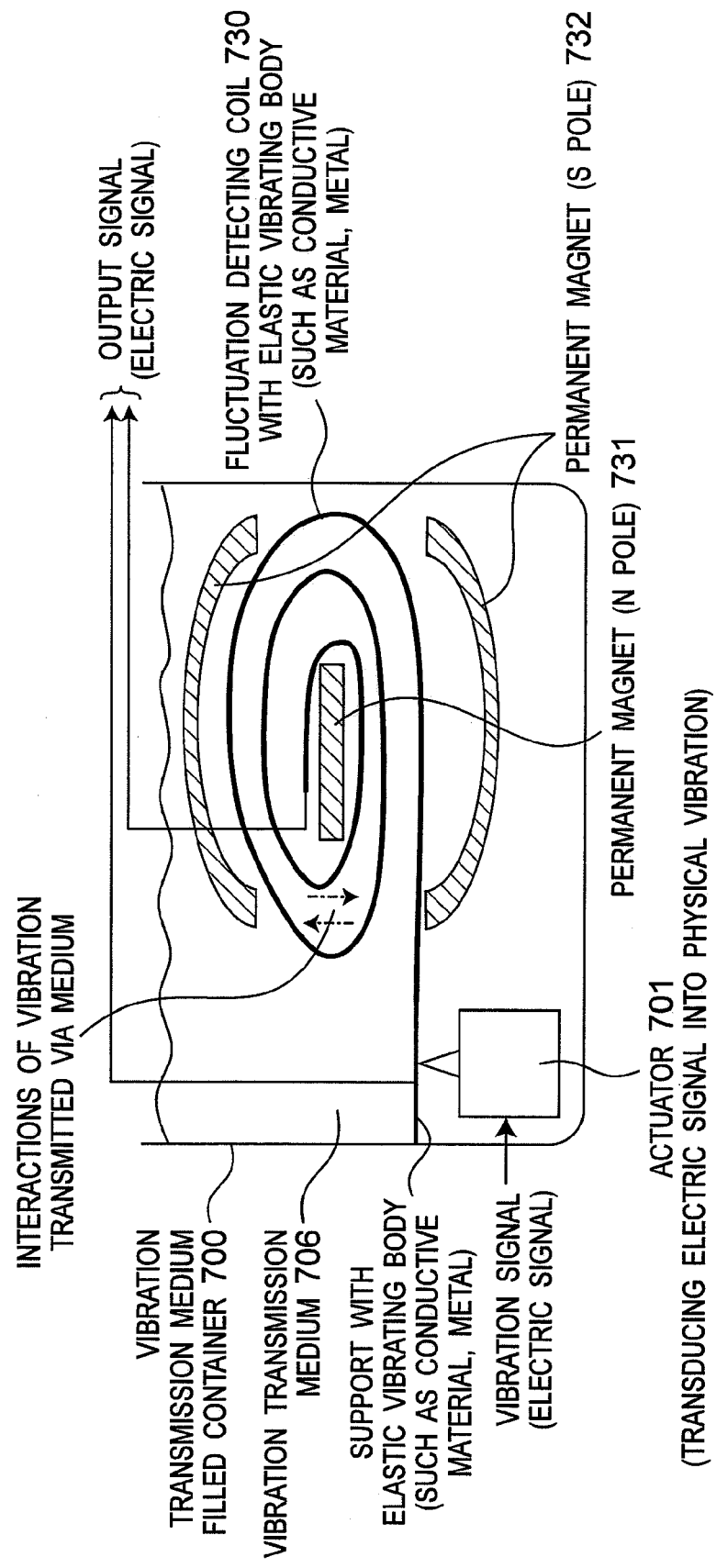
Figure 77:
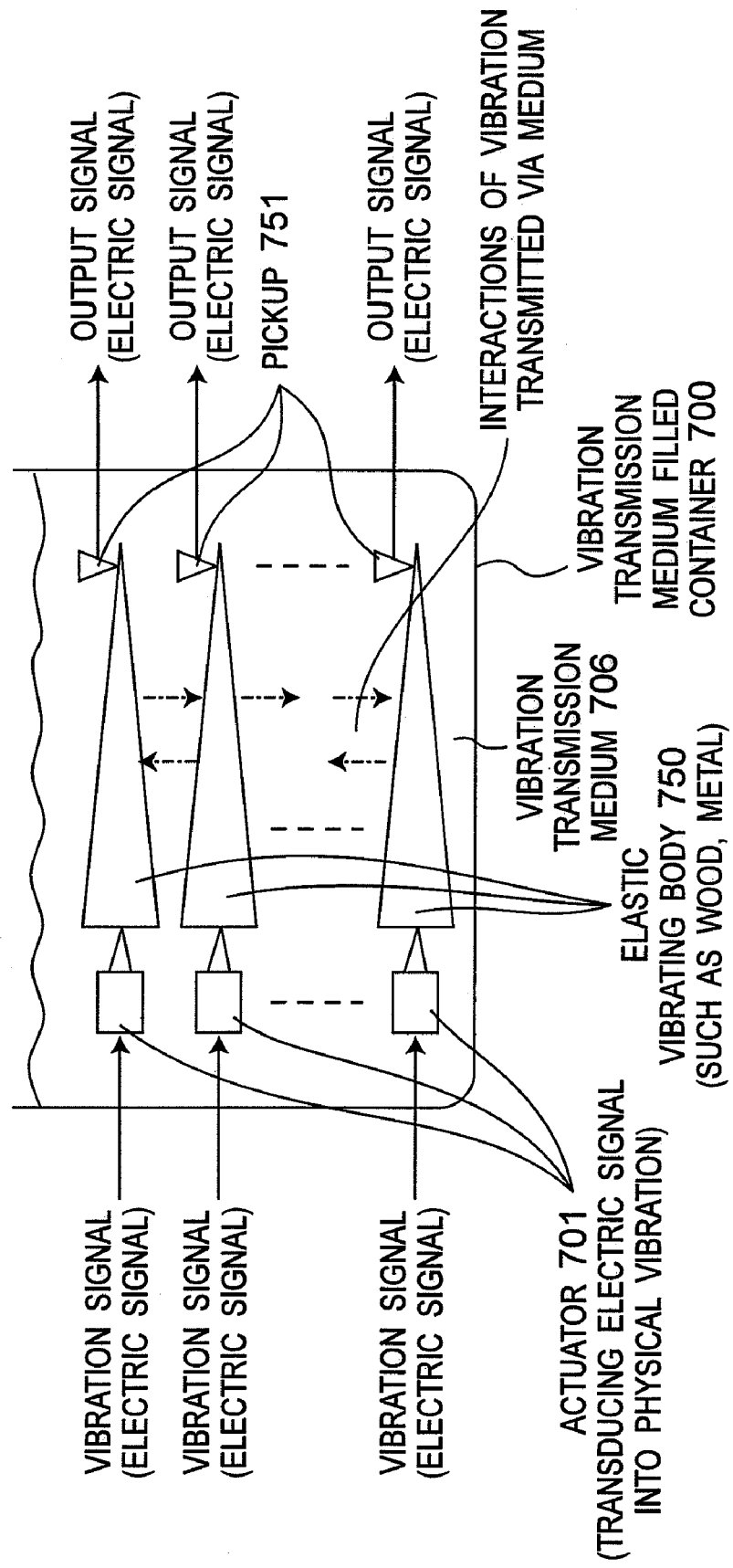
Figure 78:
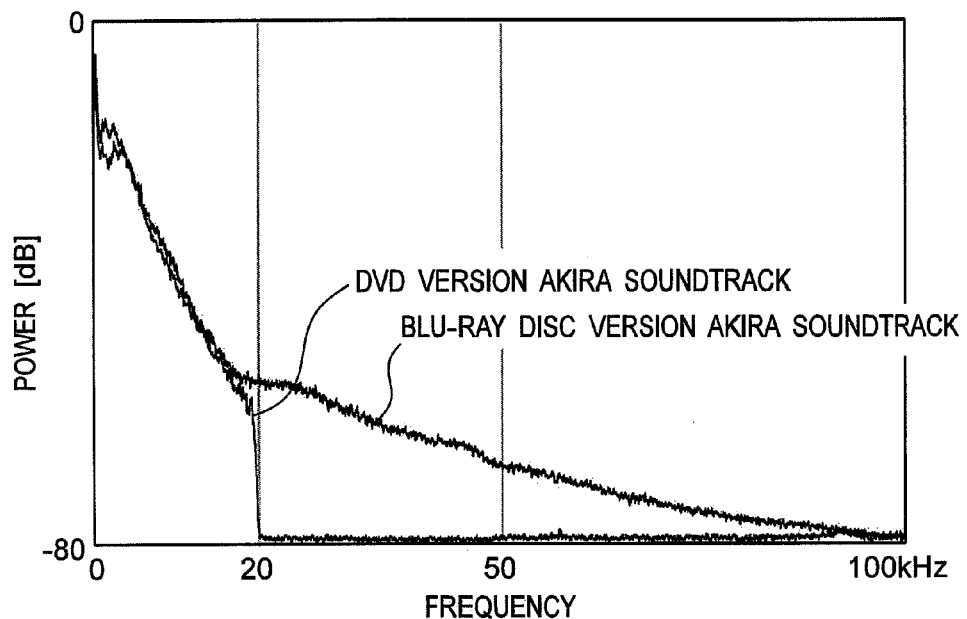
Figure 79:
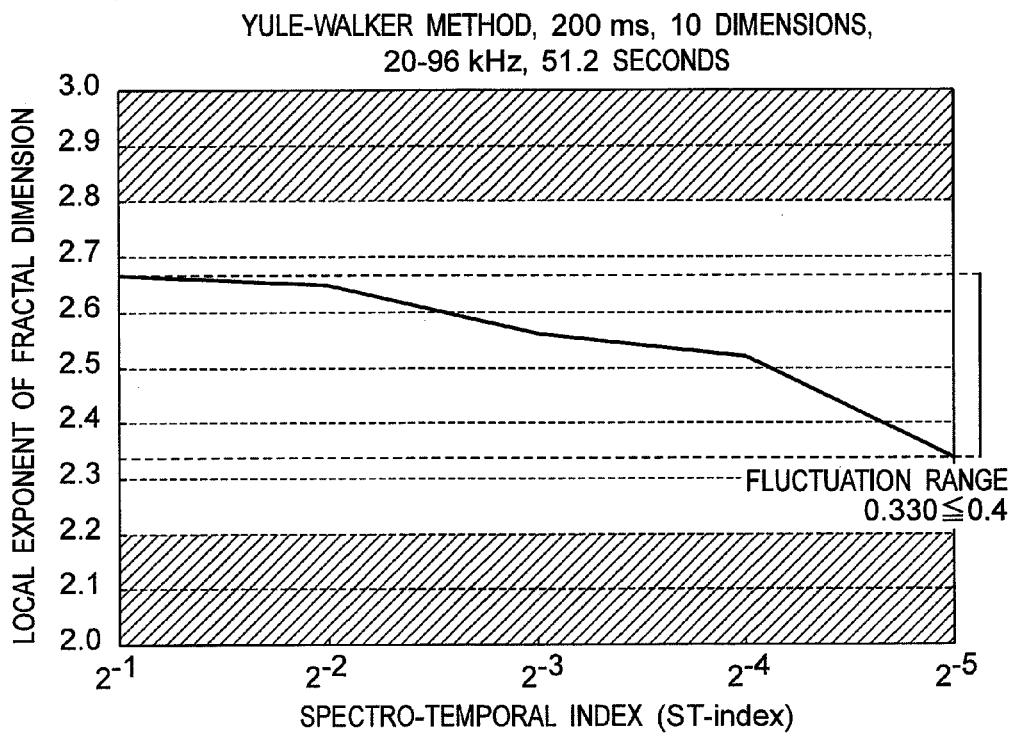
Figure 80:
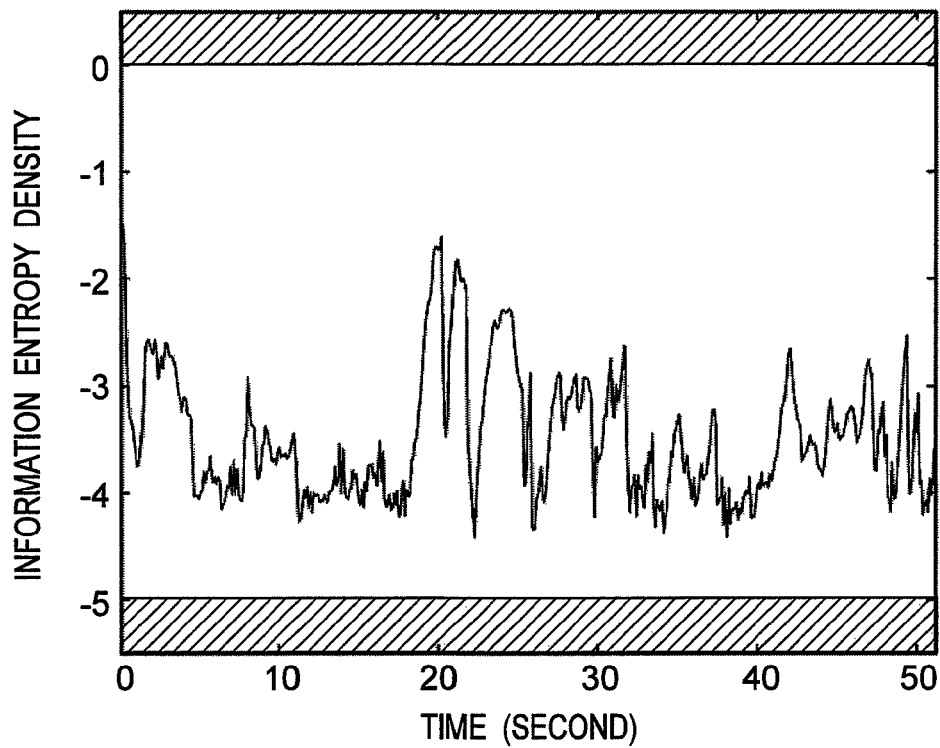
Figure 81:
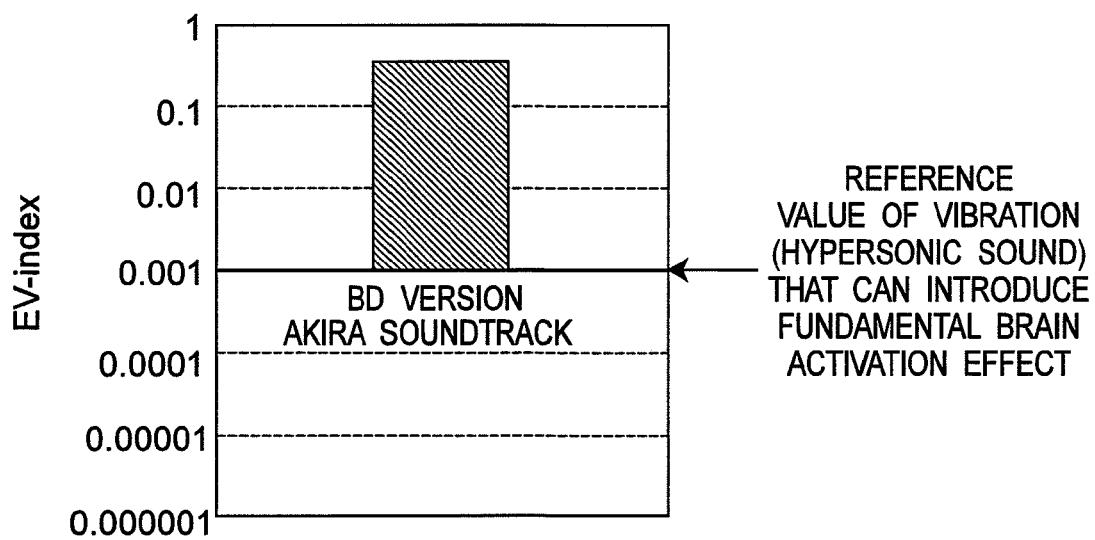
Figure 82:
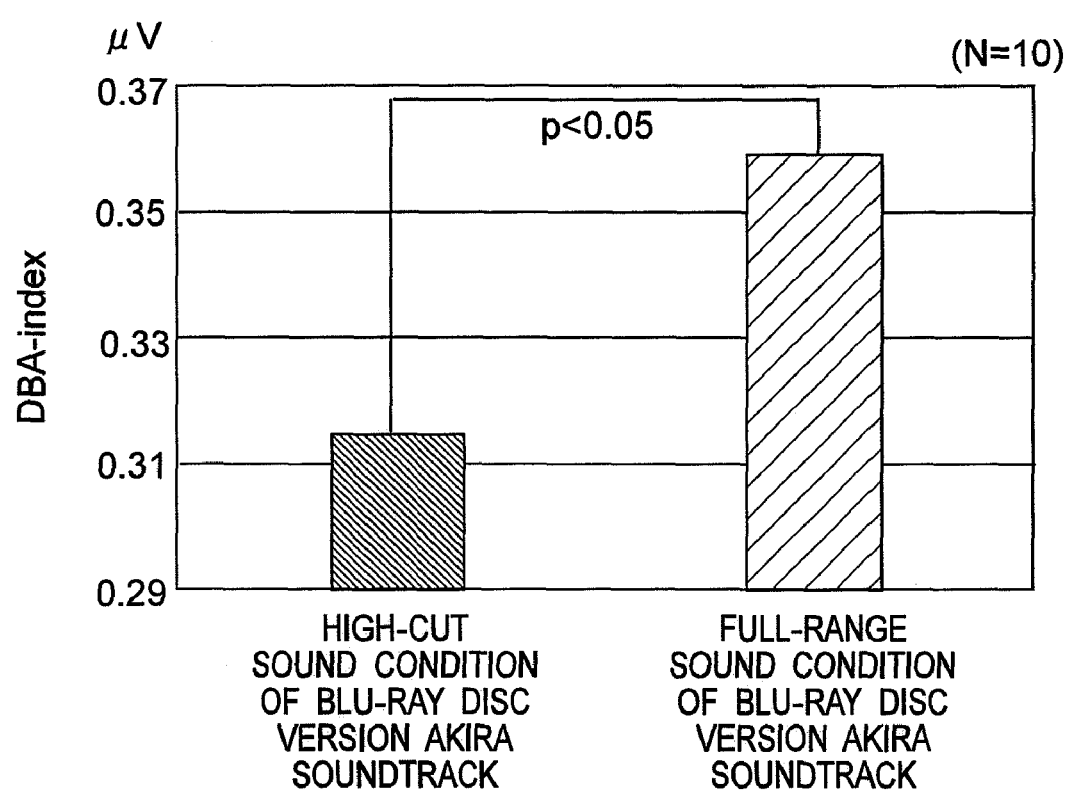
Figure 83:
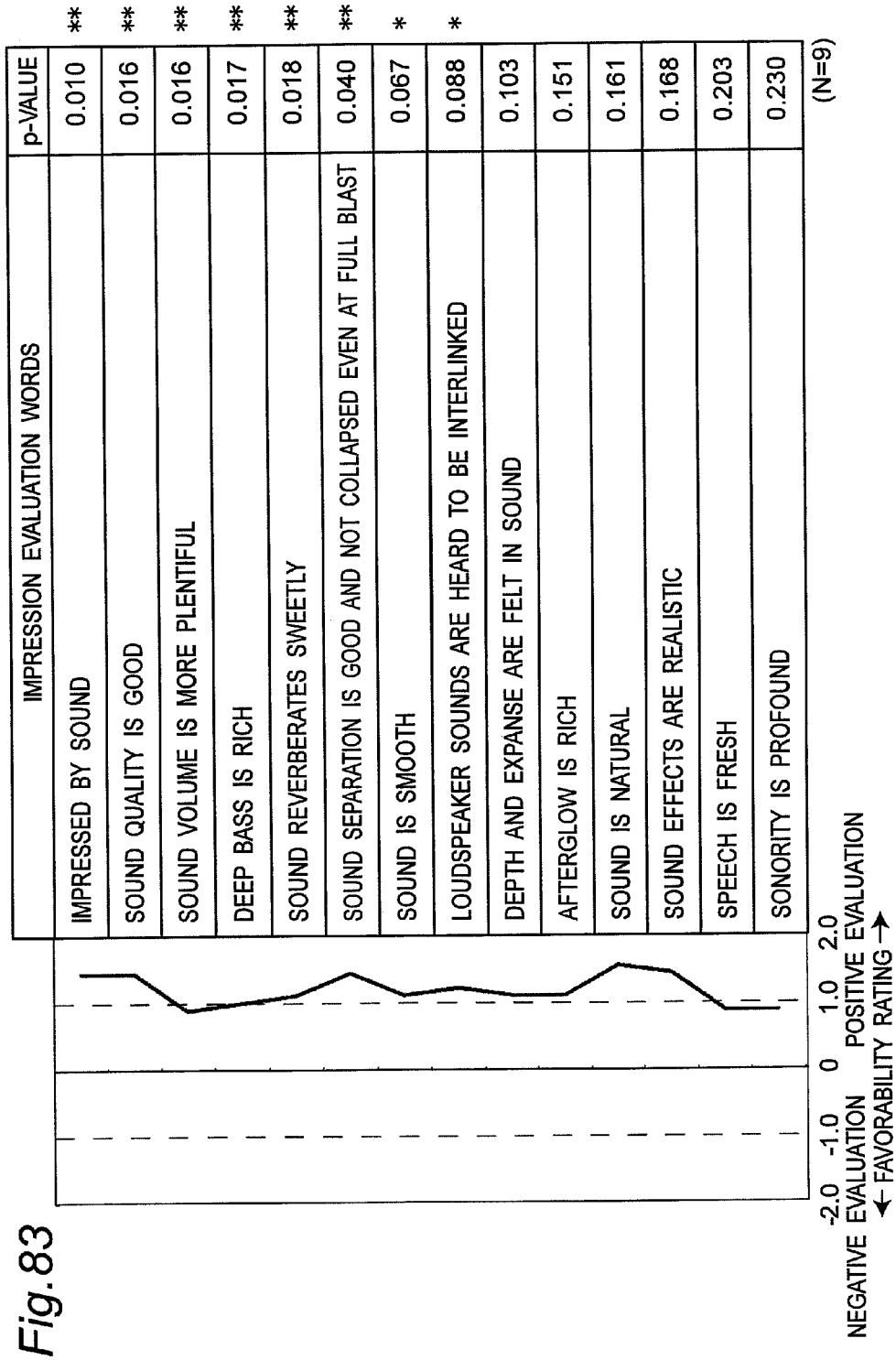
Figure 84:
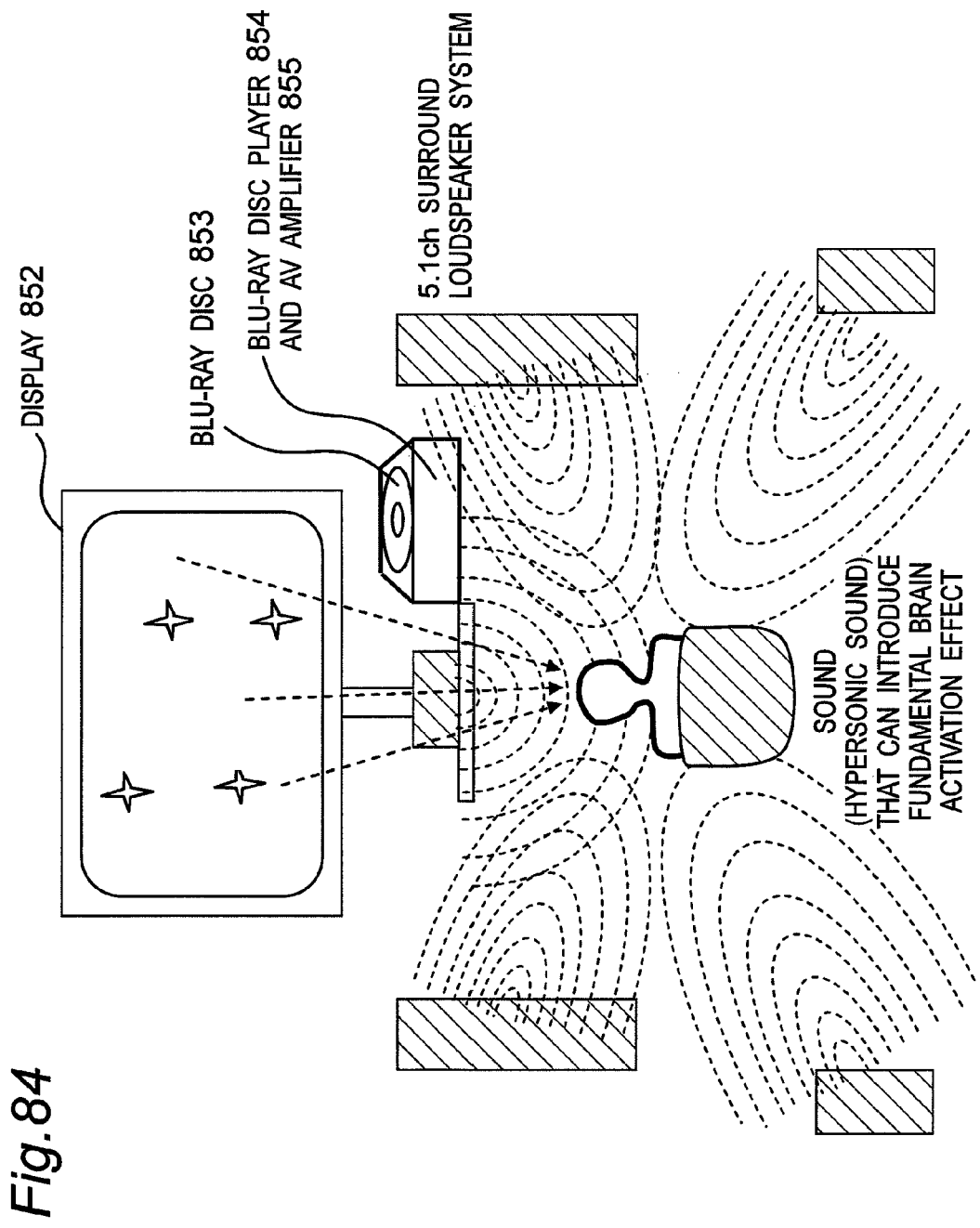
Figure 85:
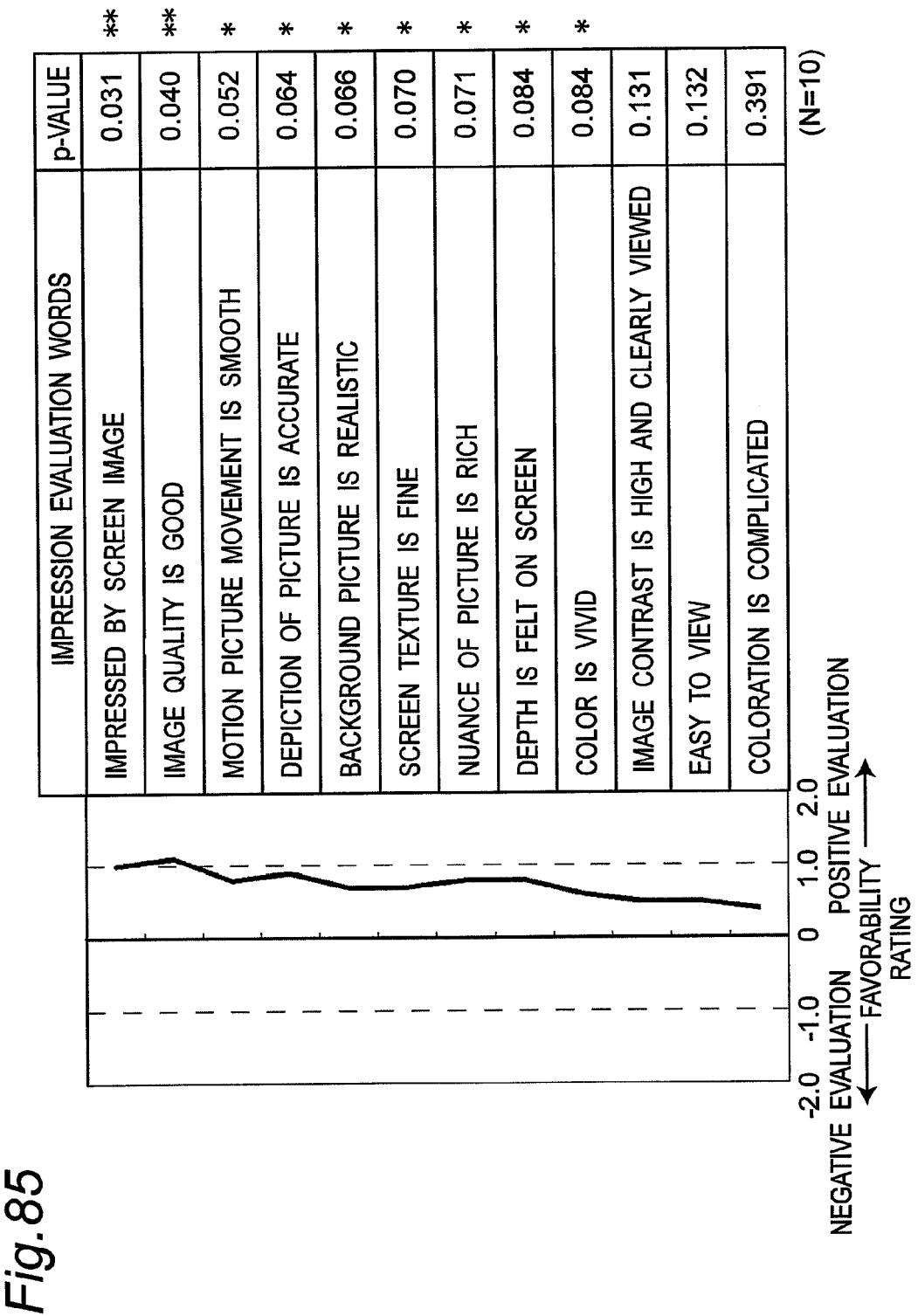
Figure 86:
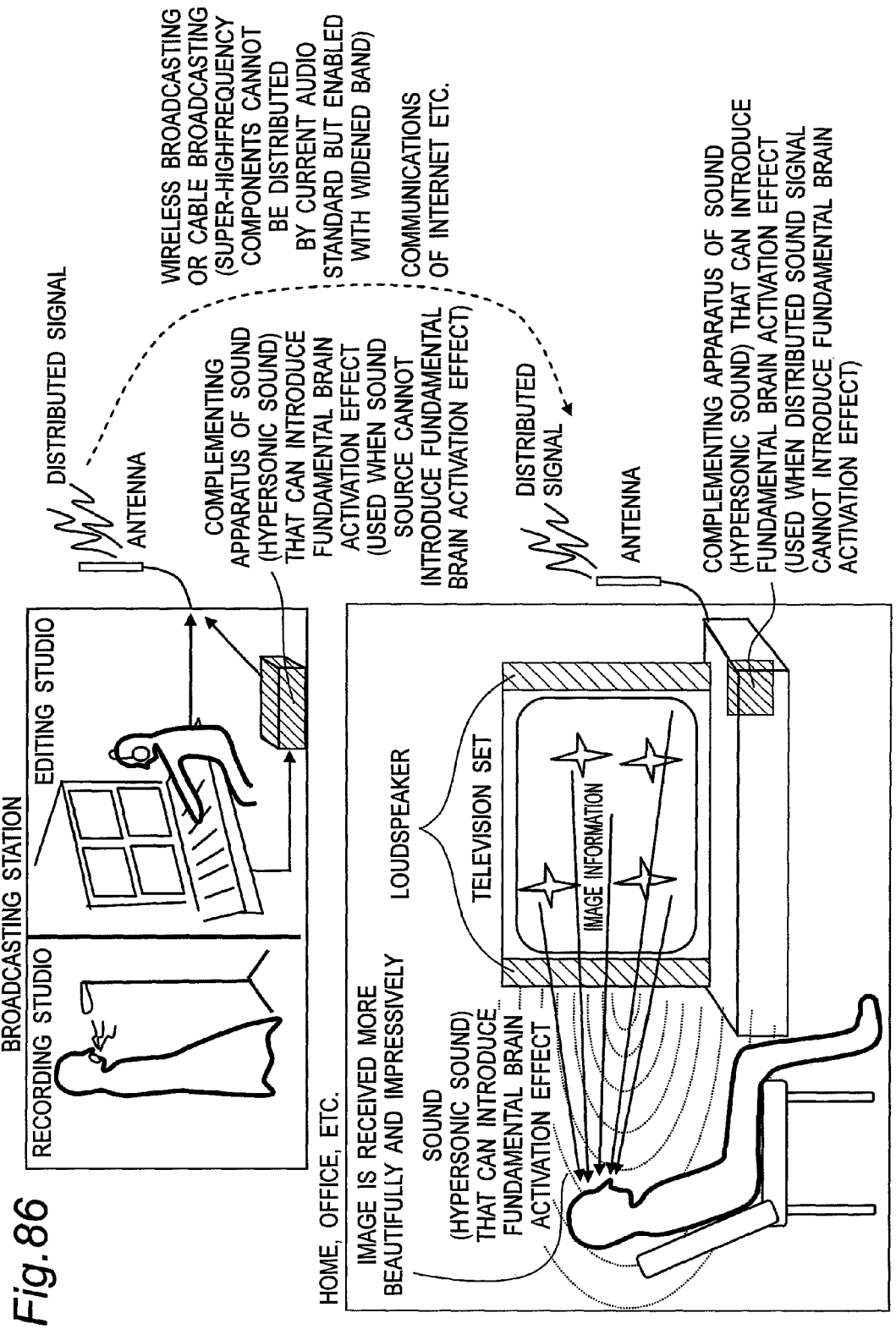
Figure 87:
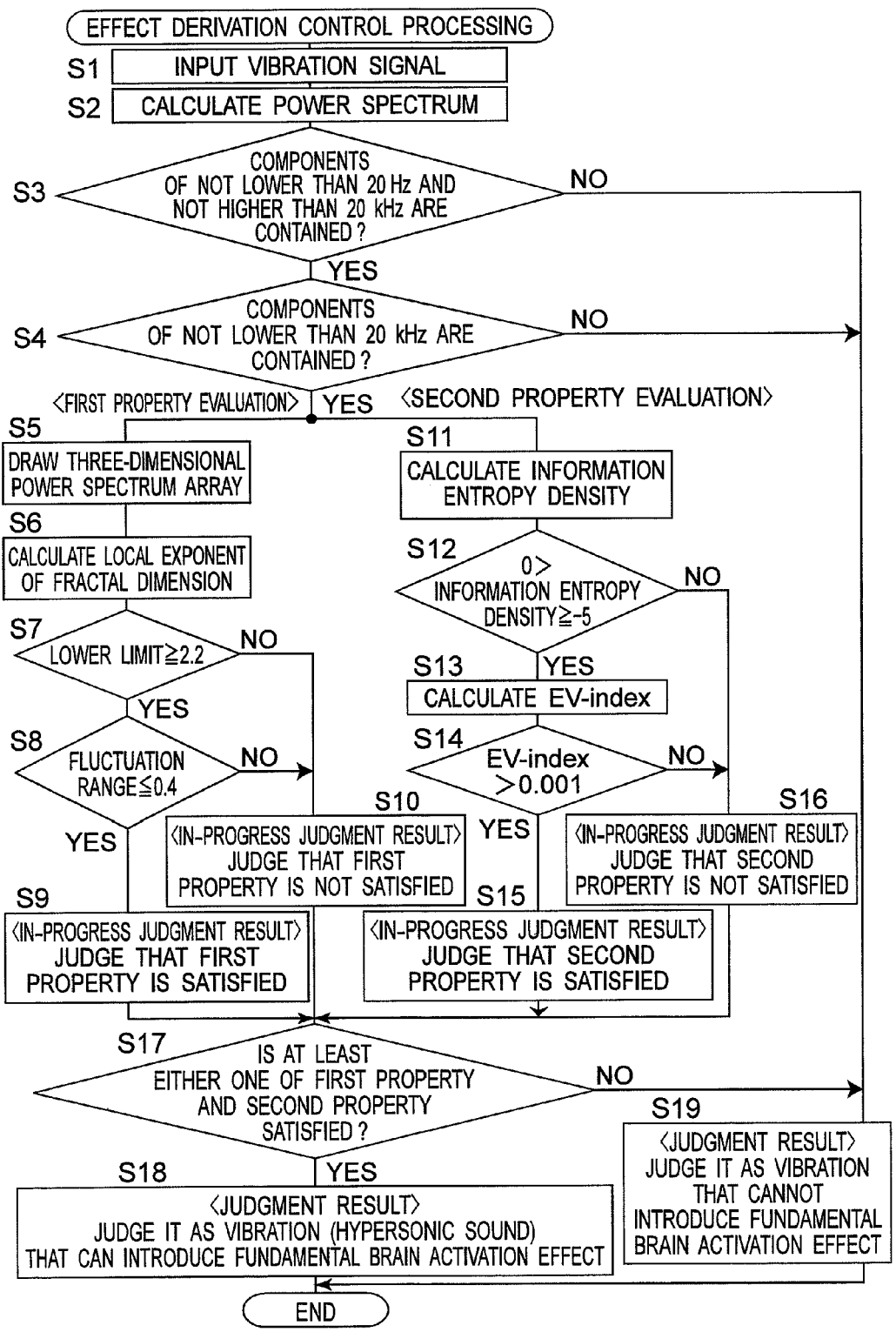
Figure 88:
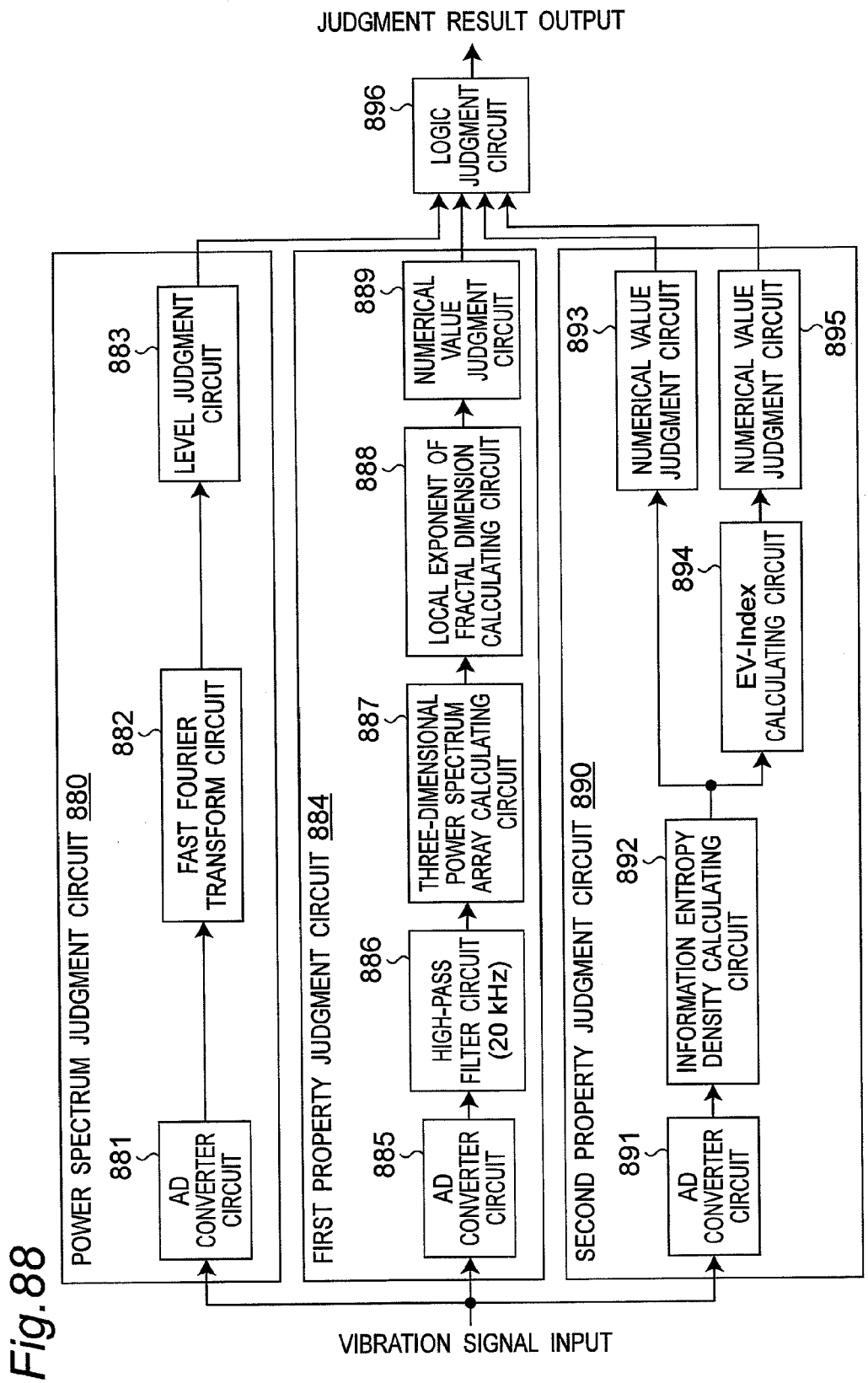
Figure 90A:
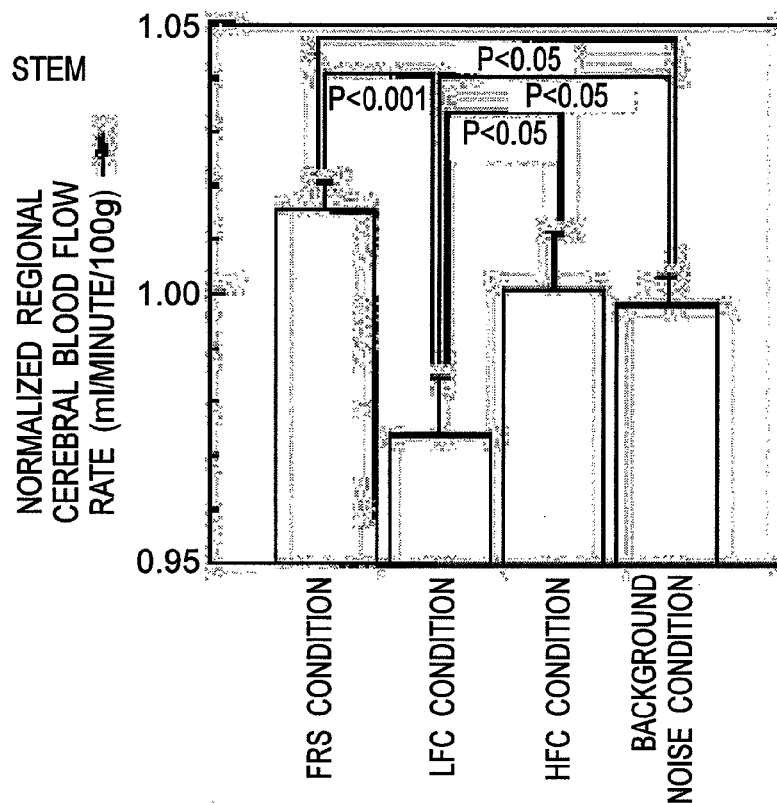
Figure 90B:
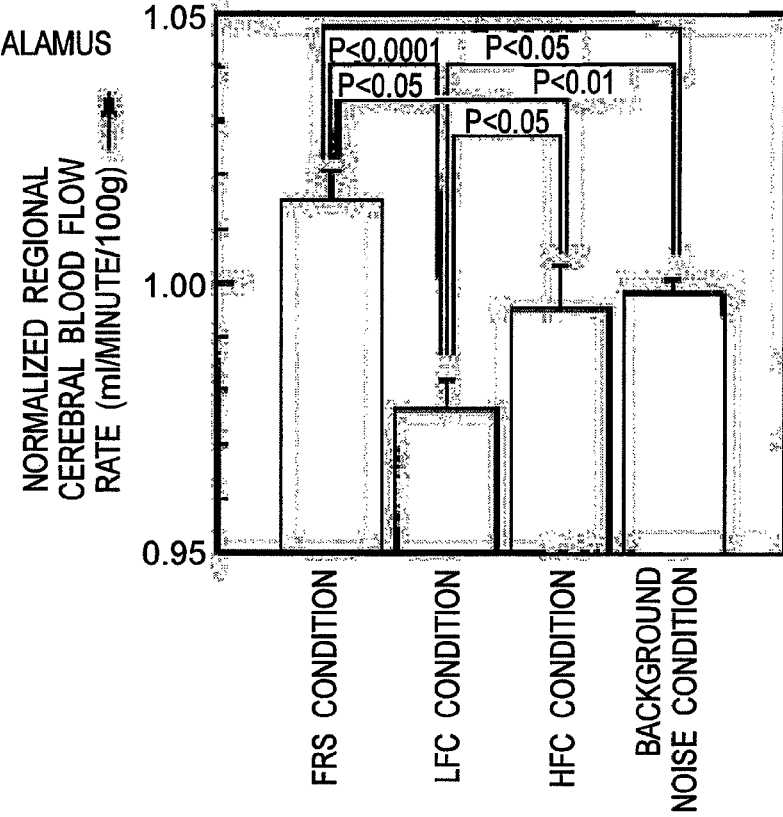
Figure 91:
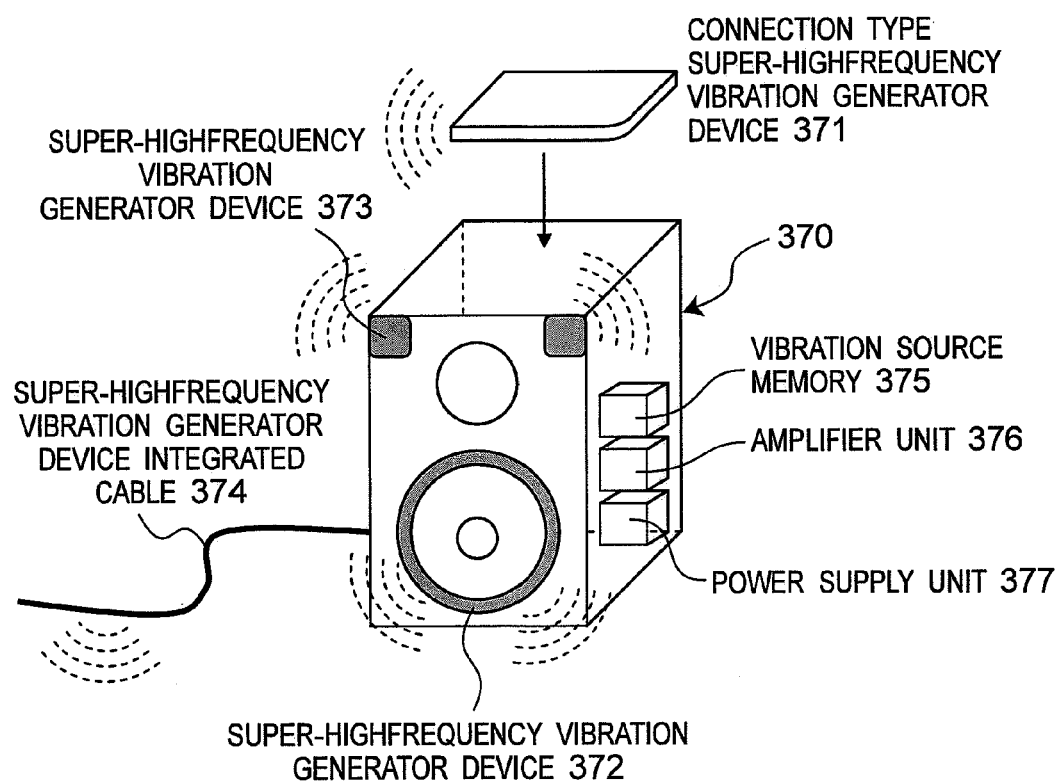
Figure 92:
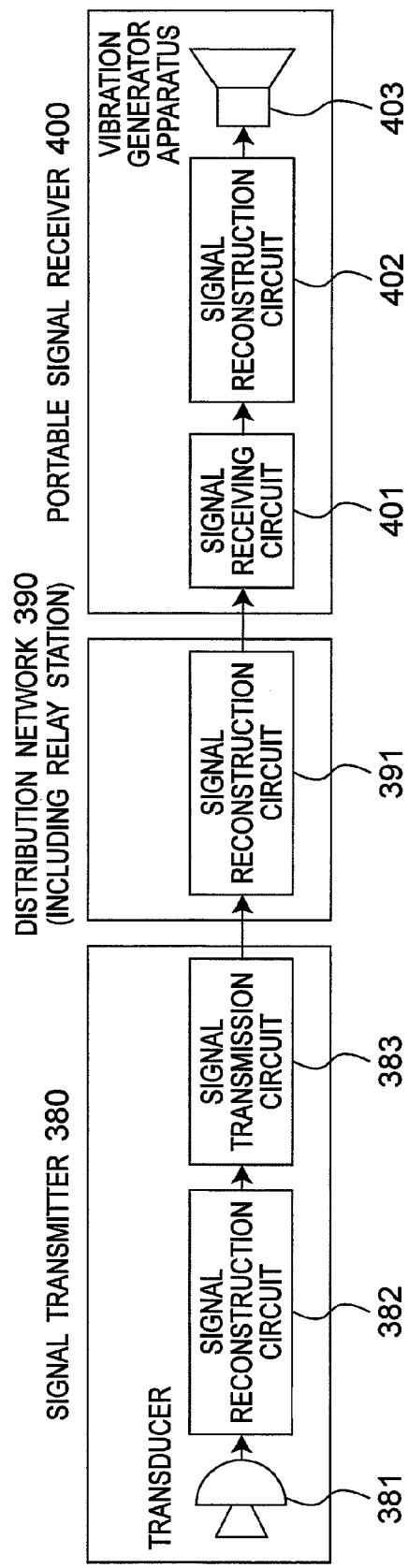
Figure 93:
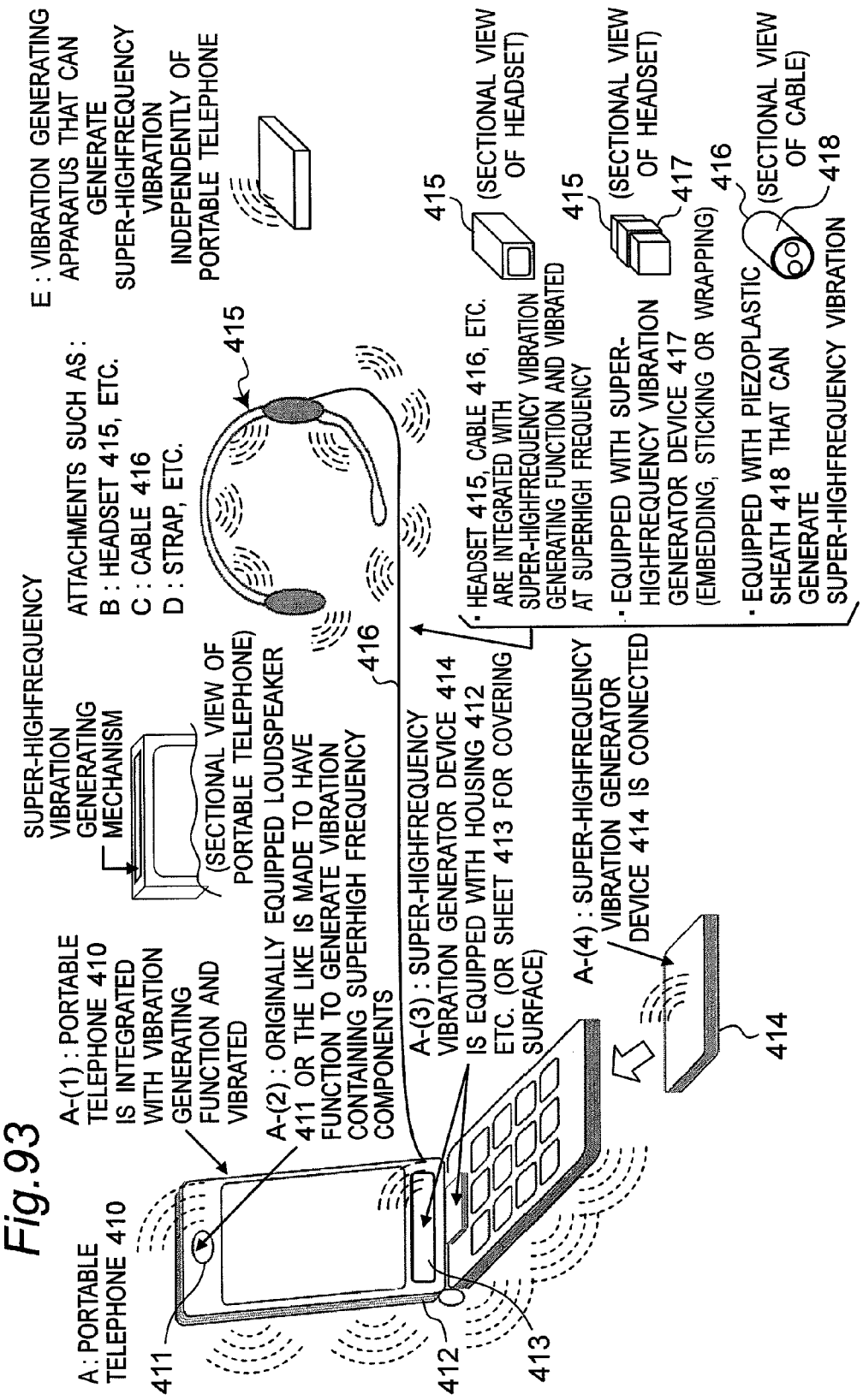
Figure 94:
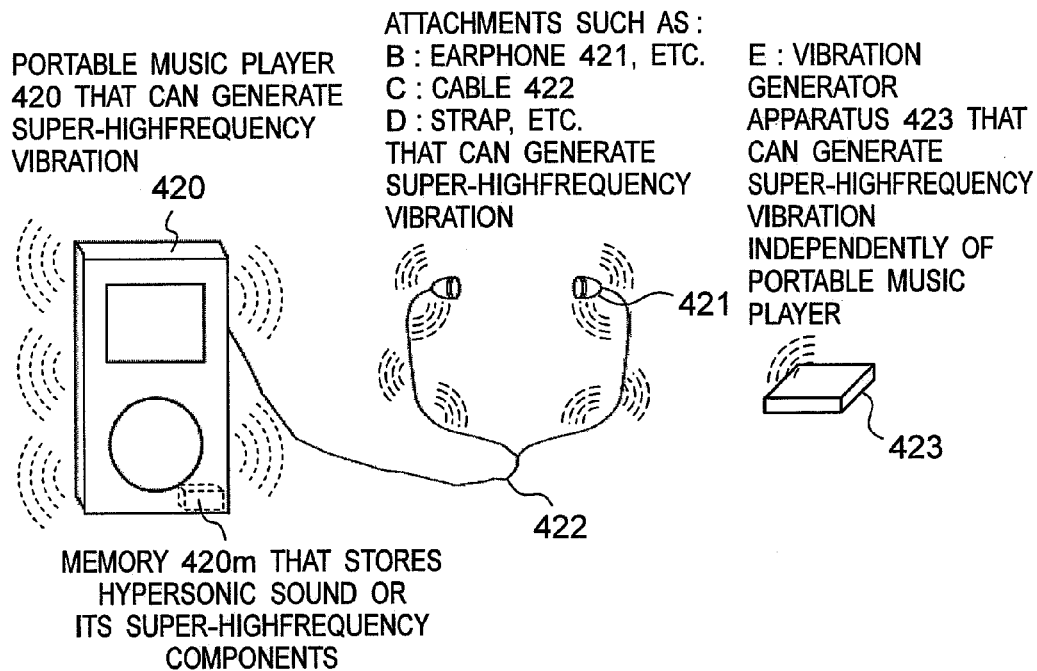
Figure 95:
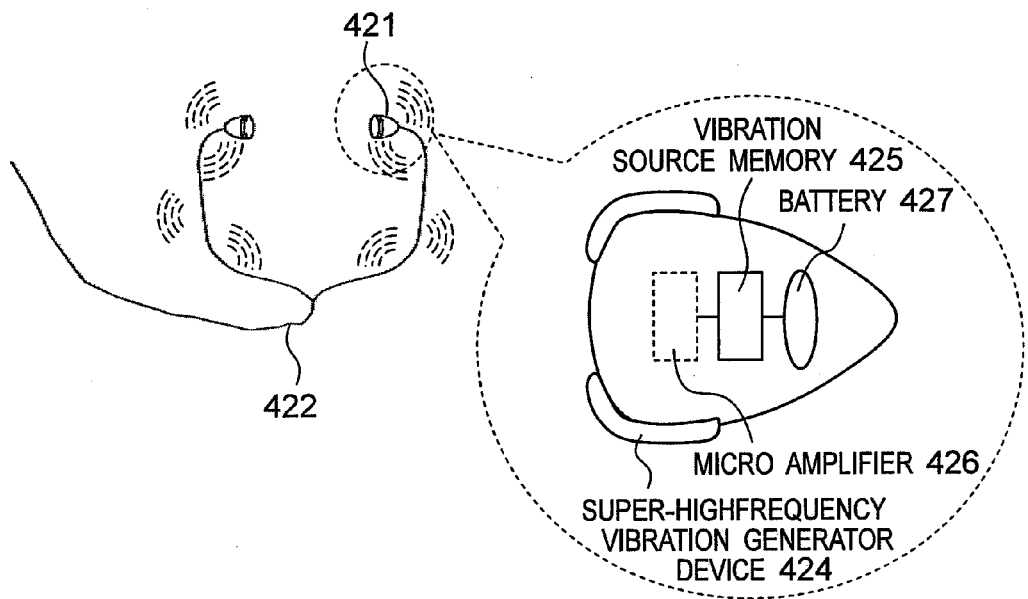
Figure 96:
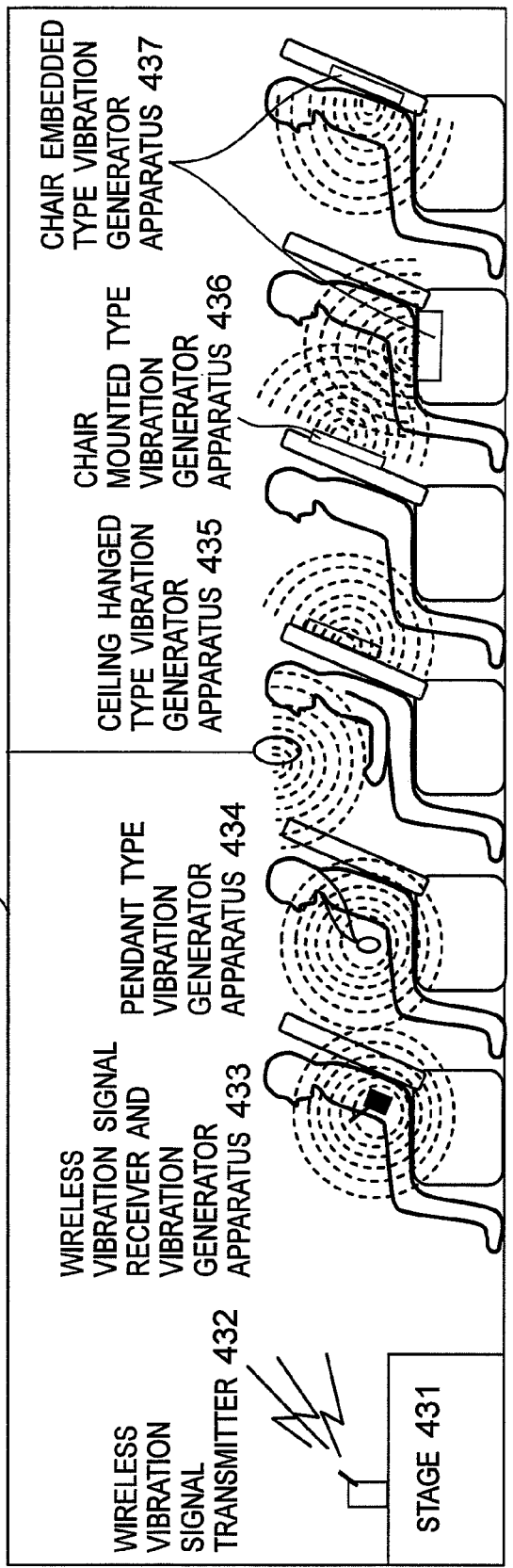
Figure 97:
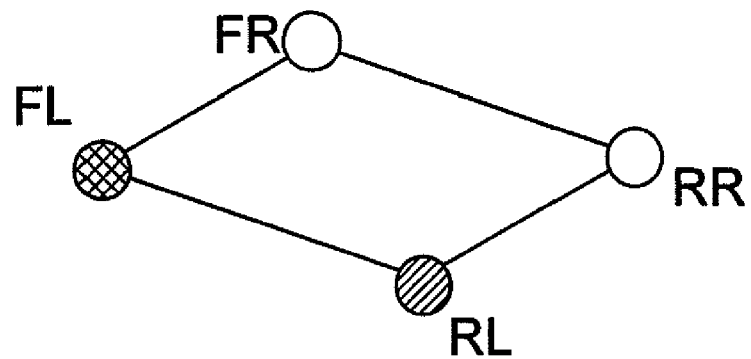
Figure 98:
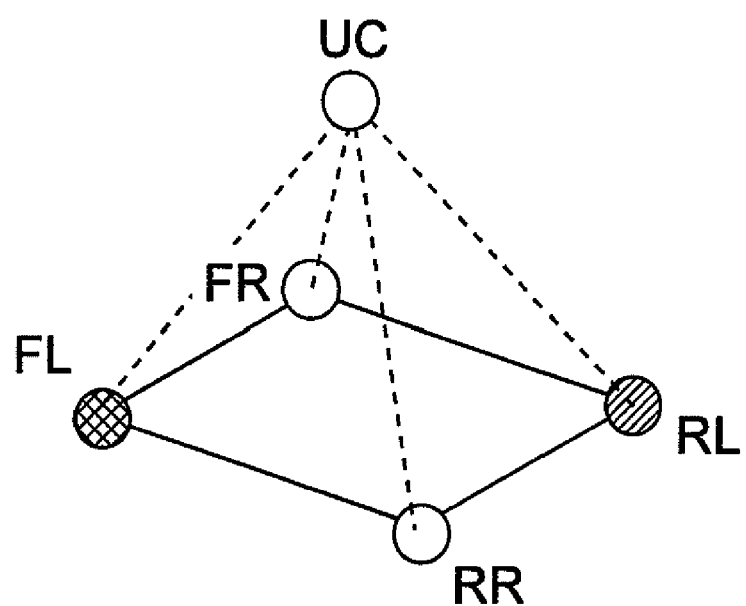
Figure 99:
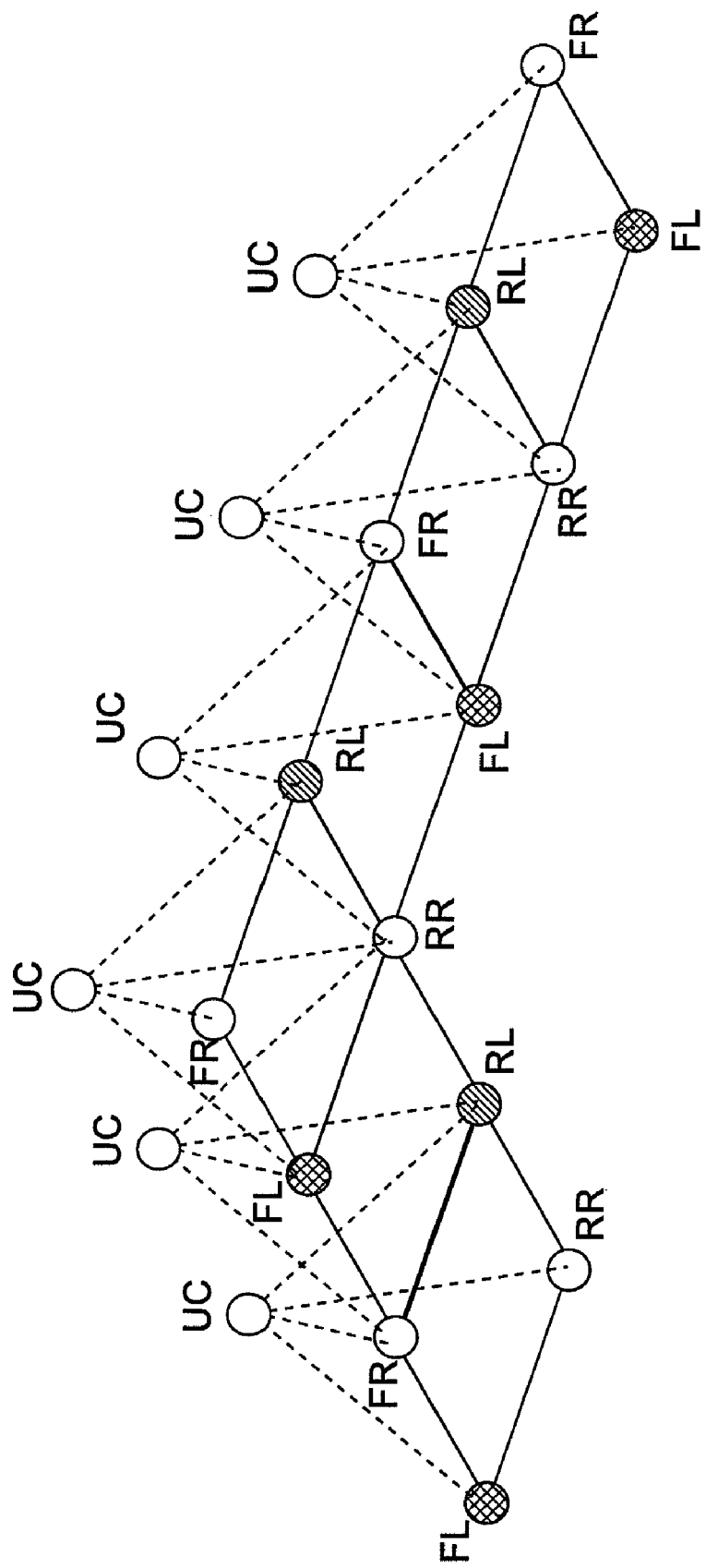
Figure 100:
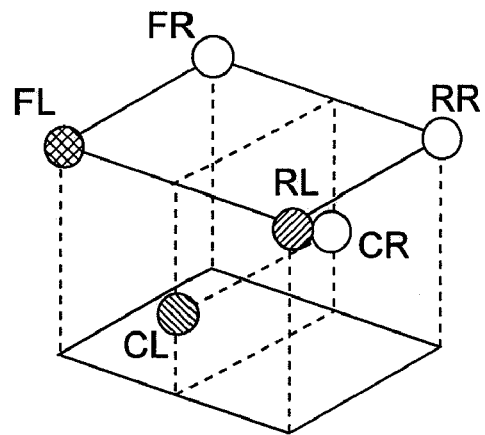
Figure 101:
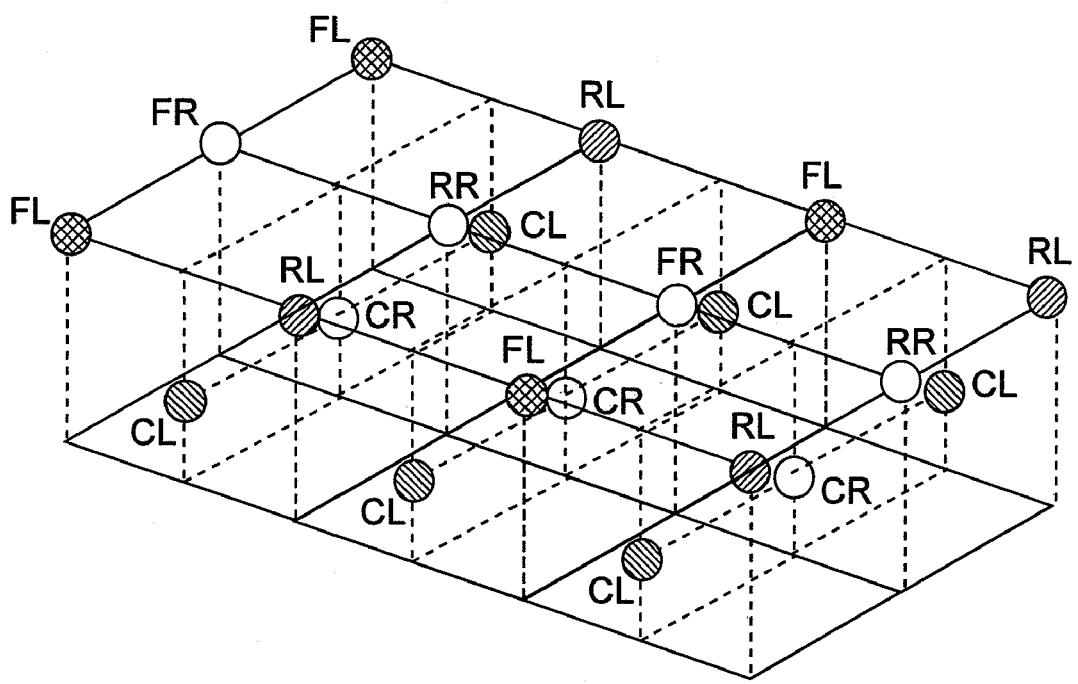
Figure 104:
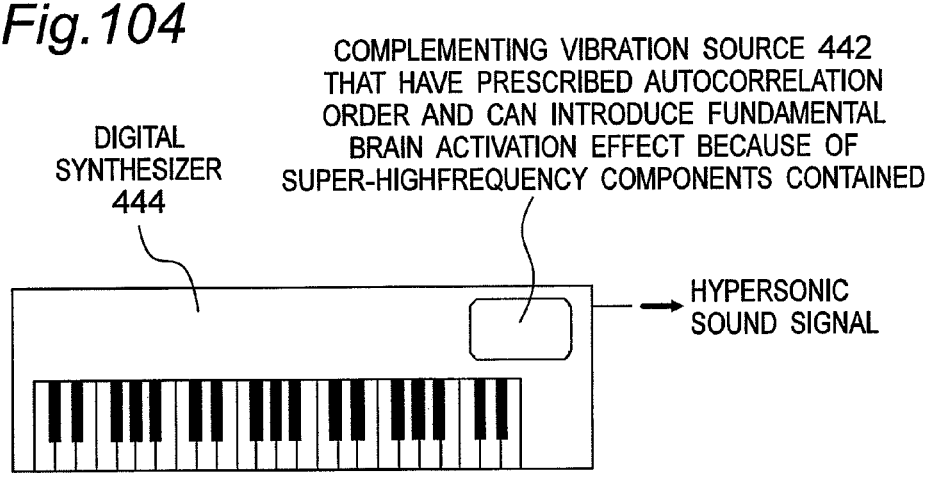
Figure 105:
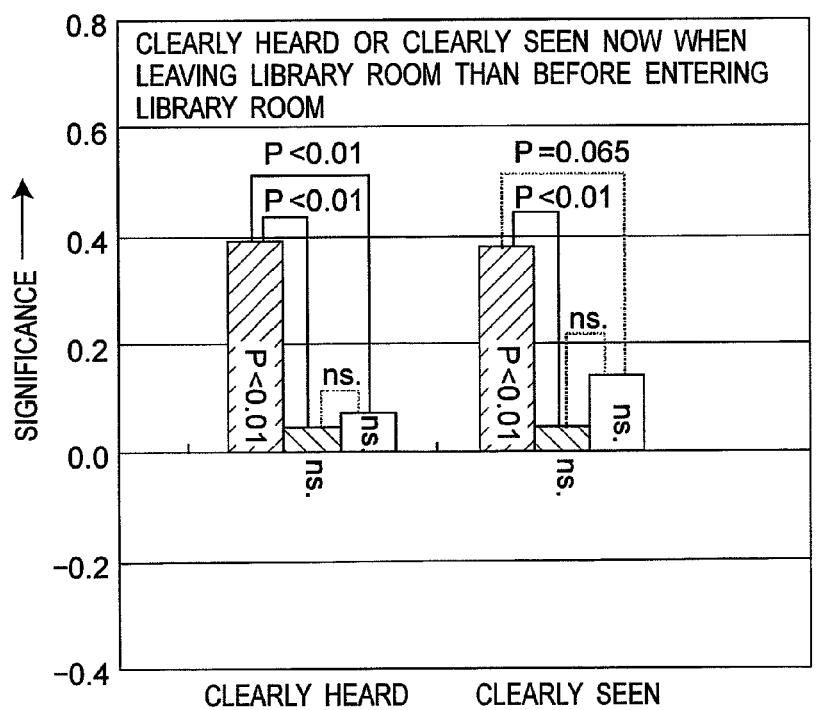
Figure 106:
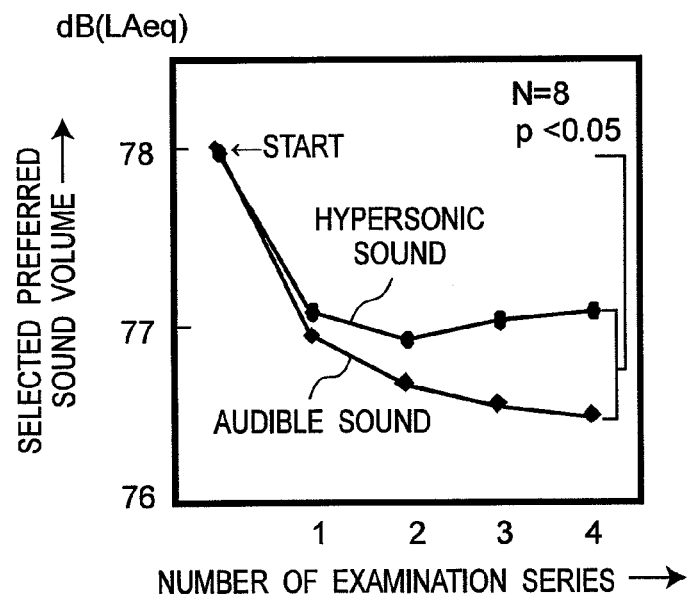
Figure 107:
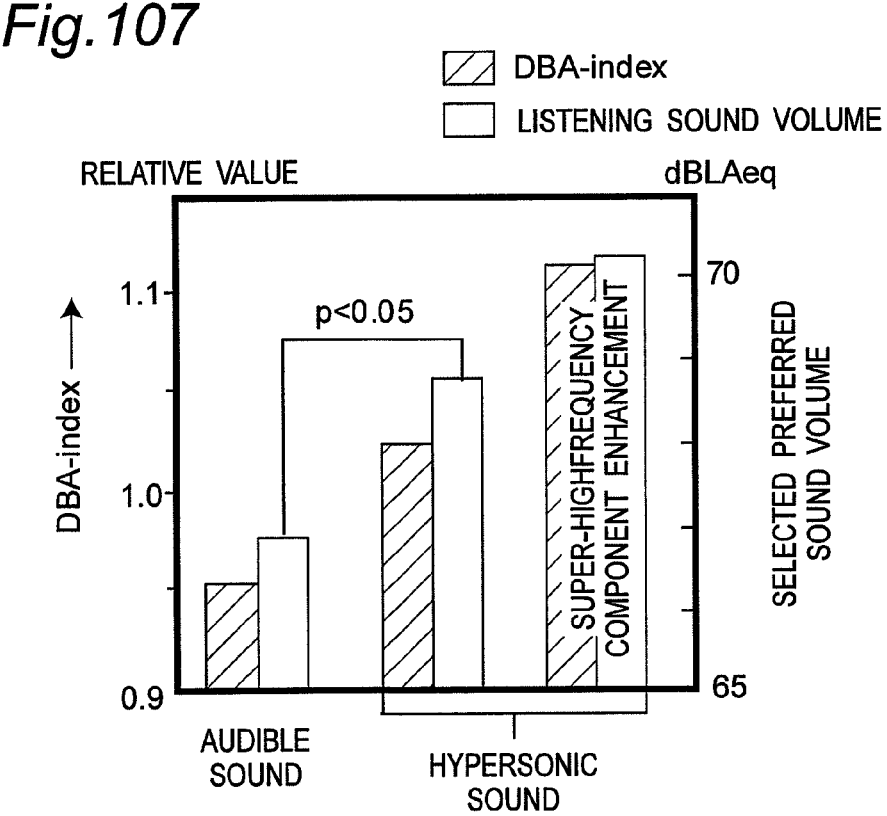
Figure 108:
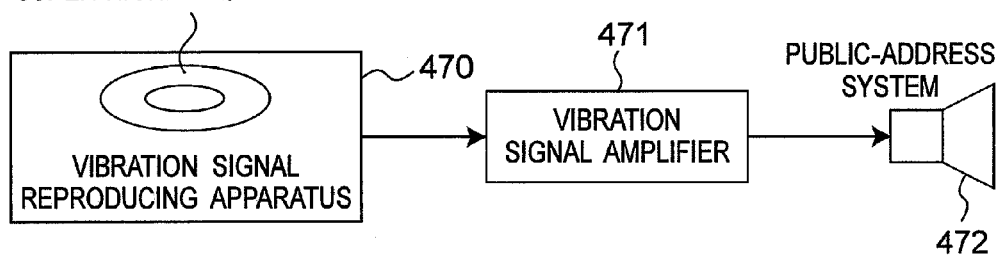
Figure 109:
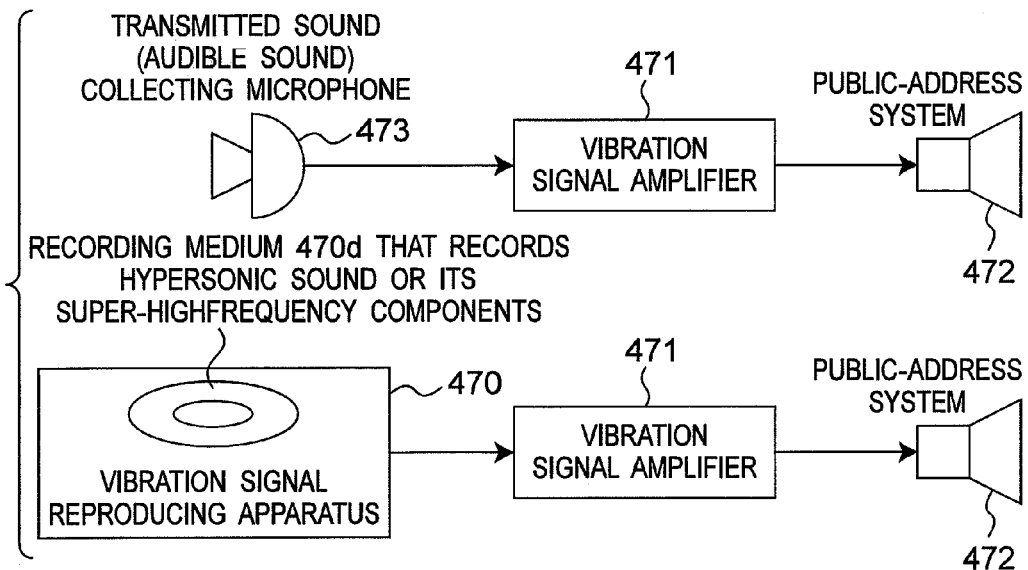
Figure 110:
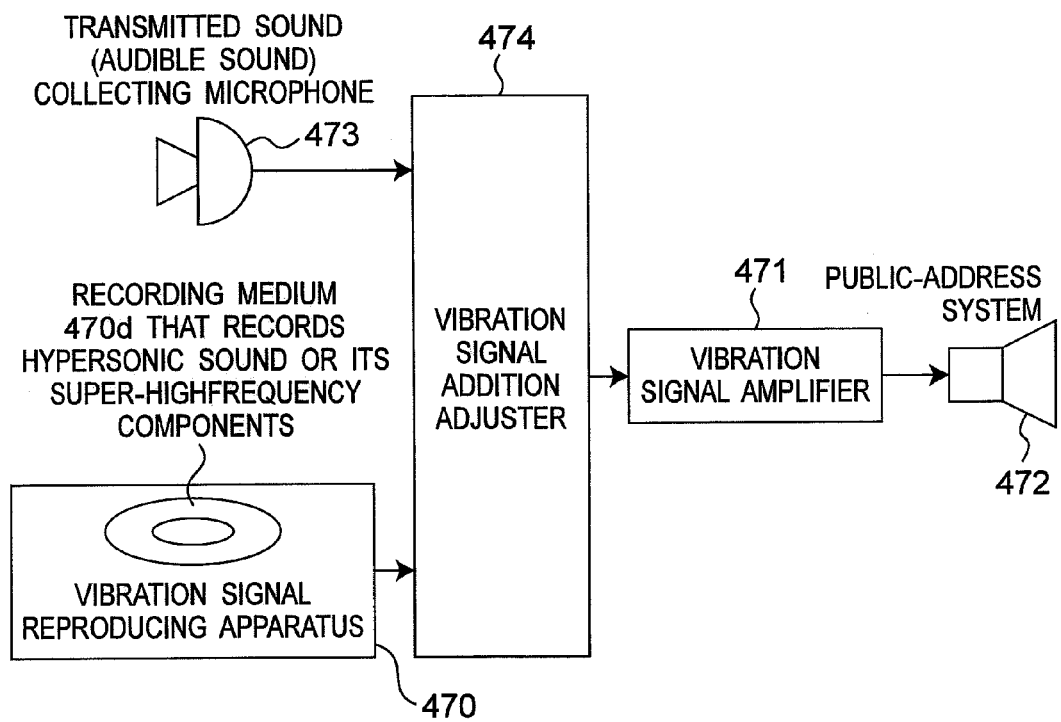
Figure 111:
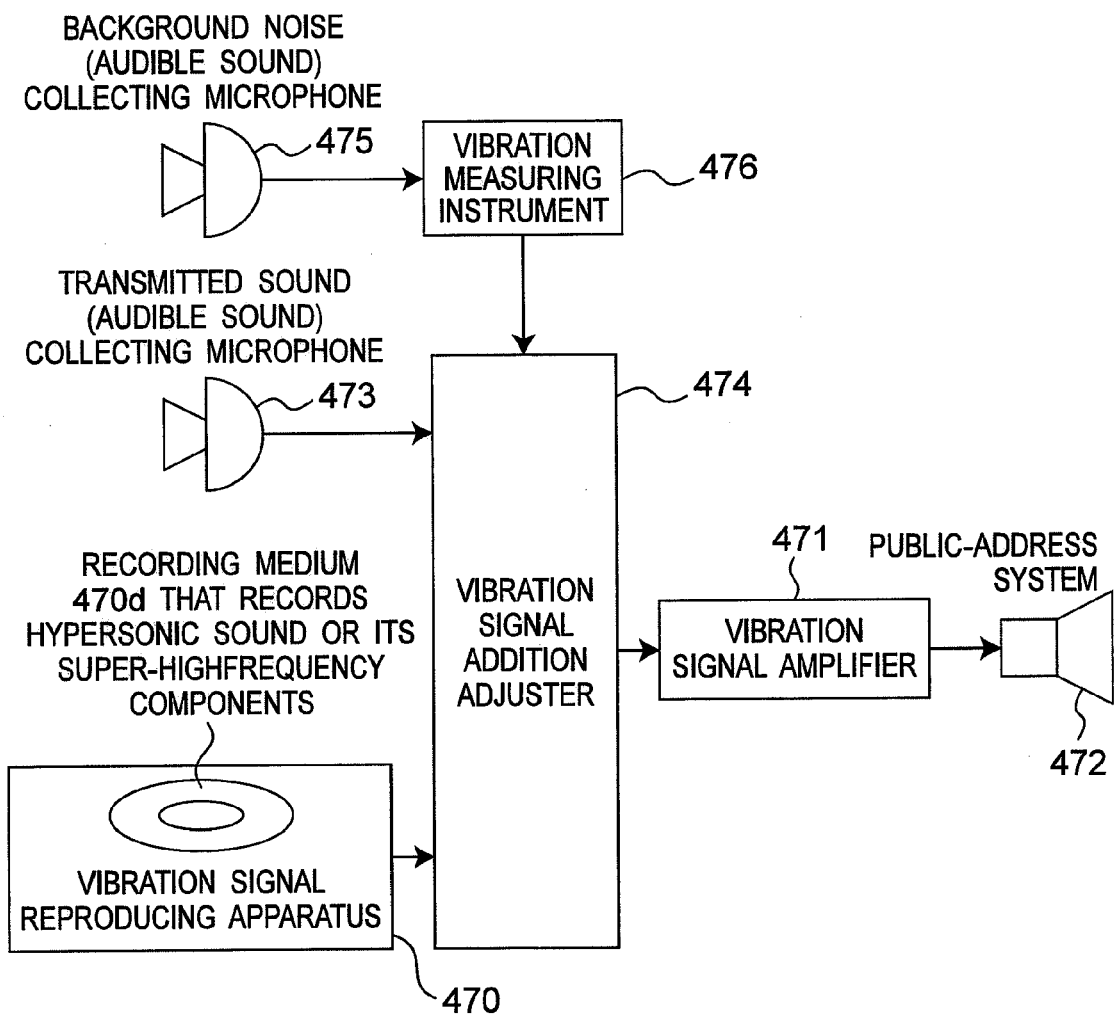
Figure 112:
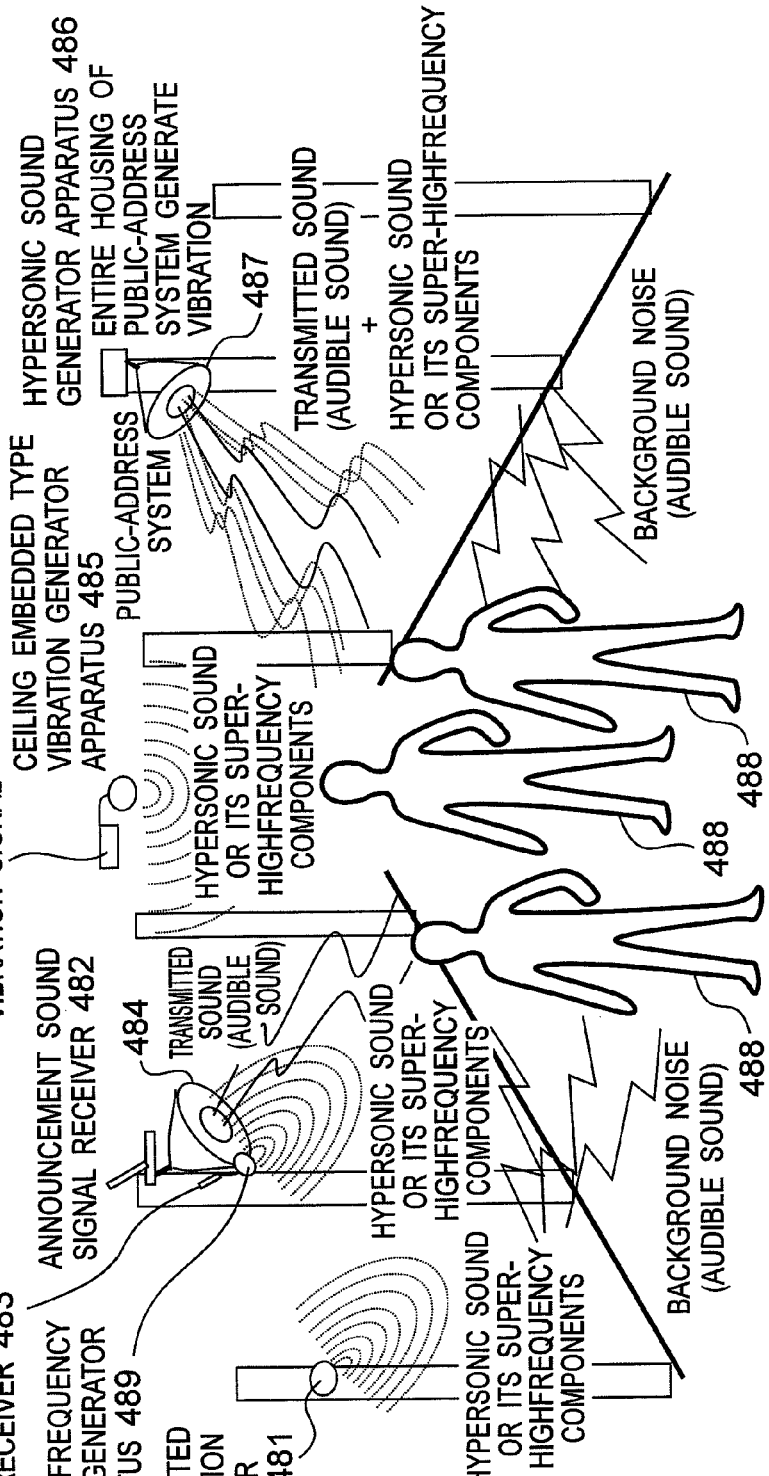
Figure 113:
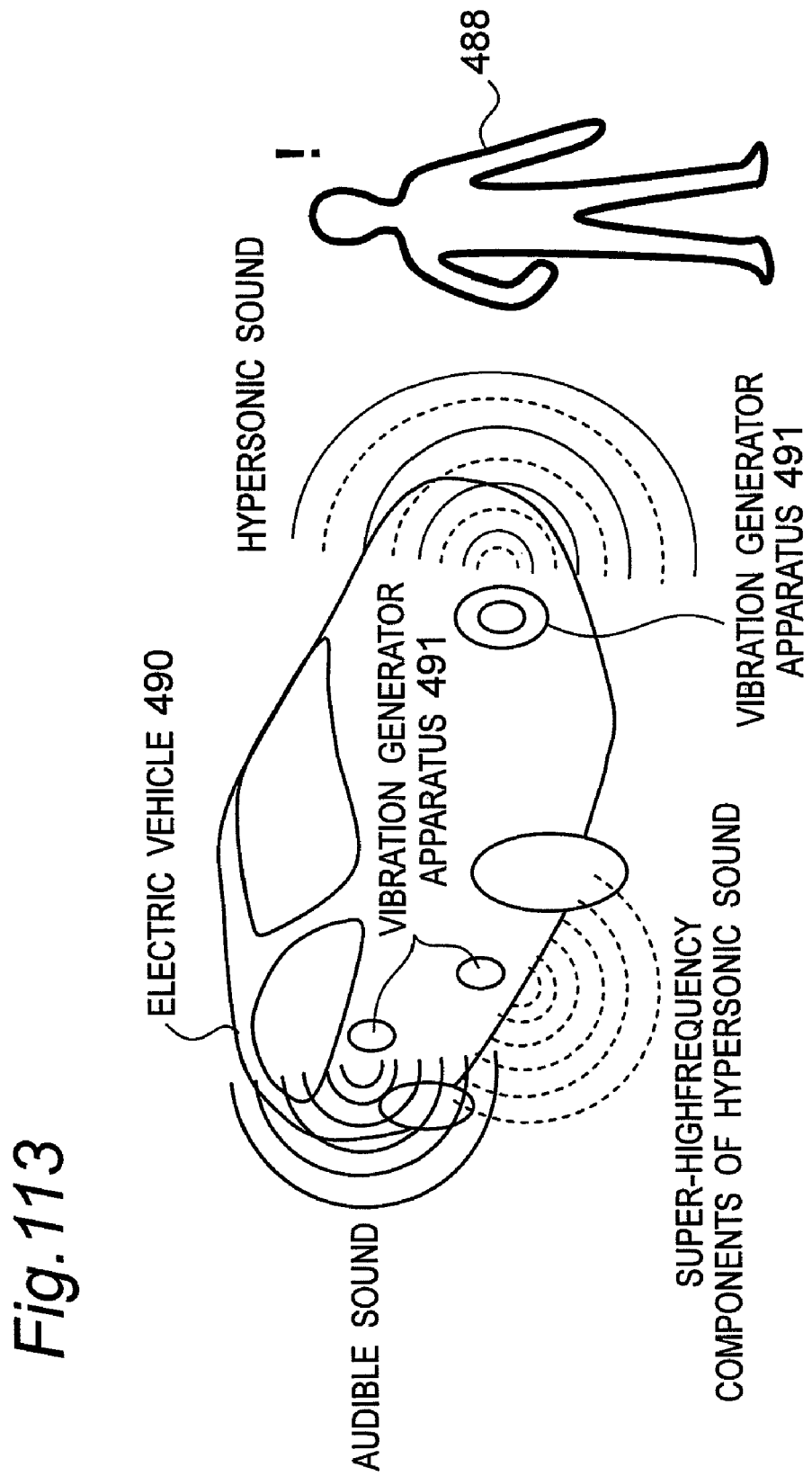
Figure 114:
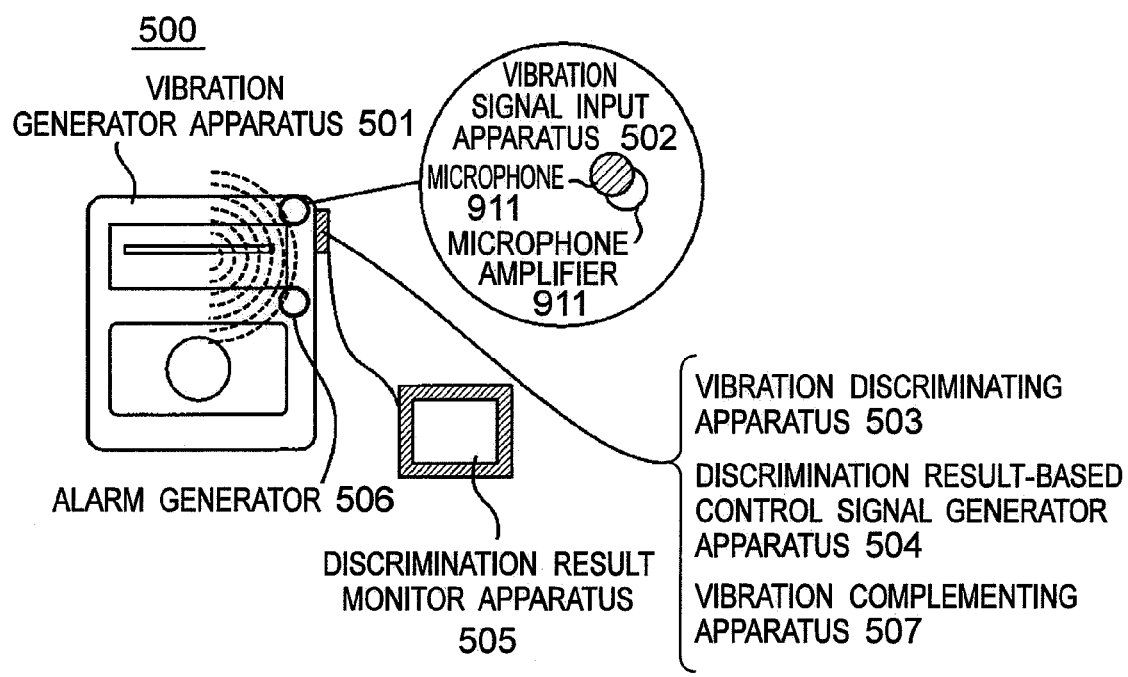
Figure 115:
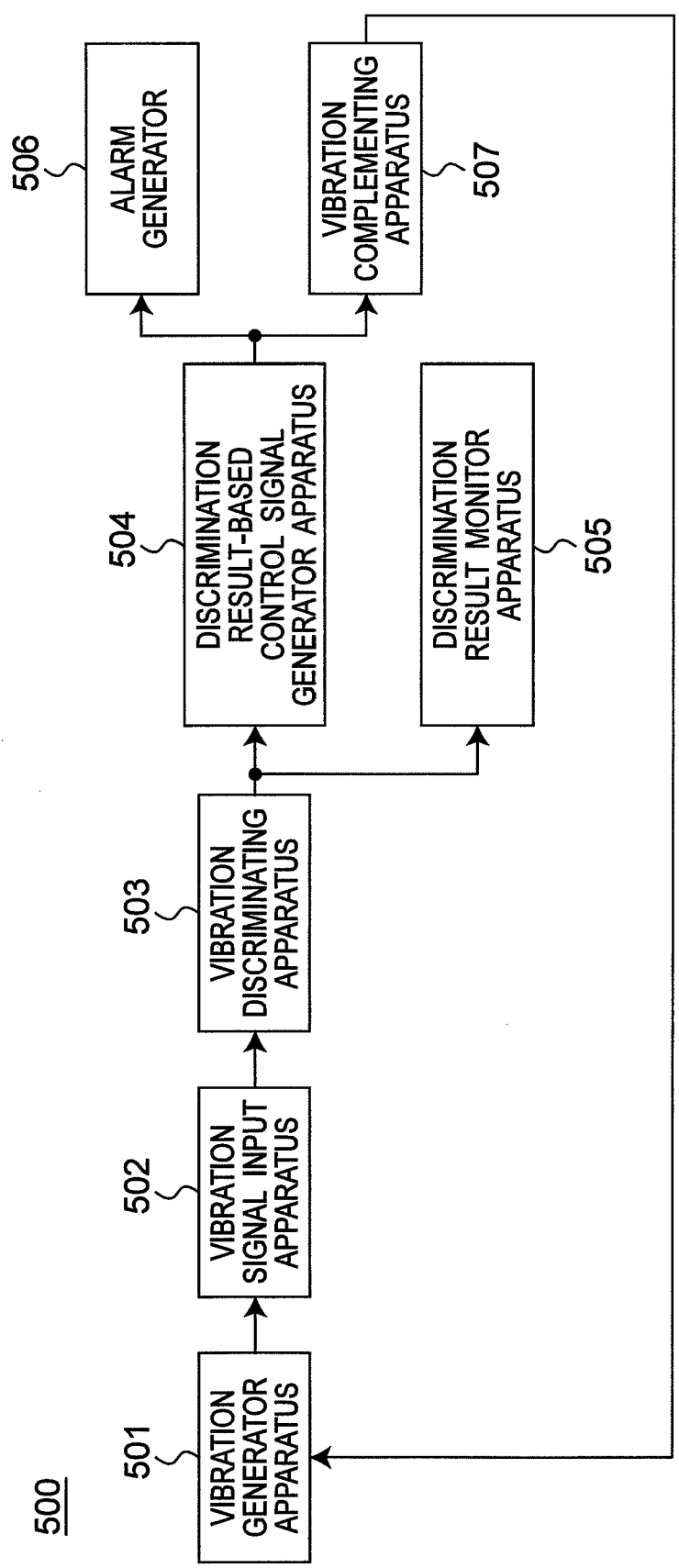

capable of introducing the fundamental brain activation effect by processing the 1-bit quantization noise owned by a high-speed sampling 1-bit quantization system according to the second preferred embodiment;

FIG. 71 is a block diagram showing a vibration signal generating apparatus that imparts the predetermined autocorrelation order owned by a vibration (hypersonic sound) capable of introducing the fundamental brain activation effect by performing processing based on a transfer function representing the property of the autocorrelation order of a reference vibration signal capable of introducing the fundamental brain activation effect to a vibration signal that does not introduce the fundamental brain activation effect according to the second preferred embodiment;

FIG. 72 is a block diagram showing a vibration (hypersonic sound) generating apparatus (exemplified apparatus employing a moving magnet type fluctuation detector device) capable of introducing the fundamental brain activation effect using an elastic vibrating object according to the second preferred embodiment;

FIG. 73 is a block diagram showing a vibration (hypersonic sound) generating apparatus (exemplified apparatus employing a capacitor type fluctuation detector device) capable of introducing the fundamental brain activation effect using an elastic vibrating object according to the second preferred embodiment;

FIG. 74 is a block diagram showing a vibration (hypersonic sound) generating apparatus capable of introducing the fundamental brain activation effect using a spiral spring shaped elastic vibrating object according to the second preferred embodiment;

FIG. 75 is a block diagram showing a vibration (hypersonic sound) generating apparatus (exemplified apparatus that makes an elastic vibrating object function as a fluctuation detecting coil) capable of introducing the fundamental brain activation effect using an elastic vibrating object according to the second preferred embodiment;

FIG. 76 is a block diagram showing a vibration (hypersonic sound) generating apparatus (exemplified apparatus that makes an elastic vibrating object as a fluctuation detecting coil) capable of introducing the fundamental brain activation effect using an elastic vibrating object according to the second preferred embodiment;

FIG. 77 is a block diagram showing a vibration (hypersonic sound) generating apparatus (exemplified apparatus that concurrently uses a plurality of vibration generating apparatuses each employing an elastic vibrating object) capable of introducing the fundamental brain activation effect using an elastic vibrating object according to the second preferred embodiment;

FIG. 78 is a spectral diagram showing a power spectrum of a vibration signal recorded on the soundtracks of a "DVD version AKIRA" and a "Blu-ray Disc version AKIRA" measured in the second preferred embodiment;

FIG. 79 is a graph showing a local exponent of fractal dimension of the vibration signal of the "Blu-ray Disc version AKIRA soundtrack" measured in the second preferred embodiment;

FIG. 80 is a graph showing an information entropy density of the vibration signal of the "Blu-ray Disc version AKIRA soundtrack" measured in the second preferred embodiment;

FIG. 81 is a graph showing an entropy variation index (EV-index) of the vibration signal of the "Blu-ray Disc version AKIRA soundtrack" measured in the second preferred embodiment;

FIG. 82 is a graph showing a deep brain activity index (DBA-index) recorded from a listener under a high-cut sound condition and a full-range sound condition generated by using the "Blu-ray Disc version AKIRA soundtrack" measured in the second preferred embodiment;

FIG. 83 is a graph and a table showing an impression evaluation of sounds evaluated by a listener on the high-cut sound condition and the full-range sound condition generated by using the "Blu-ray Disc version AKIRA soundtrack" measured in the second preferred embodiment;

FIG. 84 is a perspective view showing an example of an apparatus that leads to an increase in the impression of image representation and an improvement in image quality by using a hypersonic sound as a sound to be recorded on the soundtrack in a video-and-audio complex package media such as a Blu-ray Disc according to a third preferred embodiment;

FIG. 85 is a graph and a table showing an impression evaluation of screen images evaluated by a listener on the high-cut sound condition and the full-range sound condition generated by using the "Blu-ray Disc version AKIRA soundtrack" according to a third preferred embodiment;

FIG. 86 is a perspective view showing an improvement in aesthetic sensibility at the time of watching TV by the fundamental brain activation effect according to the third preferred embodiment;

FIG. 87 is a flow chart showing a derivation control process of the fundamental brain activation effect according to a fifth preferred embodiment;

FIG. 88 is a block diagram showing a structural example of a circuit for performing the derivation control process of the fundamental brain activation effect according to the fifth preferred embodiment;

FIG. 89 is an external view showing an example of a vibration generating apparatus installed in a station yard according to a modified preferred embodiment of the second preferred embodiment;

FIG. 90 is a graph showing a regional cerebral blood flow rate normalized to each frequency component, or the experimental results measured by the apparatus of FIG. 15, in which (a) is a graph showing a regional cerebral blood flow rate in the position of the brain stem, and (b) is a graph showing a regional cerebral blood flow rate in the position of the left thalamus region;

FIG. 91 is a perspective view showing an example of a vibration generating apparatus provided with a function to generate a hypersonic sound or the vibration of its super-high-frequency components by only giving an independent vibration generating function to a loudspeaker system itself and connecting it to certain equipment or by itself according to the first preferred embodiment;

FIG. 92 is a block diagram of a vibration generating apparatus applied to portable equipment or a distribution network to it according to the first preferred embodiment;

FIG. 93 is a perspective view of a vibration generating apparatus applied to a portable telephone according to the first preferred embodiment;

FIG. 94 is a perspective view of a vibration generating apparatus applied to a portable music player according to the first preferred embodiment;

FIG. 95 is a perspective view of a vibration generating apparatus solely of an earphone according to the first preferred embodiment;

FIG. 96 is a perspective view showing an example in which a vibration (hypersonic sound) capable of introducing the fundamental brain activation effect because it has a predetermined autocorrelation order and contains super-high-frequency components at a close distance to audiences in the space of a theater, a hall, an auditorium, or the like according to the first preferred embodiment;

FIG. 97 is a perspective view showing an ordinary prior art 4-channel surround loudspeaker arrangement;

FIG. 98 is a perspective view showing a double helical matrix loudspeaker arrangement according to the first preferred embodiment;

FIG. 99 is a perspective view showing an arrangement such that the double helical matrix loudspeaker arrangements are consecutively arranged in two directions according to the first preferred embodiment;

FIG. 100 is a perspective view showing a six-dimension consecutive matrix loudspeaker arrangement according to the first preferred embodiment;

FIG. 101 is a perspective view showing an arrangement such that six-dimension consecutive matrix loudspeaker arrangements are consecutively arranged in two directions according to the first preferred embodiment;

FIG. 102 is a table showing major differences between a hypersonic therapy according to the first preferred embodiment and the conventional musicotherapy;

FIG. 103 is a block diagram showing an example of a vibration complementing apparatus to add a vibration signal (hypersonic sound signal) that can introduce the fundamental brain activation effect to an original vibration signal that does not introduce the fundamental brain activation effect and is outputted from an electronic musical instrument or the like inclusive of a digital synthesizer according to the second preferred embodiment;

FIG. 104 is a perspective view showing an example of a vibration complementing apparatus to add a vibration signal (hypersonic sound signal) that can introduce the fundamental brain activation effect to an original vibration signal that does not introduce the fundamental brain activation effect and is outputted from an electronic musical instrument or the like inclusive of a digital synthesizer according to the second preferred embodiment;

FIG. 105 is a graph showing an effect of making a listener more clearly recognize sensory information of a sound and the like by sensitizing the sensibility to a sensory information input by heightening the activities of the thalamus and the brain stem included in the listener's fundamental brain network system among the two effects of the hypersonic sound, or psychological experimental results according to a fourth preferred embodiment;

FIG. 106 is a graph showing an effect of making a listener feel a vibration input of a large sound volume comfortable by increasing the aesthetic sensibility to sensory information by inducing activation of the reward system nerve circuit included in the listener's fundamental brain network system among the two effects of the hypersonic sound, or the psychological experimental results of the fourth preferred embodiment;

FIG. 107 is a graph indicating that the effect of increasing the aesthetic sensibility to sensory information and thereby making the listener feel the vibration input of a large sound volume comfortable appears more intensely when the super-high-frequency components contained in the hypersonic sound are heightened by inducing activation of the reward system nerve circuit included in the listener's fundamental brain network system among the two effects of the hypersonic sound, or the psychological experimental results of the fourth preferred embodiment;

FIG. 108 is a block diagram showing an example in which a transmission sound (audible sound) and a hypersonic sound or its super-high-frequency components are recorded in mixture by a predetermined balance, and the signal is reproduced by using a public-address system having a faithful response performance according to the fourth preferred embodiment;

FIG. 109 is a block diagram showing an example in which a transmission sound (audible sound) and a hypersonic sound or its super-high-frequency components are generated by using different public-address systems with different sound sources according to the fourth preferred embodiment;

FIG. 110 is a block diagram showing an example in which a transmission sound (audible sound) and a hypersonic sound or its super-high-frequency components are synthesized on the spot and generated from one public-address system according to the fourth preferred embodiment;

FIG. 111 is a block diagram showing an example in which a background noise (audible sound) is collected by a microphone, the feature of the background noise (audible sound) is measured based on the collected vibration signal, and a transmission sound (audible sound) and a hypersonic sound or its super-high-frequency components are adjusted in conformity to measured data according to the fourth preferred embodiment;

FIG. 112 is a perspective view showing an example in which the vibration generating apparatus of the fourth preferred embodiment is installed in a station yard;

FIG. 113 is a perspective view showing an example of an application to an electric vehicle according to the fourth preferred embodiment;

FIG. 114 is a perspective view showing an example of a vibration monitoring system that performs adjustment of vibration generating setting by feedback to the vibration generating apparatus by using a judgment result on the autocorrelation order owned by a vibration according to the fifth preferred embodiment; and FIG. 115 is a block diagram showing an example of a vibration monitoring system that performs adjustment of vibration generating setting by feedback to the vibration generating apparatus by using the judgment result on the autocorrelation order owned by the vibration according to the fifth preferred embodiment.

BEST MODE FOR CARRYING OUT THE PRESENT INVENTION

Preferred embodiments of the present invention will be described below with reference to the drawings. It is noted that like components are denoted by like reference numerals in the following preferred embodiments.

First Preferred Embodiment

In the first preferred embodiment of the present invention, a vibration generating apparatus and method are described below.

The vibration generating apparatus and method of the first preferred embodiment is characterized in that it generates a natural vibration, an artificial vibration, a synthesized vibration and the like, which are vibrations having the essential conditions that they contain the audible range components of the vibration components within a range of 20 Hz to 15 kHz or 20 kHz in the audible frequency range perceivable as a sound by human beings and super-high-frequency components within a range exceeding the audible frequency range up to a predetermined maximum frequency (e.g., 88.2 kHz, 96 kHz, 100 kHz, 176.4 kHz, 192 kHz, 200 kHz, 300 kHz, 500 kHz or 1 MHz), and the vibrations have an "autocorrelation order" (i.e., internal correlation property which is widely contained in natural conformation) represented by at least either one of a first property and a second property described in detail hereinbefore and immediately hereinafter, and therefore, they can introduce the effect (fundamental brain activation effect) of activating the fundamental brain including the brain stem, thalamus and hypothalamus, which are the regions to bear the fundamental functions of the human brain and the neural network (fundamental brain network) projected from the fundamental brain to the various other brain regions.

The first property has the feature of the following fractal nature such that the shape of the three-dimensional power spectrum array of the components exceeding 20 kHz of a vibration signal has a complexity with a self-similarity. That is, a "local exponent of fractal dimension" that represents the self-similarity of the shape consistently has a value of not smaller than 2.2 and not greater than 2.8 unlike the number of dimensions two of the "topological dimension" of a plane and also unlike the number of dimensions three of the "topological dimension" of a cube within a range in which a "spectro-temporal index" serving as a scale for measuring local exponent of fractal dimension is within a range of $2^{-1}$ to $2^{-5}$, and the local exponent of fractal dimension does not largely change and falls within a fluctuation range of 0.4 even when the spectro-temporal index changes in the range of $2^{-1}$ to $2^{-5}$.

In this case, it is assumed that the three-dimensional power spectrum array of a vibration signal is obtained by digitizing a signal for 51.2 seconds of a vibration served as a candidate of the vibration that can introduce the fundamental brain activation effect with a sampling frequency of 192 kHz and a quantization bit count of 24 bits or 12 bits, normalizing the variance of the whole signal, dividing the whole into a unit analysis interval duration of 200 milliseconds and a unit analysis interval overlap of 50%, performing power spectrum estimation by an autocorrelation model of ten dimensions for each interval by using the Yule-Walker method, extracting band components ranging from 20 kHz to 96 kHz exceeding the human audible range upper limit from the obtained power spectrum and three-dimensionally extracting its time change with the transverse axis (from left to right) served as linear representation of frequency, the anteroposterior axis (from this side to the depth) served as linear representation of time, and the vertical axis (from downside to upside) served as logarithmic representation of power at each time point of each frequency component.

Moreover, the "local exponent of fractal dimension" is a value obtained by inverting the sign of the inclination (i.e., local inclination of the graph) of a straight line that interconnects two mutually adjacent points when the logarithm of the length of one side of a reference box (i.e., a cube or rectangular parallelepiped serving as a "measure") for use upon calculating the fractal dimension of a curved surface by using the box-counting method is plotted on the transverse axis, the logarithm of a necessary minimum number of reference boxes for covering a three-dimensional power spectrum array curved surface with the reference boxes of the size is plotted on the vertical axis, and the necessary number of reference boxes is plotted with respect to the reference box of a different size.

Further, the "spectro-temporal index" is a normalized representation of the length of one side of the reference box used upon calculating the local exponent of fractal dimension of the three-dimensional power spectrum array curved surface by using the box-counting method as a ratio to the entire frequency bandwidth (transverse axis) and the entire time (anteroposterior axis) of the three-dimensional power spectrum array of the analysis object.

The second property means that the time series of a vibration signal is neither completely predictable and regular nor completely unpredictable and random, and the degree of the predictability or the irregularity changes with time. That is, it means that the "information entropy density" representing the irregularity of time series data has neither a value smaller than −5 expressed by a completely determinate regular signal like a sine wave nor zero expressed by a completely random signal like a white noise but consistently has a value within a range of not smaller than −5 and not greater than zero, and in addition, the value does not have a temporally constant value like a sine wave and a white noise, whereas the "entropy variation index" (hereinafter abbreviated as EV-index), which represents the degree of time change of the information entropy density, has a value of not smaller than 0.001 for 51.2 seconds.

In this case, the "information entropy density" of the time series data of a vibration signal is defined as obtained by digitizing a signal for 51.2 seconds of a vibration served as a candidate of the vibration that can introduce the fundamental brain activation effect by a sampling frequency of 192 kHz and a quantization bit count of 24 bits or 12 bits, dividing the whole into a unit analysis interval duration of 200 milliseconds and a unit analysis interval overlap of 50%, performing power spectrum estimation by an autocorrelation model of ten dimensions for each interval by using the Yule-Walker method, and being calculated from the obtained power spectrum. Moreover, the "entropy variation index (EV-index)" is the variance of all the analysis object intervals of the information entropy density for each unit analysis interval.

Also, the first preferred embodiment is characterized by being configured so that a vibration having the feature of the autocorrelation order is generated by radiating the vibration generated by one or more vibration generating apparatuses existing in a space into the space or by making the vibrations become added together or mutually interfere in the space or by making the entire space resonate with the vibrations. Moreover, the first preferred embodiment provides a vibrating object, or body, that is gas, liquid, solid or a complex of them in a vibrational state having the feature of the autocorrelation order. Further, the generated vibration signal that can introduce the fundamental brain activation effect is recorded preferably in, for example, a recording medium such as an optical disk, a memory or a hard disk, a network server or the like, which can be read by a computer or transmitted by a communication apparatus, a communication system, a broadcasting system or the like preferably by wire, wirelessly or infrared-ray communications.

Next, an implemental example of fundamental brain activation by a vibration generated to have a predetermined property is described below. First of all, the super-high-frequency components of the essential condition is described below.

Figure 1:
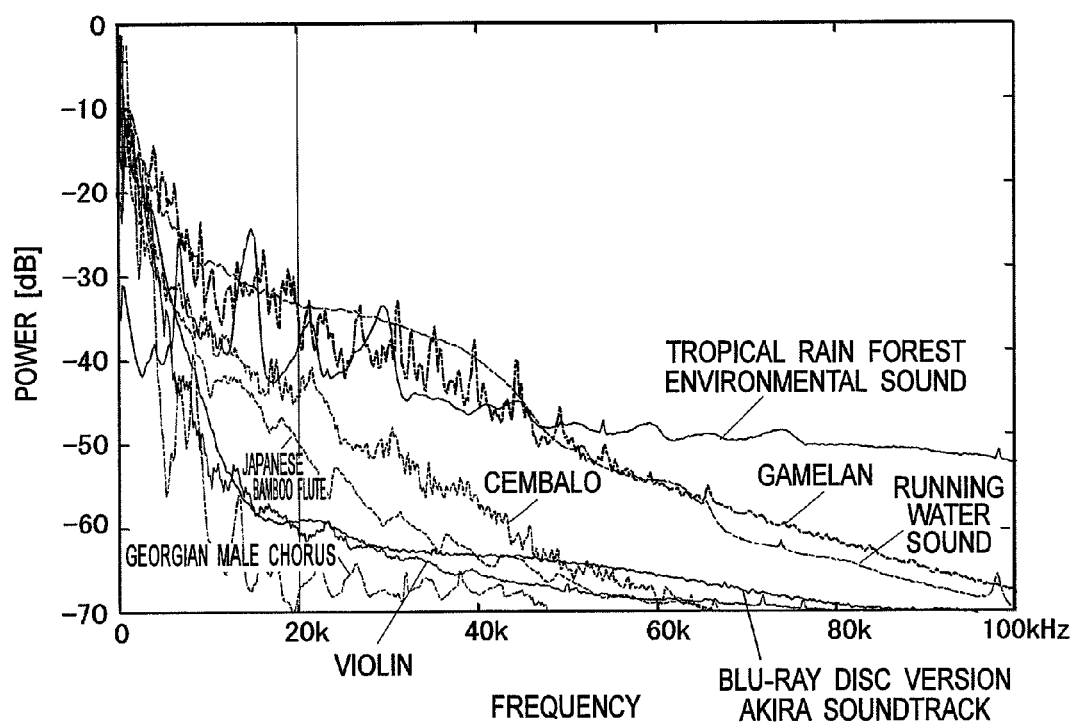
FIG. 1 is a spectral diagram showing a frequency spectrum of a vibration that contains audible range components of vibration components in the audible frequency range and super-high-frequency components exceeding the audible frequency range.

FIG. 1 is a spectral diagram showing a frequency spectrum of a vibration that contains audible range components of vibration components in the audible frequency range and super-high-frequency components exceeding the audible frequency range. That is, with regard to an example of a vibration having components in the audible frequency range from 20 Hz to 15 kHz or 20 kHz perceivable as a sound by human beings and super-high-frequency components within a range exceeding the audible frequency range up to a predetermined maximum frequency (the maximum frequency is 100 kHz in FIG. 1), its power spectrum obtained by the FFT method is shown in FIG. 1.

Reference is next made to the "autocorrelation order". An additive set of elements inclusive of atoms and molecules constituting the inorganic material world has such a feature that the thermal entropy, i.e., "randomness" unidirectionally increases with time in conformity to the second law of thermodynamics. On the other hand, complex structures existing in the natural world including lives are ingenerated as a consequence that the elements including atoms and molecules having such features are self-organized according to a certain "order" different from the deterministic regularity represented by the Euclidean geometry and the Cartesian mathematics. Such a feature is typically observed in the vital phenomena of cells and the living bodies constituted based on the mechanisms of, for example, the hierarchies of biomolecules, control of vital activities by genes and energy utilization using adenosine triphosphate and structures generated by them. Similar tendencies can be found in, for example, the compositions of rocks, geographic formations and crystal structures also in the native structures besides the vital phenomena. Further, similar structures can be found also in artificial objects highly adaptive to the senses and sensibilities of "human beings as living matters" ingenerated as one of the self-organized native structures, such as Japanese gardens of high naturalness and folk instrument sounds.

The concept representing such a "structurized order that is complex but not random" widely seen in the structures of high naturalness concerning the vital phenomena is referred to as an "autocorrelation order". This is a concept comprehensively representing the universal phenomena of organizing in accordance with the correlation internally contained or ingeneration of a structure by organizing. The structure ingenerated by the autocorrelation order possibly represents the features of, for example, self-similarity expressed by a fractal dimension, a time series structure representing the information entropy density in a moderate range that is neither completely random nor completely regular, and further a temporal structural transformation and chaos. The autocorrelation order is the concept that includes the features owned by these complex systems.

Reference is next made to the first property on the autocorrelation order. The intricate complex structures owned by the native structures of the natural world often exhibit shapes, when its details are magnified, quite similar to the unmagnified shapes (e.g., branches of trees, veins of leaves, coastlines, human internal blood vessel distribution, and pulmonary alveolus distribution in the lung). As described above, in a case where resembling structures are recurrently duplicated from a rough level to a detailed level within a definite range, a fractal dimension that represents the configurational complexity and self-similarity within the range has a constant value different from the topological dimension.

The present inventor and others discovered that, when the spectro-temporal structure of a vibration signal in the super-high-frequency range exceeding the upper limit at 20 kHz of the human audible range was indicated as a three-dimensional power spectrum array curved surface, the structure had a recurrent complexity in a manner similar to that of the native structures, and therefore, when the fractal dimension was obtained by using a "measure" having a size within a definite range, the vibration capable of introducing the fundamental brain activation effect had a property that the local exponent of the fractal dimension fell within a definite range even if the size of the "measure" changed.

On the other hand, the fractal dimension of the three-dimensional power spectrum array of a vibration not having the fundamental brain activation effect, such as the vibration signals of a white noise or a sine wave has a value of two, which is the topological dimension of a plane, or a value close to it, and the local exponent of the fractal dimension largely varies depending on the size of the "measure".

In this case, the "local exponent of fractal dimension" is a value obtained by inverting the sign of the inclination of a straight line that interconnects two mutually adjacent points when the logarithm of the length of one side of a reference box (i.e., a cube or rectangular parallelepiped serving as the "measure") for use upon calculating the fractal dimension of a curved surface by using the box-counting method is plotted on the transverse axis, the logarithm of a necessary minimum number of reference boxes for covering a three-dimensional power spectrum array curved surface with the reference boxes of the size is plotted on the vertical axis, and the necessary number of reference boxes is plotted with respect to the reference box of a different size.

In general, when the fractal dimension is obtained by using the box-counting method, the value obtained by inverting the sign of the inclination of a regression line obtained from the aforementioned graph becomes the fractal dimension. Therefore, the local exponent of fractal dimension becomes the local inclination (i.e., derivative) of the graph. The derivative value is obtained from a difference in the case of discretized data.

Figure 2:
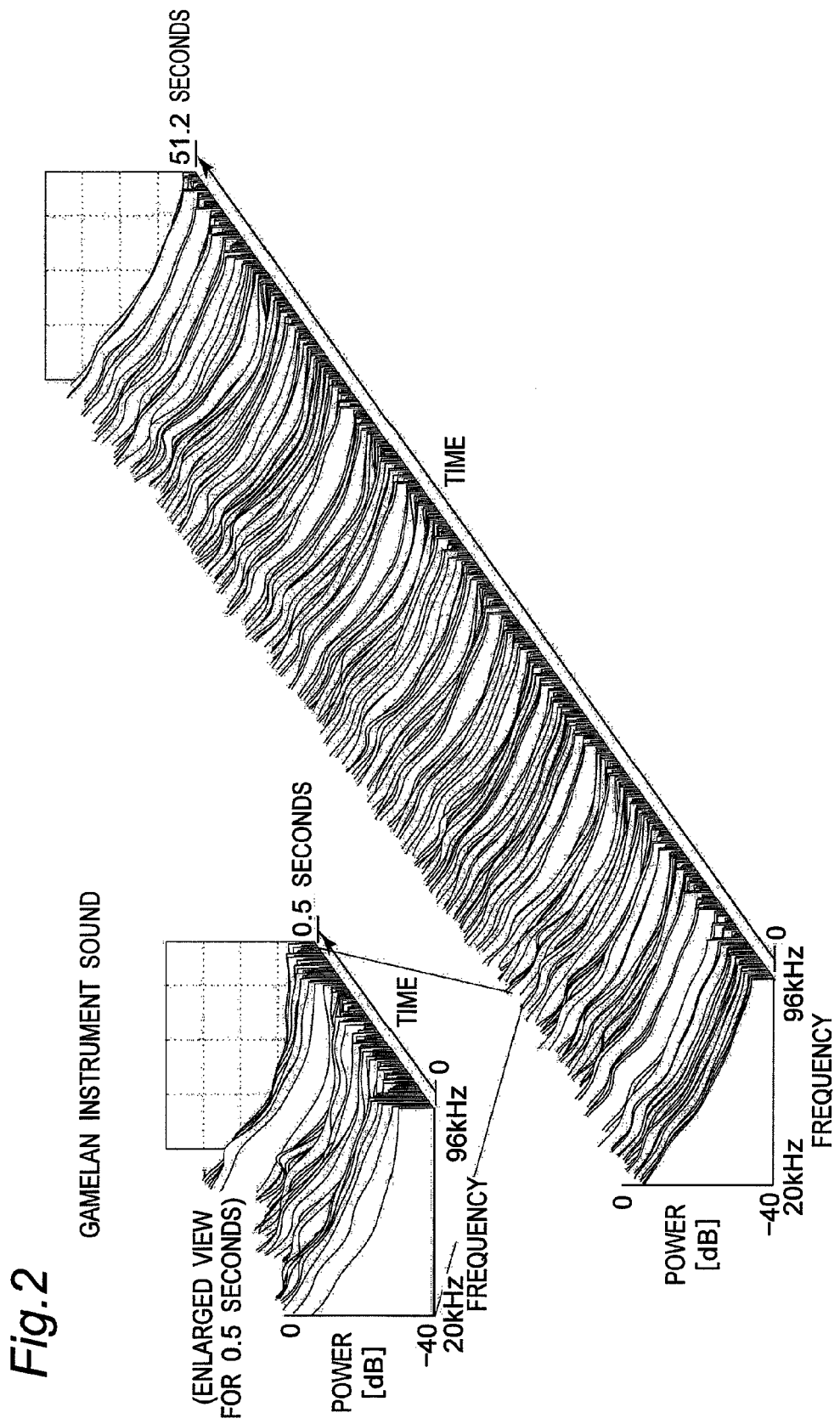
FIG. 2 is a chart showing a three-dimensional power spectrum array of a gamelan instrument sound.
Figure 3:
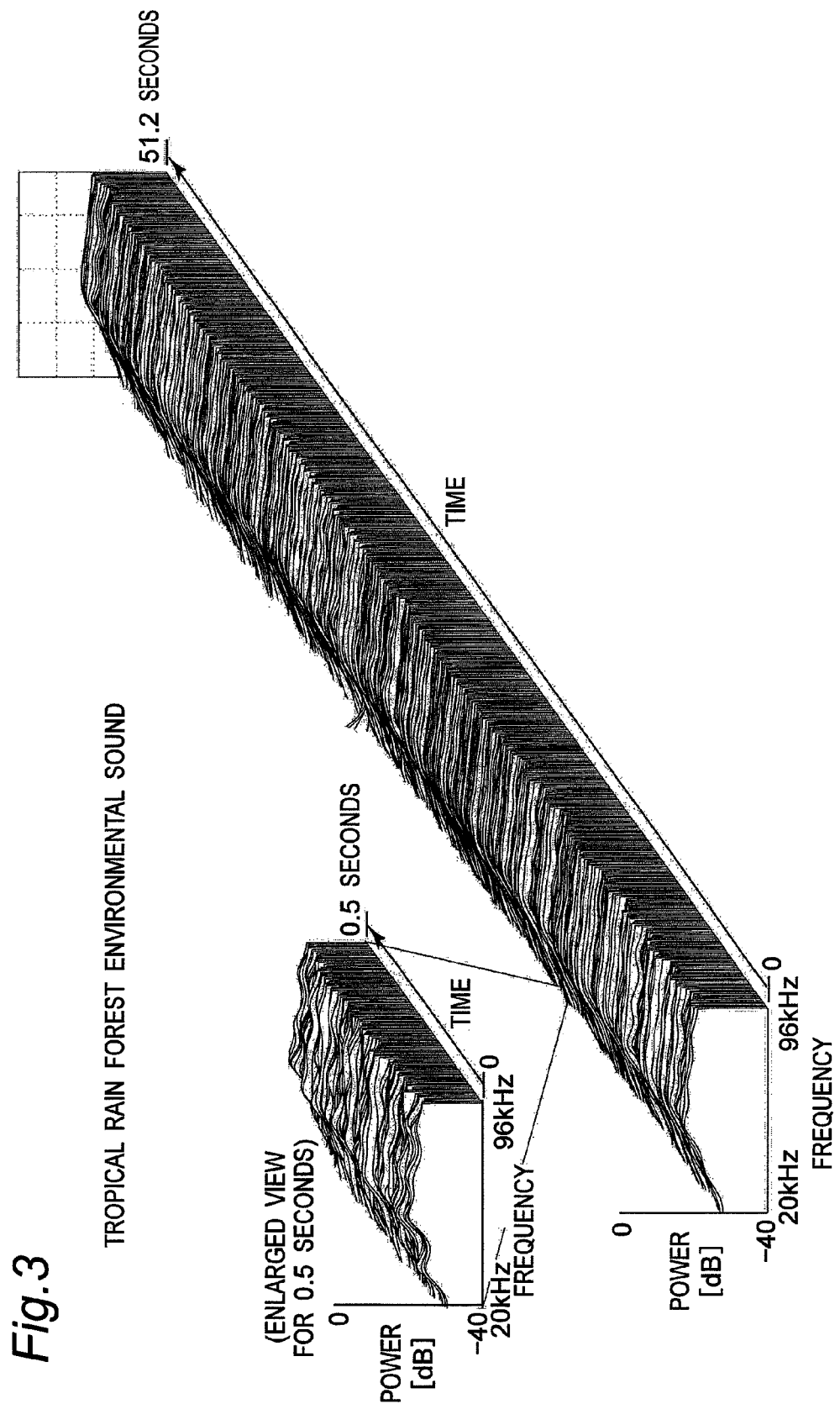
FIG. 3 is a chart showing a three-dimensional power spectrum array of a tropical rain forest environmental sound.

FIG. 2 is a chart showing a three-dimensional power spectrum array of a gamelan instrument sound, and FIG. 3 is a chart showing a three-dimensional power spectrum array of a tropical rain forest environmental sound. In this case, FIGS. 2 and 3 show examples of three-dimensional power spectrum arrays ranging from the human audible range upper limit of not lower than 20 kHz up to 96 kHz produced for examining the first property on the autocorrelation order of a vibration having super-high-frequency components. These are obtained by digitizing a signal for 51.2 seconds of a vibration by a sampling frequency of 192 kHz and a quantization bit count of 24 bits or 12 bits, normalizing the variance of the whole signal, dividing the whole into a unit analysis interval of 200 milliseconds and a unit analysis interval overlap of 50%, performing power spectrum estimation by an autocorrelation model of ten dimensions for each interval by using the Yule-Walker method, extracting band components ranging from 20 kHz to 96 kHz exceeding the human audible range upper limit from the obtained power spectrum and three-dimensionally extracting its time change with the transverse axis (from left to right) served as the linear representation of frequency, the anteroposterior axis (from this side to the depth) served as the linear representation of time, and the vertical axis (from downside to upside) served as the logarithmic representation of power at each time point of each frequency component.

Figure 4:
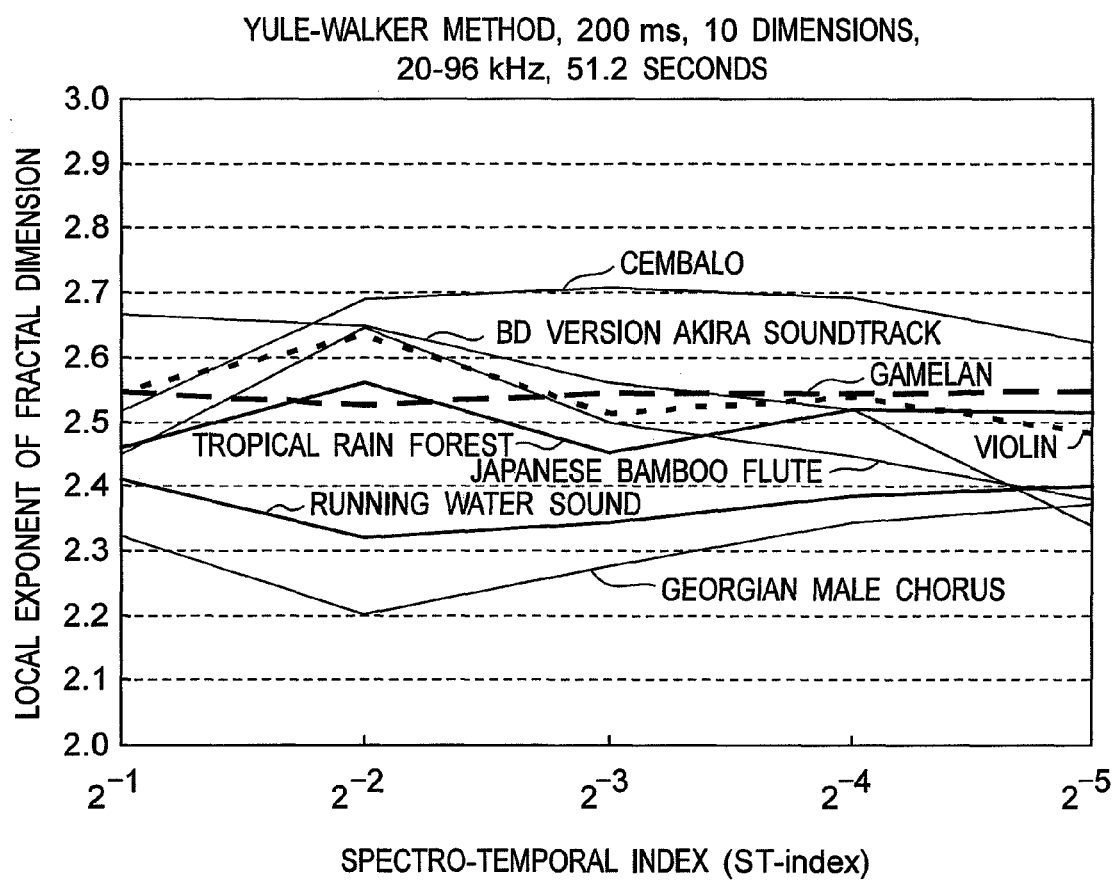
FIG. 4 is a graph showing an example of a local exponent of fractal dimension of a spectro-temporal structure of a vibration that satisfies a first property on an autocorrelation order according to the present invention.

FIG. 4 is a graph showing an example of a local exponent of fractal dimension of a spectro-temporal structure of a vibration that satisfies the first property on the autocorrelation order according to the present invention. In this case, the local exponent of fractal dimension of the obtained three-dimensional power spectrum array curved surface is calculated by using the box-counting method. It is noted that a calculation method is described in a "supplementary explanation of the calculating formula" described later. Referring to FIG. 4, regarding these vibrations, the local exponent of fractal dimension that represents the complexity and self-similarity of the shape of the three-dimensional power spectrum array of the components exceeding 20 kHz consistently has a value of not smaller than 2.2 and not greater than 2.8, which is greater than the dimension number two of the topological dimension owned by a plane-like figure even when the "spectro-temporal index" (ST-index) that serves as a reference to measure it changes within a range of $2^{-1}$ to $2^{-5}$, and its fluctuation range falls within 0.4. The local exponent of fractal dimension within a range in which the "spectro-temporal index" (ST-index) of the vibration that satisfies the first property on the autocorrelation order is $2^{-1}$ to $2^{-5}$ is shown in FIG. 5.

Although the maximum value of the data exemplified in this case is 2.709, the value changes depending on how to take a sample to be analyzed and possibly has a value up to 2.8.

In this case, the "spectro-temporal index" (ST-index) represents the length of one side of a reference box used upon calculating the local exponent of fractal dimension of the three-dimensional power spectrum array curved surface by using the box-counting method, the length being normalized as a ratio to the entire frequency bandwidth (transverse axis) and the entire time (anteroposterior axis) of the three-dimensional power spectrum array of the analysis object.

Figures 6, 7:
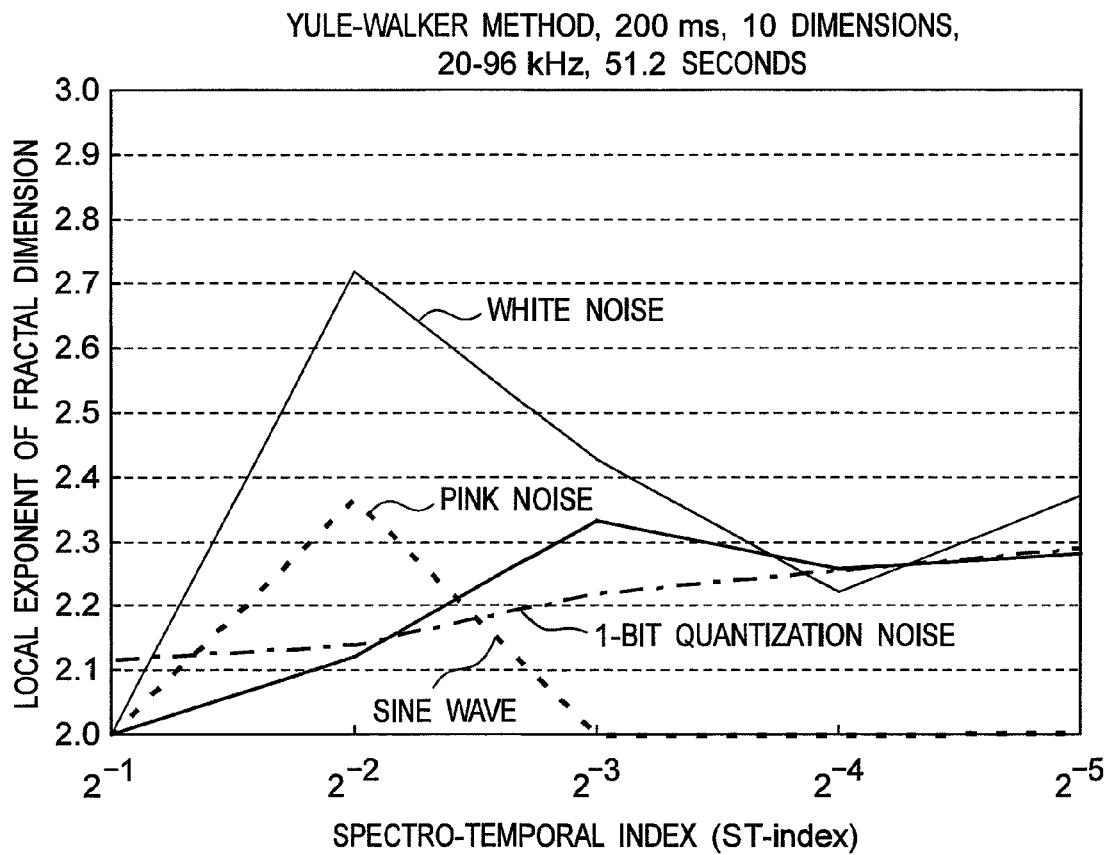
FIG. 6 is a graph showing an example of the local exponent of fractal dimension of the spectro-temporal structure of a vibration that does not satisfy the first property on the autocorrelation order of the present invention.
FIG. 7 is a table showing a local exponent of fractal dimension of a vibration that does not satisfy the first property on the autocorrelation order within a range in which the spectro-temporal index (ST-index) is $2^{-1}$ to $2^{-5}$.

FIG. 6 is a graph showing an example of the local exponent of the fractal dimension of the spectro-temporal structure of a vibration that does not satisfy the first property on the autocorrelation order according to the present invention. As is apparent from FIG. 6, examples of vibrations that do not satisfy the first property on the autocorrelation order among vibrations having the super-high-frequency components are shown. In these examples, the local exponent of fractal dimension has a value smaller than 2.2 when the spectro-temporal index is within the range of $2^{-1}$ to $2^{-5}$. That is, the local exponent of fractal dimension has a value smaller than 2.2 when the spectro-temporal index is $2^{-1}$ in the case of a white noise, when the spectro-temporal index is $2^{-1}$ and $2^{-2}$ in the case of a pink noise and a 1-bit noise or when the spectro-temporal index is $2^{-1}$, $2^{-3}$, $2^{-4}$ and $2^{-5}$ in the case of a sine wave. Further, in the case of the white noise, the fluctuation range of the local exponent of fractal dimension indicates a value greater than 0.4. Moreover, the local exponent of fractal dimension of the vibration that does not satisfy the first property on the autocorrelation order when the spectro-temporal index is within the range of $2^{-1}$ to $2^{-5}$ is shown in FIG. 7.

Reference is next made to the second property on the autocorrelation order. Many of time series having the autocorrelation order observed in the natural world exhibit a structure that is neither completely random nor completely regular. That is, they are neither the time series that are completely random and have no predictability like a white noise nor the time series that are completely predictable and have a determinate regularity like a sine wave, and they coexistently have inherent predictability and irregularity commensurate with the autocorrelation order.

The present inventor and others discovered that the vibration capable of introducing the fundamental brain activation effect had its signal coexistently having moderate predictability and irregularity and the autocorrelation structure changed with time. In contrast to this, a vibration of which the time series is completely irregular and which does not have predictability at all, such as a white noise, does not introduce the fundamental brain activation effect. Likewise, a vibration of which the time series is completely regular and the predictability is determinate, such as a sine wave, does not introduce the fundamental brain activation effect.

Therefore, when the "information entropy density" that is the index of the irregularity of the signal is obtained, the vibration that can introduce the fundamental brain activation effect indicates a value within a definite range between the vibration like, for example, a white noise that is completely irregular and unpredictable and the vibration like, for example, a sine wave that is completely regular and determinate. In contrast to this, the information entropy density theoretically consistently has a maximum value in the case of a vibration constituted of a completely irregular signal like, for example, a white noise among the vibrations that do not introduce the fundamental brain activation effect, and likewise, it theoretically consistently has a minimum value in the case of a vibration constituted of a completely determinate signal like, for example, a sine wave among the vibrations that do not introduce the fundamental brain activation effect. Further, in contrast to the fact that the information entropy density indicates fluctuations temporally in excess of a definite range since the autocorrelation structure changes with time in the case of the vibration that can introduce the fundamental brain activation effect, it consistently indicates a constant value in the case of the vibration like, for example, a white noise that does not introduce the fundamental brain activation effect.

Figure 8:
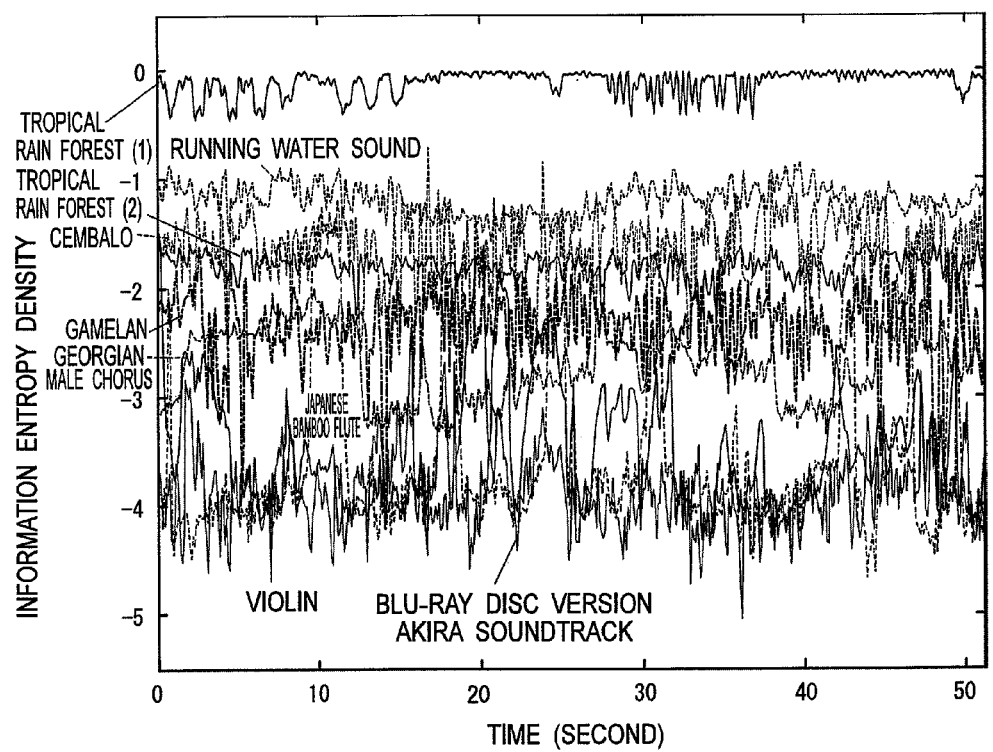
FIG. 8 is a graph showing an example of the information entropy density and its time change of a vibration that satisfies a second property on the autocorrelation order of the present invention.

FIG. 8 is a graph showing an example of the information entropy density and its time change of a vibration that satisfies the second property on the autocorrelation order of the present invention. In this case, the information entropy density of a vibration are obtained by digitizing a signal for 51.2 seconds of a vibration served as an analysis object by a sampling frequency of 192 kHz and a quantization bit count of 24 bits or 12 bits, dividing it into a unit analysis interval of 200 milliseconds and a unit analysis interval overlap of 50%, performing power spectrum estimation by an autocorrelation model of ten dimensions of the time series signal for each interval by using the Yule-Walker method, and being calculated from the obtained power spectrum based on a predetermined calculating formula (See the "supplementary explanation of the calculating formula" described later). It is noted that the signal capable of introducing the fundamental brain activation effect has its information entropy density consistently assuming a value within a range of not smaller than −5 and smaller than zero and has a large time change as described in detail later with reference to FIG. 10.

Figure 9:
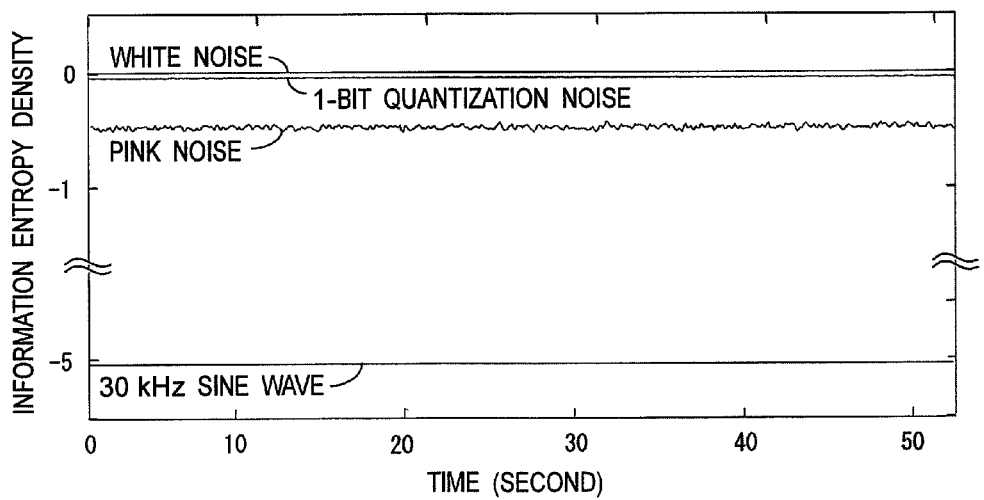
FIG. 9 is a graph showing an example of the information entropy density and its time change of a vibration that does not satisfy the second property on the autocorrelation order of the present invention.

FIG. 9 is a graph showing an example of the information entropy density and its time change of a vibration that does not satisfy the second property on the autocorrelation order of the present invention. As is apparent from FIG. 9, among the vibrations that do not introduce the fundamental brain activation effect, the information entropy density of the white noise consistently has a value of zero, and that of the sine wave consistently has a value of not greater than −5, also exhibiting flat forms with no time change. The pink noise and the 1-bit quantization noise have a value of not smaller than −5 and smaller than zero and exhibit almost no time change.

Figure 10:
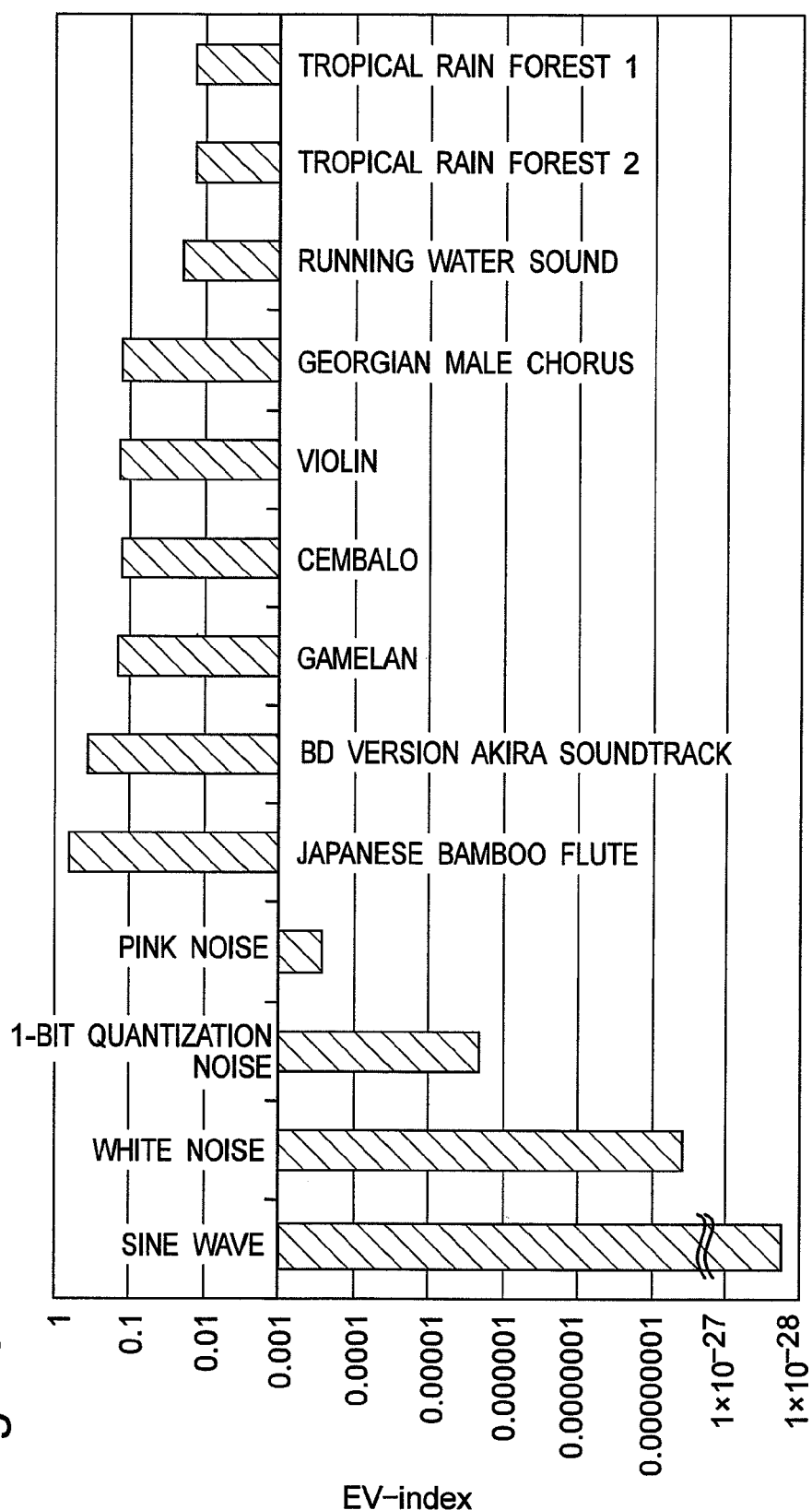
FIG. 10 is a graph showing an example of the entropy variation index (EV-index) of vibrations that satisfy the second property on the "autocorrelation order" of the present invention and vibrations that do not satisfy it according to the present invention.

Regarding the vibrations shown in FIGS. 8 and 9, the "entropy variation index" (EV-index) that represents the degree of temporal change of the information entropy density is indicated by the graph of FIG. 10 where the vertical axis represents the logarithm. That is, FIG. 10 is a graph showing an example of the entropy variation index (EV-index) of vibrations that satisfy the second property on the "autocorrelation order" of the present invention and vibrations that do not satisfy it according to the present invention. The entropy variation index (EV-index) is the variance of the information entropy densities for the unit analysis intervals across all the analysis intervals. In contrast to the fact that the entropy variation index (EV-index) has a value of not smaller than 0.001 in the case of the vibrations that satisfy the second property shown in FIG. 8, the entropy variation index (EV-index) has a value smaller than 0.001 in the case of the vibrations that do not satisfy the second property shown in FIG. 9. It is noted that the theoretical upper limit value of the entropy variation index (EV-index) is observed in such a case that the information entropy density alternately has the values of −5 and zero and it is 6.2622 under the conditions described above.

As described above, the vibration has such essential necessary conditions as having audible range components of vibration components in the audible frequency range perceivable as a sound by the auditory sensation of human beings, and as having super-high-frequency components within a range exceeding the audible frequency range up to a predetermined maximum frequency. The vibration also has the feature represented by at least either one of the first property and the second property, can introduce the effect (fundamental brain activation effect) of activating the fundamental brain including the brain stem, thalamus and hypothalamus, which are the regions that bear the fundamental functions of the human brain to which the vibration is applied, and then, can introduce the same effect of activating the neural network (fundamental brain network) projected from the fundamental brain to the various other brain regions. Therefore, the vibration has the same meanings as a hypersonic sound.

Next, an implemental example, in which the gamelan instrument sound of a percussion instrument made of bronze in Bali of Indonesia, or a typical aerial vibration that satisfies the essential conditions and the first property and the second property on the autocorrelation order is applied to a human being to introduce the fundamental brain activation effect is described below.

Figure 11:
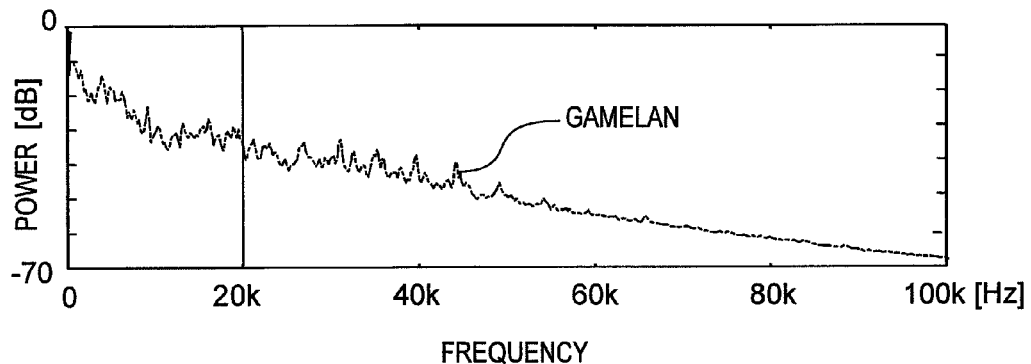
FIG. 11 is a spectral diagram of the average power spectrum of the gamelan instrument sound.

FIG. 11 shows the average power spectrum of the aerial vibration of the gamelan instrument sound, obtained by the FFT method. The sound sufficiently has super-high-frequency components having an upper limit reaching 100 kHz and satisfies the essential conditions of the present invention with regard to the frequency components.

Figure 12:
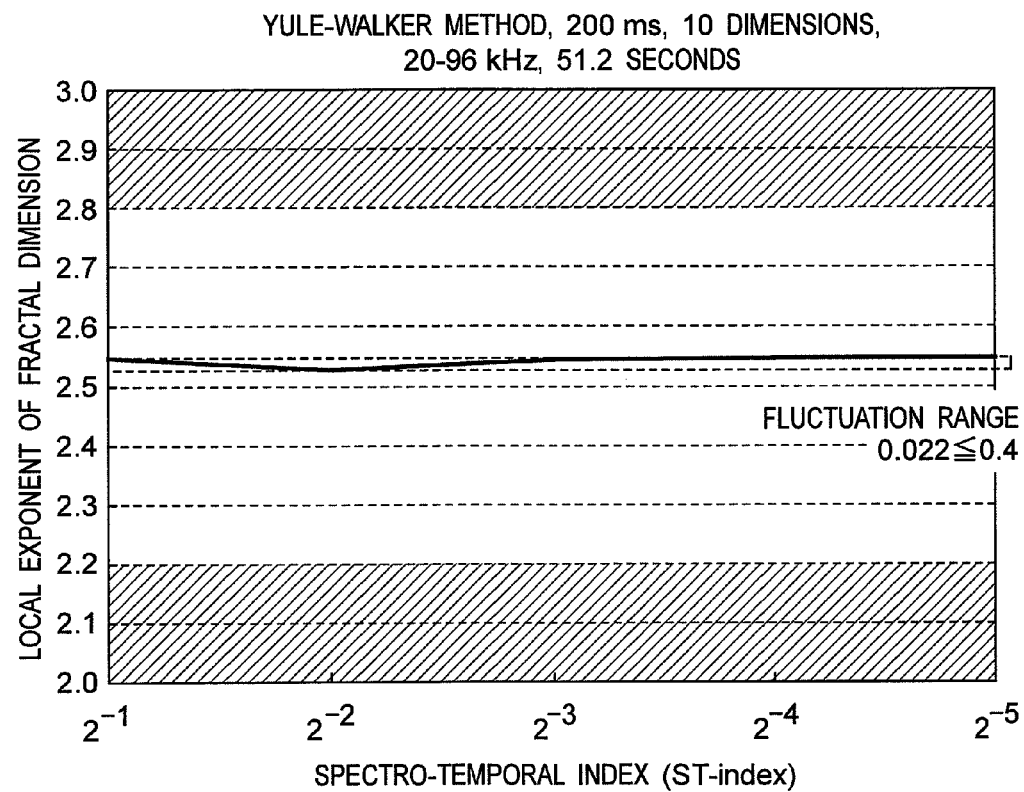
FIG. 12 is a graph showing a local exponent of fractal dimension of the gamelan instrument sound.

FIG. 12 shows the local exponent of fractal dimension obtained by a predetermined method with regard to the first property on the autocorrelation order of the gamelan instrument sound. Since the local exponent of fractal dimension consistently has a value of not smaller than 2.2 and the fluctuation range is not greater than 0.4, the first property is satisfied.

Figure 13:
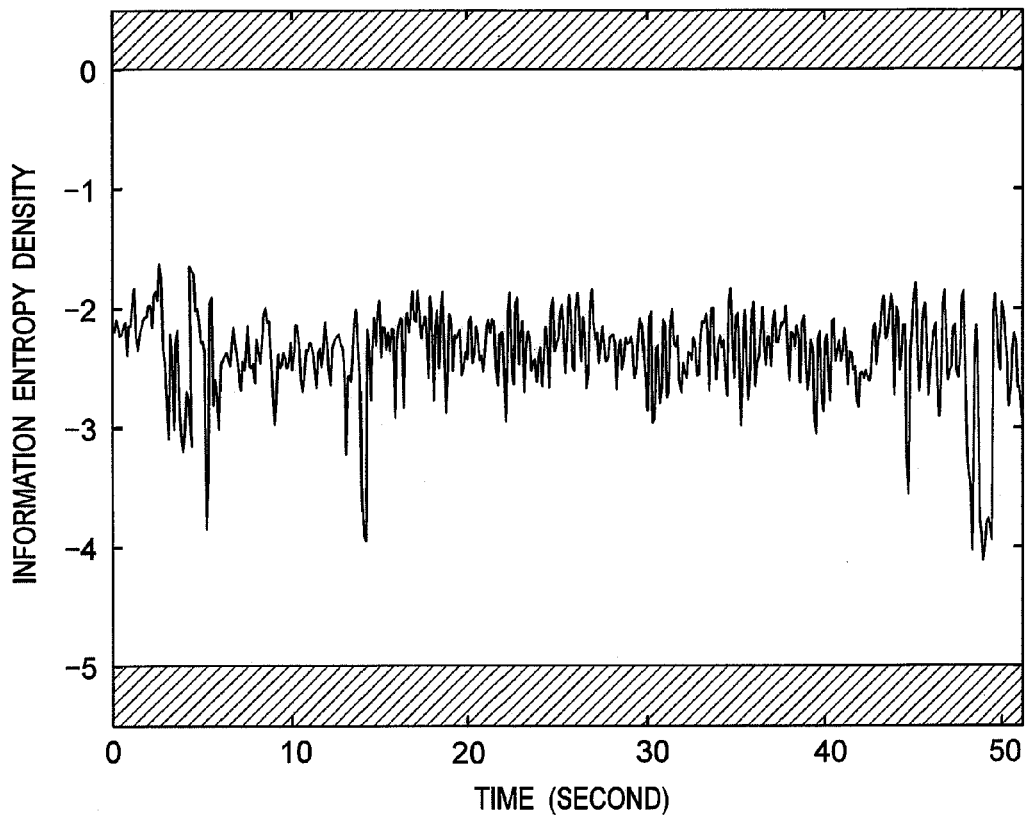
FIG. 13 is a graph showing an information entropy density of the gamelan instrument sound.
Figure 14:
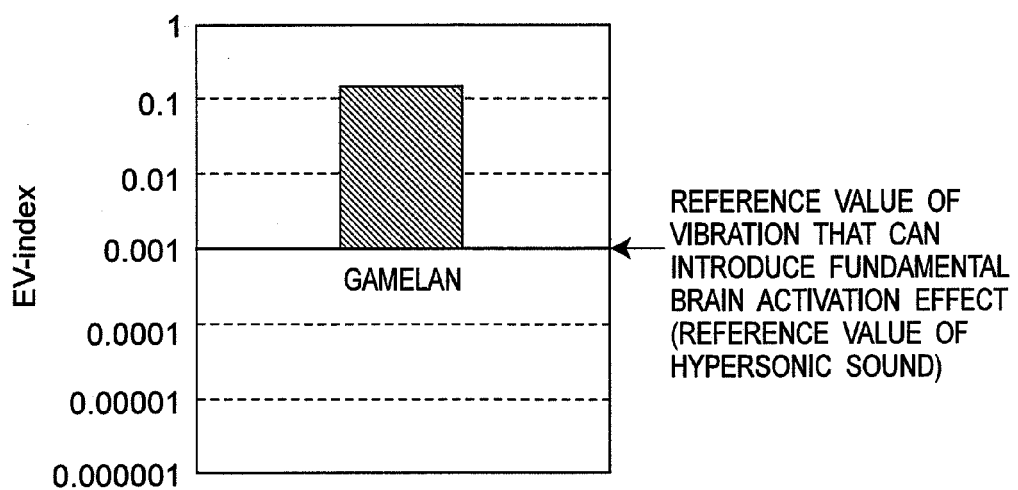
FIG. 14 is a graph showing an entropy variation index (EV-index) of the gamelan instrument sound.

FIG. 13 shows the information entropy density obtained by a predetermined method with regard to the second property on the autocorrelation order of the gamelan instrument sound. As is apparent from FIG. 13, the information entropy density consistently has a value of not smaller than −5 and smaller than zero. FIG. 14 shows the entropy variation index (EV-index) obtained by a predetermined method. As is apparent from FIG. 14, the entropy variation index (EV-index) has a value greater than 0.001. For the above-mentioned reasons, the gamelan instrument sound satisfies the second property on the autocorrelation order.

FIG. 15 is a block diagram of a vibration generating apparatus including a configuration of a positron emission tomography (PET) and a brain wave measurement apparatus used in the present implemental example and a perspective view showing a room 20 for generating a vibration by the vibration generating apparatus.

As shown in FIG. 15, an instrument sound obtained by giving a performance with a gamelan 1 is collected by a microphone 2. The microphone 2 transduces the inputted instrument sound into an analog electric signal, and outputs the transduced analog electric signal to an AD converter 4 via a preamplifier 3. The AD converter 4 performs AD conversion of the inputted analog electric signal into a digital signal by a sampling frequency of 1.92 MHz by, for example, a high-speed sampling 1-bit quantization system devised by Dr. Yoshio Yamasaki, and outputs the resulting signal to a magnetic recording part 11.

A magnetic recording and reproducing device 10 is a so-called digital signal recorder that includes a magnetic recording part 11, a magnetic recording head 12, a magnetic reproducing head 14 and a magnetic reproducing part 15 to record a digital signal on a magnetic tape 13 or to reproduce and output the digital signal recorded on the magnetic tape 13. In this case, the magnetic recording and reproducing device 10 has a uniform frequency characteristic in a frequency domain reaching 150 kHz with a prior art DAT in which a digital signal having undergone AD conversion by the high-speed sampling 1-bit quantization system devised by Dr. Yoshio Yamasaki is recorded. The magnetic recording part 11 modulates a carrier wave signal in accordance with the digital signal inputted from the AD converter 4 by a predetermined digital modulation system and records the modulated signal on the magnetic tape 13 running in the predetermined direction 16 indicated by the arrow by using the magnetic recording head 12. Meanwhile, the magnetic reproducing part 15 reproduces the modulated signal recorded on the magnetic tape 13 by using the magnetic reproducing head 14, demodulates the reproduced modulated signal by a digital demodulation system reverse to the aforementioned digital modulation system and takes out the digital signal.

The demodulated digital signal is subjected to DA conversion into the original analog signal by a DA converter 5 and thereafter outputted via a reproducing amplifier 6. An output analog signal from the reproducing amplifier 6 is inputted to a right side loudspeaker 9aa and a left side loudspeaker 9ab capable of generating a signal in a frequency domain of 20 kHz to 150 kHz via a switch SW1, a high-pass filter 7a having a cutoff frequency of 22 kHz and a power amplifier 8a and also inputted to a right side loudspeaker 9ba and a left side loudspeaker 9bb capable of generating a signal of not higher than 20 kHz via a switch SW2, a low-pass filter 7b having a cutoff frequency of 22 kHz and a power amplifier 8b. Therefore, the crossover frequency of the two filters 7a and 7b is 22 kHz.

The loudspeakers 9aa, 9ab, 9ba and 9bb are placed in the room 20 of a sound insulation room that is acoustically shielded, and the loudspeakers 9aa, 9ab, 9ba and 9bb are applied to a listener 30 who is the test human subject by transducing the inputted signal into a vibration.

Detection electrodes are placed at, for example, twelve scalp points (Fp1, Fp2, F7, Fz, F8, C3, C4, T5, Pz, T6, O1, O2) conforming to the International 10-20 method on the scalp of the listener 30, and a brain wave detecting and transmitting apparatus 32 connected to the detection electrodes convert the brain waves detected by the detection electrodes into a wireless signal and transmit it from an antenna 33 toward an antenna 34. The wireless signal of the brain waves is received by the antenna 34 and thereafter outputted to a brain wave data receiving and recording apparatus 31. In the brain wave data receiving and recording apparatus 31, the received wireless signal of the brain waves is converted into a brain wave signal and recorded in a magnetic recording apparatus. Further, the brain wave signal is analyzed by an analysis computer, while changes in the brain wave are recorded and outputted by using an output device such as a CRT display and a pen recorder. On the other hand, the head portion of the listener 30 is placed held between two detecting parts of a tomographic detector apparatus 42, and a detection signal from the tomographic detector apparatus 42 is transmitted to a tomographic apparatus 41. Subsequently, the tomographic apparatus 41 executes predetermined tomographic analysis processing based on the inputted detection signal and displays a tomographic chart of the analysis result on a built-in CRT display.

In the vibration generating apparatus and the room 20 configured as above, when the switches SW1 and SW2 are both turned on, an instrument sound performed by using the gamelan 1 is recoded on the magnetic tape 13 in the magnetic recording and reproducing device 10. Subsequently, when it is reproduced, the reproduced vibration substantially identical to the instrument sound of the gamelan 1, i.e., both of audible range components (LFC) and super-high-frequency components (HFC) having a predetermined autocorrelation order can be applied to the listener person 30 by using the loudspeakers 9aa, 9ab, 9ba and 9bb. This condition is referred to as a full-range state condition (FRS condition, hereinafter). In this case, by turning on and off the switches SW1 and SW2, the vibration of the gamelan instrument sound of various frequency components can be generated by the loudspeakers 9aa, 9ab, 9ba and 9bb. That is, when only the switch SW1 is turned on, a vibration of only the super-high-frequency components (HFC) of not lower than 22 kHz is applied to the listener person 30. This condition is referred to as an HFC alone condition. On the other hand, when only the switch SW2 is turned on, a vibration of only the audible range components (LFC) of not higher than 22 kHz is applied to the listener 30. This condition is referred to as an LFC alone condition. When both the switches SW1 and SW2 are turned off, background noise components (hereinafter referred to as background noise components) of the baseline based on aerial vibrations generated by the equipment in the room 20 and negligibly weak thermal noise components of the power amplifiers 8a and 8b are applied to the listener 30. This condition is referred to as a background noise condition.

The activity of the fundamental brain was measured by recording simultaneously or solely the regional cerebral blood flow and the brain wave of the listener, to whom the vibration of the gamelan instrument sound was applied.

FIG. 16 is a projection chart showing brain regions where the regional cerebral blood flow in the FRS condition that the audible range components and the super-high-frequency components are simultaneously applied is significantly increased by contrast to the LFC alone condition that only the audible range components are applied, or experimental results measured by the apparatus of FIG. 15. FIG. 16($a$) is a projection chart (sagittal projection chart) along the sagittal suture of the listener's cranium, FIG. 16($b$) is a projection chart (coronal projection chart) along his or her coronal suture, and FIG. 16($c$) is a horizontal plane projection chart of them. That is, FIG. 16 is a projection chart showing a region 101 corresponding to Tarailach coordinates (x, y, z)=(4 mm, −26 mm, −8 mm) where the regional cerebral blood flow in the FRS condition is significantly increased by contrast to the LFC alone condition, i.e., the brain stem, and a region 102 corresponding to Tarailach coordinates (x, y, z)=(−16 mm, −18 mm, 0 mm), i.e., the left thalamus region in the present preferred embodiment. As is apparent from FIG. 16, it can be understood that the regional cerebral blood flow is significantly increased in the brain stem and the left thalamus region in the FRS condition that the audible range components and the super-high-frequency components are simultaneously applied in comparison with the LFC alone condition that only the audible range components are applied to the listener 30.

FIG. 90 is a graph showing a regional cerebral blood flow rate normalized to each frequency component, or the experimental results measured by the apparatus of FIG. 15, in which FIG. 90($a$) is a graph showing a regional cerebral blood flow rate in the position of the brain stem, and FIG. 90($b$) is a graph showing a regional cerebral blood flow rate in the position of the left thalamus region. As is apparent from FIG. 90, it can be understood that the regional cerebral blood flow rate is significantly reduced in the LFC alone condition that only the audible range components are applied in the brain stem and the left thalamus region in comparison with also the FRS condition and the background noise condition.

Figure 17:
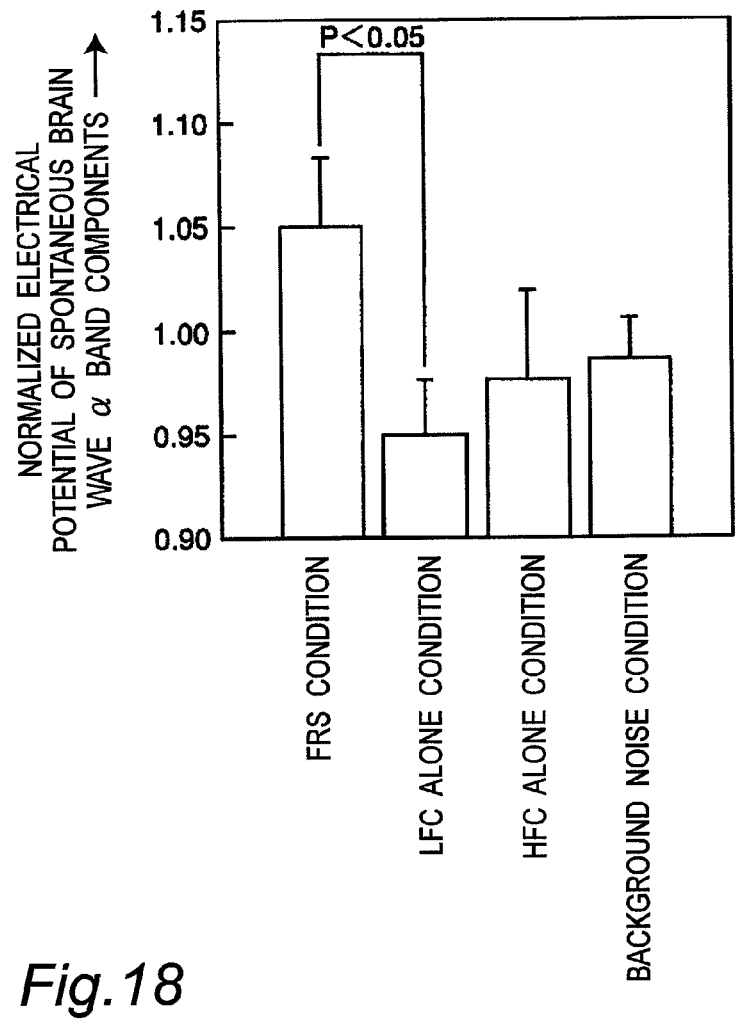
FIG. 17 is a graph showing a normalized electric potential of spontaneous a rhythm of brain wave band components normalized to each frequency component, or the experimental results measured by the apparatus of FIG. 15.

FIG. 17 is a graph showing a normalized electric potential (square root of power) of the α wave band components (8 to 13 Hz) of spontaneous brain wave normalized to each frequency component, or the experimental results measured by the apparatus of FIG. 15. As is apparent from FIG. 17, it can be understood that the α wave band components of the spontaneous brain wave are increased in the FRS condition that the audible range components and the super-high-frequency components are simultaneously applied in comparison with the LFC alone condition that only the audible range components are applied, the HFC alone condition that only the super-high-frequency components are applied and the background noise condition that only the background noise components are applied to the listener 30.

The brain stem and the thalamus where it is indicated that the regional cerebral blood flow is increased in FIG. 16 are, so to speak, the regions corresponding to the "crest" at which the statistical significance is maximized. Then, accordingly, in order to depict the overview of the neural network to which these brain regions belong, a typical spatial pattern included in the fluctuations of the entire data was extracted as a principal constituent by using a principal component analysis, and the principal constituent including the brain stem and the thalamus was searched from there.

Figure 18:
FIG. 18 is a chart showing a cross section of a fundamental brain network image extracted as a second principal constituent by a principal component analysis of regional cerebral blood flow data, or the experimental results measured by the apparatus of FIG. 15.

FIG. 18 is a chart showing a sagittal cross section (sagittal cross section) of an image depicted as the principal constituent including the brain stem and the thalamus by the principal component analysis of regional cerebral blood flow data, or the experimental results measured by the apparatus of FIG. 15. As a result of the principal component analysis, a "fundamental brain network" that included the entire neural network based in the "fundamental brain" including the hypothalamus in addition to the brain stem and the thalamus shown in FIG. 16 projected on the fundamental brain to the prefrontal region and the cingulate gyrus was depicted as a second principal constituent that indicated the second greatest fluctuation in the whole. It is noted that the first principal constituent is considered to be the reactions of the auditory area and the like to the audible range sound.

The fundamental brain serving as an internal structure is unitarily comprehensively responsible for generation of reactions of pleasure, beauty and emotion in a human being and includes the reward system nerve circuit inclusive of the monoamine neural system and the opioid neural system closely related to behavioral control. When the activity of the fundamental brain and the neural network (fundamental brain network system) widely projected therefrom to the whole brain is improved, there are produced the effects of enhancing the aesthetic sensitivity to various general sensory inputs inclusive of sounds, enhancing the reactions of pleasure, beauty and emotion and intensifying the behavior of positively receiving such sensory inputs (sensory receiving behavior or approaching behavior).

Conversely, it has been discovered that the activity abnormalities of the fundamental brain and the fundamental brain network (fundamental brain network system) led to various mental disorders directly caused by the malfunctions of the monoamine neural system, such as depression, schizophrenia, dementia, chronic fatigue syndrome and attention-deficit hyperactivity disorder, and induce various mental and behavioral abnormalities such as suicide and self-injurious behaviors and abnormal exaltation of aggressiveness, which caused serious problems in the modern society.

In addition, the fundamental brain is the ultimate center of the autonomic nerve system and the endocrine system and responsible for the function to maintain the constancy (homeostasis) of the whole body and the biophylactic function by controlling the immune system via these, and the activity abnormality of the fundamental brain has close relations to the onset of the lifestyle-related diseases of metabolic syndromes such as hypertension, hyperlipemia and diabetes, cancer, cerebrovascular disorder and cardiopathy, immune abnormalities including allergy such as pollinosis and atopic dermatitis, which are rapidly increasing in the modern society, by conducting a failure in the homeostatic maintenance function.

Figure 19:
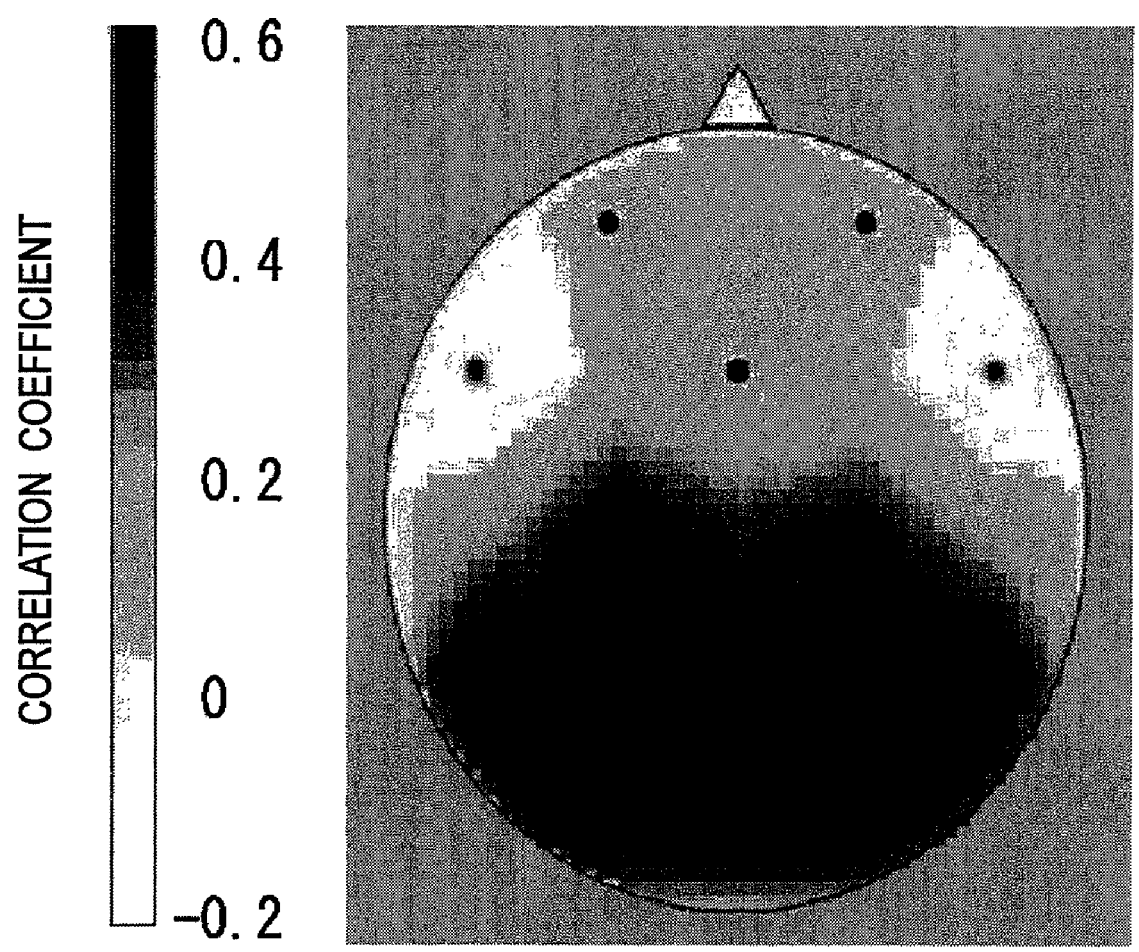
FIG. 19 is a chart showing a scalp distribution of a correlation coefficient between the normalized electric potential of spontaneous brain wave α2 band component and changes in the activity intensity of the fundamental brain network, or the experimental results measured by the apparatus of FIG. 15.

Further, referring to FIG. 19, band components of spontaneous brain waves fluctuating in parallel with changes in the activity intensity of the fundamental brain network system depicted in FIG. 18 were obtained. The spontaneous brain waves measured from twelve electrodes (Fp1, Fp2, F7, Fz, F8, C3, C4, T5, Pz, T6, O1, O2) arranged on the scalp in conformity to the International 10-20 method were divided into $\delta$ band (2 to 4 Hz), $\theta$ band (4 to 8 Hz), $\alpha1$ band (8 to 10 Hz), $\alpha2$ band (10 to 13 Hz) and $\beta$ band (13 to 30 Hz), and the electric potential (square root of power) of each band component was calculated for each electrode to examine which electrode and which band component the electric potential was recorded from and had correlations to the changes in the activity intensity of the fundamental brain network system derived from regional cerebral blood flows measured simultaneously. As a result, the electric potentials of the $\alpha2$ band components of the brain waves recorded from seven electrodes (C3, C4, T5, Pz, T6, O1, O2 by the International 10-20 method) placed in the center region, the parietal region and the occipital region on the scalp statistically significantly indicated positive correlations to the changes in the activity intensity of the fundamental brain network shown in FIG. 18.

FIG. 19 is a chart showing a scalp distribution of a correlation coefficient between the electric potential of the brain wave $\alpha2$ band component and the changes in the activity intensities of the fundamental brain network system, or the experimental results measured by the apparatus of FIG. 15. Based on these results, a value, which was obtained by normalizing and averaging the electric potential values of the brain wave $\alpha2$ band components recorded from the seven electrodes (C3, C4, T5, Pz, T6, O1, O2 by the International 10-20 method) in the center region, the parietal region and the occipital region, statistically significantly indicating positive correlations to the changes in the activity intensity of the fundamental brain network, was defined as a deep brain activity index (DBA-index). The deep brain activity index (DBA-index) can be used as an index to reflect the activities of the fundamental brain network system based on brain wave data that can be simply recorded without performing the regional cerebral blood flow measurement that needs a large-scale apparatus.

Next, an implemental example in which, by using a gamelan instrument sound of an aerial vibration that has super-high-frequency components, or the essential condition as a vibration that can introduce the fundamental brain activation effect and satisfies the first property and the second property on the autocorrelation order and brain wave measurement of a human being to whom it is applied, a super-high-frequency vibration exceeding the human audible range upper limit is received by the "body surface" and introduces the fundamental brain activation effect is described below.

In a human being, aerial vibrations at frequencies exceeding 20 kHz are scarcely transmitted to hair cells that transduce a mechanical vibration into a neural activity because of the mechanical properties of the auditory ossicles in the middle ear and the basilar membrane inside the cochlea in the inner ear. This suggests that a certain reception response system other than the human airway auditory system is concerned in the reception of the super-high-frequency components having the feature of the autocorrelation order essential for introducing the fundamental brain activation effect by a human being.

Accordingly, in order to examine whether the fundamental brain activation effect is a normal sole response of the airway auditory system or concerned in the reception response system other than it in the experiment according to the present implemental example, the frequency components of a gamelan instrument sound of a typical aerial vibration that contains super-high-frequency components of the essential condition as a vibration capable of introducing the fundamental brain activation effect and satisfies the first property and the second property on the autocorrelation order are filtered and separated into audible range components of not higher than 22 kHz and super-high-frequency components of not lower than 22 kHz. Then, by selectively representing the super-high-frequency components to the airway auditory system under the condition that the audible range components were presented to the airway auditory system or by conversely representing the super-high-frequency components to the body surface that presumably included various other vibration reception systems excluding the airway auditory system, it was determined to examine by comparison whether a difference might occur between both of them in the generation of the fundamental brain activation effect and what sort of difference it was when a difference took place.

Figure 20:
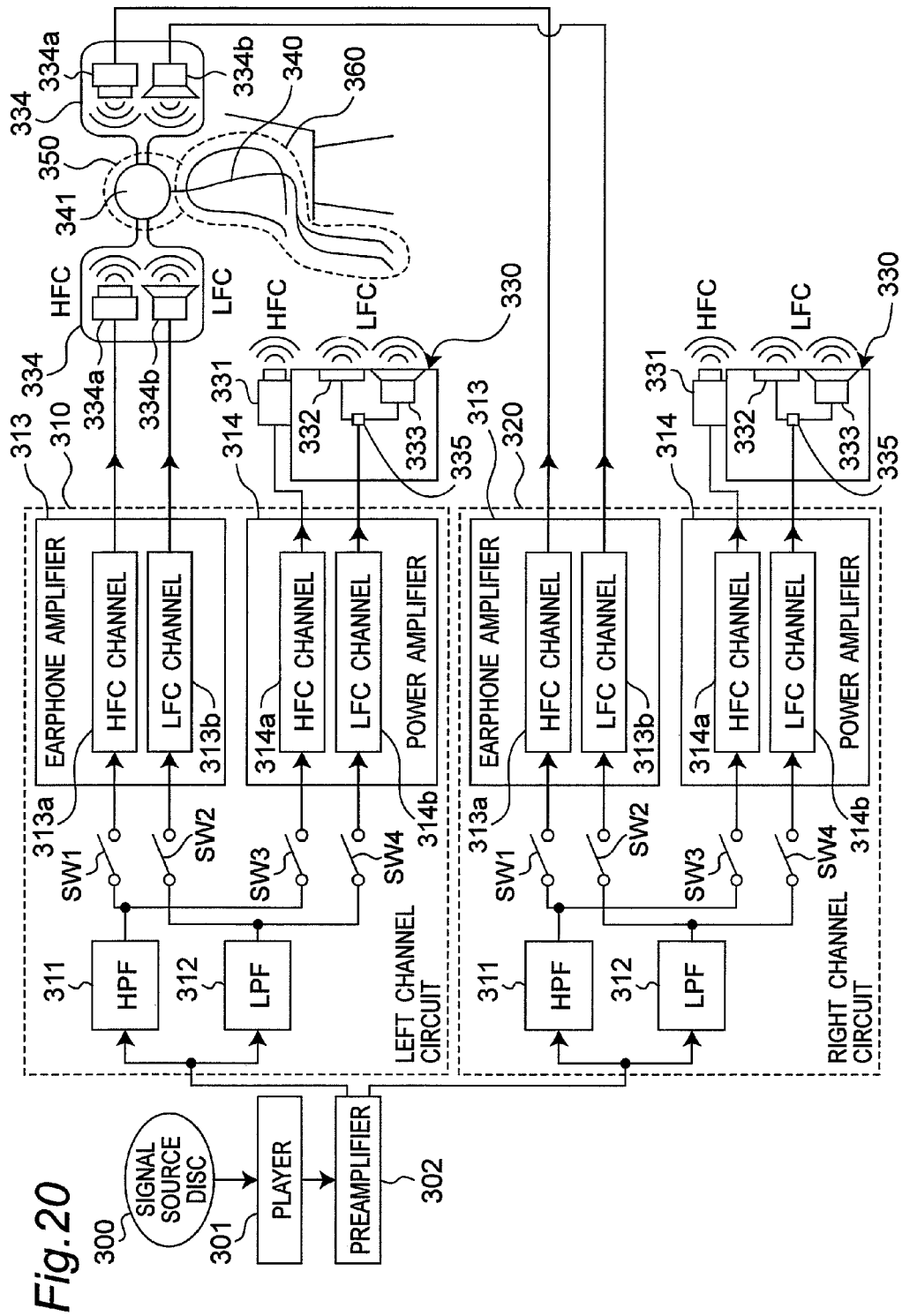
FIG. 20 is a block diagram showing a configuration of a vibration generating apparatus that is an earphone experimental apparatus used in the first preferred embodiment.

In this case, FIG. 20 is a block diagram showing a configuration of a vibration generating apparatus that is an earphone experimental apparatus used in the present preferred embodiment. In the experimental apparatus of FIG. 20, by using a high-pass filter and a low-pass filter 311 and 312 having an attenuation rate of 80 db/oct. and a pass-band frequency domain ripple of ±1 dB, with a crossover frequency set at 22 kHz, respective stereo sound source signals were each filtered and separated into audible range components and super-high-frequency components. Both of them were independently amplified and thereafter separately or simultaneously presented via earphones 334 and 334 and loudspeaker systems 330 and 330.

Referring to FIG. 20, a predetermined signal source disc 300 is set in a player 301 to generate the signal data of the vibration of the gamelan instrument sound. The signal data is subjected to DA conversion and amplification by a preamplifier 302 and thereafter inputted to the high-pass filters (HPFs) 311 and the low-pass filters (LPFs) 312 of a left channel circuit 310 and a right channel circuit 320. The left channel circuit 310 and the right channel circuit 320 are configured mutually similarly by including the high-pass filter (HPF) 311, the low-pass filter (LPF) 312, four switches SW1, SW2, SW3 and SW4, an earphone amplifier 313 configured of an HFC channel earphone amplifier 313a for the super-high-frequency components and an LFC channel earphone amplifier 313b for the audible range components, and a power amplifier 314 configured of an HFC channel power amplifier 314a for the super-high-frequency components and an LFC channel power amplifier 314b for the audible range components. In both the channel circuits 313 and 314, an electric signal of the super-high-frequency components (HFC) outputted from the high-pass filter 311 is outputted to a tweeter earphone device 334a of the earphone 334 via the switch SW1 and the HFC channel earphone amplifier 313a, and is outputted to a tweeter 331 of the loudspeaker system 330 via the switch SW3 and the HFC channel power amplifier 314a. Moreover, an electric signal of the audible range components (LFC) outputted from the low-pass filter 312 is outputted to a full-range earphone device 334b for audible range reproduction of the earphone 334 via the switch SW2 and the LFC channel earphone amplifier 313b, and is outputted to a full-range loudspeaker 332 and a woofer 333 for audible range reproduction via the switch SW4, the LFC channel power amplifier 314b and a power distribution network 335 of the loudspeaker system 330.

In this case, one pair of loudspeaker systems 330 and 330 is placed on the left and right sides of a listener 340, and one pair of earphones 334 and 334 are inserted in the external auditory meatuses of both ears of the listener 340. Depending on the following experimental conditions, the head 341 of the listener 340 is substantially wholly covered with a full-face helmet 350, and the substantial whole body except for the head 341 of the listener 340 is substantially wholly covered with an acoustically insulating sound-insulation full body coat 360. Moreover, the switches SW1, SW2, SW3 and SW4 are turned on or off depending on the following experimental conditions. In this case, one pair of loudspeaker systems 330 and 330 was placed in a position at a distance of 2.0 m apart from the ears of the listener 340. Moreover, one pair of earphones 334 and 334 was provided by an originally developed insertion type having no ear pad. The auditory meatus insertion portion of the earphone 334 forms a housing structure of a thickness of two to three millimeters formed by injection molding of a rigid plastic and has two vibration generating earphone devices 334a and 334b for the super-high-frequency components (HFC) and the audible range components (LFC), respectively, in each of the right and left channels.

The brain wave experiment was constituted of four sub-experiments. That is, the experimental conditions of these four sub-experiments are as follows.

(1) Both of the audible range components (LFC) and the super-high-frequency components (HFC) are presented via the loudspeaker systems 330 and 330.

(2) Both of the audible range components (LFC) and the super-high-frequency components (HFC) are presented via the earphones 334 and 334.

(3) The audible range components (LFC) are presented via the earphones 334 and 334, and the super-high-frequency components are presented via the loudspeaker systems 330 and 330.

(4) The audible range components (LFC) are presented via the earphones 334 and 334, and the super-high-frequency components are presented via the loudspeaker systems 330 and 330, whereas, in order not to expose the head 341 and the body surface of listener 340 to the super-high-frequency components (HFC), those portions are covered with the full face helmet 350 and the sound-insulating full body coat 360, which are sound insulators.

Two conditions were compared with each other in each of all the sub-experiments. That is, the conditions are the full-range state condition (hereinafter referred to as the FRS condition) that the audible range components (LFC) and the super-high-frequency components (HFC) are simultaneously presented and the LFC alone condition that only the audible range components (LFC) are presented. All the experiments were carried out in a sound insulation room.

In each of the experiments, two trials of each of the FRS condition and the LFC alone condition were carried out at inter-trial intervals of several minutes. In each trial, the gamelan instrument sound was presented for 400 seconds. The brain wave measuring method and the method of obtaining the deep brain activity index (DBA-index) are similar to the methods described in detail hereinabove with reference to FIGS. 18 and 19.

Since the temporal data of the brain wave exhibited an apparent delay to the sound presentation, statistical evaluations of a difference between the FRS condition and the LFC alone condition were performed by using the t-test having correspondence to the entire interval of 400 seconds, the latter half of 200 seconds and the final 100 seconds.

Figure 21:
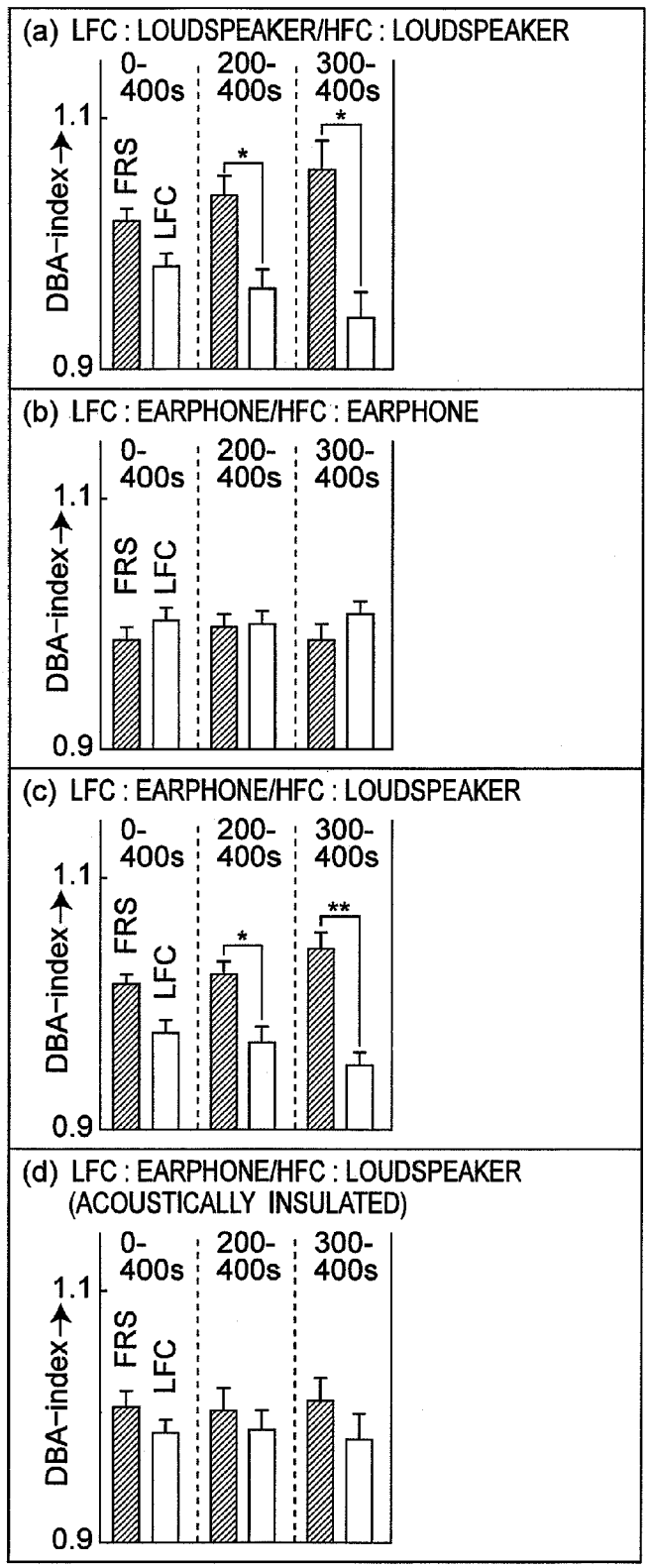
FIG. 21 is a graph showing a deep brain activity index (DBA-index) of each case, or experimental results measured by the system of FIG. 20.

Next, experimental results are described below. FIG. 21 is a graph showing a DBA-index of each case, or the experimental results measured by the system of FIG. 20, and it indicates the average value and the standard error of all the listeners. First of all, as shown in FIG. 21(a), it was confirmed that, when the audible range components (LFC) and the super-high-frequency components (HFC) were presented to the listeners 340 via the loudspeaker systems 330 and 330, the DBA-index had significantly increased values under the FRS condition in comparison with the values under the LFC alone condition, and the fundamental brain activation effect was generated. The increase in the DBA-index was more remarkable approaching the latter half of the sound presentation period. This fact well coincides with the past reports of the present inventor and others who express that the development and disappearance of the fundamental brain activation effect are accompanied by a time delay.

Next, as shown in FIG. 21(b), when both the super-high-frequency components (HFC) and the audible range components (LFC) were selectively presented to only the airway auditory system via the earphones 334 and 334, no difference was recognized in the DBA-index between the FRS condition and the LFC alone condition, and the development of the fundamental brain activation effect was not discovered.

In contrast to it, as shown in FIG. 21(c), when the super-high-frequency components (HFC) were selectively presented via the loudspeaker systems 330 and 330 under the condition that the audible range components (LFC) were selectively presented to only the airway auditory system via the earphones 334 and 334, the DBA-index was significantly increased in the FRS condition in comparison with the LFC alone condition, and it was confirmed that the fundamental brain activation effect was generated. Also, in this case, the increase in the DBA-index was more remarkable as getting closer to the latter half of the sound presentation period.

Further, as shown in FIG. 21(d), when the super-high-frequency components (HFC) sent off via the loudspeaker systems 330 and 330 were highly attenuated by placing a sound-insulating material in a position immediately before reaching the listener's body to be disturbed from reaching the his or her body in an experiment of the same setting, the difference in the DBA-index between the FRS condition and the LFC alone condition exhibited no statistical significance, and the development of the fundamental brain activation effect was remarkably suppressed.

If the above-mentioned knowledges are generalized, it is indicated that the airway auditory system is not singly concerned in the generation of the fundamental brain activation effect introduced by the vibration having the super-high-frequency components as the essential condition and satisfies the first property or the second property on the autocorrelation order to human beings, but some reception response system residing at or having a window on the body surface is concerned in it.

Next, an example of an apparatus that generates a vibration capable of introducing the fundamental brain activation effect by using an existing object is described below. An example of a vibration generating apparatus that generates a vibration (hypersonic sound) that contains audible range components and super-high-frequency components and can introduce the fundamental brain activation effect with the aforementioned predetermined autocorrelation order as described above is described below. An example of a vibration generating apparatus that generates the predetermined vibration (hypersonic sound) by using an existing object (gas, liquid, solid) is first described, and an example of a vibration generating apparatus that generates the predetermined vibration (hypersonic sound) from a vibration signal of electricity, light or the like is subsequently described.

As shown in FIGS. 1, 3, 4, 8 and 9, natural environmental sounds of the tropical rain forests, or the most powerful candidate of the environments where the human genes have been evolutionally formed abundantly contain super-high-frequency components that extends far beyond the upper limit at 20 kHz at the human audible frequency upper limit and have the predetermined autocorrelation order. In contrast to this, the environmental sounds in cities where the modern people live contain almost no such super-high-frequency components and have the possibilities of introducing no fundamental brain activation effect and deteriorating the fundamental brain activity in comparison with the background noise environment (See, for example, FIGS. 90 and 17). The activity abnormality of the fundamental brain network system of neuronal projection from there has a close relation to the modern diseases inclusive of the lifestyle-related diseases that are currently rapidly increasing by inducing various mental and behavioral disorders and conducting failures in the homeostatic function and the biophylactic function of the whole body. Therefore, paying attention to the fact that the mental and behavioral disorders, the lifestyle-related diseases and so on are increasing specifically and rapidly in the current cities, it is highly possible that one of the causes is ascribed to the fact that the sound environments of the current cities largely deviate from the feature of the natural environmental sounds of the tropical rain forests, which is the most powerful candidate of environments where the human genes have been evolutionally formed, and contain almost no super-high-frequency component having the predetermined autocorrelation order.

In order to solve this problem, it is very effective to install a vibration generating apparatus that can generate a vibration (hypersonic sound) capable of introducing the fundamental brain activation effect because it contains super-high-frequency components having the predetermined autocorrelation order in a variety of spaces inclusive of city spaces, generate a hypersonic sound and apply the same to human beings. Moreover, when a hypersonic sound is generated by using an existing object, it is acceptable to transduce the vibration generated on the spot into an electric signal by using a transducer and record the same. By so doing, it becomes possible to record and reproduce the hypersonic sound in and from package media and distribute it via communications and broadcastings, and this increases a chance that more people receive the hypersonic sound even if they are not in the same space as that of the vibration generating apparatus using the existing object. By abundantly receiving the hypersonic sound, the fundamental brain activation effect is introduced, and it is expected to solve the psychosomatic problems that the modern people confront.

First of all, an example of a vibration generating apparatus and a vibration signal generating apparatus that generate a hypersonic sound by using an existing object (gas, liquid, solid) is described.

FIGS. 22 to 28 show examples of vibration generating apparatuses that generate a vibration (hypersonic sound) which contains audible range components and super-high-frequency components having the predetermined autocorrelation order and can introduce the fundamental brain activation effect by flowing a liquid while making the liquid collide with obstacles. As shown in FIGS. 1, 4, 8 and 10, a running water sound is a vibration that coexistently has the audible range components and the super-high-frequency components and the first property and the second property on the autocorrelation order and can introduce the fundamental brain activation effect. In the apparatus examples described below, a vibration containing the super-high-frequency components having the predetermined autocorrelation order is generated by making a liquid current inclusive of a water current collide with the obstacles with a set liquid current. By thus generating a vibration (hypersonic sound) that contains the audible range components and the super-high-frequency components and has the feature of the predetermined autocorrelation order, the effects of inducing activation of the fundamental brain and the fundamental brain network (fundamental brain network system) including the reward system neural circuit responsible for the generation of reactions of pleasure, beauty and emotion, and the nerve center of the autonomic neural circuit, the endocrine system and the immune system responsible for homeostatic maintenance and biophylaxis in a human being and consequently enhancing the aesthetic sensitivity and ameliorating and improving the physical state are obtained.

Figure 22:
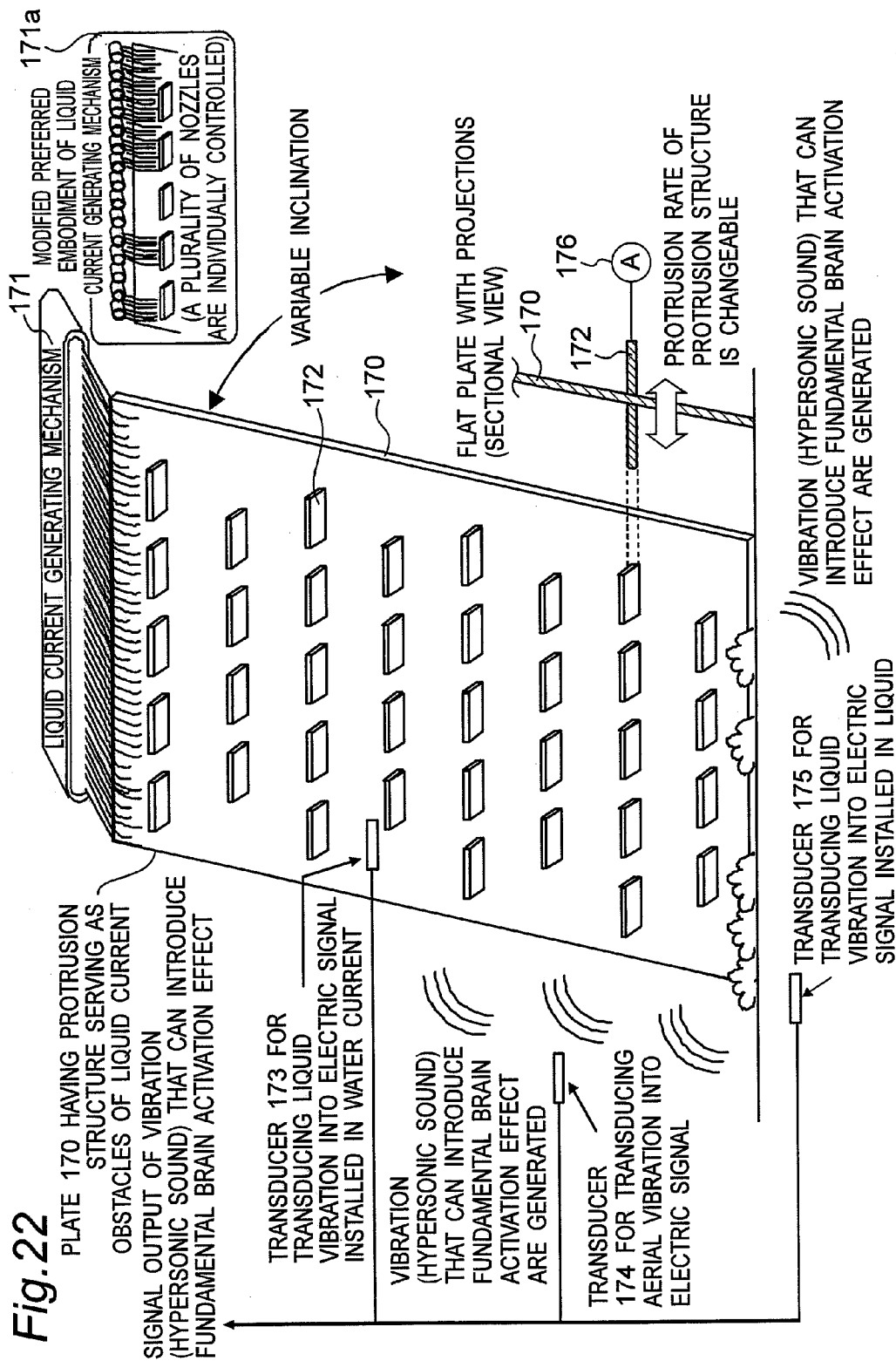
FIG. 22 is a perspective view and a sectional view showing an example of a vibration generating apparatus that generates a vibration (hypersonic sound) capable of introducing the fundamental brain activation effect by using a liquid current according to the first preferred embodiment.

FIG. 22 is a perspective view and a sectional view showing an example of a vibration generating apparatus that generates a vibration (hypersonic sound) that contains audible range components and super-high-frequency components having the predetermined autocorrelation order and can introduce the fundamental brain activation effect by using a liquid current such as a water current according to the present preferred embodiment. FIG. 22 is a vibration generating apparatus constituted of a structure of a flat plate 170 that has one or more obstacle structures such as protrusions of which the positions and the protrusion dimensions are variable and can be set in a position angled in excess of zero degrees and not greater than 90 degrees with respect to the horizontal plane, a liquid current generating device 171 that makes a liquid such as water flow downward on the surface of the flat plate 170, and transducers 173, 174 and 175 that transduce a vibration generated when the liquid is made to flow downward in this system into an electric signal.

The liquid made to flow out of the liquid current generating device 171 positioned in an upper portion of the structure of the flat plate 170 flows downward while colliding with protrusions 172 set on the flat plate 170, jumping over the protrusions 172, flowing round the protrusions 172 or leaping in droplets in the process of flowing downward on the surface of the structure of the flat plate 170. At the time, the liquid generates a vibration (hypersonic sound) capable of introducing the fundamental brain activation effect because it contains super-high-frequency components having the predetermined autocorrelation order. By transducing the thus generated aerial vibration and vibration of the liquid into an electric signal, a signal of a vibration (hypersonic sound) capable of introducing the fundamental brain activation effect can be obtained. The liquid current generating device 171 generates a vibration (hypersonic sound) capable of effectively introducing the fundamental brain activation effect by controlling the flow rate per unit time and the fluctuations of the liquid. For example, the height of the protrusions 172 is controllably configured of an actuator 176. Moreover, the protrusions 172 served as the obstacle of the liquid current may have a shape inclusive of the examples indicated by protrusions 172a to 172i of various shapes as shown in the modified preferred embodiment (sectional view) of FIG. 23 or have them mixed together. Moreover, by rotation of the protrusions 172 with respect to the plate surface, a direction in which the colliding liquid effectively vibrates can be set. It is noted that the axis of rotation of the protrusions 172 may be perpendicular, horizontal or diagonal to the plate surface. As shown in the liquid current generating mechanism 171a of the modified preferred embodiment of FIG. 22, it is also possible to install a plurality of nozzles and control the nozzle position and the flow rate per unit time of the liquid flow by individually controlling them.

Figure 24:
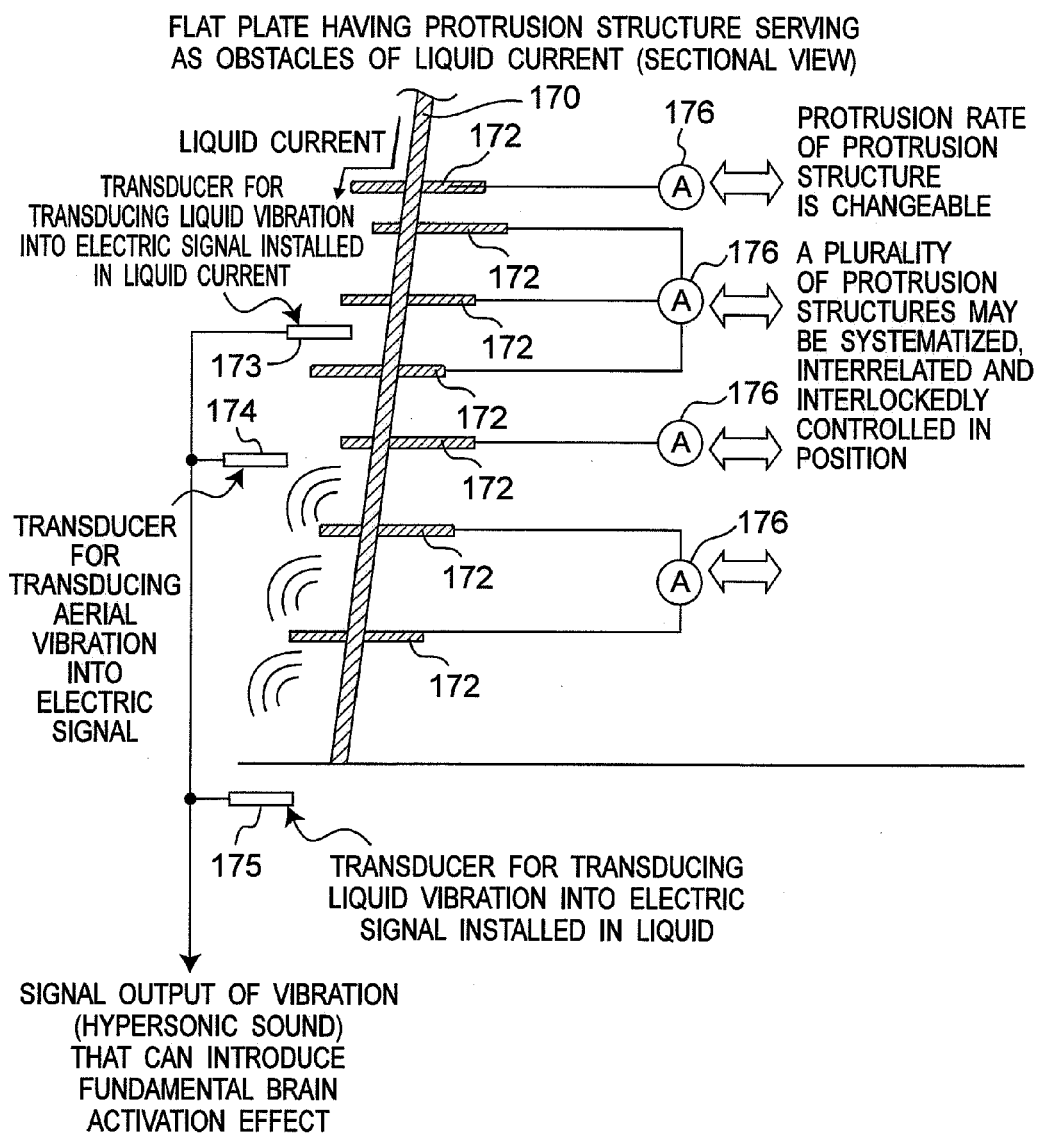
FIG. 24 is a sectional view of an example in which the position control of the protrusion is systematized and interrelated according to the first preferred embodiment.

FIG. 24 is a perspective view showing an example in which the position control of the protrusions is systematized and correlated according to the present preferred embodiment. That is, FIG. 24 is a modified preferred embodiment of the position control mechanism of the protrusions served as the obstacle of the liquid current in the vibration generating apparatus shown in FIG. 22. Referring to FIG. 24, the protrusions 172 can effectively generate a vibration (hypersonic sound) capable of introducing the fundamental brain activation effect by changing the protruding manner of the protrusions that mutually adjoin vertically and horizontally and thereby making them have a specific positional relation. FIG. 24 is an example in which a group configured of a plurality of protrusions is collectively controlled in position with such an effective combination maintained. Moreover, the height of the protrusions 172 is configured to be controllable by the actuator 176.

Figure 25:
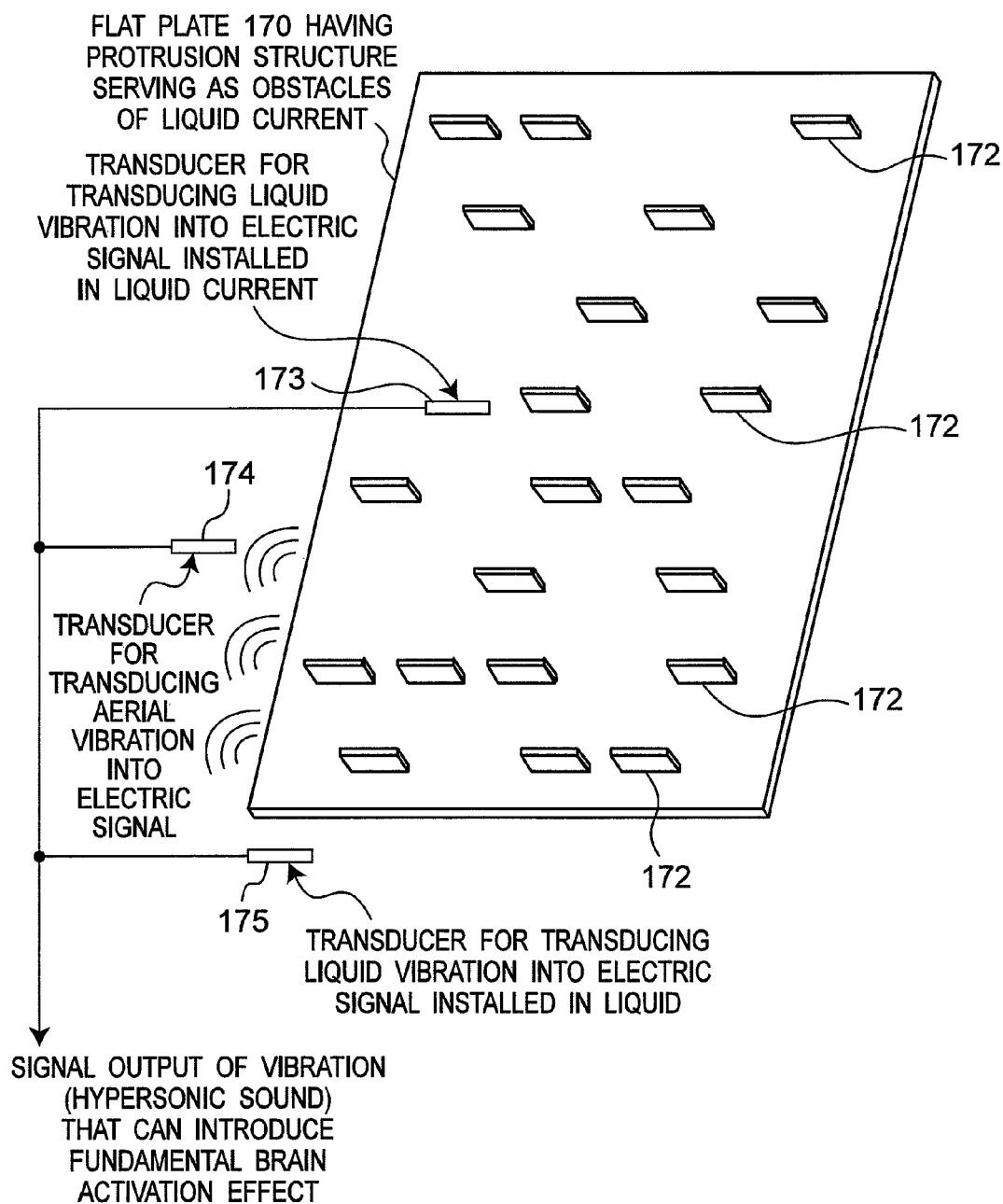
FIG. 25 is a perspective view showing an example in which the arrangement of protrusions served as the obstacle of the liquid current is not regular according to the first preferred embodiment.

FIG. 25 is a perspective view showing an example in which the arrangement of the protrusions served as the obstacle of the liquid current is not regular according to the present preferred embodiment. In FIG. 22, the protrusions 172 are arranged regularly and orderly, and the flow path of the liquid current consequently becomes orderly. The flow rates of the liquid flowing through the flow paths become equalized between corresponding ones, and the vibration (hypersonic sound) capable of introducing the fundamental brain activation effect is generated comparatively evenly from the entire plate surface. On the other hand, in FIG. 25, by irregularly arranging the protrusions 172, the flow paths become unevenly distributed, and changes occur in the liquid flow rates of the flow paths. As a result, a bias is generated in the spatial distribution and the distribution in the liquid of the vibration (hypersonic sound) capable of introducing the fundamental brain activation effect, and therefore, it becomes possible to perform multi-channel recording effective in transducing the vibration signal into an electric signal by making use of this. Moreover, by moving the transducer for transducing into the electric signal from immediately near a certain flow path to immediately near another flow path or by similar measure at this time, dynamic variations of a kind that cannot be generated in the flow rate change in the same flow path can be added to the vibration signal in the moving process.

Figure 26:
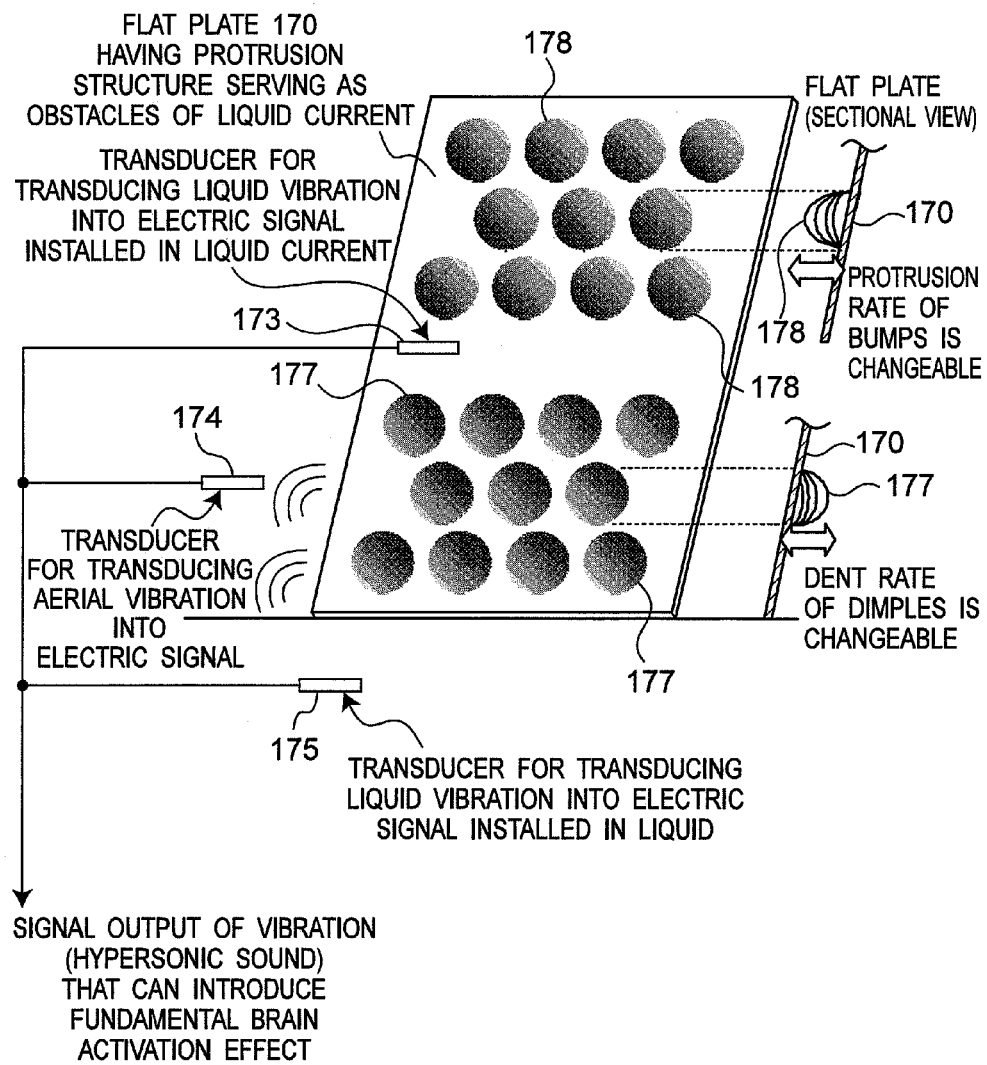
FIG. 26 is a perspective view and a sectional view showing an example in which a structure served as the obstacle of the liquid current has a bump shape or a dimple shape according to the first preferred embodiment.

FIG. 26 is a perspective view and a sectional view showing an example in which a protrusion structure served as an obstacle of a liquid current has a bump shape (e.g., a depth variable type round bump 178) or a dimple shape (e.g., a height variable type round dimple 177) according to the present preferred embodiment. That is, FIG. 26 is a modified preferred embodiment of the shape of the structure that becomes the obstacle of the liquid current in the vibration generating apparatus shown in FIG. 22. Referring to FIG. 26, the height of the bump 178 or the height of the dimple 177 is variable. At the bump 178 and the dimple 177, a structure having a plurality of shapes may coexist in mixture.

Figure 27:
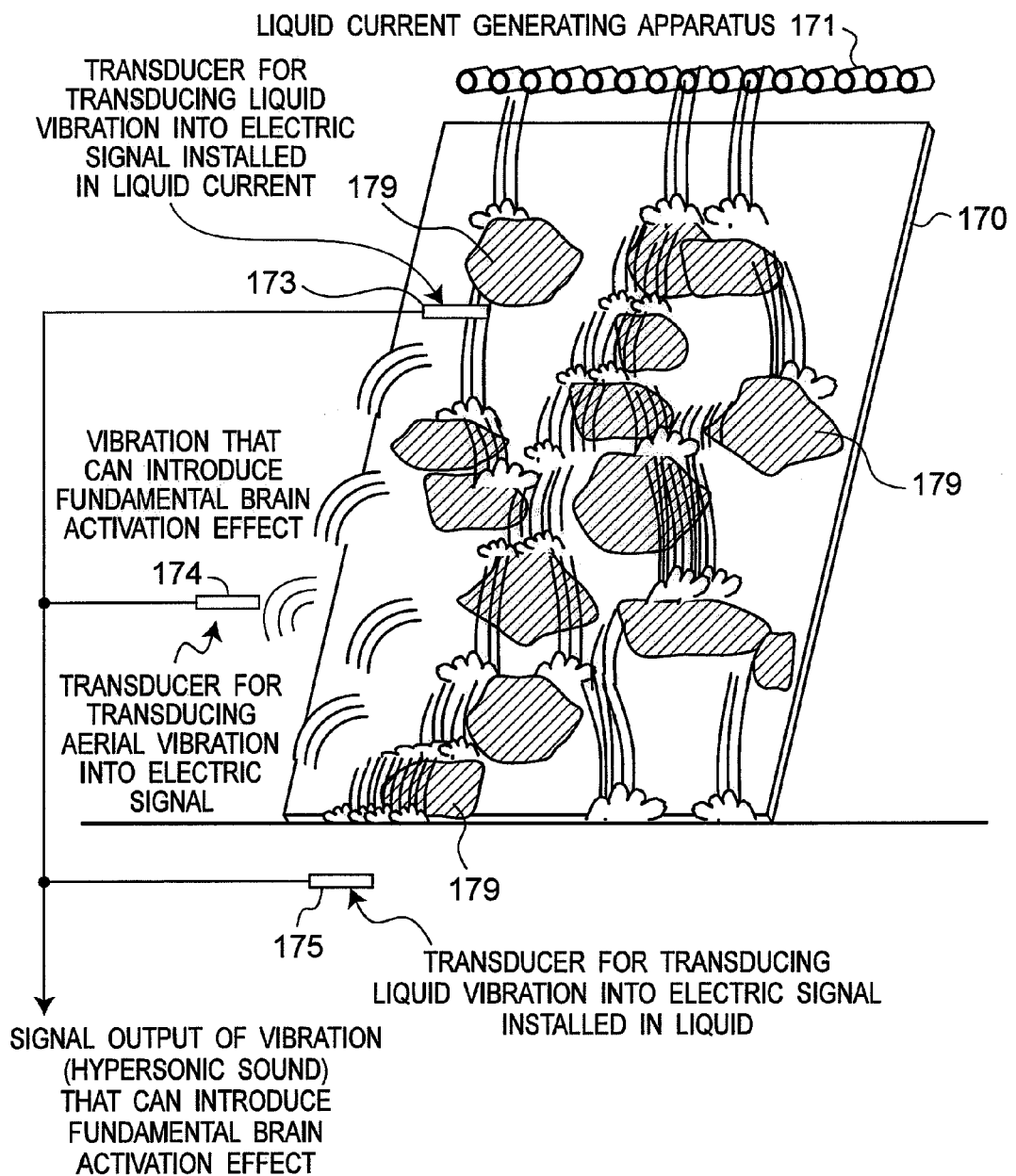
FIG. 27 is a perspective view showing an example in which a protrusion structure served as the obstacle of the liquid current has an irregular configuration and is irregularly arranged according to the first preferred embodiment.

FIG. 27 is a perspective view showing an example in which a protrusion structure served as the obstacle of the liquid current has an irregular configuration and is irregularly arranged according to the present preferred embodiment. In FIG. 22, the protrusions 172 having a plate-like simple shape are orderly regularly arranged. On the other hand, protrusions 179 having complicated configurations like natural stones are irregularly arranged. With this arrangement, a water current having complicated flow paths and obstacle structures actually existing in fields and mountains and the like is imitated in a controlled configuration is generated, thereby allowing a vibration (hypersonic sound) capable of introducing the fundamental brain activation effect to be generated.

Figure 23:
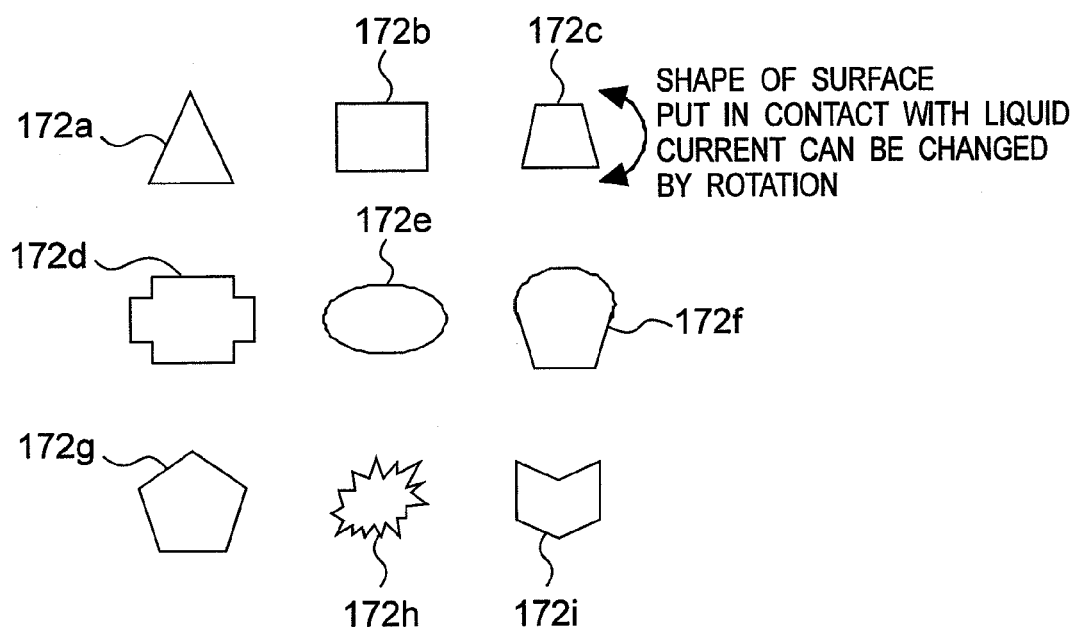
FIG. 23 is a sectional view showing examples of the shape of protrusions served as an obstacle of the liquid current of FIG. 22.
Figure 28:
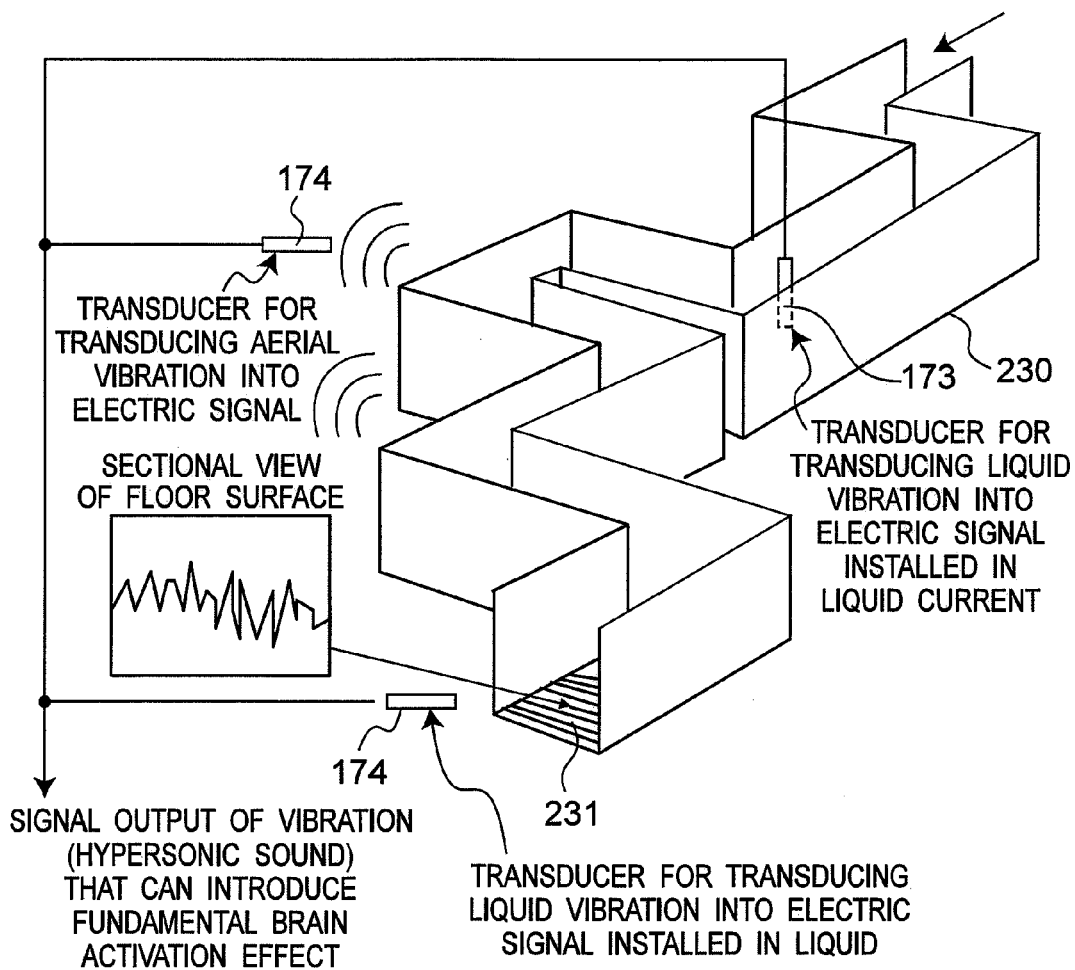
FIG. 28 is a perspective view and a sectional view showing an example (horizontal path) of a vibration generating apparatus that generates a vibration (hypersonic sound) capable of introducing the fundamental brain activation effect by using a liquid current according to the first preferred embodiment.

FIG. 28 is a perspective view and a sectional view showing an example (horizontal path) of a vibration generating apparatus that generates a vibration (hypersonic sound) which contains audible range components and super-high-frequency components having the predetermined autocorrelation order and can introduce the fundamental brain activation effect by using a liquid current such as a water current according to the present preferred embodiment. That is, FIG. 28 is a modified preferred embodiment in which the plate-like structure has an angle set at zero degrees or close to zero degrees with respect to the horizontal plane in the vibration generating apparatus shown in FIG. 22. Referring to FIG. 28, a liquid waterway 230 has a plurality of bends in an intricate structure, and its floor surface 231 has a complicated asperity structure as shown in the sectional view of FIG. 28. Each of the structures becomes an obstacle in the liquid flow, and a vibration (hypersonic sound) capable of introducing the fundamental brain activation effect can be generated by flowing the liquid while making it collide with those obstacles. It is noted that the bend angle of the waterway 230 where the liquid flows may be an angle other than 90 degrees shown in the figure. Moreover, it is acceptable to draw a continuous curve. Further, the obstacle structures of the protrusions 172 as shown in FIGS. 22 and 23, the protrusion structures 177 and 178 as shown in FIG. 26 and the protrusion structure 179 as shown in FIG. 27 may be arranged on the bottom surface and the walls in the paths.

Figure 29:
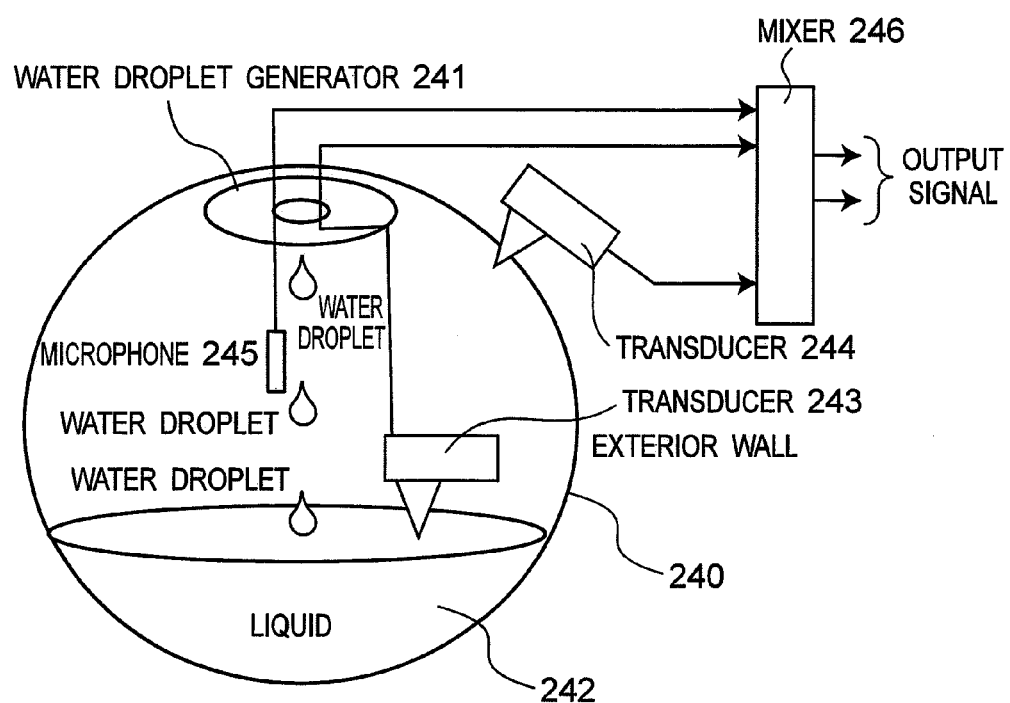
FIG. 29 is a block diagram showing an example of a vibration generating apparatus that generates a vibration (hypersonic sound) capable of introducing the fundamental brain activation effect by dripping water according to the first preferred embodiment.

FIG. 29 is a block diagram showing an example of a vibration generating apparatus and a vibration signal generating apparatus that generates a vibration (hypersonic sound) that contains audible range components and super-high-frequency components having the predetermined autocorrelation order and can introduce the fundamental brain activation effect by dropping a liquid current such as a water current according to the present preferred embodiment. The apparatus of FIG. 29 has a water drop generator 241 that continuously drops water droplets to the inside of, for example, a spherical apparatus housing 240, the apparatus housing 240 that reserves the liquid 242 of the dropped water droplets, transducers (or microphones) 243, 244 and 245 that transduce vibrations from the reserved liquid and the exterior wall into an electric signal, and an audio mixer 246 that adds the vibration signals together, and outputs an output signal of the addition result. In this case, the object to be dropped may be a liquid other than water or a solid such as pebbles. The liquid to be reserved may be water or a liquid other than water. Moreover, the water droplet generator 241 may be able to adjust a water droplet size and a drop frequency so as to effectively generate a vibration (hypersonic sound) capable of introducing the fundamental brain activation effect. Moreover, the exterior wall of the apparatus housing 240 that encloses a space above the liquid level may take any varied shape, material, hardness, surface shape and volume so that the sound generated by the collision of the dropped object against the liquid surface resonates with the space enclosed by the exterior wall. A naturally formed cave or the like may be utilized as the exterior wall. By thus generating the vibration (hypersonic sound) that contains the audible range components and the super-high-frequency components and has the predetermined autocorrelation order, the effects of inducing activation of the fundamental brain network system including the reward system neural circuit responsible for the generation of reactions of pleasure, beauty and emotion, and the nerve center of the autonomic neural circuit, the endocrine system and the immune system responsible for homeostatic maintenance and biophylaxis in a human being and consequently enhancing the aesthetic sensitivity and ameliorating and improving the physical state are obtained.

Figure 30:
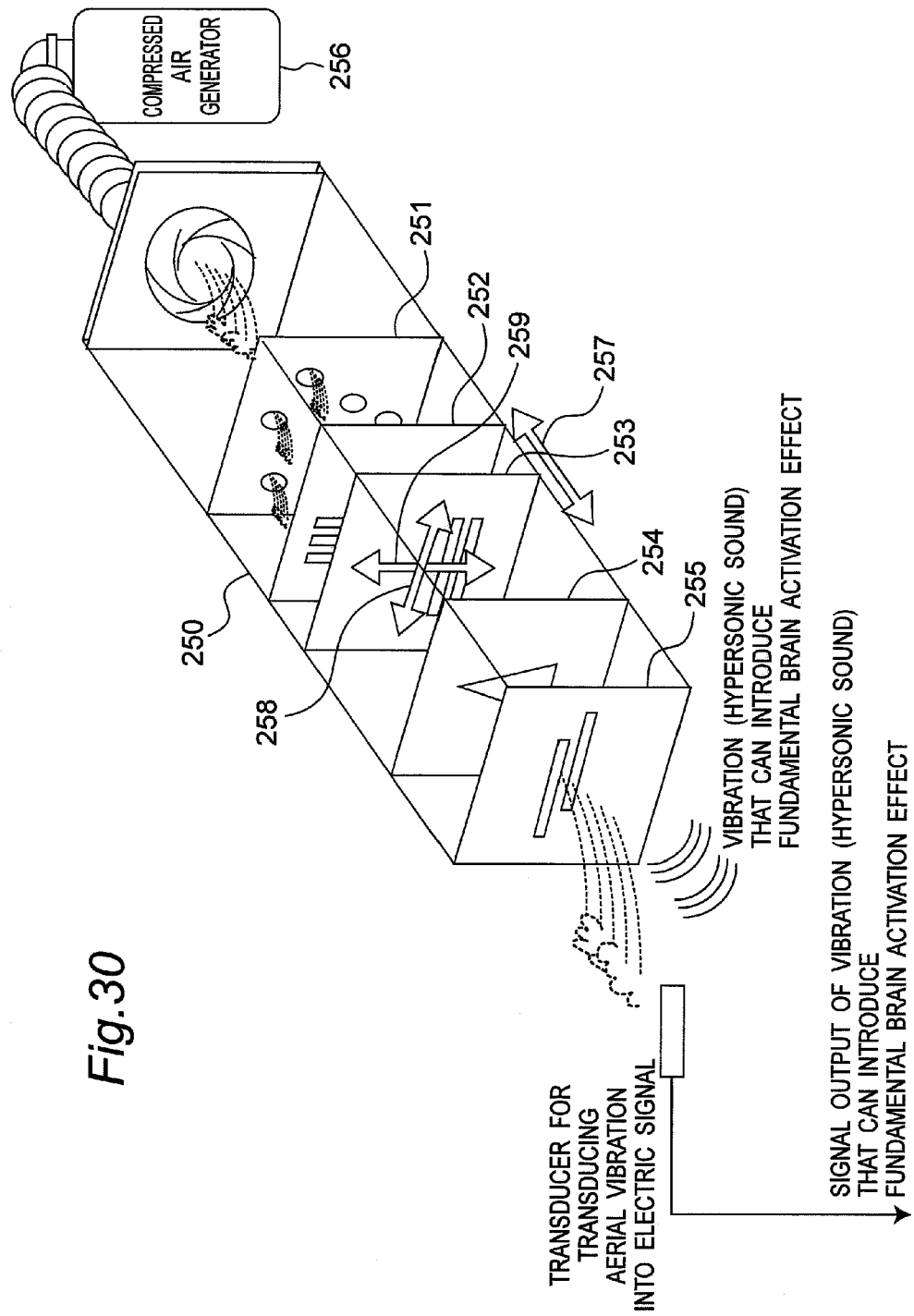
FIG. 30 is a perspective view showing an example of a vibration generating apparatus that generates a vibration (hypersonic sound) capable of introducing the fundamental brain activation effect by an airflow passing through gaps according to the first preferred embodiment.

FIG. 30 is a perspective view showing an example of a vibration generating apparatus that generates a vibration (hypersonic sound) that contains audible range components and super-high-frequency components having the predetermined autocorrelation order and can introduce the fundamental brain activation effect by an air flow passing through gaps according to the present preferred embodiment. That is, FIG. 30 is an example of a vibration generating apparatus that generates a vibration (hypersonic sound) capable of introducing the fundamental brain activation effect by complicated turbulent flows and the like generated when air flows at various speeds pass through the gaps of various shapes. The apparatus of FIG. 30 is constituted of a compressed air generator 256 that generates an air flow by releasing a propeller-shaped rotor blade or compressed air, a rectangular parallelepiped apparatus housing 250 connected to it, and partition plates 251 to 255 that partition the inside of it. In this case, it is acceptable to provide an apparatus that controls the speed of the air flow by changing the rotating speed of the rotor blade and the size of the release port of compressed air, an apparatus such that air flows pass through a plurality of gaps having various shapes and sizes, and an apparatus that changes the positions of the gaps as indicated by the arrows 257 to 259. It is acceptable to provide an apparatus such as a resonance box or a resonance tube having a function to amplify and generate an aerial vibration that satisfies the conditions of the aforementioned properties by resonating it with the aerial vibration generated from the vibration generating apparatus. Further, it is acceptable to provide a mechanism that generates a vibration (hypersonic sound) capable of introducing the fundamental brain activation effect as an electric signal by taking the vibration generated by the apparatus out of a space in the vicinity of the partitions the exterior wall of the flow path or the like that form the gaps through which the air flows pass and transducing it into an electric signal. By thus generating the vibration (hypersonic sound) that contains the audible range components and the super-high-frequency components and has the predetermined autocorrelation order, the effects of inducing activation of the fundamental brain network system including the reward system neural circuit responsible for the generation of reactions of pleasure, beauty and emotion, and the nerve center of the autonomic neural circuit, the endocrine system and the immune system responsible for homeostatic maintenance and biophylaxis in a human being and consequently enhancing the aesthetic sensitivity and ameliorating and improving the physical state are obtained.

Figure 31:
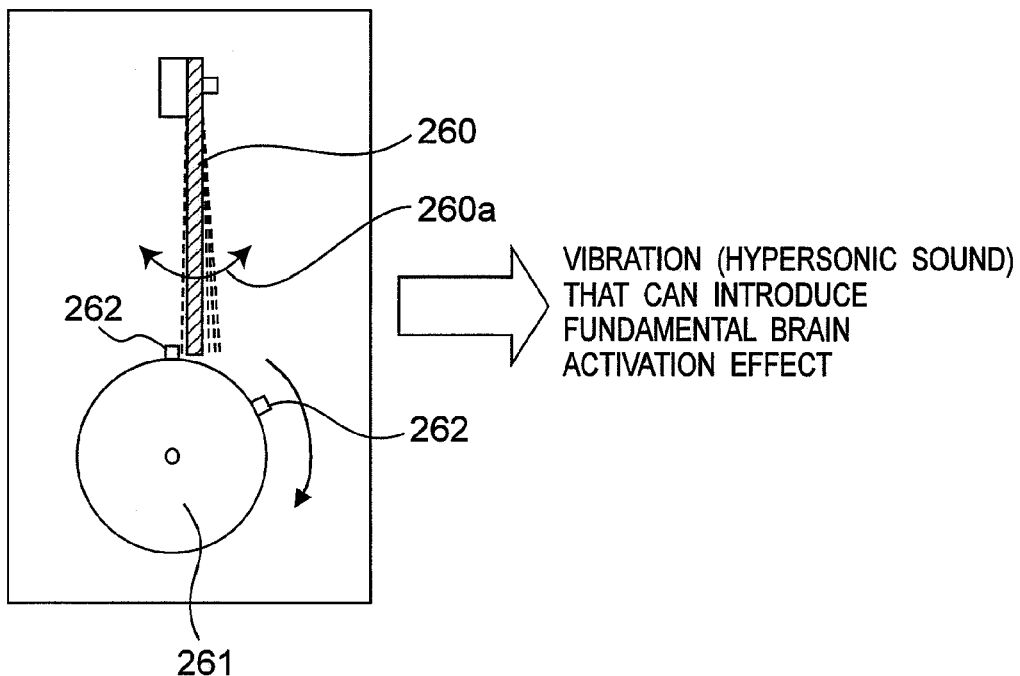
FIG. 31 is a side view showing an example of a vibration generating apparatus that generates a vibration (hypersonic sound) capable of introducing the fundamental brain activation effect by flipping a metal piece according to the first preferred embodiment.

FIG. 31 is a side view showing an example of a vibration generating apparatus that generates a vibration (hypersonic sound) that contains audible range components and super-high-frequency components having the predetermined autocorrelation order and can introduce the fundamental brain activation effect by flipping a metal piece according to the present preferred embodiment. Referring to FIG. 31, a vibration that can introduce the fundamental brain activation effect is generated by fixing one end of a strip-shaped metal piece 260 made of, for example, iron, copper or the like and flipping the other end by using a protrusion 262 that is made of a metal or the like and fixed to the outer surface of a rotating cylindrical member 261. It is acceptable to provide an apparatus such as a resonance box or a resonance tube having a function to amplify and generate an aerial vibration that satisfies the conditions of the aforementioned properties by resonating it with the aerial vibration generated from the vibration generating apparatus. Moreover, it is acceptable to provide a mechanism that generates a vibration (hypersonic sound) capable of introducing the fundamental brain activation effect as an electric signal by transducing the vibration generated by the apparatus into the electric signal. Moreover, there may be a plurality of metal pieces 260 on the flipping side, and the kind of the material of the metal piece 260 may be a metal or an alloy made of iron, copper, gold, silver, bronze, brass, titanium, magnesium, zirconium or the like, which has physical properties suitable for generating a vibration having an autocorrelation order structure. The protrusion 262 on the flipping side may be made of plastic, ceramics or the like, which has physical properties suitable for generating a vibration having an autocorrelation order structure besides the aforementioned metals and alloys. Moreover, the protrusion 262 on the flipping side may be stuck to, for example, a rotating disc or a moving planar surface instead of the cylinder. By thus generating the vibration (hypersonic sound) that contains the audible range components and the super-high-frequency components and has the feature of the predetermined autocorrelation order, the effects of inducing activation of the fundamental brain network system including the reward system neural circuit responsible for the generation of reactions of pleasure, beauty and emotion, and the nerve center of the autonomic neural circuit, the endocrine system and the immune system responsible for homeostatic maintenance and biophylaxis in a human being and consequently enhancing the aesthetic sensitivity and ameliorating and improving the physical state are obtained.

Next, an example of an apparatus that generates a vibration that can introduce the fundamental brain activation effect from a vibration signal is described below. In this case, an example of a vibration generating apparatus that generates the predetermined vibration from a vibration signal of electricity, light or the like among the examples of vibration generating apparatuses that generate a vibration (hypersonic sound) that contains audible range components and super-high-frequency components having the predetermined autocorrelation order and can introduce the fundamental brain activation effect is described below.

First of all, an example of an apparatus that generates a vibration (hypersonic sound) capable of introducing the fundamental brain activation effect from a single vibration signal via a single vibration generating mechanisms is described below.

Figure 32:
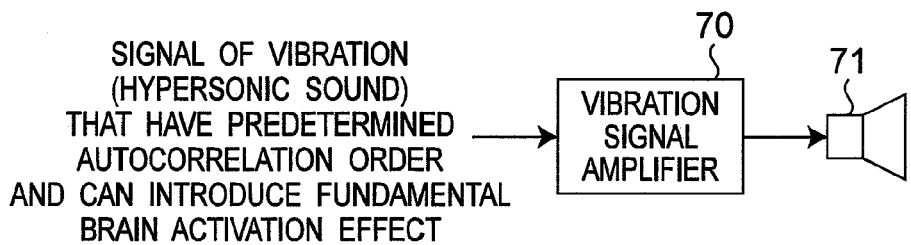
FIG. 32 is a block diagram of an apparatus that amplifies an input signal in a vibration signal amplifier and generates a vibration from a vibration generating mechanism according to the first preferred embodiment.

FIG. 32 is a block diagram of an apparatus that amplifies an input signal by a vibration signal amplifier and generates a vibration from a vibration generating mechanism according to the present preferred embodiment. Referring to FIG. 32, an input signal of a vibration (hypersonic sound) that contains the audible range components and the super-high-frequency components having the predetermined autocorrelation order and can introduce the fundamental brain activation effect is inputted to a vibration signal amplifier 70 and amplified in power, and thereafter, the amplified vibration signal is radiated from a loudspeaker 71 by being transduced into an aerial vibration. By thus generating the vibration (hypersonic sound) that contains the audible range components and the super-high-frequency components and has the feature of the predetermined autocorrelation order, the effects of inducing activation of the fundamental brain network system including the reward system neural circuit responsible for the generation of reactions of pleasure, beauty and emotion, and the nerve center of the autonomic neural circuit, the endocrine system and the immune system responsible for homeostatic maintenance and biophylaxis in a human being and consequently enhancing the aesthetic sensitivity and ameliorating and improving the physical state are obtained.

It is noted that the signal inputted to the apparatus shown in FIG. 32 may be a signal inputted from a broadcasting receiver, a receiver of a signal that is distributed and delivered from the Internet line, a telephone line or the like, a signal inputted from a vibration signal synthesizing apparatus of a synthesizer or the like or a signal inputted by transducing the vibration of a solid, liquid, gas or the like into an electrical variation by a transducer. Further, the loudspeaker 71 may be a transducer that generates a solid vibration or a liquid vibration.

Figure 33:
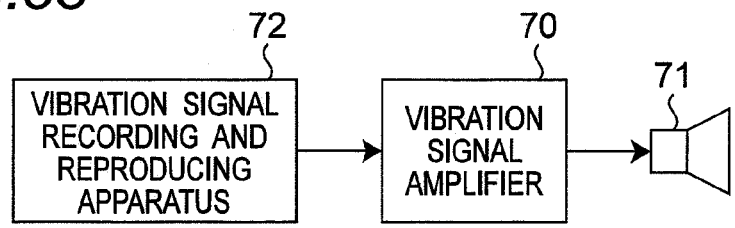
FIG. 33 is a block diagram of an apparatus that amplifies a vibration signal reproduced by using a vibration signal recording and reproducing apparatus in a vibration signal amplifier and generates a vibration from a loudspeaker according to the first preferred embodiment.

FIG. 33 is a block diagram of an apparatus that amplifies a vibration signal reproduced by using a vibration signal recording and reproducing apparatus in a vibration signal amplifier and generates a vibration from a loudspeaker according to the present preferred embodiment. Referring to FIG. 33, an electric signal of a vibration (hypersonic sound) that contains audible range components and super-high-frequency components having the predetermined autocorrelation order and can introduce the fundamental brain activation effect is previously recorded in a variety of memories including a recording medium such as the optical disks inclusive of Blu-ray Discs, and thereafter, the recorded electric signal is reproduced by a vibration signal recording and reproducing apparatus 72. Next, the electric signal of the vibration that can introduce the fundamental brain activation effect is inputted to a vibration signal amplifier 70 and amplified in power, and thereafter, the amplified vibration signal is radiated from a loudspeaker 71 by being transduced into an aerial vibration.

The above is a method for generating an actual vibration by transducing the signal inputted to the loudspeaker, and in this case, there is such a problem that the listener cannot receive the hypersonic sound if the super-high-frequency components are in a deficient state at the stage of the vibration signal inputted to the loudspeaker.

As a measure for solving this problem, an independent vibration generating function is given to the loudspeaker system itself, and a function to generate a hypersonic sound or the vibration of its super-high-frequency components by only connecting it to some equipment or being solely used is provided.

FIG. 91 shows one example of a vibration generating apparatus 370 of a loudspeaker system regarding a concrete method. As a vibration sources, the loudspeaker system itself is equipped with the attachment apparatuses of a memory 375 that previously stores the signals of a hypersonic sound or its super-high-frequency components as a vibration source, and an amplifier unit 376, a power supply unit 377 and so on for driving a loudspeaker or a super-high-frequency vibration generating device by the signal. Moreover, a built-in apparatus that generates the super-high-frequency components having the predetermined autocorrelation order in the loudspeaker system may be provided.

As a vibration generating mechanism, there are means as described below besides the generation of a vibration that contains the super-high-frequency components having the predetermined autocorrelation order by using the vibration generating mechanism of the loudspeaker itself. A vibration generating function is integrated in the loudspeaker system, and the housing itself or the like is vibrated. Otherwise, super-high-frequency vibration generating devices 372 and 373 are provided for (embedded in, stuck to or wrapped around) the housing or the like. Moreover, the outside of the housing or the like is covered with a material of piezoplastic or the like. Further, the super-high-frequency vibration generating devices 372 and 373 are connected to generate a vibration. Moreover, it is possible to provide a super-high-frequency vibration generating device for a cable 374 that connects equipment to the loudspeaker system.

A power supply method may be achieved by feeding power from an external power supply or providing a built-in power supply unit 377 or a battery (primary cell (dry battery), secondary cell (storage battery), built-in fuel cell, etc.) Moreover, as a method for feeding power from the connected equipment, there are the method of feeding power by a phantom system, i.e., feeding power by superimposing a dc power source on the audio cable and the method of making audio signal transmission and power feeding coexist by an USB cable or the like. Beside them, a wireless power feeding mechanism may be provided.

With these arrangements, the listener becomes able to receive the hypersonic sound even if a loudspeaker is connected to equipment not having the function to generate a vibration signal of the super-high-frequency band, and this enables not only prevention of a deterioration in the fundamental brain activation effect and assurance of safety but also production of the positive effects of ameliorating and improving the psychosomatic state through the activation of the fundamental brain network system.

Figure 34:
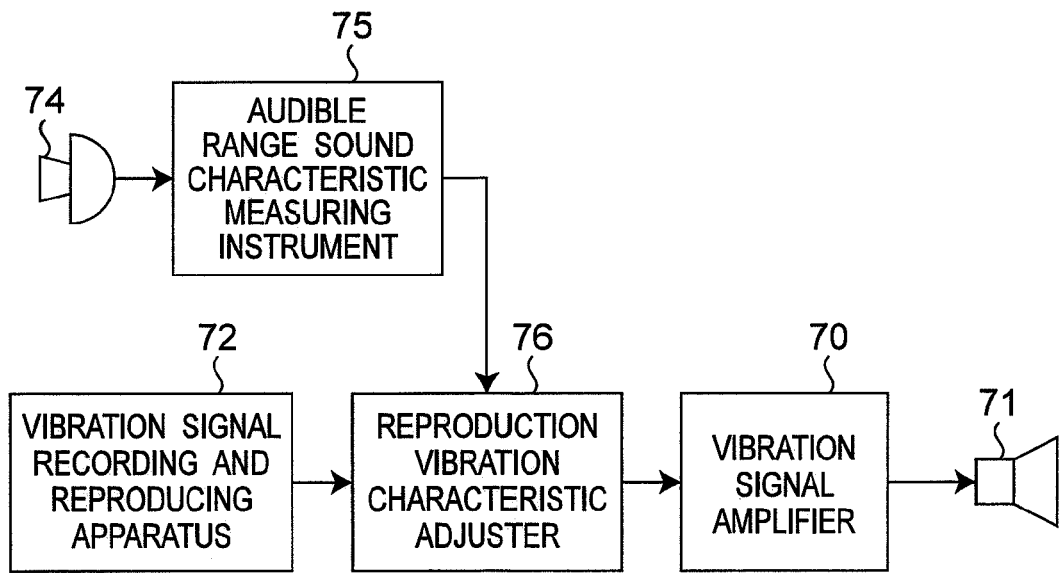
FIG. 34 is a block diagram showing an example of a vibration generating apparatus having a function to adjust the generated vibration by using a reproduction vibration characteristic adjuster according to the first preferred embodiment.

FIG. 34 is a block diagram showing an example of a vibration generating apparatus having a function to adjust the generated vibration by using a reproduction vibration characteristic adjuster according to the present preferred embodiment. Referring to FIG. 34, an electric signal of a vibration (hypersonic sound) that contains audible range components and super-high-frequency components having the predetermined autocorrelation order and can introduce the fundamental brain activation effect is previously recorded in a variety of memories including recording media such as optical disks inclusive of Blu-ray Discs, the recorded electric signal is thereafter reproduced by the vibration signal recording and reproducing apparatus 72, and the reproduced electric signal is inputted to a reproduction vibration characteristic adjuster 76. On the other hand, an audible range sound characteristic measuring instrument 75 collects by a microphone 74 the audible range components of the vibration existing in the ambient environment of the subject person to whom a vibration is applied, analyzes the feature of the vibration based on the signal of the collected audible range components, and outputs the obtained analysis data to the reproduction vibration characteristic adjuster 76. The reproduction vibration characteristic adjuster 76 adjusts the characteristics of the vibration signal so that the signal of the previously recorded vibration (hypersonic sound) capable of introducing the fundamental brain activation effect is reproduced in the most appropriate state in accordance with the feature analysis data of the audible range components, and outputs the adjusted vibration signal to the vibration signal amplifier 70. The vibration signal amplifier 70 subjects the inputted vibration signal to DA conversion and thereafter to power amplification, so that the resulting signal is transduced into an aerial vibration, outputted and radiated via the loudspeaker 71.

Further, the reproduction vibration characteristic adjuster 76 adjusts the reproduction level of the super-high-frequency components of the vibration capable of introducing the fundamental brain activation effect so that the components are increased or decreased at a constant ratio to the power of the audible range components measured by, for example, the audible range sound characteristic measuring instrument 75. According to the experimental results by the present inventor and others, it has been clarified that, when the super-high-frequency components in the vibration (hypersonic sound) that can introduce the fundamental brain activation effect is increased or decreased, the degree of the fundamental brain activation effect is increased or decreased in accordance with it. Accordingly, it is preferable that the reproduction is made by adjusting the power of the super-high-frequency components to the most effective level. Moreover, it is acceptable to arrange the spectro-temporal structure of the super-high-frequency components of the vibration (hypersonic sound) that can introduce the fundamental brain activation effect to a state highly adaptable to the spectro-temporal structure or the autocorrelation order owned by the audible range components measured by using the audible range sound characteristic measuring instrument 75 or to emphasize or restrain the autocorrelation order.

Although the signal recording and reproducing apparatus of FIG. 34 is configured so that the vibration (hypersonic sound) capable of introducing the fundamental brain activation effect is radiated to the listener's substantial whole body via the loudspeaker 71, it is acceptable to apply the audible range components of the vibration to only the listener's auditory sensation via the earphone and earphone or the like. Moreover, although the style that the vibration signal recorded in the recording medium is reproduced by using the vibration signal recording and reproducing apparatus 72 is shown in FIG. 34, the signal inputted to the reproduction vibration characteristic adjuster 76 may be a signal inputted from a broadcasting receiver, a receiver of a signal that is distributed and delivered from the Internet line, a telephone line or the like, a signal inputted from a vibration signal synthesizing apparatus of a synthesizer or the like or a signal inputted by transducing the vibration of a solid, liquid, gas or the like into an electrical variation by a transducer.

Figure 35:
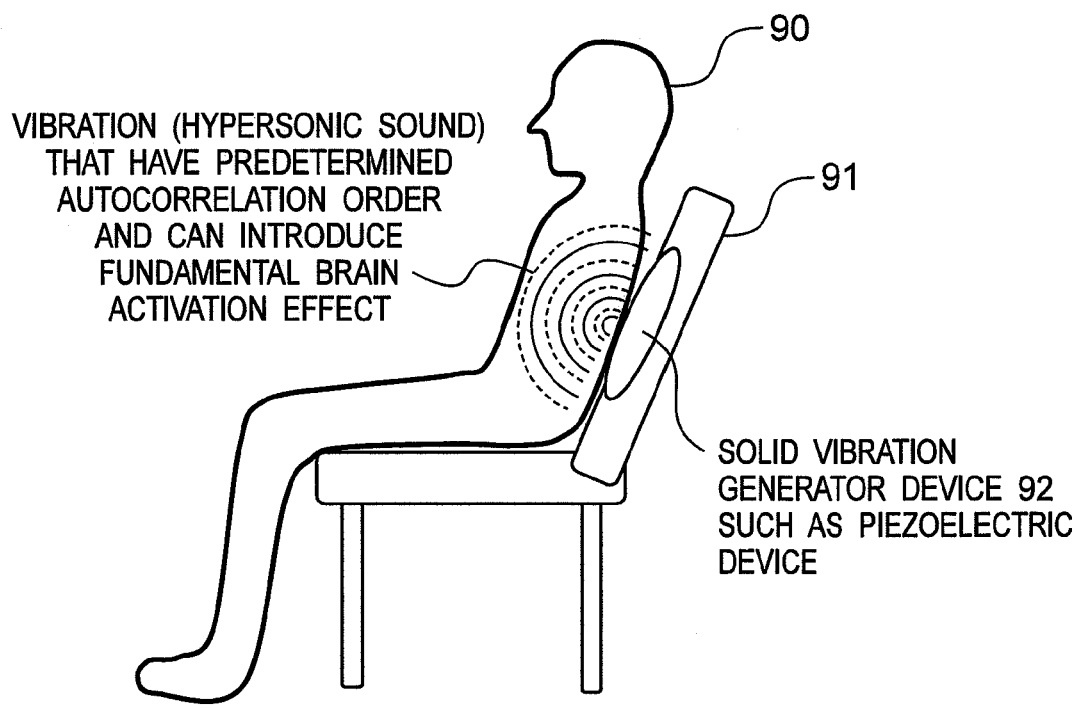
FIG. 35 is a side view showing an example of an apparatus that applies from a body surface a vibration (hypersonic sound) capable of introducing the fundamental brain activation effect via a solid vibration generating mechanism according to the first preferred embodiment.

FIG. 35 is a side view showing an example of an apparatus that applies a vibration (hypersonic sound) that contains audible range components and super-high-frequency components having the predetermined autocorrelation order and can introduce the fundamental brain activation effect via the body surface and the auditory system with intervention of a solid vibration generating mechanism according to the present preferred embodiment. In the implemental example of FIG. 35, an example in which a vibration (hypersonic sound) that can introduce the fundamental brain activation effect is generated with intervention of a solid vibration generating device 92 such as a piezoelectric device embedded in a chair 91 or the like on which a person 90 to whom the vibration signal is applied sits is described. As shown in FIG. 35, the super-high-frequency components of the vibration (hypersonic sound) that can introduce the fundamental brain activation effect are received from the body surface, and the audible range components of the vibration are received by the auditory system, introducing the fundamental brain activation effect.

Figure 36:
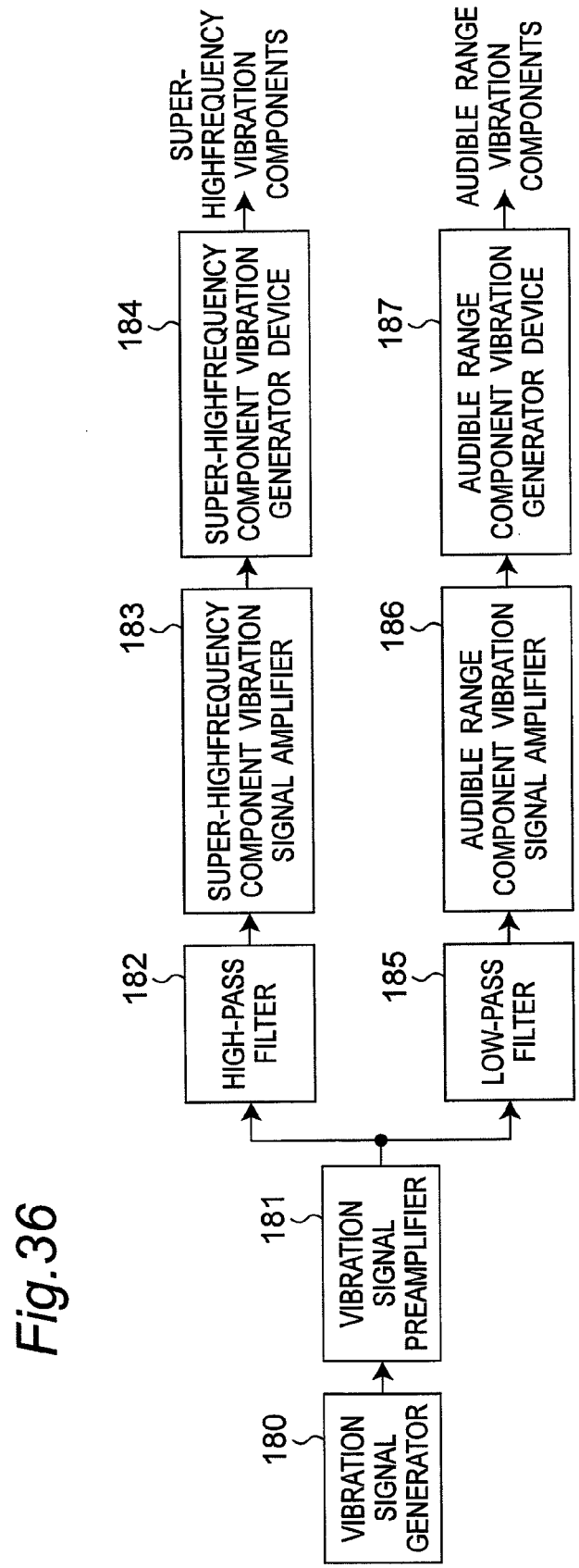
FIG. 36 is a block diagram of an apparatus that generates a vibration (hypersonic sound) capable of introducing the fundamental brain activation effect via a plurality of vibration generating mechanisms from signals diverging from a single vibration signal according to the first preferred embodiment.

FIG. 36 is a block diagram of an apparatus that generates vibration capable of introducing the fundamental brain activation effect via a plurality of vibration generating mechanisms from signals diverging from a single vibration signal of a vibration (hypersonic sound) that contains audible range components and super-high-frequency components having the predetermined autocorrelation order and can introduce the fundamental brain activation effect according to the present preferred embodiment. Referring to FIG. 36, by amplifying and filtering a signal of a vibration (hypersonic sound) that can introduce the fundamental brain activation effect from a vibration signal generator 180 (constituted of, for example, a vibration signal storage device and its reproducing device) by a vibration signal preamplifier 181 using, for example, a low-pass filter 185 and a high-pass filter 182 of which the cutoff frequency is set to 20 kHz at the human audible frequency upper limit, the vibration components containing the audible range components and the super-high-frequency components are extracted. Thereafter, by transducing the vibration components into vibrations via respective separate vibration generating devices 184 and 187, a vibration (hypersonic sound) that can introduce the fundamental brain activation effect is generated. In this case, the super-high-frequency components of the vibration (hypersonic sound) that can introduce the fundamental brain activation effect may be applied as an aerial vibration by a loudspeaker or the like or applied directly to the body surface by putting a vibration generating mechanism in contact with the body. Moreover, there may be a plurality of vibration generating devices 184 and 187 for the super-high-frequency components and the audible range components, respectively. Moreover, the cutoff frequency of the low-pass filter for extracting the super-high-frequency components may be lowered to, for example, about 16 kHz in accordance with the frequency at the audible range upper limit of the person to whom it is applied. Further, the low-pass filter 185 for extracting the audible range components may be removed.

Next, an example of a headphone/earphone type vibration generating apparatus according to the present preferred embodiment is described. It was indicated that the airway auditory system was not singly concerned in the fundamental brain activation effect introduced by a hypersonic sound to human beings, but some reception response system residing at or having a window on the body surface was concerned in it (See FIG. 21). Therefore, the fundamental brain activation effect cannot effectively be introduced by applying the vibration to only the airway auditory system by using a headphone, earphone or the like. Moreover, when the frequency response characteristic of the headphone, earphone or the like in the super-high-frequency band is not sufficient, only the audible range components containing no super-high-frequency component are applied in a state extremely close to the human body. Therefore, it is highly possible to deteriorate the fundamental brain activity in comparison with that in the ordinary background noise state (See FIGS. 90 and 17), which leads to such a problem that a risk of significantly threatening the health of the listener who uses the headphone, earphone or the like.

In order to solve this problem, in the present implemental example, super-high-frequency vibration generating devices are placed on the headphone, earphone or the like so that the vibration containing the super-high-frequency components having the predetermined autocorrelation order can be applied to the listener's body surface while applying the vibration containing the audible sound to the listener's airway auditory system. With this arrangement, the listener becomes able to receive the hypersonic sound, and this enables not only prevention of the deterioration in the fundamental brain activation effect and assurance of safety but also production of the positive effects of ameliorating and improving the psychosomatic state through the activation of the fundamental brain network system.

An example of a headphone is described below. FIG. 37 is a front view of a headphone type vibration generating apparatus according to the present preferred embodiment. Referring to FIG. 37, a headphone 111 is constituted of one pair of approximately cylindrical headphone housings 111*a* and 111*b* arranged oppositely to cover listener's both ears, and a headband 112 for mechanically connecting the headphone housings 111*a* and 111*b* and placing them on the listener's head 110. Ring-shaped ear pads 124 are provided for the headphone housings 111*a* and 111*b* in close contact with the peripheries of the entrances of the external auditory meatuses 110*a* on the side surfaces located on the listener side of the headphone housings 111*a* and 111*b*, and super-high-frequency component vibration generating devices 120 for generating the super-high-frequency components of the vibration that can introduce the fundamental brain activation effect are provided at the peripheral portions of the ear pads 124. Moreover, a lot of vibration generating devices 120 is provided at regular intervals on the surfaces located on the listener's head 110 side of the headband 112. Further, a plurality of super-high-frequency component vibration generating devices 120 are provided at the peripheral portions of the headphone housings 111*a* and 111*b*, a headphone cable and so on, and audible range loudspeakers 121 that generate the audible range components of the vibration that can introduce the fundamental brain activation effect are provided in places corresponding to the external auditory meatuses 110*a* on the inner side surfaces of the headphone housings 111*a* and 111*b*. The headphone cable and so on are allowed to be made of a piezoplastic material and generate a super-high-frequency vibration or to devise a design to vibrate the cable itself. The circuits and devices 115, 115, 117, 120 and 121 of the signal reproducing apparatus and a small battery 125 that supplies power necessary for generating the super-high-frequency vibration are arranged in each of the headphone housings 111*a* and 111*b*, a signal input plug 118 is connected to the input terminal of a signal band dividing circuit 115 of the signal reproducing apparatus, and the signal input plug 118 is connected to a predetermined signal reproducing apparatus. With these devices, the present vibration generating apparatus enable the application of the vibration containing the super-high-frequency components having the predetermined autocorrelation order to the listener's body surface while applying the vibration containing the audible sound to the listener's airway auditory system.

It is also possible to generate the audible range components and the super-high-frequency components from separate vibration generating devices by using separate vibration signals in FIG. 37.

Next, an example of an apparatus that generates a vibration (hypersonic sound) that can introduce the fundamental brain activation effect because it contains super-high-frequency components having the predetermined autocorrelation order by separately generating a plurality of vibration signals from a plurality of vibration generating mechanisms is described below.

Figure 41:
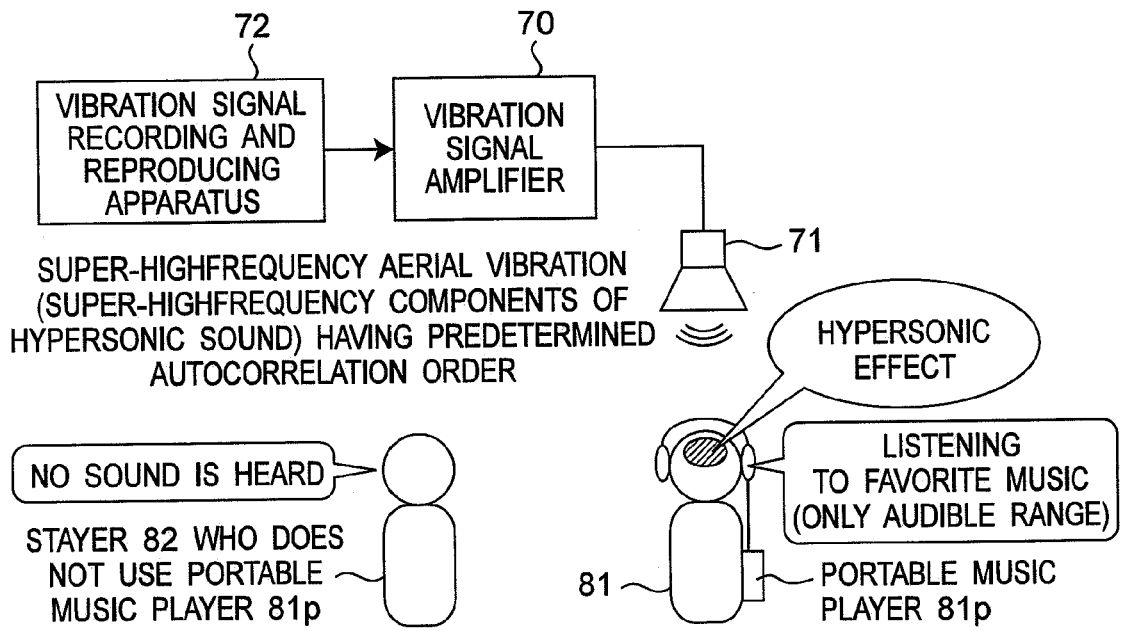
FIG. 41 is a block diagram showing an example in which audible range components are presented from a portable music player or the like by an earphone or the like, and super-high-frequency components provided for a vibration signal separately from the audible range components are presented by a loudspeaker or the like, according to the first preferred embodiment.

FIG. 41 is a block diagram showing an example of a vibration generating apparatus that presents a vibration constituted of only audible range components from a portable music player with a headphone, earphone or the like and presents a super-high-frequency vibration that cannot be heard as a sound having an autocorrelation order and can introduce the fundamental brain activation effect when coexisting with the vibration constituted of only the audible range components with a loudspeaker or the like, according to the present preferred embodiment. FIG. 41 shows a case where, in a space in which a signal of the vibration (hypersonic sound) that can introduce the fundamental brain activation effect and is outputted from, for example, the vibration signal recording and reproducing apparatus 72 is presented as an aerial vibration from the loudspeaker 71 via the vibration signal amplifier 70, a listener 81 listens to his or her favorite music with a portable music player 81*p* that the listener carries. By thus applying the vibration (hypersonic sound) that contains the audible range components and the super-high-frequency components having the predetermined autocorrelation order, the effects of inducing activation of the fundamental brain network system including the reward system neural circuit responsible for the generation of reactions of pleasure, beauty and emotion, and the nerve center of the autonomic neural circuit, the endocrine system and the immune system responsible for homeostatic maintenance and biophylaxis in the listener 81 and consequently enhancing the aesthetic sensitivity and ameliorating and improving the physical state are obtained. It is noted that, in the present implemental example, by virtue of the fundamental brain activation effect introduced by a combination of the audible range components applied to the ears of the listener 81 and the super-high-frequency components having the feature of the predetermined autocorrelation order applied to the body surface, the listener 81 enjoys a better sound quality while listening to his or her favorite music from the ordinarily used portable music player without additional investment to the apparatus, and the adverse effects on his or her health concerned when he or she listens to only the audible range components provided from the portable music player or the like can be avoided. Further, in the present implemental example, only the super-high-frequency components exceeding the audible range of the vibration (hypersonic sound) capable of introducing the fundamental brain activation effect can also be extracted by a high-pass filter or the like and presented from the loudspeaker 71. In the case, since the super-high-frequency components are not perceived, a stayer 82 who does not use the portable music player 81*p* or the like feels the space as indistinguishable from the background noise when a BGM reproducing apparatus or the like to present the audible range components in this space is not installed, and a compulsory listening situation accompanied by the conventional BGM can be eliminated.

Figure 42:
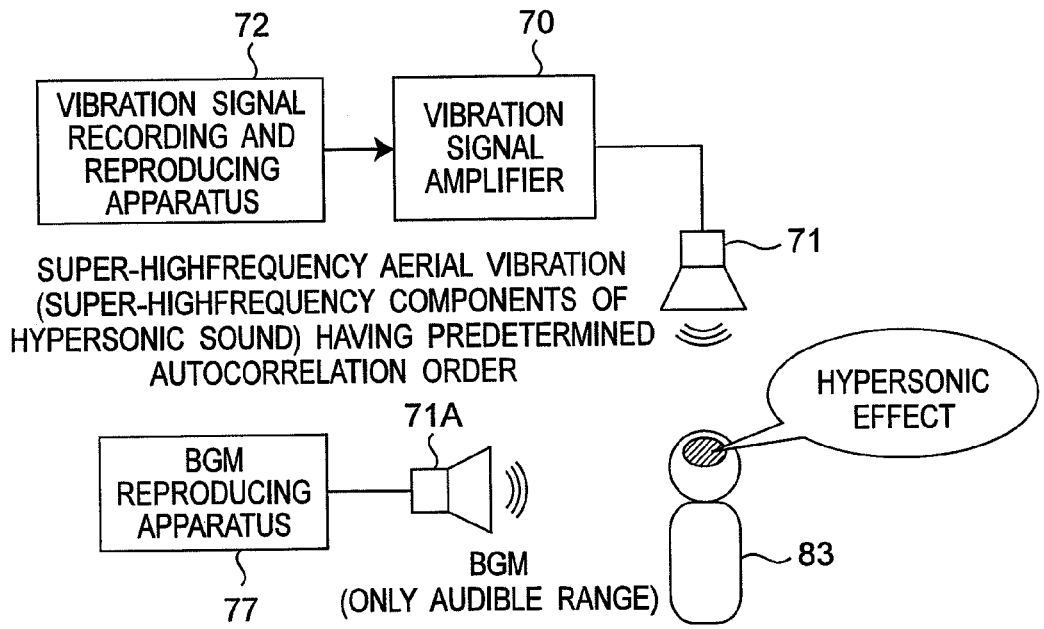
FIG. 42 is a block diagram showing an apparatus according to a modified preferred embodiment of FIG. 41.

FIG. 42 is a block diagram showing an apparatus of a modified preferred embodiment of FIG. 41. FIG. 42 is an example in which the vibration constituted of only the audible range components is presented by a loudspeaker or the like in a manner similar to that of the case of BGM and the super-high-frequency components of the vibration (hypersonic sound) that can introduce the fundamental brain activation effect having the autocorrelation order different from the vibration constituted of only the audible range components are presented by a special loudspeaker. FIG. 42 shows a case where a conventional BGM reproducing apparatus 77 is coexistently used in a space in which the super-high-frequency components of a vibration (hypersonic sound) that can introduce the fundamental brain activation effect and is outputted from, for example, the vibration signal recording and reproducing apparatus 72 is presented as a super-high-frequency aerial vibration from the loudspeaker 71 via the vibration signal amplifier 70. In the present implemental example, by virtue of the fundamental brain activation effect introduced by a combination of the super-high-frequency vibration from the loudspeaker 71 and the audible frequency vibration of the BGM (only the audible region) radiated from a prior art BGM reproducing apparatus 77 via a loudspeaker 71A, a listener 83 who is staying in the space can enjoy a better sound quality while listening to the conventional BGM music, and the adverse effects on his or her health concerned when he or she listens to only the audible range components can be avoided.

Next, an apparatus that generates a vibration that can introduce the hypersonic effect, i.e., a hypersonic sound by using portable communication equipment such as a portable telephone, a portable broadcasting receiver, a portable music player or a portable video player such as iPod (registered trademark), a portable game machine or the like is described below.

In the modern society, portable communication equipment (portable telephone, information terminals using wireless IP communications and infrared-ray communications, transceiver, income, etc.) and portable broadcasting receivers (one-segment receiver etc.), portable music players (iPod: (registered trademark), Walkman (registered trademark), etc.), portable video players, portable game machines and so on are explosively popularized. In addition, frequency of use is increased, and long-time watching and listening styles are increased. A majority of the equipment is carried for a long time and used very closely to the human body, and therefore, influences exerted on the body and spirit of the carrier person cannot be ignored. In this case is a such problem that the sound vibration generated by the portable equipment contains no super-high-frequency component and is constituted of only the audible range components, and therefore, it is highly possible that the fundamental brain activity deteriorates in comparison with that in the normal background noise state (See FIGS. 90 and 17). Using such portable equipment not only significantly threatens the health of the modern people but also induces unpleasant sensation and irritative feeling inducing stress reactions such as an increase in the adrenaline concentration, and the risks of triggering violent actions and abnormal behaviors are increased.

As shown in FIG. 92, a drastic method for solving this problem is to appropriately generate, transmit, transfer and receive a vibration (hypersonic sound) signal that can introduce the fundamental brain activation effect because it contains super-high-frequency components having the predetermined autocorrelation order in the relevant systems and make all the apparatuses concerned have the function to enable the generation of the signals as actual vibrations in the portable equipment.

In concrete, a signal transmitter 380 is first made to have a function to transduce a sound vibration into a vibration signal faithfully to the super-high-frequency band and a function to reconstruct the same vibration signal into a vibration signal (hypersonic sound signal) that can introduce the fundamental brain activation effect because it contains super-high-frequency components having the predetermined autocorrelation order by carrying out appropriate signal processing by a signal reconstruction circuit 382 for a case where the vibration signal does not contain the super-high-frequency components having the predetermined autocorrelation order and to transmit the signal by a signal transmission circuit 383.

Next, in addition to making an apparatus or a network for transmitting a vibration signal have the function of transmission faithfully to the super-high-frequency band, for example, a signal reconstruction circuit 391 is made to have a function to reconstruct the transmitted signal into a hypersonic sound signal by carrying out appropriate signal processing in a relay station of a telephone exchange office, a broadcasting station or the like for a case where the vibration signal served as a transmission material does not contain the super-high-frequency components having the predetermined autocorrelation order. In this case, the network for transmission may be not only communications and broadcastings intended for a large area but also LAN, a ubiquitous network, inter-equipment communications in a certain specific space or region.

At last, a portable signal receiver 400 includes a signal receiving circuit 401, a signal reconstruction circuit 402 and a vibration generating apparatus 403. The portable signal receiver 400 is made to have a function to achieve reconstruction into a hypersonic sound signal by carrying out appropriate signal processing in the receiver itself for a case where the vibration signal being received does not contain the super-high-frequency components having the predetermined autocorrelation order and to transduce the signal into an actual vibration and generate the vibration in addition to the function to faithfully receive the transmitted vibration signal and transduce the signal into an actual vibration.

With these arrangements, a person who carries and uses portable equipment becomes able to receive the hypersonic sound, and the positive effects of ameliorating and improving the psychosomatic state through the activation of the fundamental brain network system are obtained in addition to prevention of a deterioration in the fundamental brain activation effect and assurance of safety.

However, it is difficult to immediately achieve the drastic problem solving method as described above regarding the equipment and functions concerned in the transmission and transfer of the vibration signal. Accordingly, as a problem solving method that is more immediately effective and highly feasible, only a portable signal receiver is made to have an appropriate signal processing function and a vibration generating function. With this arrangement, it becomes possible to generate a hypersonic sound in a portable signal receiver even if the equipment and functions concerned in the transmission and transfer have limitations and able to receive only a vibration signal constituted of only the audible range components lacking the super-high-frequency components.

A concrete method to make a portable signal receiver have an appropriate signal processing function is described below.

A signal of a hypersonic sound or its super-high-frequency components is previously stored in, for example, a memory or the like provided in the portable signal receiver, and the signal of the received audible sound is complemented with a signal of the hypersonic sound or its super-high-frequency components. The complementing signal may be not only provided by one stored in the memory but also inputted from the outside of the portable signal receiver or generated inside the portable signal receiver. Moreover, the level of the complementing vibration signal can be automatically changed in correlation to the level of the received audible sound or arbitrarily adjusted by the user of the portable equipment.

The signal of the received audible sound and the signal of the hypersonic sound or its super-high-frequency components may be provided by generating an actual vibration by an identical vibration generating mechanism or generating an actual vibration by independent separate vibration generating mechanisms.

Next, a concrete vibration generating mechanism for making the portable signal receiver have an appropriate vibration generating function is described in detail below.

It is indicated that the airway auditory system is not singly concerned in the generation of the fundamental brain activation effect introduced by the hypersonic sound, but some reception response system residing at or having a window on the body surface is concerned in it (See FIG. 21). Therefore, the portable signal receiver needs not only means for applying a vibration containing the audible band to the airway auditory system but also a vibration generating mechanism capable of applying a vibration containing super-high-frequency components having the predetermined autocorrelation order to the body surface. FIG. 93 shows an example of a vibration generating mechanism that utilizes a portable telephone 410.

A. Examples of vibration generating mechanisms utilizing the main unit of the portable telephone 410 are described.

A-(1): By integrating a vibration generating function in the portable telephone 410 and vibrating the portable telephone 410 (housing 412, LCD screen, manual operation button, etc.), a vibration that contains super-high-frequency components having the predetermined autocorrelation order is generated and applied to a human being directly or via an aerial vibration.

A-(2): By making sound generating means of a loudspeaker 411 originally provided for the portable telephone 410 have an ability to faithfully reproduce a super-high-frequency vibration, a vibration that contains super-high-frequency components having the predetermined autocorrelation order is generated and applied to a human being.

A-(3): A super-high-frequency vibration generating device 414 (this may have a shape of a sheet 413 for covering the surface) is newly provided for the housing 412 or the like of the portable telephone 410, and a vibration that contains super-high-frequency components having the predetermined autocorrelation order is generated and applied to a human being.

A-(4): A super-high-frequency vibration generating device 414 is connected to the portable telephone 410, and a vibration that contains super-high-frequency components having the predetermined autocorrelation order is generated and applied to a human being.

B. Examples of vibration generating mechanisms utilizing a headset 415 used by being connected to the portable telephone 410 are described.

B-(1): By integrating a vibration generating function in a headset 415 and vibrating a headband, microphone arm, ear pad or the like, a vibration that contains super-high-frequency components having the predetermined autocorrelation order is generated and applied to a human being directly or via an aerial vibration.

B-(2): A super-high-frequency vibration generating device 417 is newly provided for (embedded in, stuck to or wound around) the headset 415, and a vibration that contains super-high-frequency components having the predetermined autocorrelation order is generated and applied to a human being.

B-(3): The outside of the headset is sheathed 418 with a material of piezoplastic or the like, and a vibration that contains super-high-frequency components having the predetermined autocorrelation order is generated from the sheath 418 and applied to a human being.

C. Examples of vibration generating mechanisms utilizing a cable 416 for connecting the portable telephone 410 with the headset 415 or the like are described.

C-(1): By vibrating an electric signal line in the cable 416, a vibration that contains super-high-frequency components having the predetermined autocorrelation order is generated and applied to a human being.

C-(2): By using a material of piezoplastic or the like for the cable sheath 418, a vibration that contains super-high-frequency components having the predetermined autocorrelation order is generated from the sheath and applied to a human being.

C-(3): A super-high-frequency vibration generating device 417 is embedded in the cable sheath, and a vibration that contains super-high-frequency components having the predetermined autocorrelation order is generated from there and applied to a human being.

C-(4): A super-high-frequency vibration generating device sheath 418 is provided for (stuck to or wrapped around) the outside of the cable, and a vibration that contains super-high-frequency components having the predetermined autocorrelation order is generated and applied to a human being.

D: A super-high-frequency vibration generating device is provided for the attachment of earphone microphone, strap, accessory, soft casing or the like belonging to the portable telephone, and a vibration that contains super-high-frequency components having the predetermined autocorrelation order is generated and applied to a human being.

E: A vibration generating apparatus capable of generating a vibration that contains super-high-frequency components having the predetermined autocorrelation order may be separately provided independently of the portable telephone.

It is noted that the vibration generating mechanisms of A to E may be combined together.

Although the examples in which the portable telephone 410 and the headset 415 or the like are connected together by wire are described here, they may be connected together wirelessly (Bluetooth (registered trademark) communications, infrared-ray communications, human body communications, etc.)

It is noted that the aforementioned vibration generating mechanisms can also be similarly provided for other portable communication equipment (information terminal, transceiver, intercom, or the like using wireless IP communications, infrared-ray communications, etc.), portable broadcasting receivers (one-segment receiver etc.) and the like.

With these arrangements, the positive effects of ameliorating and improving the psychosomatic state through the activation of the fundamental brain network system are obtained in addition to prevention of a deterioration in the fundamental brain activation effect and assurance of safety of people who carry and use portable signal receivers.

Next, examples in which a hypersonic sound is generated by making portable equipment such as portable music players (iPod (registered trademark), Walkman (registered trademark), etc.), portable video players and portable game machines have an appropriate vibration generating mechanism are described.

As a concrete example, an example of a vibration generating mechanism utilizing a portable music player such as iPod (registered trademark) is shown in FIG. 94.

In a manner similar to that of FIG. 93, concrete vibration generating mechanisms that generate vibrations containing super-high-frequency components include: A. a vibration generating mechanism utilizing the main unit of a portable music player 420 (including a memory 420*m* that stores a hypersonic sound or its super-high-frequency components); B. a vibration generating mechanism utilizing an earphone 421 or the like; C. a vibration generating mechanism utilizing a cable 422; D. a vibration generating mechanism utilizing other attachments such as a strap; and E. means for utilizing a vibration generating apparatus 423 independent of the portable music player. Moreover, the vibration generating mechanisms of A to E may be combined together.

It is noted that the aforementioned vibration generating mechanisms can also be similarly provided for a portable video player, a portable game machine and the like. Lately, combining of the functions of the portable equipment is promoted as exemplified by fusion of a portable telephone and a portable player, and therefore, the examples described with reference to FIGS. 93 and 94 may be partially or totally put into practice in combination.

With these arrangements, people who carry and use portable signal receivers become able to receive a hypersonic sound, and the positive effects of ameliorating and improving the psychosomatic state through the activation of the fundamental brain network system are obtained in addition to prevention of a deterioration in the fundamental brain activation effect and assurance of safety.

Further, as a highly feasible simpler method, by only giving an independent vibration generating function to the earphone, headset, or the like, which have conventionally been considered to be attachments to the portable equipment, they are provided with a function to generate a vibration of a hypersonic sound or its super-high-frequency components by being connected to some equipment or solely.

With this arrangement, the listener becomes able to receive a hypersonic sound by merely connecting the earphone, headset or the like described in the present implemental example even to various kinds of apparatuses, inclusive of the portable telephone and the portable music player, which can generate only an audible sound. FIG. 95 shows an example of an earphone 421.

Regarding a power supply method, it is acceptable to integrate a primary cell (dry battery) 427 such as a button battery or a built-in secondary cell (storage battery) or a built-in fuel cell in the housing of the earphone 421 as an example of integrating a battery in the housing of the earphone 421. Moreover, there is a method for feeding power by a phantom system, i.e., feeding power by superimposing a dc power on the audio cable as an example of supplying power from the connected equipment. Otherwise, it is acceptable to feed power by making audio signal transmission coexist with power feed by an USB cable or the like or feed power by connection with an electric cable other than the audio signal cable. Besides this, a wireless power feeding mechanism may be provided.

As a vibration source, a memory 425 to previously store the signal of a hypersonic sound or its super-high-frequency components is provided inside the housing of the earphone 421, partway on the cable 422 and so on. Moreover, a built-in apparatus that artificially generates super-high-frequency components having the predetermined autocorrelation order inside the earphone 421 may be provided. Further, a built-in micro amplifier 426 for amplifying a vibration signal may be provided if circumstances require.

There are following means as a vibration generating mechanism for generating a vibration that contains super-high-frequency components having the predetermined autocorrelation order.

A vibration generating function is integrated in the earphone 421, and the housing, an ear pad or the like itself is vibrated. Otherwise, a super-high-frequency vibration generating device is provided for (embedded in, stuck to or wrapped around) the housing of the earphone 421, ear pad or the like. Moreover, the outside of the housing of the earphone 421, ear pad or the like is coated with a material of piezoplastic or the like.

Moreover, means for utilizing the cable 422 include vibrating the electric signal wire in the cable 422, using a material of piezoplastic or the like for the cable sheath, embedding a super-high-frequency vibration generating device in the cable sheath and providing (sticking, wrapping, etc.) a super-high-frequency vibration generating device on the outside of the cable.

These vibration generating mechanisms may be combined together. Moreover, the headset, headphone and the like are allowed to have a similar function.

With these arrangements, the user of the earphone 421 or the like becomes able to receive a hypersonic sound whatever equipment is used in combination, and the positive effects of ameliorating and improving the psychosomatic state through the activation of the fundamental brain network system are obtained in addition to prevention of a deterioration in the fundamental brain activation effect and assurance of safety.

In common to all the problem solving methods described above, by taking advantage of, for example, the fact that not only the airway auditory system but also some reception response systems existing on the body surface are concerned in the development of the hypersonic effect in a situation where a problem easily occurs if an audible sound is environmentally heard in a manner similar to that of public spaces and the like (See FIG. 21), only the super-high-frequency components having the predetermined autocorrelation order are applied to the body surface while the audible sound is applied to the airway auditory system of the portable equipment user. By so doing, the fundamental brain activation effect of the portable equipment user can be introduced without generating the audible sound that exerts influences on the surroundings.

Moreover, the hypersonic sound itself including the audible sound may be applied to the body of the portable equipment user in a situation in which no problem occurs even if the audible sound is heard in the surroundings in a manner similar to that of a private space.

Next, an example in which portable equipment and a vibration generating apparatus capable of generating a vibration that contains super-high-frequency components having the predetermined autocorrelation order independently of it are used together is described.

Figure 43:
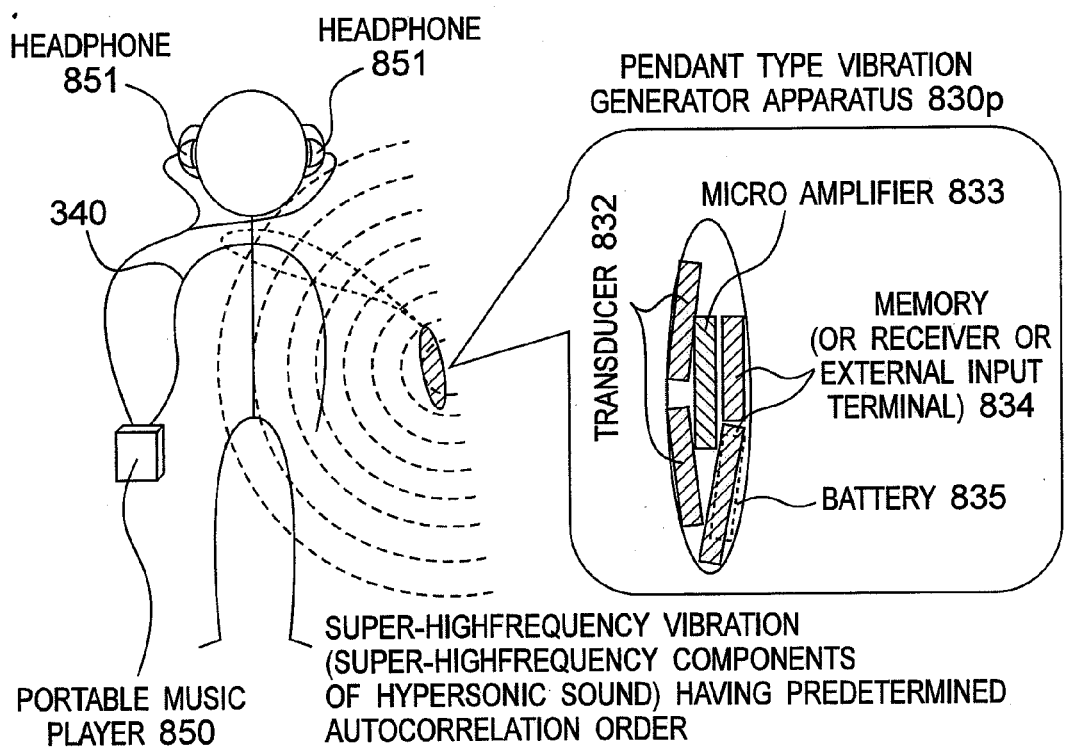
FIG. 43 is a perspective view and a sectional view of a portable terminal plus pendant type vibration generating apparatus according to the first preferred embodiment.

FIG. 43 is a perspective view and a sectional view of a portable terminal plus accessory type vibration generating apparatus according to the present preferred embodiment. FIG. 43 shows an example in which a pendant type vibration generating apparatus 830$p$ utilizing an accessory such as a pendant is used. The super-high-frequency components of a signal of a vibration (hypersonic sound) that can introduce the fundamental brain activation effect because it contains super-high-frequency components having the predetermined autocorrelation order and is inputted from a memory (or a receiver or an external input terminal) 834 in the vibration reproducing apparatus 830$p$ is reproduced by the vibration reproducing apparatus 830$p$ through a micro amplifier 833 and a transducer 832, allowing the super-high-frequency components of the vibration (hypersonic sound) that can introduce the fundamental brain activation effect to be applied to the body surface of the listener 340 who wears the accessory. By thus applying the vibration (hypersonic sound) that contains the audible range components and the super-high-frequency components and has the feature of the predetermined autocorrelation order, the effects of inducing activation of the fundamental brain network system including the reward system neural circuit responsible for the generation of reactions of pleasure, beauty and emotion, and the nerve center of the autonomic neural circuit, the endocrine system and the immune system responsible for homeostatic maintenance and biophylaxis in the listener 340 and consequently enhancing the aesthetic sensitivity and ameliorating and improving the physical state are obtained. In this case, the listener who wears the accessory can avoid the negative influence due to his or her listening to the vibration constituted of only the audible range components even when listening to a music, broadcast sound, voice or the like in the audible frequency range and is allowed to enjoy the fundamental brain activation effect by virtue of the coexistence of the music, broadcast sound, voice or the like in the audible frequency range with the super-high-frequency components of the vibration (hypersonic sound) that can introduce the fundamental brain activation effect.

Next, an example of a vibration generating mechanism that effectively applies a vibration containing super-high-frequency components having the predetermined autocorrelation order to the body surface by utilizing an accessory such as a broach worn extremely closely to the body is described. FIG. 38($a$) is a front view of an accessory (broach) type vibration generating apparatus according to the present preferred embodiment, FIG. 38($b$) is a its right side view, and FIG. 38(c) is its rear view. Referring to FIG. 38, a plurality of super-high-frequency component vibration generating devices 120 for generating super-high-frequency components in a vibration (hypersonic sound) signal that can introduce the fundamental brain activation effect having the autocorrelation order are provided embedded in the front surface and the rear surface of a broach type vibration generating apparatus 160. Moreover, a signal reproducing apparatus is provided embedded in the broach type vibration generating apparatus 160. A battery socket cover 161 and a memory socket cover 162 are provided on the rear surface of the broach type vibration generating apparatus 160, and a clasp 164 for hanging the broach is connected to a clasp fastening portion 163 located in an upper part of the broach type vibration generating apparatus 160. A super-high-frequency vibration generating device may be attached to this clasp. In the broach type vibration generating apparatus 160, signal data of a vibration (hypersonic sound) that can introduce the fundamental brain activation effect is previously stored in a non-volatile solid memory 201 of, a flash memory or the like. At the time of reproducing, the signal data of the vibration that can introduce the fundamental brain activation effect read from the solid memory 201 is subjected to DA conversion and power amplification in a micro amplifier 202 and thereafter outputted to the super-high-frequency component vibration generating devices 120 to generate and radiate super-high-frequency vibrations.

As described above, the super-high-frequency components can be simply effectively applied to the body surface by embedding a lot of super-high-frequency component vibration generating devices 120 in the broach type vibration generating apparatus 160. In this case, the audible range components are applied to the listener by a loudspeaker, headphone or the like. Although the broach type vibration generating apparatus 160 is described in the preferred embodiment of FIG. 38, the present invention is not limited to this, and it may be one that uses an accessory such as a pendant head, a loop tie clasp or the like.

Next, an example of a vibration generating mechanism that effectively applies a vibration that contains super-high-frequency components having the predetermined autocorrelation order to the body surface by utilizing clothes or the like to cover the body is described. FIG. 39(a) is an external view of clothes embedded type vibration generating apparatus according to the present preferred embodiment, and FIG. 39(b) is its internal view. Referring to FIG. 39, a lot of super-high-frequency component vibration generating devices 120 for generating the super-high-frequency components of a vibration (hypersonic sound), that has the predetermined autocorrelation order and can introduce the fundamental brain activation effect, are provided on the substantially entire surface inside a shirt 210, outer sleeve portion, collar portion and the like. Moreover, a signal reproducing apparatus 200 is provided in the vicinity of the hem portion of the shirt 210. In the shirt 210, a conductive plastic fiber coated with a nonconductive plastic is woven into a fabric in concrete, and part of the conductive plastic fiber is used as wiring between the signal reproducing apparatus 200 and the super-high-frequency component vibration generating devices 120. Moreover, it is acceptable to weave a piezo fiber and use this as a super-high-frequency vibration generating device. According to the shirt 210 configured as above, a lot of super-high-frequency component vibration generating devices 120 are embedded in the shirt 210 to generate a super-high-frequency vibration on the whole body, allowing the super-high-frequency components to be simply effectively applied to the listener without using a loudspeaker system. In this case, the audible range components are applied to the listener by a loudspeaker, headphone or the like.

Figure 40:
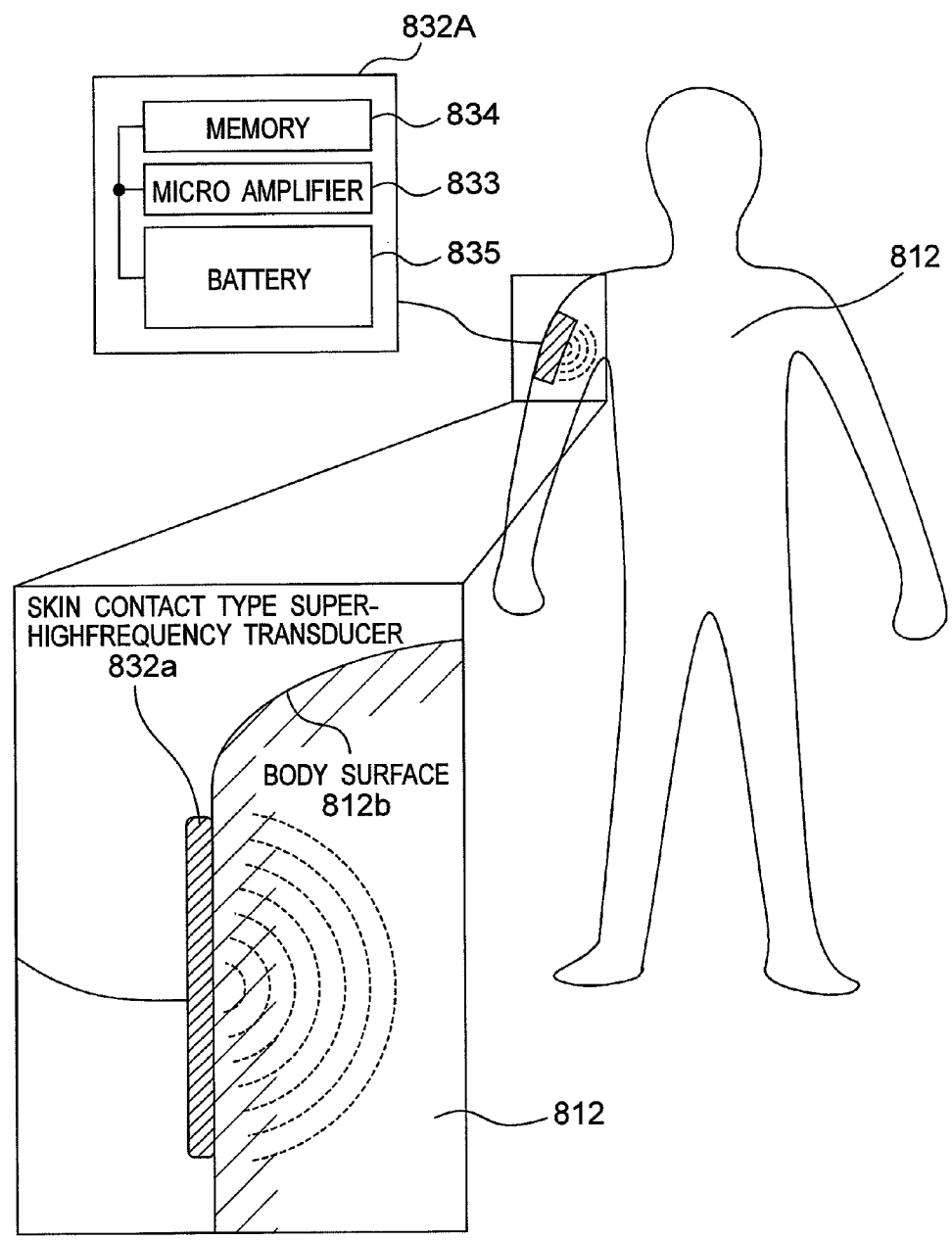
FIG. 40 is a sectional view and a block diagram of a body surface attachment type vibration generating apparatus according to the first preferred embodiment.

Next, an example of a vibration generating mechanism that effectively applies a vibration that contains super-high-frequency components having the predetermined autocorrelation order to the body surface in close contact with the skin is described. FIG. 40 is a sectional view and a block diagram of the body surface attachment type vibration generating apparatus according to the present preferred embodiment. That is, an apparatus for transmitting the super-high-frequency components of a vibration (hypersonic sound), that has the predetermined autocorrelation order and can introduce the fundamental brain activation effect to the skin not without interposition of air by attaching a vibration generating apparatus 832A in close contact with the skin of the listener 812 as the configuration of the vibration generating apparatus 832A using a skin contact type super-high-frequency transducer 832a, is described. In the vibration generating apparatus 832A, the super-high-frequency components of a vibration signal that can introduce the fundamental brain activation effect and is stored in a memory 834, received wirelessly or by wire or inputted from the outside are sent off wirelessly or by wire via a micro amplifier 833 that amplifies and transmits the components. A skin contact type super-high-frequency transducer 832a, which is a film-shaped vibration generating apparatus of a compact actuator, a piezoelectric device or the like, is implemented by being directly closely fixed to the body surface 812b of the skin or the like by a plaster, a supporter or the like, and the super-high-frequency components of the vibration (hypersonic sound) that can introduce the fundamental brain activation effect are transmitted directly to the skin. In this case, the audible range components are applied to the listener by a loudspeaker, headphone or the like.

Next, an example of a vibration generating apparatus for generating a hypersonic sound at close range to audiences in a space of a theater, a hall, an auditorium or the like according to the present preferred embodiment is described. In a large-capacity indoor space of a theater, a hall, an auditorium or the like, an electro-acoustic public-address system is used for making mainly the audible sound sufficiently reach the depth of the audience seats. However, there is such a problem that the super-high-frequency components of a hypersonic sound are disadvantageously largely attenuated by air absorption even if they are generated on the stage, and it is extremely difficult to make them reach the audiences at the depth of the audience seats with regard to both the direct sound and the public-address sound.

In order to solve this problem, it is effective to individually generate a hypersonic sound or its super-high-frequency components at close range to the audiences. With this arrangement, the super-high-frequency components can be made to reach the audiences without being largely attenuated. As a result, the effects of inducing activation of the fundamental brain network system including the reward system neural circuit responsible for the generation of reactions of pleasure, beauty and emotion, and the nerve center of the autonomic neural circuit, the endocrine system and the immune system responsible for homeostatic maintenance and biophylaxis and consequently enhancing the aesthetic sensitivity and ameliorating and improving the physical state are obtained.

FIG. 96 is a perspective view of a vibration generating apparatus for generating a vibration (hypersonic sound) that can introduce the fundamental brain activation effect because it contains super-high-frequency components having the predetermined autocorrelation order at close range to audiences in a space of a theater, a concert hall 430, an auditorium or the like according to the present preferred embodiment. FIG. 96 shows a stage 431, a wireless vibration signal transmitter 432, a wireless vibration signal receiver and vibration generating apparatus 433, a pendant type vibration generating apparatus 434, a ceiling hanged type vibration generating apparatus 435, a chair mounted type vibration generating apparatus 436 and a chair embedded type vibration generating apparatus 437. That is, the super-high-frequency vibration generating apparatus of the present preferred embodiment is embedded in the back of a seat in front of an audience or his or her own seat. Otherwise, it may be arranged hanged from the ceiling or extended from a wall surface or a pillar. Moreover, it may be arranged attached to an accessory such as a pendant or clothes that the audience wears, a portable telephone, a portable music player or the like. Otherwise, the audience may sit wearing a super-high-frequency vibration generating apparatus integrated with a wireless vibration signal receiver. A signal of a hypersonic sound or its super-high-frequency components may be sent off from the stage 431 by wire or wirelessly (electromagnetic waves, infrared rays, LAN, Bluetooth (registered trademark), etc.) or recorded in a memory or the like and integrated in each vibration generating apparatus. It becomes possible for all the audiences to receive the hypersonic sound by the method as described above.

As described above, it becomes possible to effectively generate the vibration that that has the predetermined autocorrelation order and can introduce the fundamental brain activation effect in spaces where many unspecified people gather in a manner similar to that of public institutions, commercial facilities, public transports and the like by separately generating a plurality of vibration signals from a plurality of vibration generating mechanisms. That is, it is effectively achieved to introduce the fundamental brain activation effect into the subject person by applying the vibration or its super-high-frequency components that can introduce the fundamental brain activation effect in the spaces where many unspecified people gather and integrating it with a sound in the audible range from the portable music player that the subject person carries in the space, the sound presenting apparatus of BGM or the like installed in the space. In this case, there are the features that every one can listen to mutually different sounds in the audible range by using the portable player or the like, and all of the people who are in an identical space can enjoy the fundamental brain activation effect while permitting individual differences in the favor pertaining to musics.

In the implemental example described in detail hereinabove with reference to FIGS. 41 to 43 and FIGS. 91 to 96, it is acceptable to use one recording medium or recording and reproducing apparatus having one channel, record the signal of the vibration (hypersonic sound) that has the predetermined autocorrelation order and can introduce the fundamental brain activation effect over a plurality of channels or provide two or more recording and reproducing apparatuses.

Next, an implemental example corresponding to a vibration generating space is described below.

The natural environmental sounds of the tropical rain forests, or the most powerful candidate of the environments where the human genes have been formed through evolution abundantly contain super-high-frequency components that largely exceed 20 kHz at the human audible frequency upper limit and have the predetermined autocorrelation order as shown in FIGS. 1, 3, 4, 8 and 9. In contrast to this, environmental sounds in cities where the modern people live contain almost no such super-high-frequency components, and this does not introduce the fundamental brain activation effect but possibly deteriorate the fundamental brain activity in comparison with that in the background noise environment (See FIGS. 90 and 17). The activity abnormality of the fundamental brain network system of intracerebral projection from there have close relations to the onset of the lifestyle-related diseases that are rapidly increasing in the modern society as a consequence of inducing various mental and behavioral disorders and conducting failures in the homeostatic function and the biophylactic function. Therefore, paying attention to the fact that the mental and behavioral disorders, the lifestyle-related diseases and so on are increasing specifically and rapidly in the modern cities, it is highly possible that a cause is ascribed to the fact that the sound environments in the modern cities largely deviate from the environmental sounds of the tropical rain forests, or the most powerful candidate of the environments where the human genes have been formed through evolution and contain almost no such super-high-frequency components having the predetermined autocorrelation order.

In order to solve this problem, it is extremely effective to generate a vibration (hypersonic sound) that can introduce the fundamental brain activation effect because it contains super-high-frequency components having the predetermined autocorrelation order in various spaces inclusive of urban spaces and achieve a vibration generating space where human beings located there can effectively receive the hypersonic sound. By abundantly receiving the hypersonic sound, it can be expected to introduce the fundamental brain activation effect and solve the problems in the psychosomatic health aspects that the modern people confront.

First of all, an example in which a vibration generating space is achieved in a private space is described.

Figure 44:
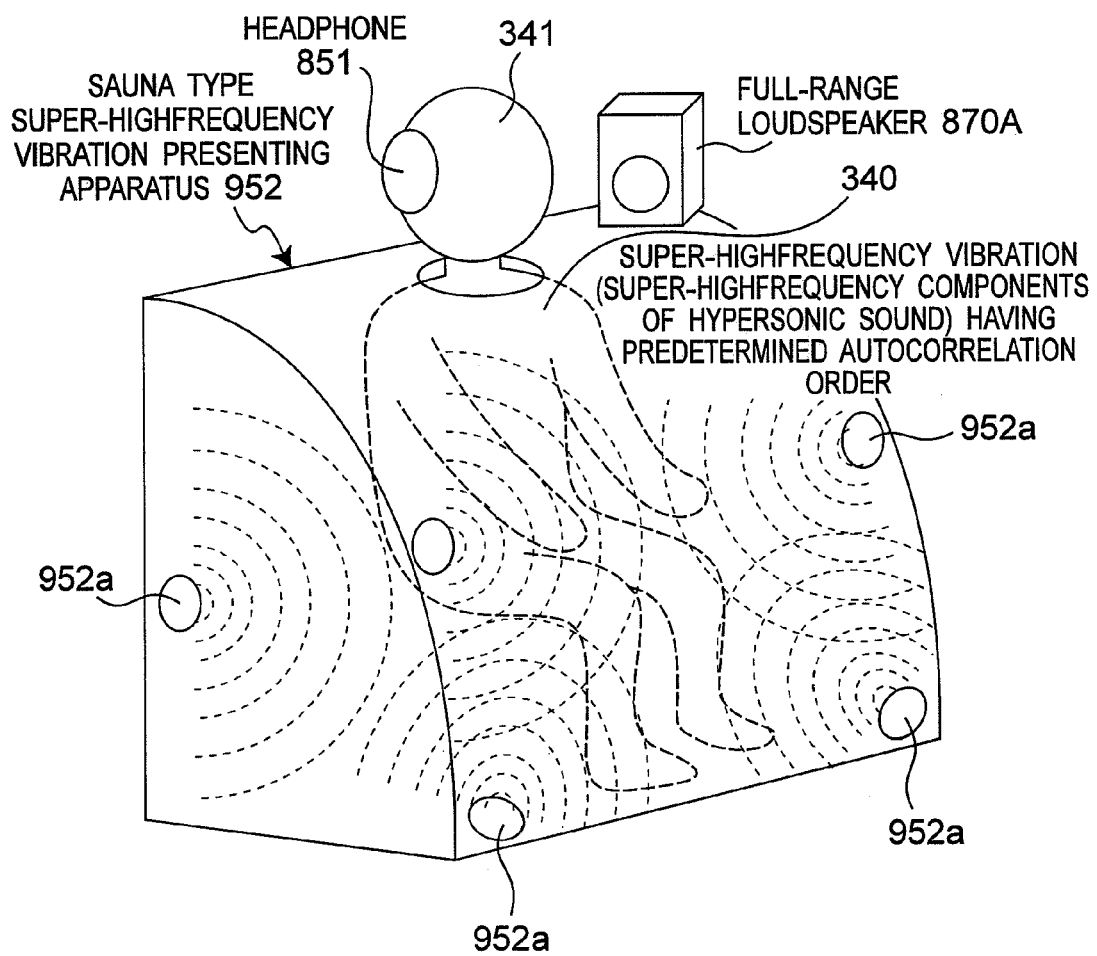
FIG. 44 is a perspective view showing an example of a sauna type vibration presenting apparatus according to the first preferred embodiment.

FIG. 44 is a perspective view showing an example of a sauna type vibration presenting apparatus according to the present preferred embodiment. The sauna type personal space of FIG. 44 is an example of a space in which a vibration (hypersonic sound) that can introduce the fundamental brain activation effect is presented by applying from a headphone or a loudspeaker the audible range components as an aerial vibration in a space where the head is projecting, applying the super-high-frequency components of the vibration that has the predetermined autocorrelation order and can introduce the fundamental brain activation effect from a loudspeaker installed in a space where body parts other than the head are located and adding together the operative effects of both of them. In this case, by entering a sauna type super-high-frequency vibration presenting apparatus 952 in which a lot of super-high-frequency transducers 952a are placed, the super-high-frequency vibration can be poured extremely effectively onto the body surface. A lot of super-high-frequency transducers 952a in the sauna are similar to those of the aforementioned preferred embodiments. In this case, the listener 340 who is in the sauna is listening to the sound at the audible range frequencies by using a headphone 851 or the like or listening to the sound at the audible range frequencies by the airway auditory system including the head by using a full-range loudspeaker 870A or the like. In this case, by virtue of the coexistence of the super-high-frequency components having the predetermined autocorrelation order applied to the body surface, the person can effectively enjoy the fundamental brain activation effect. By thus generating the vibration (hypersonic sound) that contains the audible range components and the super-high-frequency components and has the feature of the predetermined autocorrelation order, the effects of inducing activation of the fundamental brain network system including the reward system neural circuit responsible for the generation of reactions of pleasure, beauty and emotion, and the nerve center of the autonomic neural circuit, the endocrine system and the immune system responsible for homeostatic maintenance and biophylaxis in the listener 340 and consequently enhancing the aesthetic sensitivity and ameliorating and improving the physical state are obtained.

Next, an example in which a vibration generating space is achieved in a space inside a vehicle such as a passenger vehicle is described.

Figure 45:
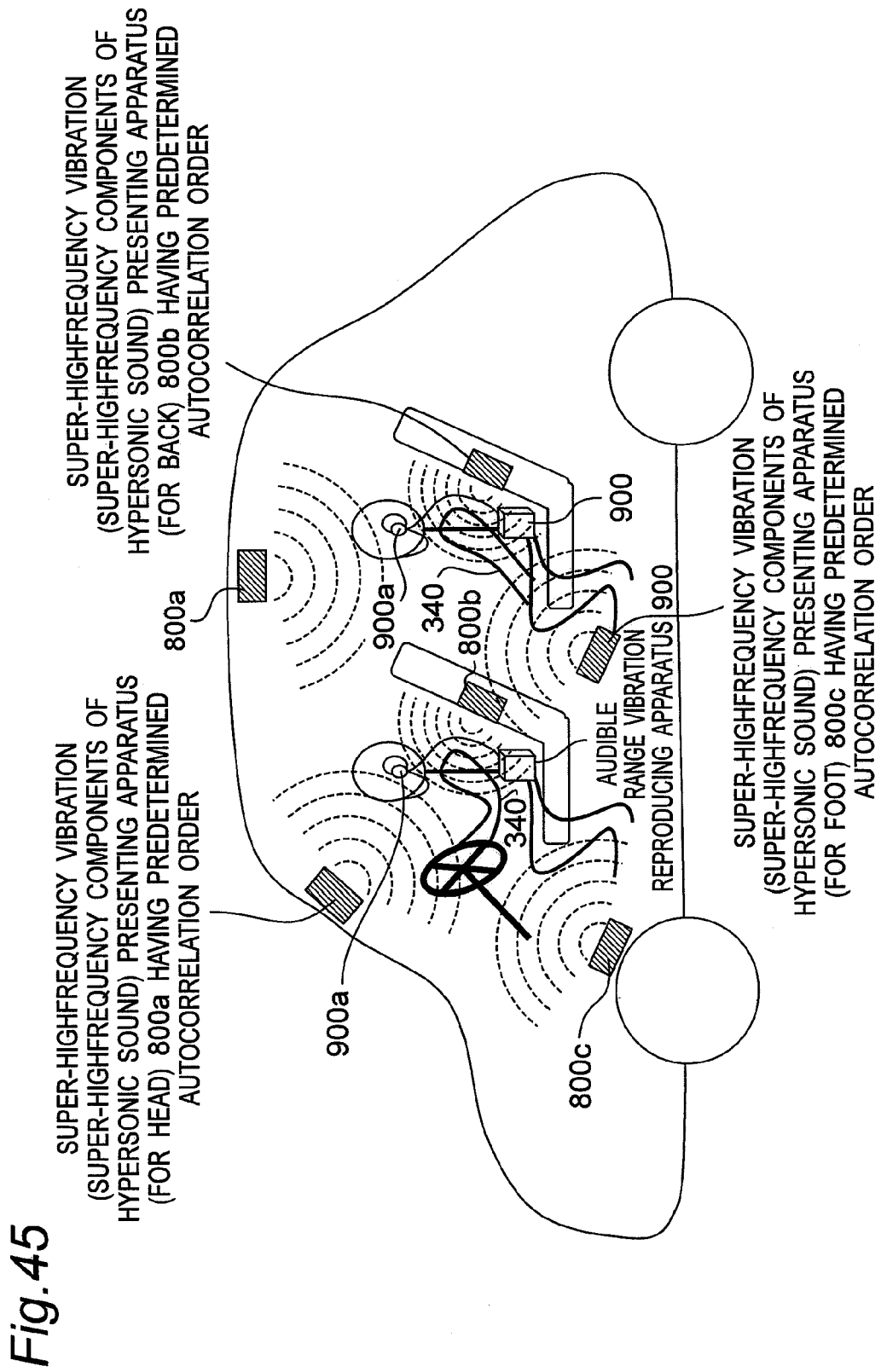
FIG. 45 is a side view showing an example of a vibration presenting apparatus in a vehicle according to the first preferred embodiment.

FIG. 45 is a side view showing an example of a vibration presenting apparatus in a vehicle according to the present preferred embodiment. FIG. 45 is an example of a space in which a vibration (hypersonic sound) that can introduce the fundamental brain activation effect is presented by applying the audible range components of the vibration (hypersonic sound) that contains the audible range components and the super-high-frequency components having the predetermined autocorrelation order and can introduce the fundamental brain activation effect from an audible range component reproducing apparatus such as a portable player in a vehicle and additionally applying the super-high-frequency components from a loudspeaker installed in the space or a vibration generating apparatus embedded in a seat, those components coexisting. In this case, the super-high-frequency components are presented from super-high-frequency vibration presenting apparatuses 800a, 800b and 800c installed in places inside the vehicle and applied to the portions of the face, body, back and so on of the person in the vehicle. These presenting apparatuses may present an identical vibration source or use different vibration sources together. In this case, mutually different listeners 340 in the same vehicle can enjoy the fundamental brain activation effect while listening to their mutually different favorite audible sounds by using an audible range vibration reproducing apparatus 900 such as a portable player and a headphone 900a or the like.

Figure 46:
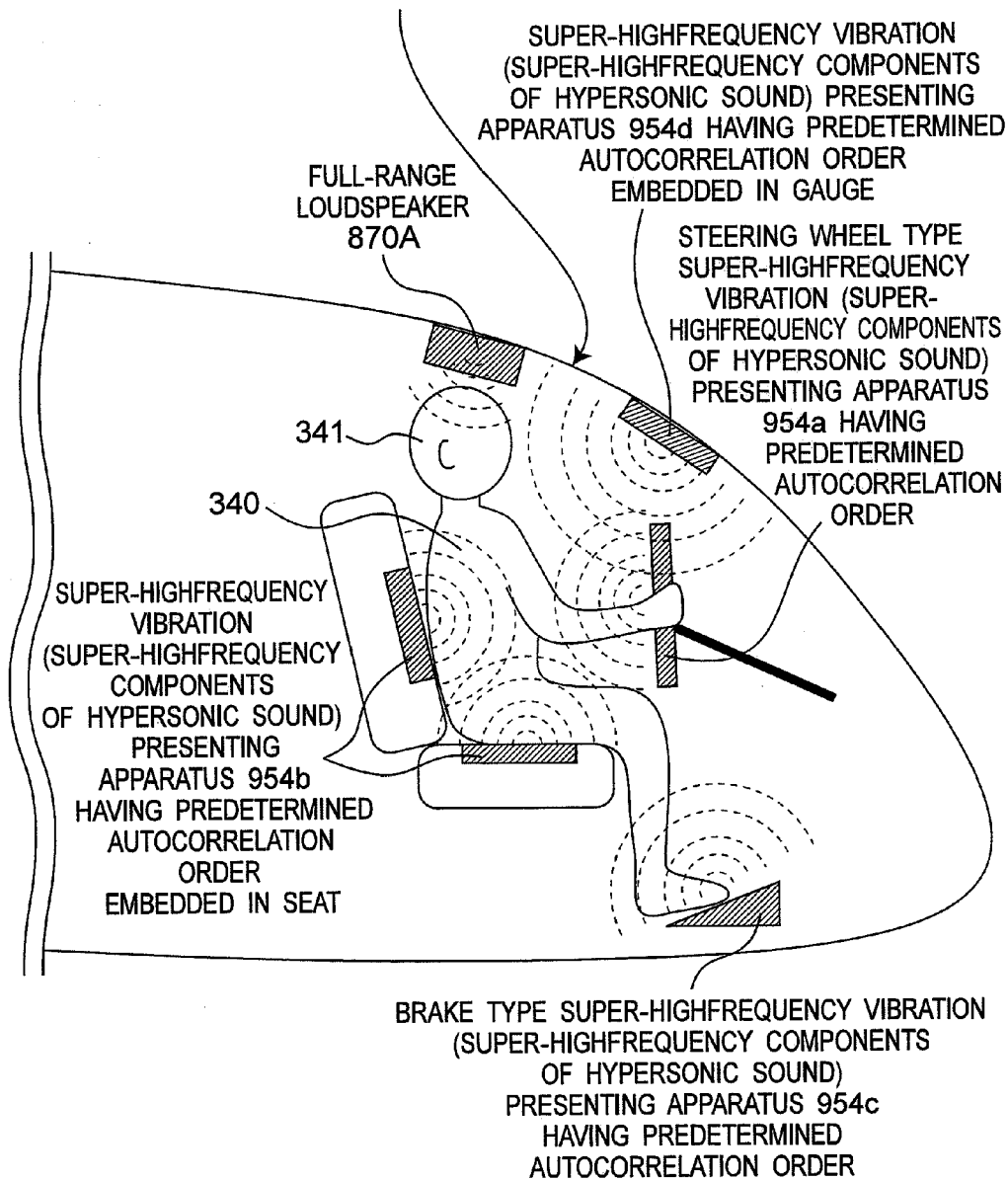
FIG. 46 is a side view showing an example of a vibration presenting apparatus in a driver's seat or a cockpit of public transportation according to the first preferred embodiment.

FIG. 46 is a side view showing an example of a vibration presenting apparatus at the driver's seat or the cockpit of a public transportation according to the present preferred embodiment. FIG. 46 shows a vibration generating space that can introduce the fundamental brain activation effect into the listener 340, or the pilot by applying a vibration (hypersonic sound) that contains audible range components and super-high-frequency components having the predetermined autocorrelation order and can introduce the fundamental brain activation effect to the listener 340, or the pilot from a full-range loudspeaker installed in the space at the driver's seat or the cockpit of a public transportation or the like and additionally effectively applying the super-high-frequency components of the vibration from vibration generating apparatuses embedded in the seat, a brake type steering gear or the like, those components coexisting. In this case, the cockpit of an airplane 954 having a plurality of super-high-frequency vibration presenting apparatuses 954a to 954d is shown by a partially broken external view. By navigating in a state in which the plurality of super-high-frequency vibration presenting apparatuses 954a to 954d are arranged in the cockpit room or the cockpit seat of the airplane 954 (this may be a vehicle such as locomotive, train, ocean vessel, car, or manned rocket besides the airplane), the super-high-frequency vibration can be effectively presented to the body surface. The super-high-frequency vibration presenting apparatuses 954a to 954d effectively present the super-high-frequency vibration to the body surface by generating the super-high-frequency vibration by a vibration generating apparatus in a manner similar to that of the aforementioned preferred embodiments. In this case, the listener 340, or the pilot can effectively enjoy the fundamental brain activation effect by interactions with the super-high-frequency vibration even when he or she is listening to a music, broadcast sound, voice or the like within the audible range frequencies by using a general loudspeaker, a headphone or the like. With this arrangement, it can be expected to promote the pilot's psychosomatic health, maintain the arousal level, prevent the human error, and promote the safety of the navigation. It is noted that this apparatus is not limited to the cockpit room and the cockpit seat but allowed to be installed in crew's rooms, trainman seats, passenger rooms and passenger seats.

Next, an example in which a vibration generating space is achieved by utilizing walls is described.

Figure 47:
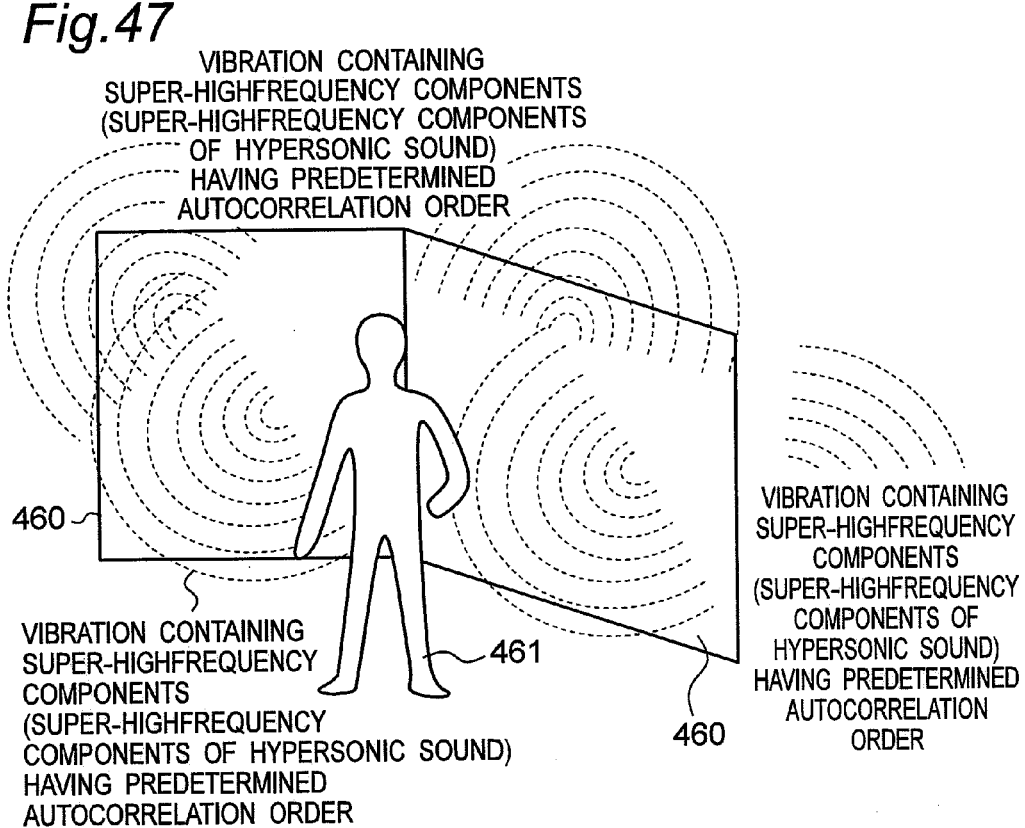
FIG. 47 is a perspective view showing an example in which the walls themselves constituting a space vibrate to generate super-high-frequency components according to the first preferred embodiment.

FIG. 47 is a perspective view showing an example of a space in which the walls themselves constituting the space vibrate to generate super-high-frequency components having the predetermined autocorrelation order according to the present preferred embodiment. FIG. 47 shows an example of a vibration generating space for generating a vibration (hypersonic sound) that contains audible range components and super-high-frequency components having the predetermined autocorrelation order and can introduce the fundamental brain activation effect in the space by the vibration of the walls themselves constituting the space and applying it to a listener 461. The walls 460 may vibrate by being driven by an electric signal or secondarily vibrate by the propagation of a vibration generated by a vibrating object of a solid, liquid or gas installed in the space or outside the space. For example, by generating a vibration having the conditions of the predetermined properties when an instrument sound, voice or vocal sound performed in the hall space, a sound generated by an PA system or the like propagates to the walls in a concert hall or the like, and applying it to the audiences, a vibration generating space that can introduce the fundamental brain activation effect is provided.

Next, an example of a vibration generating space that applies in common a hypersonic sound or its super-high-frequency components to a plurality of persons who are listening to individual audible sounds in a public space or the like is described.

Figure 48:
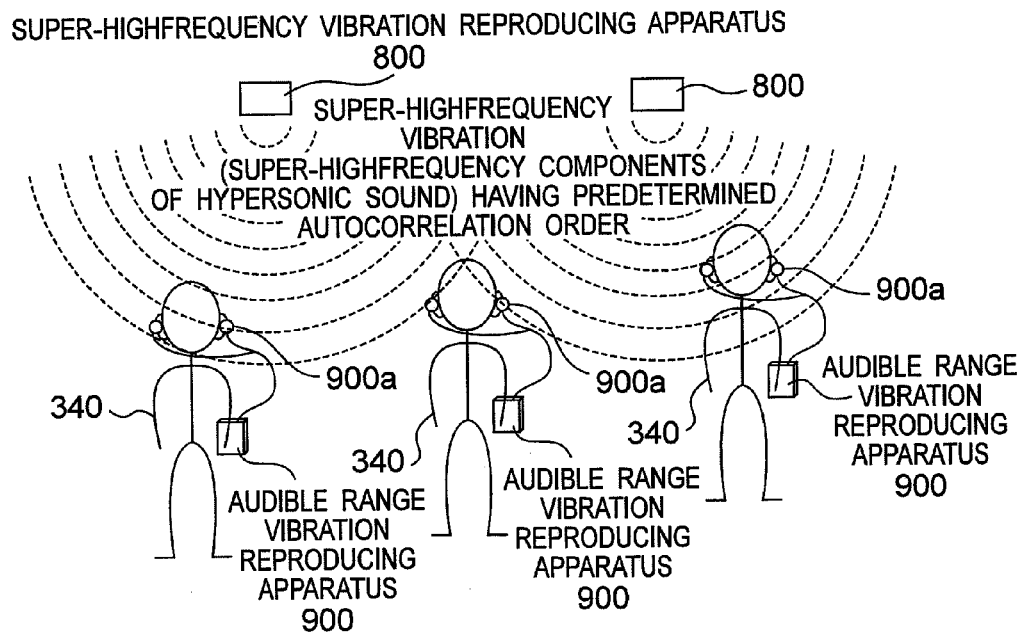
FIG. 48 is a plan view showing an example of a space in which portable players are combined with a vibration generating apparatus that simultaneously applies a super-high-frequency to a plurality of persons according to the first preferred embodiment.

FIG. 48 is a side view showing an example of a space in which a portable player that reproduces audible range vibration components is combined with a vibration generating apparatus that simultaneously applies the super-high-frequency components of a vibration (hypersonic sound) that has the predetermined autocorrelation order and can introduce the fundamental brain activation effect to a plurality of persons according to the present preferred embodiment. For example, the super-high-frequency components of the vibration (hypersonic sound) that can introduce the fundamental brain activation effect are reproduced from a super-high-frequency vibration reproducing apparatus 800 installed in a public space of, for example, a public road, a plaza, an office, a waiting area or the like and applied to the body surfaces of listeners 340. In this case, the reproduced super-high-frequency vibration, that has the predetermined autocorrelation order and is inaudible as a sound are common to all the listeners 340. Under this condition, audible range vibrations are reproduced by audible range vibration reproducing apparatuses 900 such as portable music players, and the listeners listen to them by, for example, headphones 900a. In this case, the listeners 340 may be listening to mutually different their favorite musics or the like.

Figure 49:
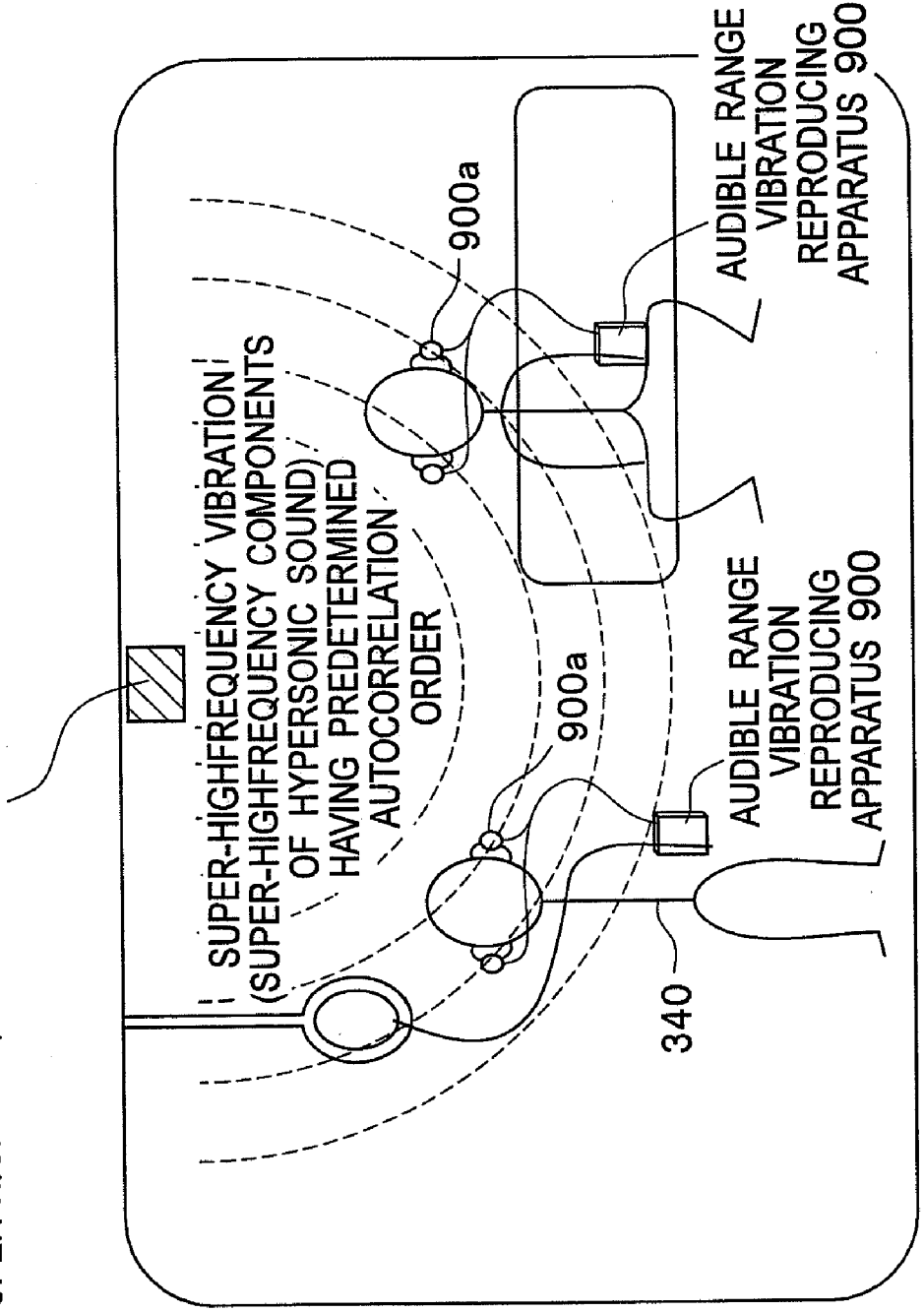
FIG. 49 is a plan view showing a modified preferred embodiment of the apparatus of FIG. 48.

FIG. 49 is a side view showing a modified preferred embodiment of the apparatus of FIG. 48. FIG. 49 shows a configuration that applies a vibration (hypersonic sound) that can introduce the fundamental brain activation effect to a plurality of listeners 340 in a train, a bus, the passenger room of an airplane or the like by using a vibration reproducing apparatus 800. In this case, the super-high-frequency vibration having the predetermined autocorrelation order is reproduced from the super-high-frequency vibration reproducing apparatus 800 installed in the passenger room or the like and applied to the body surfaces of the plurality of listeners 340 in the train. In this case, the reproduced super-high-frequency vibration is common to all the listeners 340. In this case, the plurality of listeners 340 in the train can concurrently enjoy the fundamental brain activation effect while listening to mutually different their favorite audible range vibrations by using portable music players or audible range vibration reproducing apparatuses 900 such as headphones for music service provided for the present vehicle.

Figure 50:
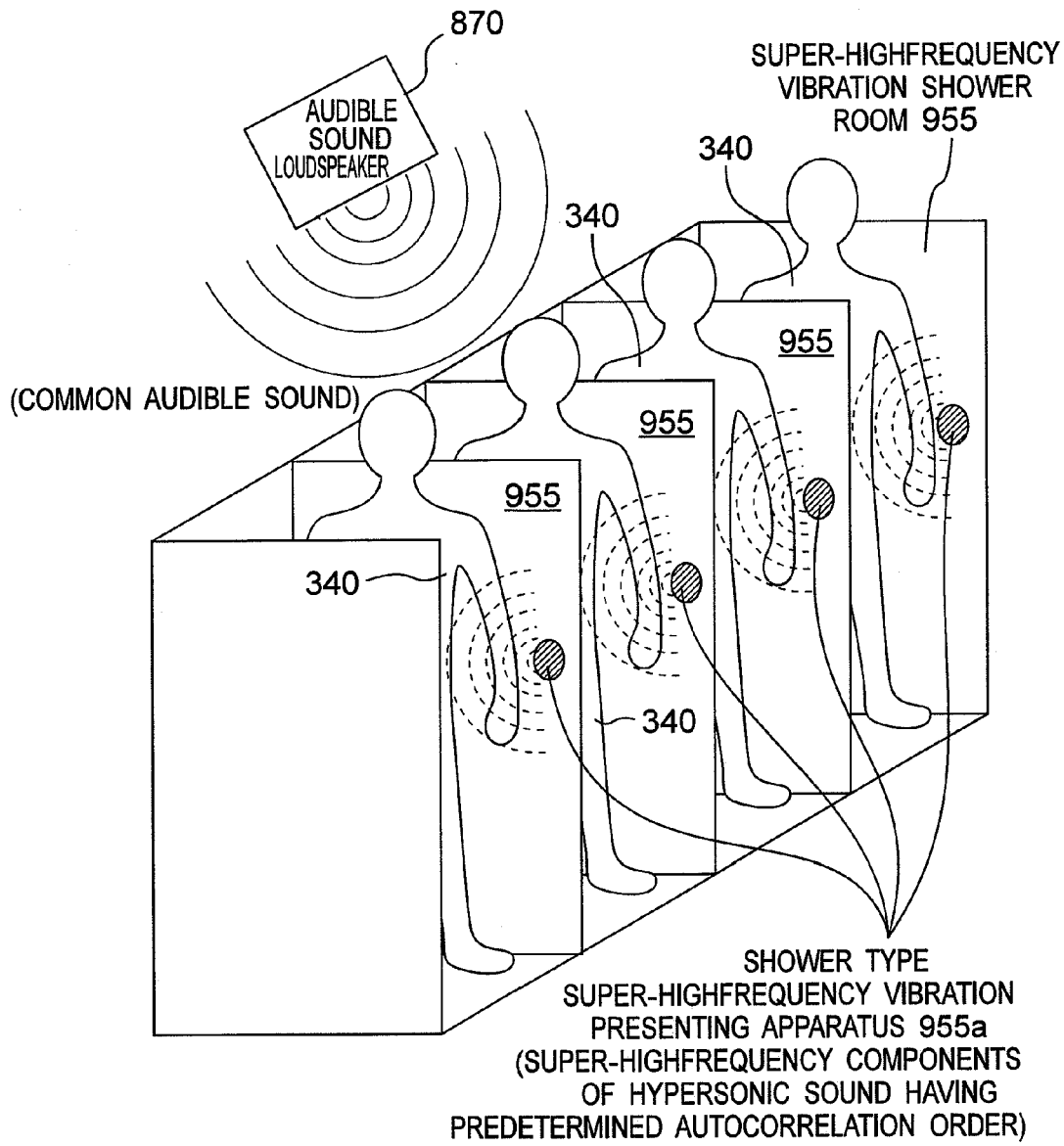
FIG. 50 is a perspective view showing a shower type vibration presenting apparatus according to the first preferred embodiment.

Next, an example of a vibration generating space that applies individual hypersonic sounds or their super-high-frequency components to a plurality of persons who are listening to a common audible sound in a public space or the like is described. FIG. 50 is a perspective view showing a shower type vibration presenting apparatus that generates a vibration (hypersonic sound) that contains audible range components and super-high-frequency components having the predetermined autocorrelation order and can introduce the fundamental brain activation effect according to the present preferred embodiment. FIG. 50 shows a plurality of shower type vibration presenting apparatuses. In this case, a plurality of persons can bath their favorite super-high-frequency vibrations in high-frequency vibration shower rooms 955 in a shower room type facility used by the plurality of persons. Referring to FIG. 50, a super-high-frequency vibration presenting apparatus 955a, that has the predetermined autocorrelation order and is installed in each super-high-frequency vibration shower room 955, allows the user to select his or her favorite super-high-frequency vibration signal having the predetermined autocorrelation order from among a number of kinds of super-high-frequency vibration signals stored in a memory and to effectively bath the same on the body surface. In this case, the user listens to common audible range music, a broadcast sound, voice or the like from a general audible sound loudspeaker 870. By virtue of the coexistence of the audible sound and the super-high-frequency components, the user can effectively enjoy the fundamental brain activation effect. It is noted that the users are allowed not to listen to the common audible sound or to listen to their individual favorite audible sounds by bringing portable players or the like.

The implemental examples of FIGS. 48 to 50 show examples of vibration generating spaces that generate fundamental brain activation vibrations from the vibration generating apparatuses installed in public spaces and the like and apply the same to a plurality of persons. In this case, it is acceptable to present only the components having frequencies of not lower than 20 kHz at the human audible range upper limit out of the vibrations having the conditions of the aforementioned properties from the fundamental brain activation vibration generating apparatus and allow the plurality of persons who are subject to the application of the vibration to listen to mutually different their favorite musics and the like by using, for example, audible range vibration generating apparatuses such as portable players. In this case, the super-high-frequency components, which have the predetermined autocorrelation order that the human being cannot feel as a sound and are radiated in the air, and the audible range components generated from the audible range vibration generating apparatuses to which the individuals are listening are added together at the place of each person, thereby generating the vibration (hypersonic sound) that satisfies the conditions of the aforementioned properties. Such a vibration generating space can be set in (1) intra-building spaces such as rooms, gateways, lobbies, passages, stairs, escalators, elevators, halls, auditoriums, gyms, stadiums, warehouses, factories, stores, video arcades, play facilities of pachinko parlors and the like, stations, and airport facilities, (2) conveyance spaces such as vehicles, trains, ocean vessels, submarines, airplanes, rockets, and playing tools, (3) outdoor spaces such as gardens, school yards, plazas, parks, amusement parks, grounds, stadiums, building rooftops, roads, bridges, farms, forests, beaches, lakes, marshes and rivers, seas, deserts, and meadows, (4) underground spaces such as caves, tunnels, mineshafts, and underground shopping centers, (5) semi-open spaces located at indoor and outdoor boundaries such as shopping street arcades, station platforms, station concourses, stadiums, and seats of racetracks, and so on. The vibration generating spaces make it possible to introduce the fundamental brain activation effect into a plurality of persons in the spaces by letting them listen to their freely selected favorite musics and the like.

Next, in order to constitute a vibration generating space, a double helical matrix coordination method and a six-dimension consecutive matrix coordination method are described as coordination method examples of arranging a plurality of loudspeakers serving as a recording and reproducing apparatus.

FIG. 97 shows the prior art normal 4-channel surround loudspeaker arrangement. In this loudspeaker arrangement, a front left loudspeaker FL and a rear left loudspeaker RL are located on the same left-hand side. Next, if a double helical matrix arrangement is provided, it is as shown in FIG. 98. Referring to FIG. 98, in contrast to the front left loudspeaker FL located on the left-hand side, the rear left loudspeaker RL is located on the right-hand side. With this arrangement, a person who is in this space is to face the sound on the left-hand side and the sound on the right-hand side whichever direction of the four directions the person faces. Moreover, the person is to listen to the sounds of all the five channels. It is also the feature of the double helical matrix that stereophonic effects and continuity are achieved by adding an upper middle loudspeaker UC.

FIG. 99 shows a case where the double helical matrixes are consecutively iteratively arranged in two directions. In the loudspeaker arrangement of FIG. 99, a person in this space is to consistently face the sound on the left-hand side and the sound on the right-hand side and listen to the sounds of all the five channels. Further, referring to FIG. 99, the sound on the left-hand side and the sound on the right-hand side intertwine with each other, and the row of the left-hand loudspeakers and the row of the right-hand loudspeakers are each helicoidal iterating the front side, the rear side, the front side, the rear side, . . . .

Next, the loudspeaker arrangement using the six-dimension consecutive matrix coordination method is described.

The 4-channel surround loudspeaker arrangement of FIG. 97 is lifted up to a predetermined height as shown in FIG. 100. Then, channels of sounds located between the front side and the rear side are added, and the loudspeakers are served as a center left loudspeaker CL and a center right loudspeaker CR. These center left loudspeaker CL and the center right loudspeaker CR are placed on the ground or at a height slightly higher than the ground. The loudspeaker arrangement of FIG. 100 is referred to as the matrix in the present implemental example. In this case, it is acceptable to use a modified inverted arrangement such that FL, FR, RL, and RR are placed at a height slightly higher than the ground and CL and CR are placed upside.

When the matrixes of FIG. 100 are arranged consecutively iteratively bidirectionally in the vertical and horizontal directions, the resulting arrangement becomes as shown in FIG.

101. Referring to FIG. 101, since there are the left sound column and the right sound column in any of the matrixes, the sound field is formed so as to be felt normal. Moreover, the front sound and the rear sound appear alternately. Further, since there is a center sound that interlinks the front sound with the rear sound, a continuous space can be felt.

It is also acceptable to reproduce only the audible range components of a vibration by using the double helical matrix coordination method, the six-dimension consecutive matrix coordination method or the like and reproduce the super-high-frequency components exceeding the human audible frequency upper limit in a stereophonic reproduction or monaural reproduction manner.

Next, an example in which a vibration generating space that can introduce the fundamental brain activation effect by using the six-dimension consecutive matrix coordination method is set in an urban district, and the activation of the fundamental brain is actually exhibited is described below.

Figure 51:
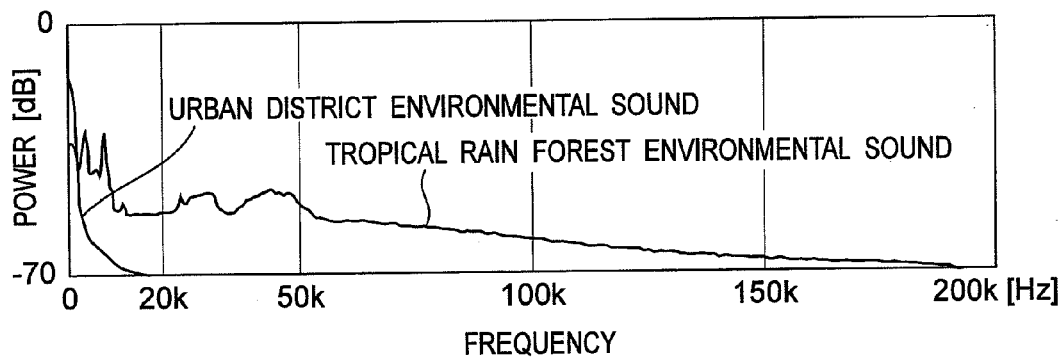
FIG. 51 is a spectral diagram of the average power spectrum of an urban district environmental sound and a tropical rain forest environmental sound for complementing, measured in the first preferred embodiment.

FIG. 51 is a spectral diagram of the average power spectrum of an urban district environmental sound and a complementing tropical rain forest environmental sound measured in the present preferred embodiment. The environmental sound in the urban district of a city cannot introduce the fundamental brain activation effect since it does not contain the super-high-frequency components having an appropriate structure. Accordingly, an example in which the tropical rain forest environmental sound of a typical aerial vibration that can introduce the fundamental brain activation effect is added in a space to the environmental sound (urban district environmental sound) that cannot introduce the fundamental brain activation effect existing originally in urban district spaces to constitute a vibration generating space that can apply them to a person in the space, and the fundamental brain activation effect is actually introduced into the person in the space is described. FIG. 51 shows the average power spectrums of the aerial vibration of the original environmental sound of the urban district and the aerial vibration of the tropical rain forest environmental sound for complementing, which are obtained by the FFT method. The environmental sound of the urban district contains only the components up to about 20 kHz and does not have the super-high-frequency components of the essential condition as a vibration (hypersonic sound) that can introduce the fundamental brain activation effect. On the other hand, the tropical rain forest environmental sound has sufficient super-high-frequency components of which the upper limit reaches 200 kHz and satisfies the condition of the frequency domain that is the essential condition of the vibration (hypersonic sound) that can introduce the fundamental brain activation effect.

Figure 52:
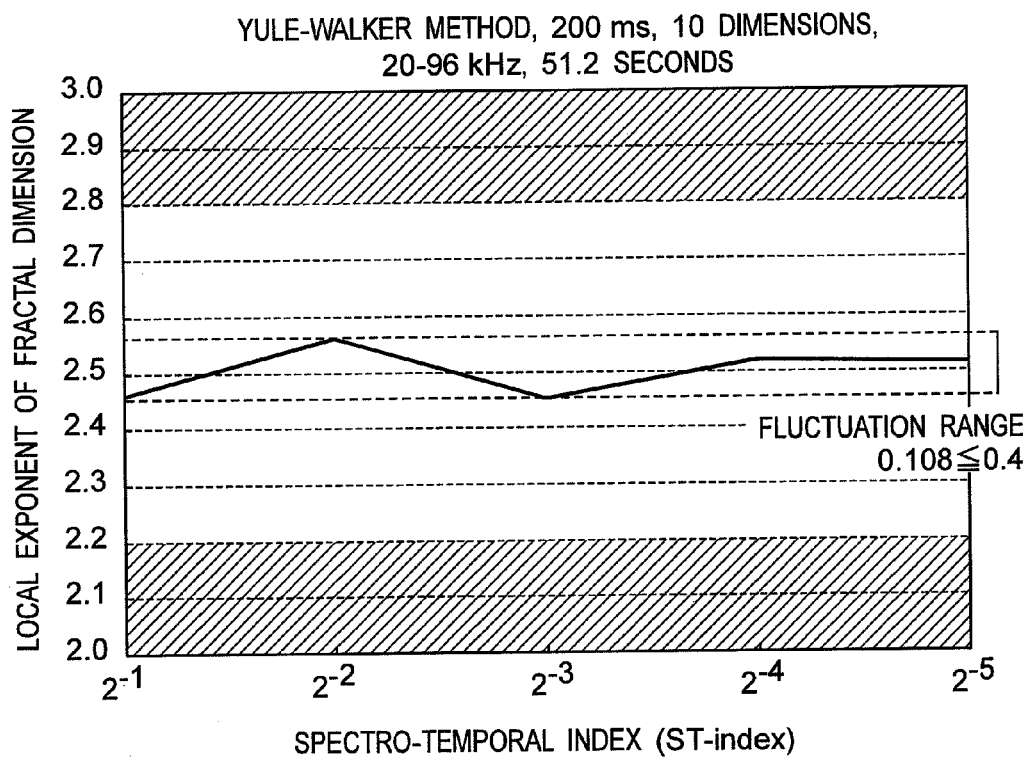
FIG. 52 is a graph showing a local exponent of fractal dimension of the tropical rain forest environmental sound applied to an urban district space, measured in the first preferred embodiment.

FIG. 52 is a graph showing a local exponent of fractal dimension of the tropical rain forest environmental sound applied to an urban district space measured in the present preferred embodiment. That is, FIG. 52 shows the local exponent of fractal dimension obtained by a predetermined method concerning the first property on the autocorrelation order of the tropical rain forest environmental sound applied in addition to the environmental sound of the urban district. The local exponent of fractal dimension of the applied tropical rain forest environmental sound consistently has a value of not smaller than 2.2 and has a fluctuation range of not greater than 0.4. Therefore, the tropical rain forest environmental sound applied in addition to the urban district environmental sound satisfies the first property on the autocorrelation order.

Figure 53:
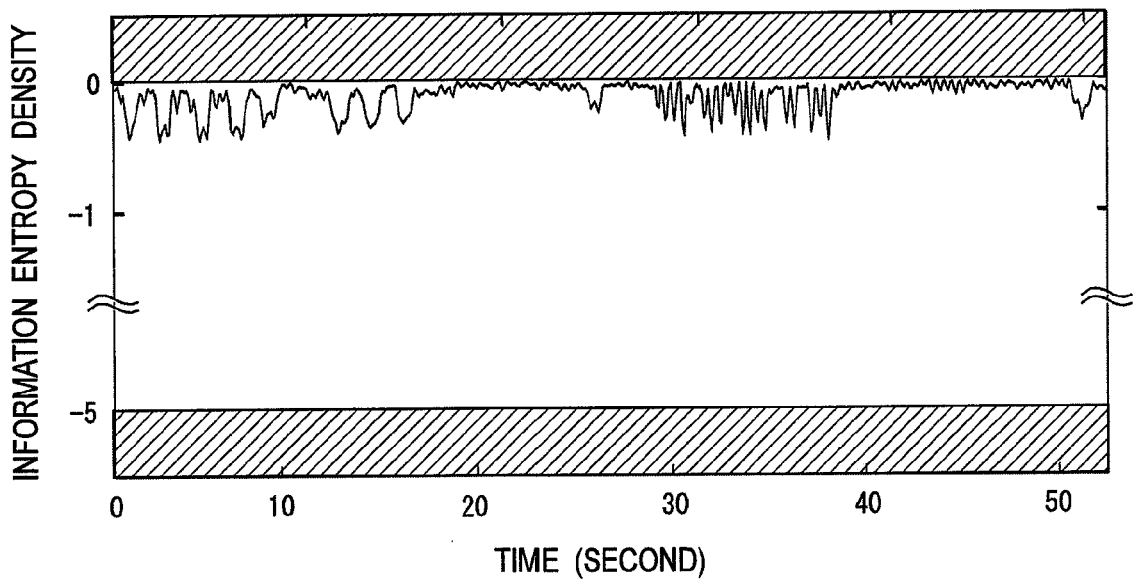
FIG. 53 is a graph showing an information entropy density of the tropical rain forest environmental sound applied to the urban district space, measured in the first preferred embodiment.
Figure 54:
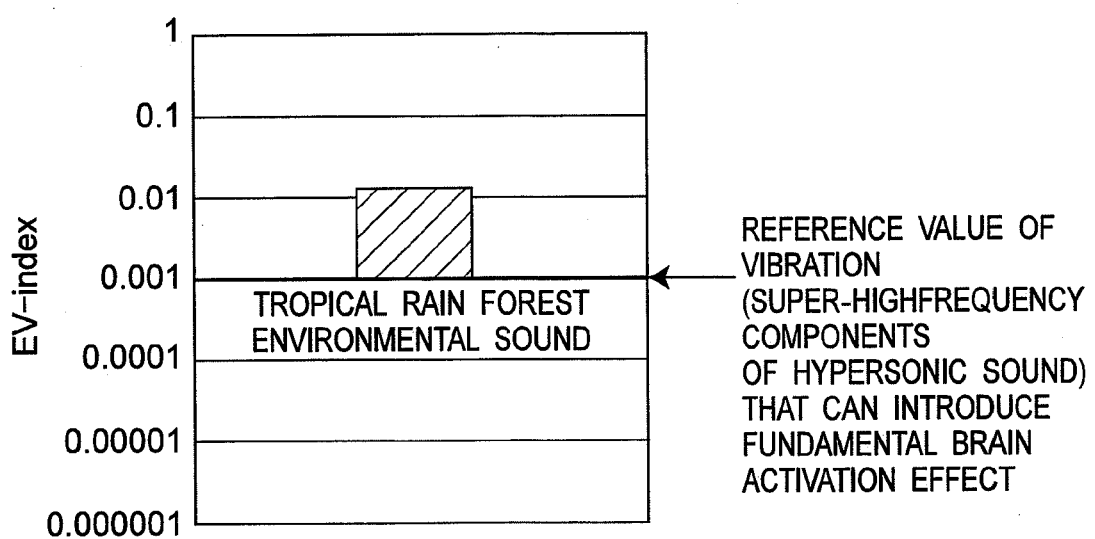
FIG. 54 is a graph showing an entropy variation index (EV-index) of the tropical rain forest environmental sound applied to the urban district space, measured in the first preferred embodiment.

FIG. 53 is a graph showing an information entropy density of the tropical rain forest environmental sound applied to the urban district space measured in the present preferred embodiment, and FIG. 54 is a graph showing an entropy variation index (EV-index) of the tropical rain forest environmental sound applied to the urban district space measured in the present preferred embodiment. As is apparent from FIG. 53, the information entropy density consistently has a value of not smaller than −5 and smaller than zero. Moreover, as is apparent from FIG. 54, the entropy variation index (EV-index) has a value greater than 0.001. For these reasons, the tropical rain forest environmental sound applied in addition to the urban district environmental sound satisfies the condition of the second property on the autocorrelation order.

Figure 55:
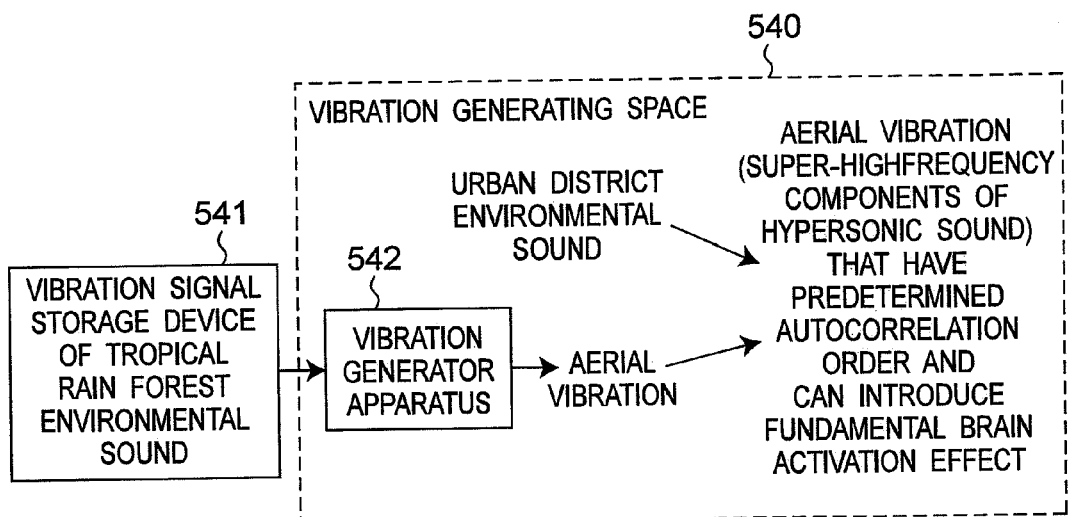
FIG. 55 is a block diagram showing a method for generating a vibration (hypersonic sound) capable of introducing the fundamental brain activation effect in an urban district space according to the first preferred embodiment.

FIG. 55 is a block diagram showing a method for generating a vibration that can introduce the fundamental brain activation effect in an urban district space according to the present preferred embodiment. As described above, in contrast to the fact that the environmental sound existing in the originally objective urban districts is a vibration that cannot introduce the fundamental brain activation effect, the tropical rain forest environmental sound applied to it is a vibration (hypersonic sound) that can introduce the fundamental brain activation effect. By generating the tropical rain forest environmental sound from the loudspeakers of a plurality of vibration generating apparatuses 542 installed in an urban district including plazas and passages as the objective space 540 and adding them in the space, a vibration capable of introducing the fundamental brain activation effect was generated. By thus generating the vibration (hypersonic sound) that contains the audible range components and the super-high-frequency components having the feature of the predetermined autocorrelation order, the effects of inducing activation of the fundamental brain network system including the reward system neural circuit responsible for the generation of reactions of pleasure, beauty and emotion, and the nerve center of the autonomic neural circuit, the endocrine system and the immune system responsible for homeostatic maintenance and biophylaxis in a human being and consequently enhancing the aesthetic sensitivity and ameliorating and improving the physical state are obtained.

Figure 56:
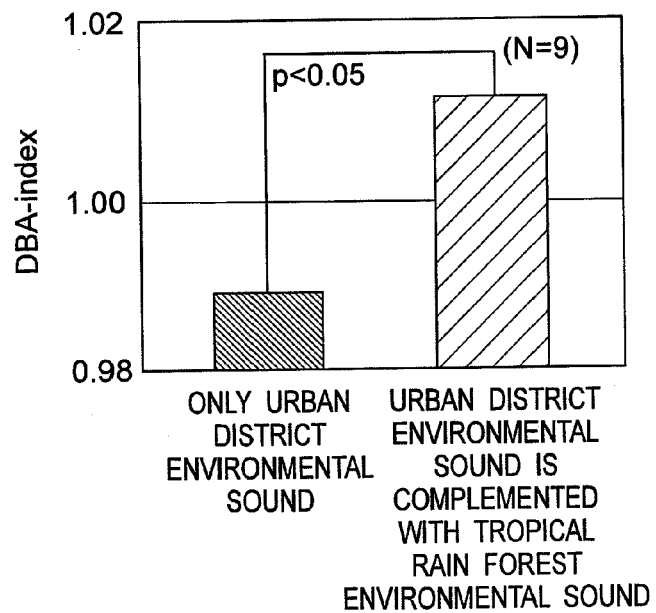
FIG. 56 is a graph showing a deep brain activity index (DBA-index) in a case where only the urban district environmental sound is applied and a case where the tropical rain forest environmental sound capable of introducing the fundamental brain activation effect is added to it, measured in the first preferred embodiment.

FIG. 56 is a graph showing a deep brain activity index (DBA-index) in a case where only the urban district environmental sound is applied and a case where the tropical rain forest environmental sound that can introduce the fundamental brain activation effect is added to it measured in the present preferred embodiment. Referring to FIG. 56 showing a brain wave measurement results, the brain waves of test human subjects staying in an urban district were measured depending on when the tropical rain forest environmental sound was applied and when it was not applied, the deep brain activity index (DBA-index) serving as an index of fundamental brain activation was obtained for each test human subject, and a statistical examination was performed based on the data of nine test human subjects. As a result, the deep brain activity index (DBA-index) was increased statistically more significantly when the tropical rain forest environmental sound capable of introducing the fundamental brain activation effect was applied than when not applied. This result indicates that, by adding together the originally existing urban district environmental sound and the tropical rain forest environmental sound capable of introducing the fundamental brain activation effect in a space, the fundamental brain of the person existing in the space is activated.

Next, "apparatus and medium for hypersonic therapy" utilizing the vibration generating space that can introduce the fundamental brain activation effect is described.

The conventionally performed musicotherapy (meaning not the active musicotherapy such that the patient himself or herself gives a performance but the passive musicotherapy of listening to a music in this case) is one alternative medicare intended for making the patient listen to his or her favorite music to induce positive sensibility reactions such as emotion and relaxation, thereby trying to link it to the recovery and improvement of psychosomatic health. However, the sensory information generally called "arts" inclusive of musics has the features of introducing emotional reactions through "likes" and "dislikes" through the work of the neural circuit such as the auditory nerve system responsible for perceptions. A first problem caused by this is the individuality of the effects. A music that induces a positive sensibility reaction perceived as "likes" to a certain patient is perceived as "dislikes" by another patient, sometimes causing no effect or conversely inducing a negative sensibility reaction. That is, due to the dependency on the individuality that holds only between a specific music and a specific patient, a specialist needs to previously individually examine what sort of music is effective for the patient and make a prescription before starting a remedy. A second problem is the situation dependency of effects. For example, a tune that a patient feels "likes" sometimes produces an adverse effect when he or she listens to it in another occasion. That is, even if an identical patient is made to listen to an identical music, it sometimes leads to different reactions depending on the patient's psychosomatic state at the time. The individuality and the situation dependency mean that universal effects cannot be expected in the musicotherapy unlike treatments with medical agents. Moreover, another problem of the musicotherapy, which should not be overlooked, is that it is influenced by the signal structure of the sound source. When a music is reproduced by using a medium like a CD that cannot record the super-high-frequency or when a music is generated by using a reproducing apparatus or a musical instrument that can only generate audible sounds, a signal structure to deteriorate the fundamental brain activity is provided, and this leads to a risk of causing adverse effects.

Against the problems owned by the conventional musicotherapy as described above, by making the patient receive the vibration (hypersonic sound) that introduces the fundamental brain activation effect because it contains super-high-frequency components having the predetermined autocorrelation order in the present implemental example, all the problems described above can be solved. The hypersonic sound has the effects of increasing the regional cerebral blood flow of the fundamental brain network system including the brain stem, thalamus and hypothalamus, which are the regions responsible for the fundamental functions of the brain and the neural projection from the fundamental brain and activating these regions. The fundamental brain activation effect introduces the effects of improving the physical activation such as homeostatic maintenance and biophylaxis of the whole body, consequently making it possible to introduce the effects of comprehensively remedying the lifestyle-related diseases of metabolic syndromes such as hypertension, hyperlipemia and diabetes, cancer, cerebrovascular disorder and cardiopathy, immune abnormalities including pollinosis and atopic dermatitis, various mental disorders such as depression, schizophrenia, dementia, chronic fatigue syndrome and attention-deficit hyperactivity disorder, behavioral abnormalities such as suicide and self-injurious behaviors, abnormal exaltation of aggressiveness and so on, which are caused by the abnormality of the fundamental brain activity and pose serious problems in the modern society. Moreover, the activation of the reward system neural network contained in the fundamental brain network system causes positive sensibility reactions such as an improvement in the comfortable sensation and the like.

As described above, the effects of the hypersonic therapy have the features that the existence of the super-high-frequency components, which are perceived as a sound like a music and do not induce the negative influences of individuality and situation dependency, serves as a key to work on the fundamental brain network system in a route different from that of the sensory nerve circuit. With a mechanism other than the emotional reactions that are unstable and have individual variations of "likes" and "dislikes" inevitably induced by a music perceived as a sound, effects that are biologically universally positive for the human race are introduced, never causing individuality and situation dependency. Therefore, the procedure of previously examining a sound effective for the patient is also unnecessary. For these reasons, the hypersonic therapy produces universal effects that statistically significantly hold between an identical vibration having a predetermined physical structure and unspecified listeners. Such effects are essentially common to the fact that a medical agent having a predetermined chemical structure develops statistically significant effects in an unspecified patient. Major differences between the conventional musicotherapy and the hypersonic therapy are shown in the table of FIG. 102.

The vibration generating apparatus for achieving the hypersonic therapy can be provided by applying any one of the vibration generating apparatuses described in the first to fourth preferred embodiments of the present application. Moreover, the patient may listen to his or her favorite music in combination with the reception of the hypersonic sound, and greater effects can be expected by a synergistic effect depending on the combining manner.

Next, an implemental example of the vibrating object is described below.

An example of a vibrating object in a vibrational state in which it vibrates in the super-high-frequency band having the feature of the predetermined autocorrelation order introduced by vibrating a gas, a liquid, a solid or the like is described below.

Figure 57:
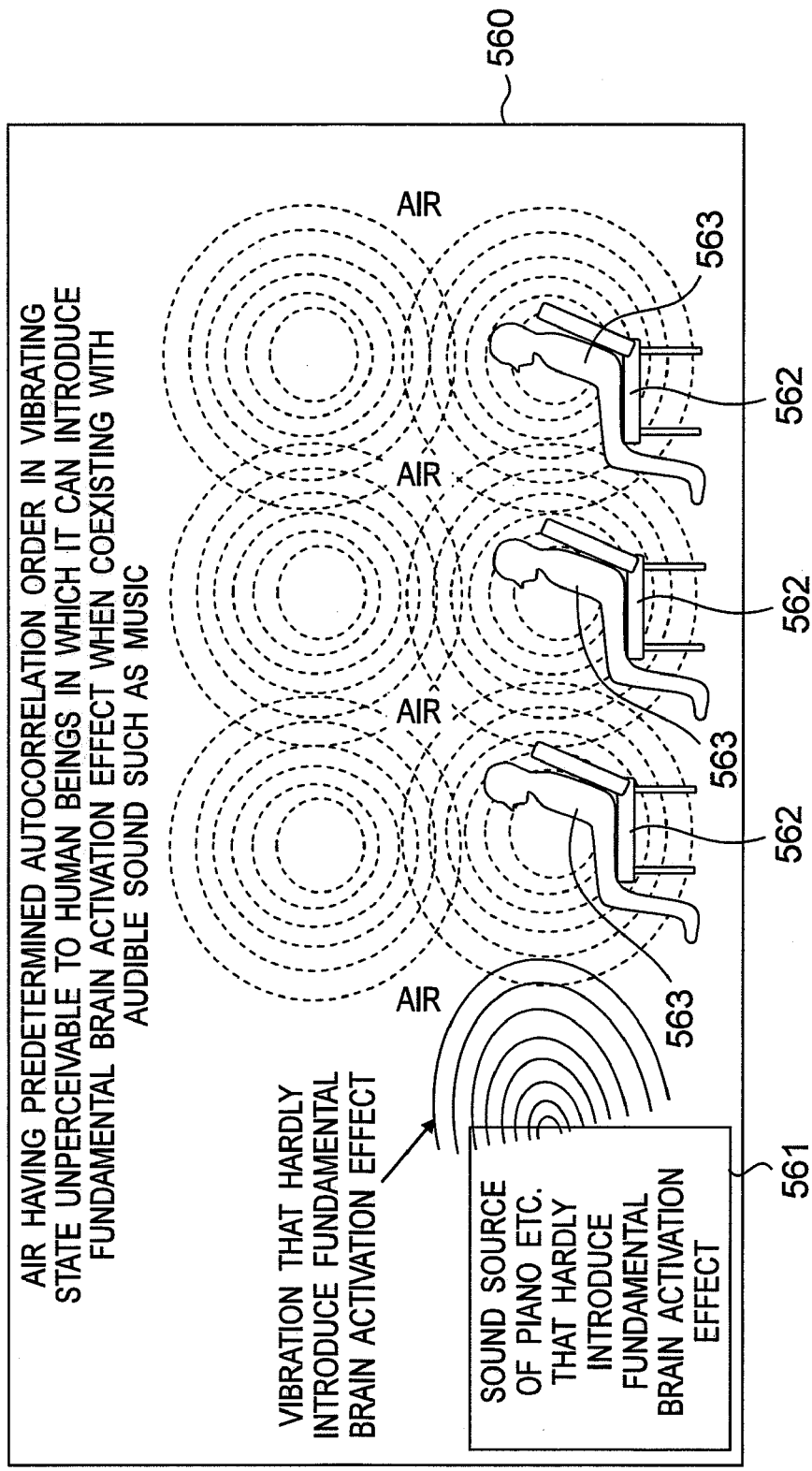
FIG. 57 is a side view showing an example of a vibrating object in a vibrational state satisfying the feature of a predetermined autocorrelation order according to the first preferred embodiment by vibrating air surrounding persons in the super-high-frequency band exceeding the audible range according to the first preferred embodiment.

FIG. 57 is a side view showing an example of a vibrating object in a vibrational state satisfying the feature of the predetermined autocorrelation order introduced by vibrating air that is the object surrounding persons in the super-high-frequency band according to the present preferred embodiment. Referring to FIG. 57, when a vibration that scarcely contain super-high-frequency components exceeding the audible range like the sound of a sound source 561 of, for example, a piano or the like is generated in the space that surrounds listeners 563 sitting on chairs 562, originally the fundamental brain activation effect is not introduced, whereas the fundamental brain activation effect can be introduced by the decisive factor of the existence of air in the vibrational state in the super-high-frequency band (inaudible). In this case, the vibrating object may be a gas, a liquid or a solid other than air.

The existence of the vibrating object in the vibrational state introduces the activation of the fundamental brain network system including the reward system neural circuit responsible for the generation of reactions of pleasure, beauty and emotion in a human being. For example, even with the performance of a music having a sound source that scarcely contains the super-high-frequency components originally having the autocorrelation order and hardly introduce the fundamental brain activation effect like, for example, a piano music, the aesthetic sensitivities of the audiences who are appreciating the music are enhanced, and the reactions of pleasure, beauty and emotion are more remarkably introduced to allow the sensuous artistic value to be heightened by activating the fundamental brain network system with the application of the present invention. In addition, by leading the autonomic neural circuit, the endocrine system and the immune system responsible for the homeostatic maintenance and biophylaxis of the whole body to satisfactory states through the fundamental brain, it can contribution to human health promotion. Needless to say, the aforementioned vibrational state of the vibrating object cannot be perceived by human beings, and therefore, it does not hinder the appreciation of music or the like. Further, even when the super-high-frequency components having the predetermined autocorrelation order are generated by, for example, an orchestra that performs on the stage of a concert hall, the super-high-frequency components are rapidly attenuated in accordance with the distance. Therefore, in contrast to the fact that the fundamental brain activation effect cannot always be introduced to all persons in back seats, the fundamental brain activation effect can be introduced to all persons in arbitrary places by virtue of the existence of the vibrating object in the aforementioned vibrational state.

Figure 58:
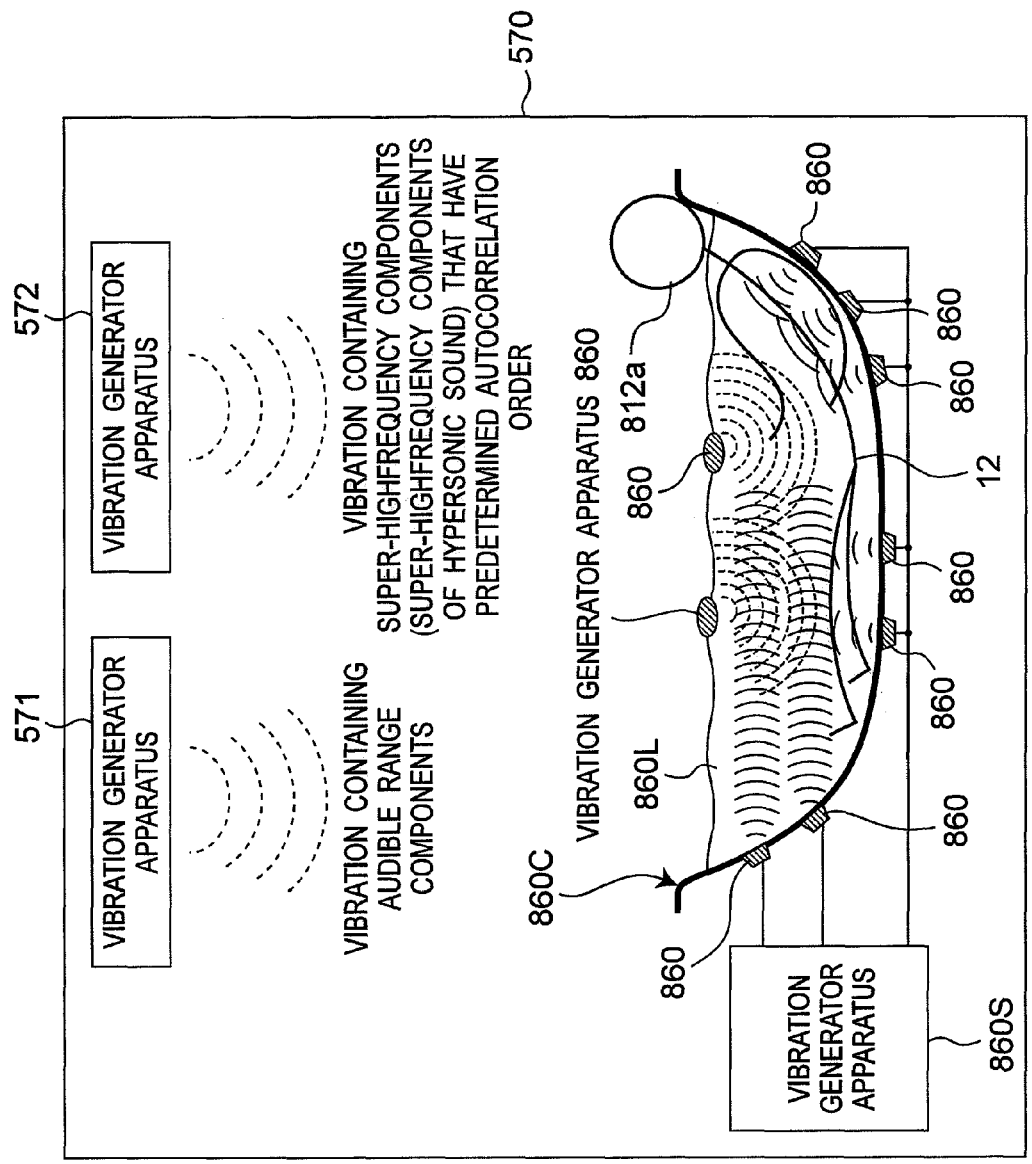
FIG. 58 is a sectional view showing an example of a vibrating object in a bathtub according to the first preferred embodiment.

FIG. 58 is a block diagram showing an example of a vibrating object in a bathtub according to the present preferred embodiment. FIG. 58 shows an example in which, by applying a vibration from vibration generating apparatuses 571, 572 and 860 installed in a bathroom and a bathtub in a space 570 of the bathroom or the like, air surrounding the head portion 812a of a listener 812 and water or hot water surrounding the human body trunk and four limbs are led to vibrating bodies that are in a vibrational state having the predetermined autocorrelation order and capable of introducing the fundamental brain activation effect. In this case, although the listener 812 is located concurrently in the two different vibrating bodies, the listener 812 may be located in a vibrational state in which either one of the liquid and the gas has the predetermined feature.

Next, an implemental example concerning a signal of a vibration (hypersonic sound) that contains audible range components and super-high-frequency components having the predetermined autocorrelation order and can introduce the fundamental brain activation effect, i.e., a vibration signal recorded in a recording medium or a vibration signal transmitted and distributed by a communication system is described below.

In the implemental examples described in detail with reference to FIGS. 51 to 56, the vibration signal of the tropical rain forest environmental sound generated in the urban district spaces corresponds to the present implemental example. The vibration signal generated in the urban district spaces was provided by "THE ENVIRONPHONY II (Universal Symphony No. 2 Environphony II)" (composed and organized by Shoji Yamashiro) of a creation constituted by adding vibration signals of a synthesized sound by a synthesizer, a native musical instrument sound and the like to the main vibration signal of the tropical rain forest environmental sound that could introduce the fundamental brain activation effect, the creation being recorded into an optical disk served as a recording medium by using the high-speed sampling 1-bit quantization system. An output signal reproduced from the vibration signal recorded in the recording medium by using a reproducing apparatus was transmitted to a plurality of vibration generating apparatuses installed in the objective urban district spaces by using an optical fiber cable. The vibration signals inputted to the vibration generating apparatuses via the transmission system was amplified, transduced into aerial vibrations by loudspeakers and presented to the spaces.

Second Preferred Embodiment

In the second preferred embodiment of the present invention, a vibration generating apparatus and method including a vibration complementing apparatus to add a vibration signal that can introduce the fundamental brain activation effect to an original vibration signal that does not introduce the fundamental brain activation effect is described below.

Almost all the audio signals in the audio formats, which are recorded in the audio information media of Compact Discs (CD), Mini Discs (MD) and solid memories widely popularized in the contemporary society and outputted by a portable player, and audio signals in the digital formats, which are transmitted and distributed via broadcasting and communication systems and so on, can neither record nor reproduce super-high-frequency components, and therefore, they are unable to generate hypersonic sounds and activate the fundamental brain. On the other hand, even in the digital media having formats capable of performing recording and transmission to a band considerably exceeding the audible range upper limit, such as Super Audio CD (SACD), DVD audio, soundtracks of Blu-ray Disc (BD) and network transmission by high-speed optical communications and the like, which have appeared in recent years, it is ordinary that they can neither generate a hypersonic sound nor introduce the fundamental brain activation effect since no super-high-frequency component is contained in the vibration signals recorded in the recording media, i.e., the contents due to limitations in the vibration generating function owned by sound sources and limitations in the capabilities of the recording and editing apparatuses and the like. Accordingly, there is such a problem that the vibrations generated by the vibration sources of the existent huge amount of record libraries and the vibration generating apparatuses not only significantly impair the sensuous artistic values because they cannot introduce the fundamental brain activation effect but also rather induce various modern diseases due to deterioration in the fundamental brain activation, and this leads to high possibilities of significantly threatening the comfort and safety of the modern people.

Against such problems, by adding the vibration signals that contain the super-high-frequency components having the predetermined autocorrelation order to the existent huge amount of original vibration signals that cannot introduce the fundamental brain activation effect by various means, the present preferred embodiment makes it possible to easily generate hypersonic sounds voluminously in quality and quantity. By applying them to human beings, the effects of inducing activation of the fundamental brain network system including the reward system neural circuit responsible for the generation of reactions of pleasure, beauty and emotion, and the nerve center of the autonomic neural circuit, the endocrine system and the immune system responsible for homeostatic maintenance and biophylaxis in a human being, consequently increasing the expressive effect of the original vibration signals inclusive of the huge amount of already accumulated record libraries, heightening the sensuous artistic value, concurrently promoting the safety of the person who listens to it, and ameliorating and improving the physical state are obtained.

The second preferred embodiment is characterized by including addition means for adding vibration signal components that can introduce the fundamental brain activation effect to an original vibration signal that is a vibration containing components within a range of 20 Hz to 15 kHz or 20 kHz in the audible frequency range perceivable as a sound by human beings and does not introduce the fundamental brain activation effect because it does not contain super-high-frequency components within a range exceeding the audible frequency range up to a predetermined maximum frequency (e.g., 88.2 kHz, 96 kHz, 100 kHz, 176.4 kHz, 192 kHz, 200 kHz, 300 kHz, 500 kHz or 1 MHz) or an original vibration signal that do not introduce the fundamental brain activation effect because it satisfies neither the first property nor the second property on the autocorrelation order while containing the super-high-frequency components, and outputs a signal of the addition result, thereby generating a vibration signal (hypersonic sound signal) having the features of the conditions of the properties. In this case, the original vibration signal is the objective vibration signal to be complemented by being inputted to the vibration complementing apparatus, or a vibration signal not having the fundamental brain activation effect because it contains no super-high-frequency component or does not have the fundamental brain activation effect because it satisfies neither the first property nor the second property on the autocorrelation order while containing super-high-frequency components.

Moreover, the second preferred embodiment is characterized by including means for generating a vibration (hypersonic sound) capable of introducing the fundamental brain activation effect by imparting either one of the first property and the second property on the autocorrelation order by processing the original vibration signal not having the fundamental brain activation effect because it satisfies neither the first property nor the second property on the autocorrelation order while containing the super-high-frequency components within the range exceeding the audible range upper limit frequency perceivable as a sound by human beings up to the predetermined maximum frequency.

Further, the second preferred embodiment is a vibration generating apparatus that performs enhancement and impartation of effective vibration components and attenuation and removal of unnecessary vibration components by using an elastic vibrating object and characterized in by including means for emphasizing the effect of a vibration (hypersonic sound) that can introduce the fundamental brain activation effect by applying a vibration signal to an elastic vibrating object, processing the vibration applied by using the applied vibration characteristics owned by the elastic vibrating object, thereby enhancing or imparting at least either one of the first property and the second property on the autocorrelation order in the signal, and attenuating or removing vibration components that cannot exist in the natural elastic vibrating object although it exists as an electric signal and do not introduce the fundamental brain activation effect.

First of all, an implemental example concerning an apparatus that complements an original vibration signal that does not introduce the fundamental brain activation effect with a vibration that can introduce the fundamental brain activation effect is described below.

Figure 59:
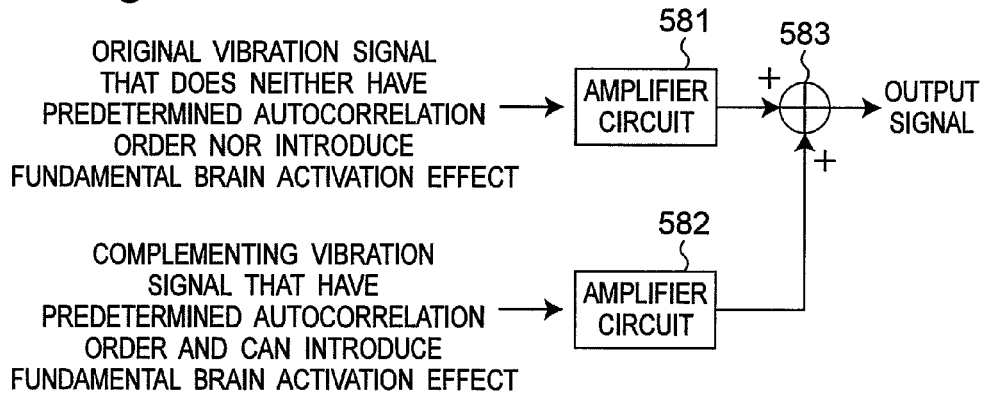
FIG. 59 is a block diagram of an apparatus that generates an output signal (hypersonic sound signal) capable of introducing the fundamental brain activation effect by adding a vibration signal, which has a predetermined autocorrelation order and can introduce the fundamental brain activation effect, to an original vibration signal that does neither have the predetermined autocorrelation order nor introduce the fundamental brain activation effect according to a second preferred embodiment of the present invention.

FIG. 59 is a block diagram of an apparatus that generates an output signal capable of introducing the fundamental brain activation effect by adding a vibration signal capable of introducing the fundamental brain activation effect (having the aforementioned autocorrelation order (and so forth in the present specification)) to an original vibration signal that does not introduce the fundamental brain activation effect (not having the aforementioned autocorrelation order (and so forth in the present specification)) according to the second preferred embodiment. It is noted that each vibration signal is generated by, for example, a vibration signal storage device and its reproducing circuit. Referring to FIG. 59, vibration signals are amplified by amplifier circuits 581 and 582 and thereafter added together by an adder 583. By this apparatus, even if a vibration signal that does neither contain super-high-frequency components nor introduce the fundamental brain activation effect like, for example, a piano sound is inputted, a vibration signal (hypersonic sound signal) that can introduce the fundamental brain activation effect can be outputted by complementing it with a vibration signal that contains super-high-frequency components and have the feature of the autocorrelation order. By thus generating the vibration (hypersonic sound) that contains the super-high-frequency components having the predetermined autocorrelation order, the effects of inducing activation of the fundamental brain network system including the reward system neural circuit responsible for the generation of reactions of pleasure, beauty and emotion, and the nerve center of the autonomic neural circuit, the endocrine system and the immune system responsible for homeostatic maintenance and biophylaxis in a human being, enhancing the aesthetic sensitivity and ameliorating and improving the physical state are obtained.

Figure 60:
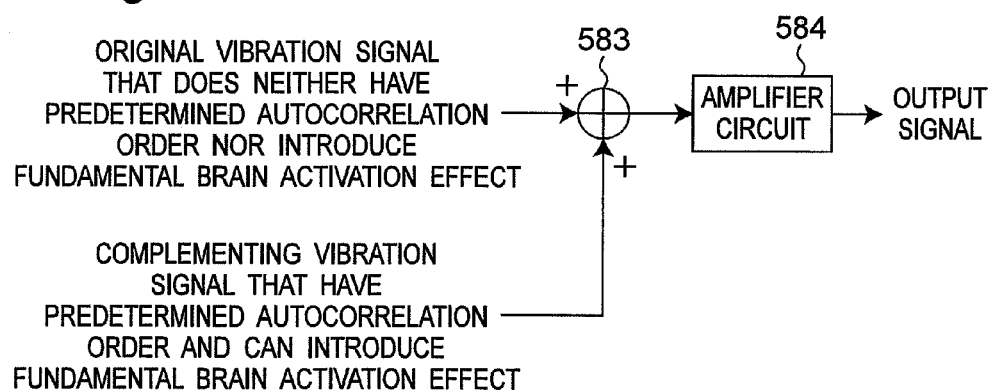
FIG. 60 is a block diagram showing a modified preferred embodiment of the apparatus of FIG. 59.

FIG. 60 is a block diagram showing a modified preferred embodiment of the apparatus of FIG. 59. Referring to FIG. 60, an original vibration signal that does not introduce the fundamental brain activation effect and a vibration signal that can introduce the fundamental brain activation effect are added together by an adder 583 and inputted to an identical amplifier 584, thereby obtaining an output signal (hypersonic sound signal) that can introduce the fundamental brain activation effect.

Figure 61:
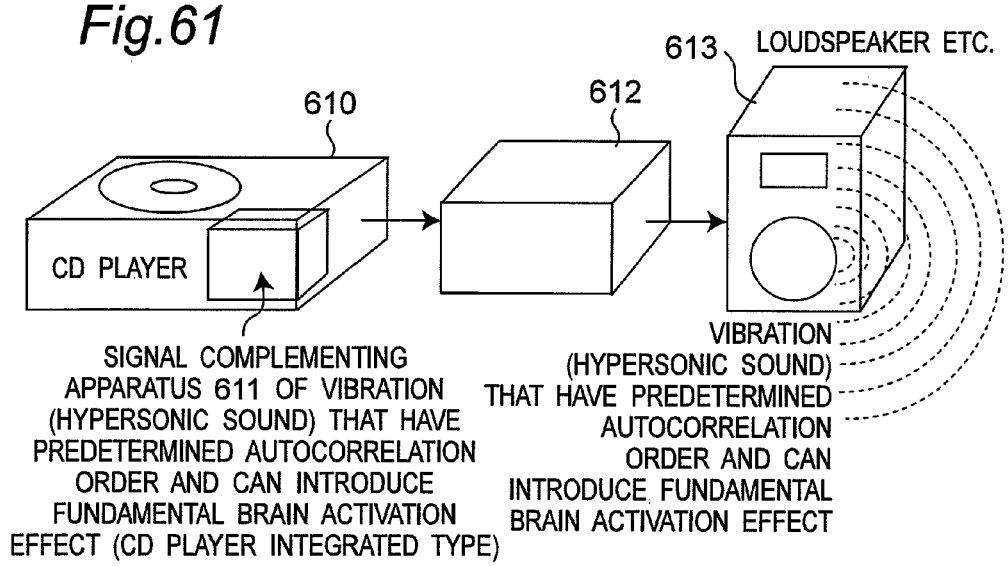
FIG. 61 is a perspective view showing an example of a vibration complementing apparatus to add a vibration signal that can introduce the fundamental brain activation effect to an original vibration that does not introduce the fundamental brain activation effect according to the second preferred embodiment.
Figure 62:
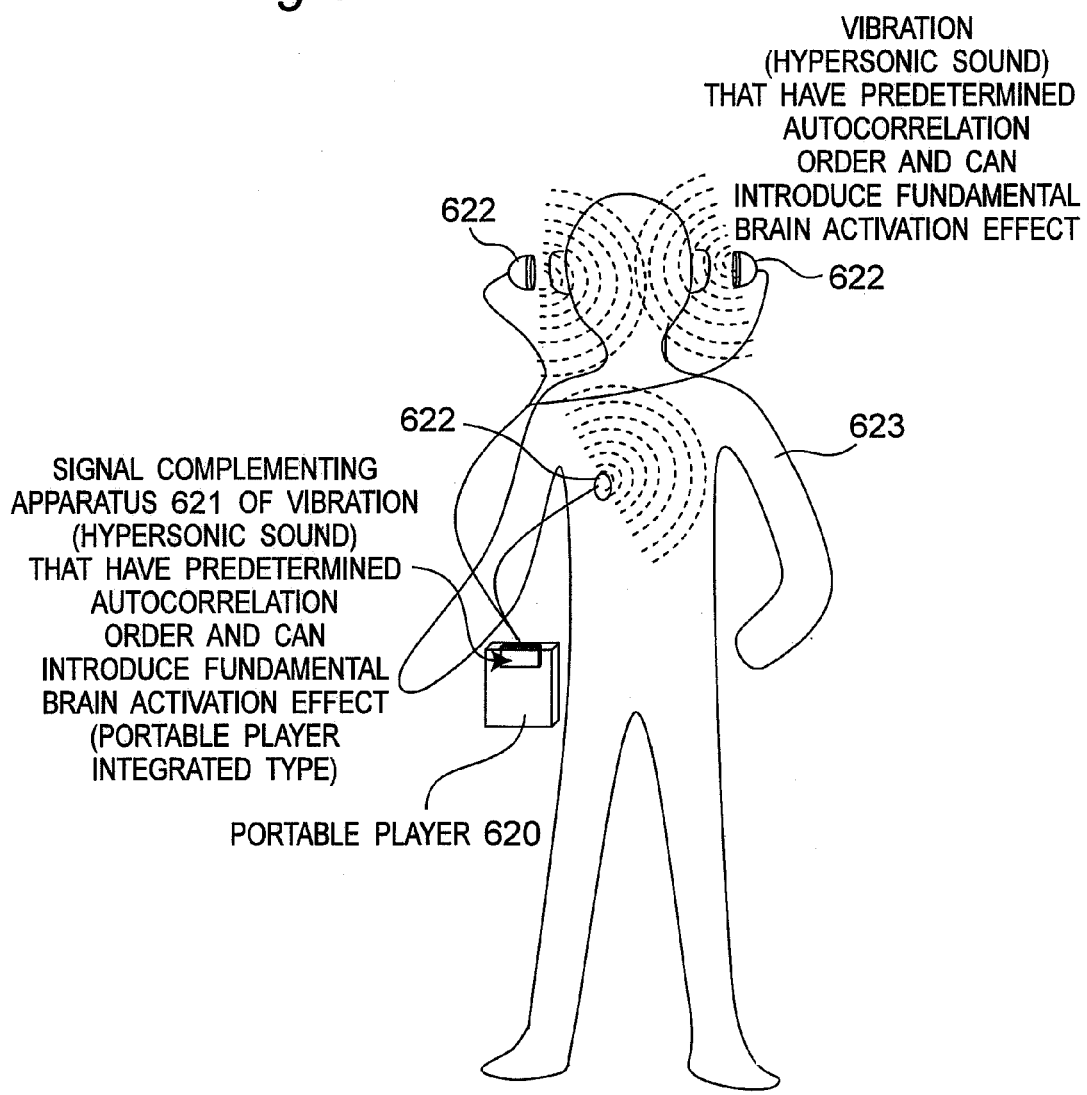
FIG. 62 is a perspective view showing an example of a vibration complementing apparatus to add a vibration signal (hypersonic sound signal) that can introduce the fundamental brain activation effect to an original vibration that does not introduce the fundamental brain activation effect and is outputted from a portable player or the like according to the second preferred embodiment.
Figure 63:
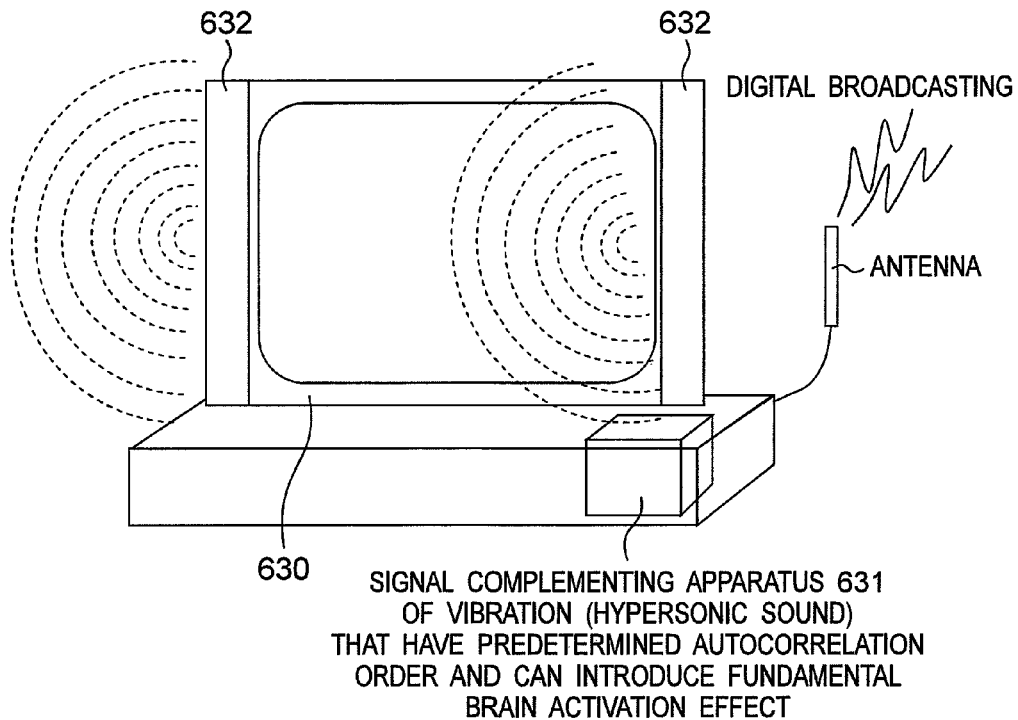
FIG. 63 is a perspective view showing an example of a vibration complementing apparatus to add a vibration signal (hypersonic sound signal) that can introduce the fundamental brain activation effect to an original vibration signal that does not introduce the fundamental brain activation effect and is outputted from a broadcasting receiver or the like according to the second preferred embodiment.

FIGS. 61 to 63 show concrete applications. Currently, a great number of digital formats that cannot record super-high-frequency components and analog systems having a bandwidth similarly incapable of recording super-high-frequency components are used in the package media and transmission and distribution of vibration signals of musics, sounds and the like via broadcastings, telecommunications and so on. However, a vibration obtained by reproducing the vibration signals recorded and transmitted by these systems cannot introduce the fundamental brain activation effect. By using the apparatus of the present invention, it becomes possible to apply a vibration (hypersonic sound) that can introduce the fundamental brain activation effect to human beings by utilizing the contents that do not introduce the fundamental brain activation effect, the contents being accumulated, transmitted and distributed by the existent systems widely popularized in the current society.

FIG. 61 is a perspective view showing an example of a vibration generating apparatus including a vibration complementing apparatus to add a vibration signal that can introduce the fundamental brain activation effect to an original vibration that does not introduce the fundamental brain activation effect according to the second preferred embodiment. That is, it is an example of a vibration complementing apparatus to add a vibration signal that can introduce the fundamental brain activation effect to an original vibration signal of the signals in the digital formats that can neither record super-high-frequency components nor introduce the fundamental brain activation effect such as the signals of music CDs. The vibration complementing apparatus 611 is mounted in a CD player 610 and internally integrated with a variety of kinds of storage devices such as a solid memory in which the vibration signal that contains super-high-frequency components and has the feature of the autocorrelation order satisfying the conditions of the aforementioned properties. This vibration complementing apparatus reads the vibration signal that can introduce the fundamental brain activation effect from the storage device, thereafter adds it to the original vibration signal that contains no super-high-frequency component read from a CD, and then outputs a vibration signal from the CD player 610. The outputted vibration signal is transduced into an aerial vibration by a loudspeaker 613 or the like via an amplifier 612. In this case, the transduced aerial vibration is the vibration (hypersonic sound) that can introduce the fundamental brain activation effect. Although the above-mentioned vibration complementing apparatus is exemplified by the CD player integrated type, it may be an external type. Moreover, although the example in which the complementing is achieved by using the vibration signal that can introduce the preset fundamental brain activation effect in this case, the complementing can also be achieved by using a vibration signal that can introduce the fundamental brain activation effect selected from a plurality of candidates by the user.

The objective original vibration signals of this vibration complementing apparatus include vibration signals recorded in digital formats that cannot record super-high-frequency components in a storage media such as DVD videos, Blu-ray Discs and hard disks, vibration signals used in equipment using formats that can neither record nor reproduce super-high-frequency components such as VR systems, attraction systems of Theme Parks, game machines and game software, vibration signals that are transmitted and distributed via broadcastings and telecommunications using formats that cannot transmit super-high-frequency components such as telephones, TV conference systems and wireless apparatuses, and vibration signals obtained by transducing the vibration of a solid, a liquid, a gas or the like into an electric signal by a transducer by using an apparatus that can neither transduce nor transmit super-high-frequency components, besides the aforementioned CDs. Moreover, even a vibration signal recorded in a format that can record super-high-frequency components in a storage medium as described above, or even a vibration signal obtained by transducing the vibration of a solid, a liquid, a gas or the like into an electric signal by a transducer by using an apparatus that can transduce and transmit super-high-frequency components, becomes the object of this vibration complementing apparatus when the vibration does neither have the required structure nor introduce the fundamental brain activation effect.

By using this apparatus, it becomes possible to apply the vibration (hypersonic sound) that can introduce the fundamental brain activation effect to human beings by utilizing the existent huge amount of contents recording the vibration signals in the digital formats that can neither record the super-high-frequency components nor introduce the fundamental brain activation effect. Moreover, it becomes possible to form a vibration (hypersonic sound) that can introduce the fundamental brain activation effect and apply it to human beings by utilizing the contents constituted of vibration signals that do not introduce the fundamental brain activation effect and are expected to be produced continuously in the future while utilizing the formats that can record super-high-frequency components.

FIG. 62 is a perspective view showing an example of a vibration complementing apparatus to add a vibration signal that can introduce the fundamental brain activation effect to an original vibration that does not introduce the fundamental brain activation effect and is outputted from a portable player or the like according to the second preferred embodiment. FIG. 62 shows an example of a vibration complementing apparatus 621 to add a vibration signal that contains super-high-frequency components having the predetermined autocorrelation order and can introduce the fundamental brain activation effect to an original vibration signal of the signals in the digital formats that can neither record super-high-frequency components nor introduce the fundamental brain activation effect such as the signal of a portable player 621. This vibration complementing apparatus 621 is mounted in the portable player 620 and internally integrated with a storage device such as a solid memory in which the vibration signal that contains super-high-frequency components and has the feature of the autocorrelation order satisfying the conditions of the aforementioned properties. The vibration complementing apparatus 621 has a function to read the vibration signal that can introduce the fundamental brain activation effect from the storage device, add it to the original vibration signal that does not contain the super-high-frequency components read from the solid memory or the like of the portable player 620 and thereafter output the vibration signal from the portable player. The added signal is applied to a person 623 by a headphone, earphone 622 or an apparatus 622 or the like to apply the vibration to the body surface. In this case, the applied vibration is the vibration (hypersonic sound) that can introduce the fundamental brain activation effect. Although the vibration complementing apparatus 620 is described by the example of the portable player integrated type, it may be an external type.

The objective original vibration signals of this vibration complementing apparatus 620 include signals in the digital formats that cannot record the super-high-frequency components transmitted and distributed via communications of the current one-segment or the like besides the signals of musics recorded in the digital formats that cannot record super-high-frequency components in a variety of kinds of storage media such as a solid memory.

By using the apparatus of this implemental example, it becomes possible to apply the vibration (hypersonic sound) that can introduce the fundamental brain activation effect to human beings by utilizing the contents of musics in the digital formats that can neither record super-high-frequency components nor introduce the fundamental brain activation effect for use in the existent portable player and the like.

FIG. 63 is a perspective view showing an example of a vibration complementing apparatus to add a vibration signal that can introduce the fundamental brain activation effect to an original vibration signal that does not introduce the fundamental brain activation effect and is outputted from a broadcasting receiver or the like according to the second preferred embodiment. FIG. 63 shows an example of a vibration complementing apparatus to add a vibration signal containing the super-high-frequency components that have the predetermined autocorrelation order and can introduce the fundamental brain activation effect to an original vibration signal of a vibration signal transmitted in a format that does neither contain the super-high-frequency components nor can introduce the fundamental brain activation effect, such as the signal of a broadcasting receiver such as a television receiver 630. This vibration complementing apparatus 631 is mounted in the broadcasting receiver such as the television receiver 630 and internally integrated with a storage device such as a solid memory in which the vibration signal that contains the super-high-frequency components and has the feature of the autocorrelation order satisfying the conditions of the aforementioned properties. This vibration complementing apparatus 631 has a function to read a vibration signal that can introduce the fundamental brain activation effect from the storage device, add it to the received vibration signal that contains no super-high-frequency component and thereafter output the vibration signal. The added signal is transduced into an aerial vibration by a loudspeaker 632 or the like attached to the broadcasting receiver. In this case, the transduced aerial vibration is the vibration (hypersonic sound) that can introduce the fundamental brain activation effect. Although the vibration complementing apparatus 631 is exemplified by the integrated type, it may be an external type. Moreover, it is possible to automatically complement the stored signal or to allow the user to select his or her favorite vibration signal to achieve the complementing.

The objective original vibration signals of this vibration complementing apparatus include signals of digital formats and analog formats that cannot transmit the super-high-frequency components transmitted and distributed via communications of the current terrestrial digital broadcastings, BS digital broadcastings, analog TV broadcastings, AM radio broadcastings, FM radio broadcastings, Internet, and the like, telephone lines, wireless communications, intercoms, interphones, and the like.

By using the apparatus of the present implemental example, it becomes possible to apply a vibration (hypersonic sound) that can introduce the fundamental brain activation effect to human beings by utilizing the vibration signals transmitted by the existing broadcastings and the like.

FIG. 103 is a block diagram showing an example of an electronic musical instrument apparatus 440 including a vibration complementing apparatus to add a vibration signal that contains super-high-frequency components having the predetermined autocorrelation order to an original vibration that does not introduce the fundamental brain activation effect and is generated by giving a performance with the electronic musical instrument 441 according to the second preferred embodiment, and FIG. 104 is a perspective view showing an example of its external appearance. The electronic musical instrument 441 such as the existent digital synthesizer 444 uses a digital format that cannot perform recording and reproducing of super-high-frequency components, and therefore, the vibration of the performance sound contains no super-high-frequency component and cannot introduce the fundamental brain activation effect. Accordingly, referring to FIGS. 103 and 104, the vibration complementing apparatus uses the vibration signal of the performance sound of the electronic musical instrument as an original vibration signal, reads a vibration signal that can introduce the fundamental brain activation effect from a complementing vibration source 442, and adds it to the original vibration signal by an adder 443, thereby outputting a signal (hypersonic sound signal) of the vibration that introduces the fundamental brain activation effect because it contains super-high-frequency components having the predetermined autocorrelation order. Although this vibration complementing apparatus is mounted in the electronic musical instrument 441 of FIG. 104, it may be external or exist independently of the electronic musical instrument 441 without being limited to this. Moreover, the complementing vibration source 442 may be internally integrated with a variety of kinds of storage devices such as a solid memory in which the vibration signal that can introduce the fundamental brain activation effect is recorded or supplied as a vibration signal that is synthesized by an analog synthesizer or the like and can introduce the fundamental brain activation effect by telecommunications or the like.

Although the digital synthesizer 444 is taken as an example above, electronic musical instruments and karaoke systems and the like besides this are allowed to have the vibration signal of their performance sounds similarly complemented with a vibration signal that can introduce the fundamental brain activation effect. Otherwise, it is also possible to transduce the vibration of the performance sound of an acoustic musical instrument into an electric signal by a microphone or the like and complement it with a vibration signal that can introduce the fundamental brain activation effect. Furthermore, complementing with a vibration signal that can introduce the fundamental brain activation effect can be similarly performed by the vibration complementing apparatus also in the so-called PA (public-address) that reproduces the performance of such musical instruments, singing and the like by once transducing it into a signal in a concert hall or the like.

Next, an implemental example corresponding to a vibration complementing apparatus combined with the existent band expanding is described below.

In recent years, a variety of band expanding methods are proposed as a technique to complement a vibration signal from which the super-high-frequency components have dropped out with super-high-frequency components. However, considering that examples in which a certain kind of artificially synthesized super-high-frequency components does not develop the fundamental brain activation effect or conversely deteriorates the fundamental brain activity are reported, there is such a problem that it is necessary to carefully examine whether the structure of the super-high-frequency components artificially expanded by a band expanding method is effective and safe for human beings.

Regarding this problem, the present implemental example obtains the effects of promoting the safety of the band-expanded vibration signal, inducing the activation of the fundamental brain network, enhancing the aesthetic sensibility and ameliorating and improving the physical state by complementing with the vibration signal of a hypersonic sound or its super-high-frequency components of which the effect of introducing the fundamental brain activation effect is guaranteed.

Figure 64:
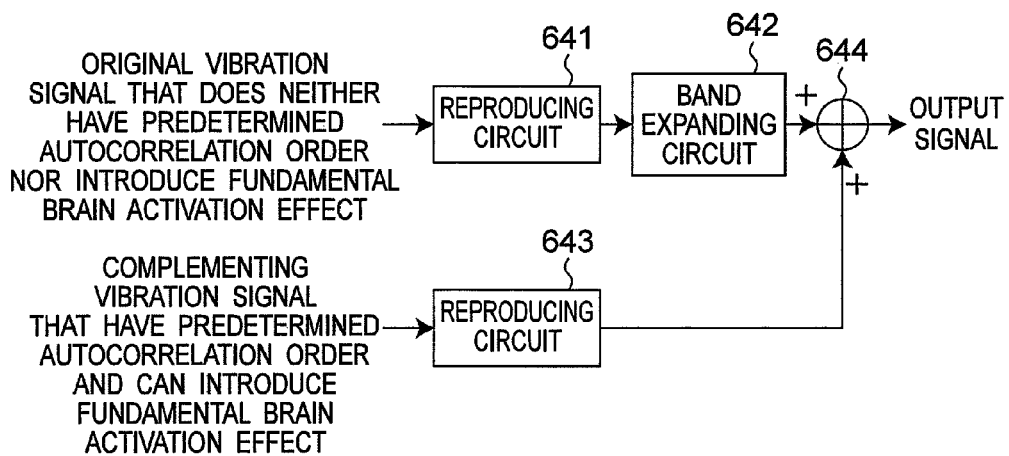
FIG. 64 is a block diagram showing an example of a vibration complementing apparatus using the band expanding means of the existing technology together with addition means of a vibration (hypersonic sound) capable of introducing the fundamental brain activation effect according to the second preferred embodiment.

FIG. 64 is a block diagram showing an example of a vibration complementing apparatus that use the band expanding means of the existing technology together with addition means of a vibration that can introduce the fundamental brain activation effect according to the second preferred embodiment. FIG. 64 shows a configuration constituted of a reproducing circuit 641 and a band expanding circuit (also generally referred to as a band expanding circuit) 642 for an original vibration signal that does neither contain super-high-frequency components nor introduce the fundamental brain activation effect, a reproducing circuit 643 for a vibration signal that can introduce the fundamental brain activation effect, and an adder 644 that adds these vibration signals together.

In this case is shown an example of an apparatus, in which the frequency domain of an original vibration signal that does not introduce the fundamental brain activation effect is expanded to a band of not lower than 20 kHz at the human audible frequency upper limit by using the existent band expanding circuit 642 (See, for example, the Patent Documents 6 and 7), and by adding a vibration signal that contain super-high-frequency components having the predetermined autocorrelation order and can introduce the fundamental brain activation effect to a signal, of which the super-high-frequency components are enabled to be generated but it is unclear whether the structure of the vibration satisfies the conditions capable of activating the fundamental brain, by the adder 644, the signal is complemented with the components that satisfy the conditions of the aforementioned properties, consequently generating an output signal (hypersonic sound signal) that can introduce the fundamental brain activation effect. Many of the existent vibration signals that do not introduce the fundamental brain activation effect in a manner similar to that of the case of, for example, the instrument sound of a piano and the existent digital media such as CD, DVD, digital broadcasting scarcely contain vibration components reaching up to 20 kHz at the human audible frequency upper limit. Particularly, if only the super-high-frequency components are added to the original vibration signal when the upper limit of the band of the original vibration is far below 20 kHz, then segmentation occurs between the original vibration and the added super-high-frequency components, and an unnatural power spectrum is to result. By using the existent band expanding circuit together with the original vibration signal having such a feature, it becomes possible to eliminate the segmentation, dropout and unnatural bend in the band between the power spectrum of the audible range components and the power spectrum of the super-high-frequency components and to obtain a more smoothly linked natural power spectrum. Moreover, by virtue of a synergistic effect of the super-high-frequency components of not lower than 20 kHz at the human audible frequency upper limit generated by band expanding and the vibration signal that can introduce the fundamental brain activation effect, a greater fundamental brain activation effect can be expected. By thus generating the vibration (hypersonic sound) that introduces the fundamental brain activation because it contains super-high-frequency components having the predetermined autocorrelation order, the effects of inducing activation of the fundamental brain network system including the reward system neural circuit responsible for the generation of reactions of pleasure, beauty and emotion, and the nerve center of the autonomic neural circuit, the endocrine system and the immune system responsible for the homeostatic maintenance and biophylaxis of the whole body in a human being, enhancing the aesthetic sensibility and ameliorating and improving the physical state are obtained.

Next, an implemental example of a vibration complementing apparatus integrated with a high-pass filter is described below.

Figure 65:
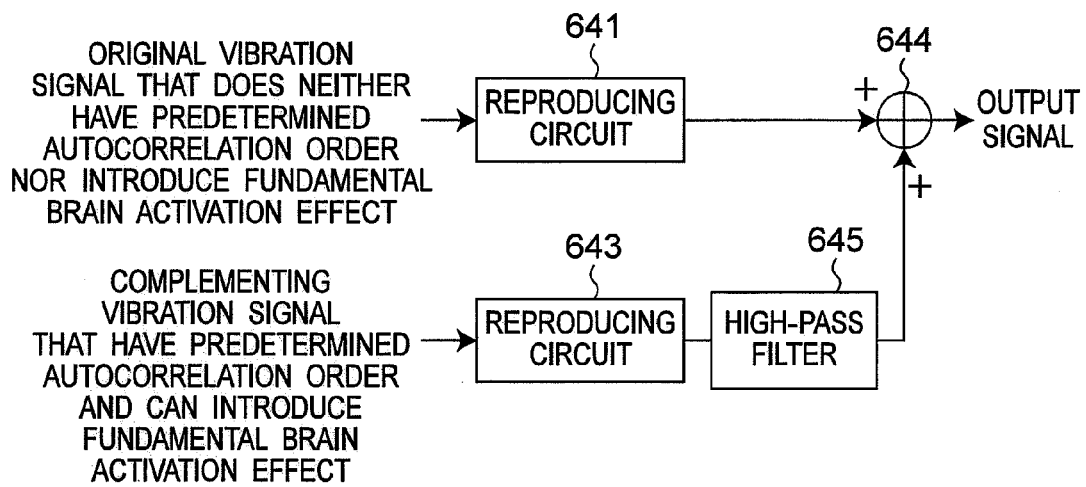
FIG. 65 is a block diagram showing an example of a vibration complementing apparatus that generates a vibration signal capable of introducing the fundamental brain activation effect as an output signal by adding a signal obtained by extracting the super-high-frequency components of a vibration signal (hypersonic sound signal) capable of introducing the fundamental brain activation effect to an original vibration signal according to the second preferred embodiment.

FIG. 65 is a block diagram showing an example of a vibration complementing apparatus that generates a vibration signal (hypersonic sound signal) that can introduce the fundamental brain activation effect as an output signal by adding a signal obtained by extracting the super-high-frequency components of a vibration signal that can introduce the fundamental brain activation effect to an original vibration signal according to the second preferred embodiment. Referring to FIG. 65, by adding a signal obtained by extracting only the super-high-frequency components by filtering a vibration signal that can introduce the fundamental brain activation effect by a high-pass filter 645 or attenuating the audible range components to a considerable extent to an original vibration signal that does neither contain super-high-frequency components nor introduce the fundamental brain activation effect by the adder 644, thereby complementing it with the components satisfying the conditions of the aforementioned properties, and an output signal (hypersonic sound signal) that can introduce the fundamental brain activation effect is generated as a result. If audible range components are contained in the vibration signal that can introduce the fundamental brain activation effect to be added to it, and when the original signal is, for example, a music, it becomes difficult to receive the original vibration as a music due to interference between both of them. Accordingly, by extracting and adding only the super-high-frequency components that are not perceivable as a sound and contained in the vibration signal that can introduce the fundamental brain activation effect, it becomes possible to introduce the fundamental brain activation effect without disturbing the reception of the audible range components of the original vibration. The high-pass filter 645 may be a band-pass filter. Moreover, the existent band expanding circuit of FIG. 64 may be used together with the original vibration signal.

Figure 66:
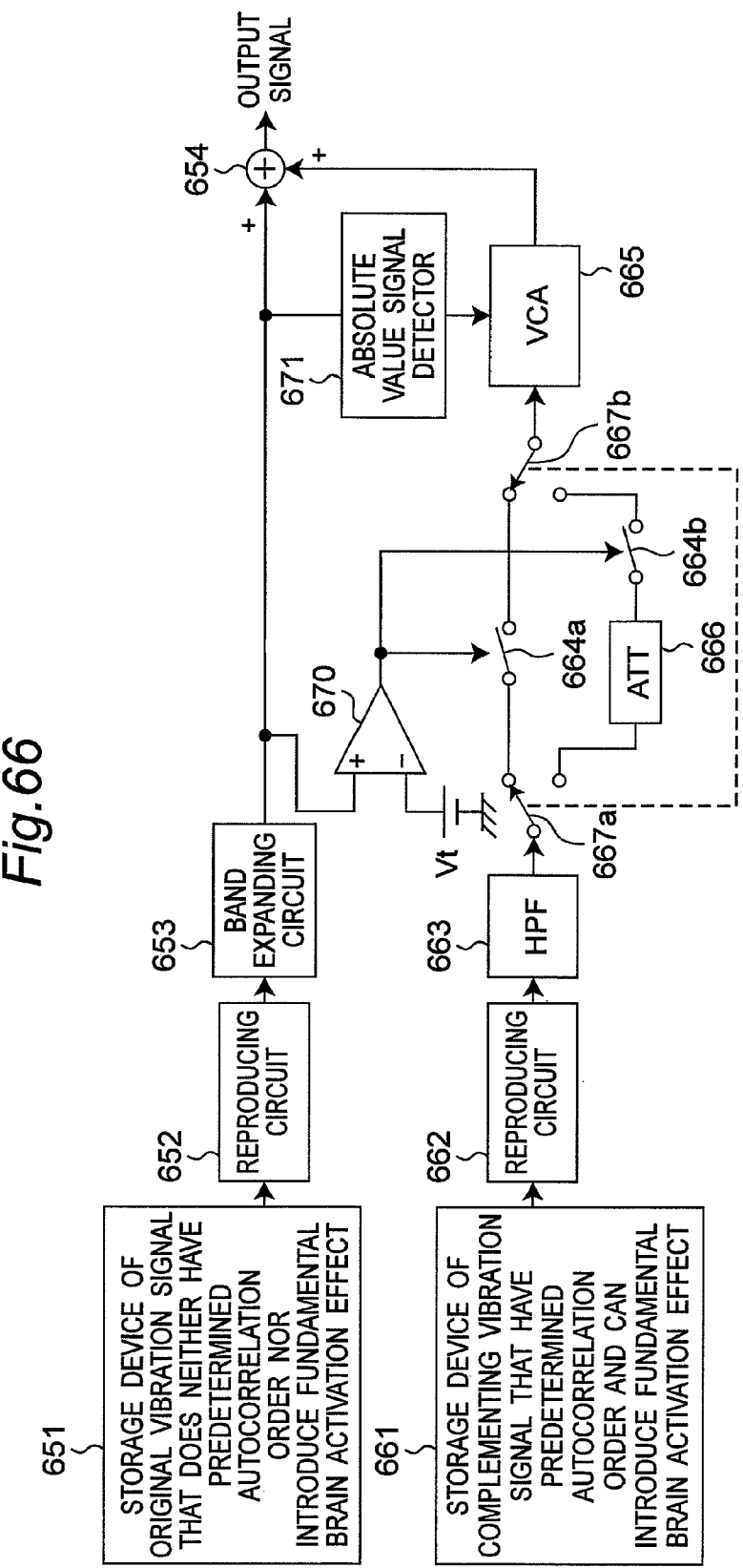
FIG. 66 is a block diagram showing an example of a complementing type vibration signal generating apparatus capable of introducing the fundamental brain activation effect concurrently using the circuits of a band expander, a high-pass filter, a gate apparatus and a voltage-controlled amplifier (VCA) according to the second preferred embodiment.

FIG. 66 is a block diagram showing an example of a complementing type vibration signal generating apparatus that can introduce the fundamental brain activation effect and use the circuit of a band expanding apparatus, a high-pass filter, a gate apparatus and a voltage-controlled amplifier (VCA) together according to the second preferred embodiment. FIG. 66 shows an example of an apparatus, in which, by using the circuit of an existent band expanding circuit 653 (corresponding to 642 of FIG. 64), a high-pass filter 663, a gate apparatus having switches 664a and 664b controlled by a comparator 670, and a voltage-controlled amplifier (VCA) 665 together, as described above, a signal component that can introduce the fundamental brain activation effect is added to the original vibration signal that does not introduce the fundamental brain activation effect at a level strongly correlated to the level of the original vibration, and an output signal (hypersonic sound signal) that can introduce the fundamental brain activation effect is generated as a result.

Data of the vibration signal is read from the storage device 651 of the original vibration signal that does not introduce the fundamental brain activation effect by a reproducing circuit 562, subjected to DA conversion and thereafter to band expanding by the band expanding circuit 653 by using the known band expanding technology and then outputted to a comparator 670, an absolute value signal detector 671 and an adder 654. On the other hand, data of the vibration signal that can introduce the fundamental brain activation effect is read from a storage device 661 of the vibration signal by a reproducing circuit 662, subjected to DA conversion, and thereafter outputted via a high-pass filter 663 and a switch 667a and via a first path of a switch 664a and a second path of an attenuator 666 and a switch 664b and via a switch 667b and a voltage-controlled amplifier (VCA) 665 to the adder 654. In this case, the switches 667a and 667b are mode switches for switchover regarding whether to pass the data through the attenuator 666, and the switches 664a and 664b are gate circuits for switchover regarding whether to pass the vibration signal of each path. The gate circuit performs control so as to turn on the switches 664a and 664b by comparing the magnitude of the vibration signal from the band expanding circuit 653 with a voltage source Vt by a comparator 670 and when it is not lower than a predetermined level. Moreover, the voltage-controlled amplifier 665 changes the level of the vibration signal from the switch 667b in accordance with the absolute value level of the vibration signal from the band expanding circuit 653.

With the above-mentioned configuration, by using the existent band expanding apparatus for the original vibration signal that does not introduce the fundamental brain activation effect, it becomes possible to eliminate the segmentation and dropout in the band between the audible range components and the super-high-frequency components and to obtain a more smoothly linked natural power spectrum. Moreover, by extracting only the super-high-frequency components by filtering the vibration signal that can introduce the fundamental brain activation effect by the high-pass filter 663 and adding it to the original vibration signal, it becomes possible to generate an output signal (hypersonic sound signal) that can introduce the fundamental brain activation effect without influencing the audible range components of the original vibration signal and accordingly without disturbing listening to the audible range components of the original vibration.

The gate apparatus has the operation of opening the gate switches 664a and 664b when the level of the original vibration signal in the signal processing system exceeds a definite value to add the vibration that can introduce the fundamental brain activation effect or closing the gate switches 664a and 664b when the level does not exceed the definite value to perform no addition. By using this apparatus, it becomes possible to avoid the generation of an unnatural state such that, when the level of the original vibration is extremely low or when almost or utterly no original vibration exists, only the super-high-frequency components that do not introduce the fundamental brain activation effect under this condition exists at a high level.

The voltage-controlled amplifier (VCA) 665 has a function to change the amplification factor of the vibration that can introduce the fundamental brain activation effect to be added in correspondence with the original vibration signal level and amplify the vibration signal that can activate the fundamental brain by the amplification factor. In the case of, for example, music, of where the level of the super-high-frequency components is high when the level of the audible range components is high, it is often the case where the levels of both of them have high correlation. By using this apparatus, it becomes possible to add the vibration signal that can introduce the fundamental brain activation effect in a more natural state correlated to the level of the original vibration. Referring to FIG. 66, these additional function apparatuses may be provided by using all of the circuit of the existent band expanding circuit 653, high-pass filter 663, and the gate apparatus having the switches 664a and 664b controlled by the comparator 670, and the voltage-controlled amplifier (VCA) 665 together or using them partially solely or in combination. For example, it is acceptable to use any one of the gate apparatus and the voltage-controlled amplifier (VCA) 665 or use the band expanding circuit 653 and the high-pass filter 663 as occasion demands.

Next, an implemental example concerning a vibration complementing apparatus using a plurality of vibration signals is described below.

Figure 67:
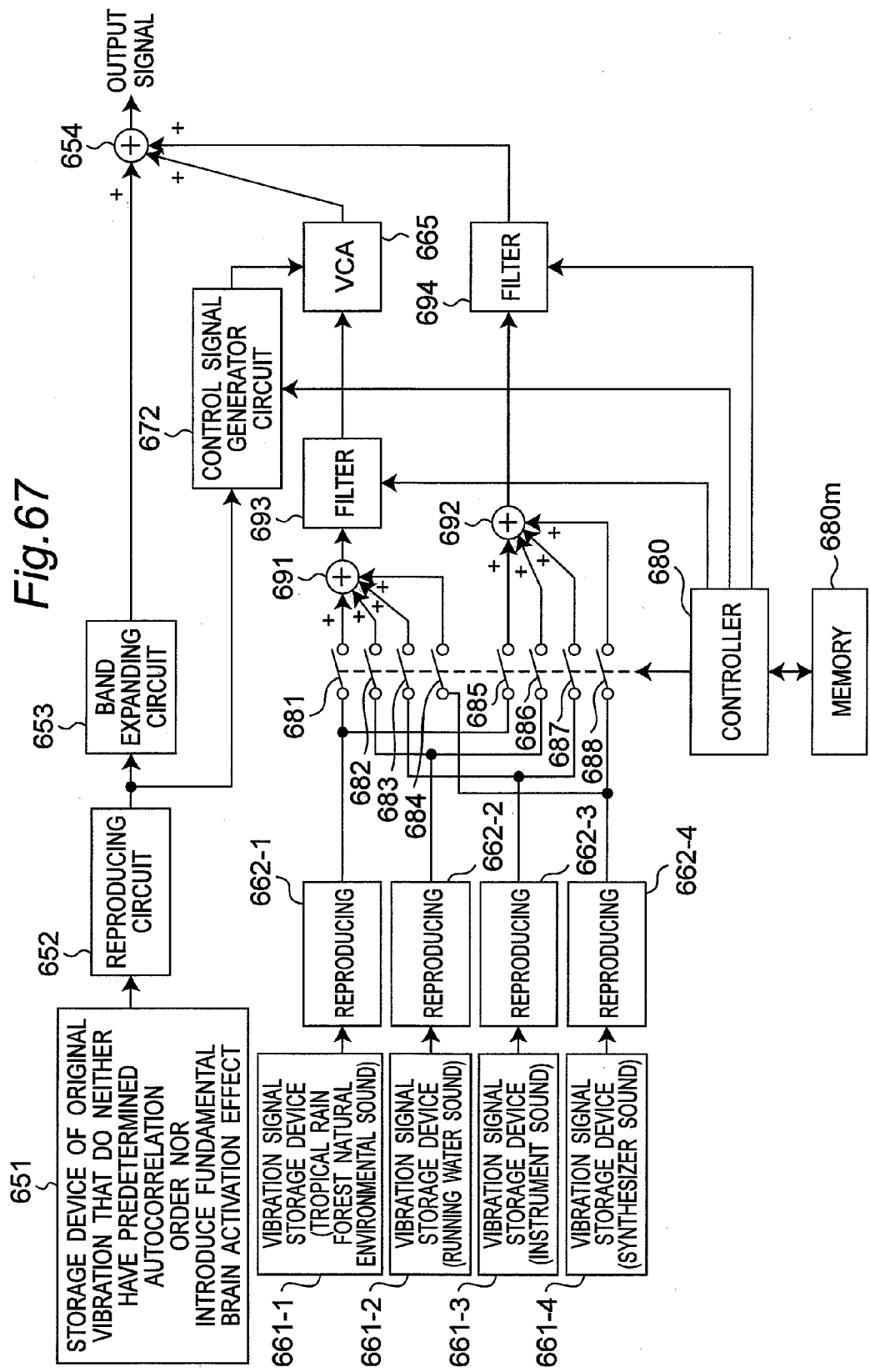
FIG. 67 is a block diagram showing an example of a vibration complementing apparatus that can add a plurality of vibrations (hypersonic sound) capable of introducing the fundamental brain activation effect according to the second preferred embodiment.

FIG. 67 is a block diagram showing an example of a vibration complementing apparatus capable of adding a plurality of vibrations that can introduce the fundamental brain activation effect according to the second preferred embodiment. FIG. 67 shows an example of a vibration complementing apparatus capable of selectively adding one or more from among the plurality of vibration signals that can introduce fundamental brain activation effect to an original vibration signal that does not introduce the fundamental brain activation effect.

Data of complementing vibration signals of a tropical rain forests natural environmental sound, a running water sound, an instrument sound and a synthesized sound are previously stored in vibration signal storage devices 661-1 to 661-4, respectively, and they are read and reproduced by respective reproducing circuits 662-1 to 662-4. Switches 681 to 684 and 685 to 688 are provided for selective switchover regarding whether to make each vibration signal pass through the voltage-controlled amplifier (VCA) 665 and whether to use it as a complementing sound source. Filters 693 and 694 are, for example, high-pass filters, band-pass filters or the like. Moreover, a control signal generating circuit 672 is a circuit such as an absolute value detector 671 to control the operation of the voltage-controlled amplifier 665. A controller 680 controls the operations of switches 681 to 684 and 685 to 688, passbands of filters 693 and 694 and the control signal generating circuit 672 based on a setting table of parameter setting and an operation program stored in a memory 680m. The setting table records settings for controlling these in accordance with the kind of the original vibration signal and/or the complementing vibration signal. In this case, the kind of the complementing vibration signal may be previously set or manually inputted as needed.

In a vibration generating apparatus including the complementing signal generating apparatus configured as above, it is possible to select any one appropriate vibration from the plurality of complementing vibration signals that can introduce the fundamental brain activation effect or to add together a plurality of them by using the controller 680. In the case, the controller 680 controls selection and addition of the complementing vibration signals according to the setting table of the parameter setting and the operation program in the memory 680m. For example, it is acceptable to select a vibration having the autocorrelation order recorded in the natural environment such as a tropical rain forest as a background vibration and consistently add the same. Moreover, in a case where the original vibration signal to be complemented is a music, it is acceptable to select a signal of a vibration having the autocorrelation order recorded by using a musical instrument of the same kind as the musical instrument used in the music as a complementing vibration signal or to add together a plurality of vibrations having the autocorrelation order recorded by using each of a plurality of musical instruments used and use the same. Further, it is also possible to extract only the super-high-frequency components by filtering the selected vibration signal that can introduce the fundamental brain activation effect by the high-pass filters 693 and 694 and add the same. Moreover, the signal level of the vibration that can introduce the fundamental brain activation effect may be amplified so as to correlate to the level of the original vibration signal by using the voltage-controlled amplifier (VCA) 665. Further, it is acceptable to adjust the gain of the amplification factor of the vibration signal that can introduce the fundamental brain activation effect with respect to the level fluctuation of the original vibration via the controller 680.

Since the amount and time duration of the hypersonic sound signal qualified as a complementing vibration signal are witheringly smaller than those of the existent huge amount of original vibration signals that cannot introduce the fundamental brain activation effect, a small amount of complementing vibration signals is to be repetitively used. In contrast to this, the actual vibrations of high naturalness such as the tropical rain forest environmental sound do not have iterative identical vibrations. Such a problem that the vibration generated by the complementing and the actual vibrations of high naturalness have mutually different features occurs at this point.

Regarding this matter, by concurrently using a plurality of complementing vibration signals, it becomes possible to generate a vibration signal that does not generate repetition remarkably for a long time even if each individual is a complementing vibration signal of a limited time duration. For example, a complementing vibration signal group constituted of a plurality of mutually independent vibration currents produced so as not to cause expressive and functional failures by any combination is configured. In this case, after performing recording so that the time durations of the vibration signals come to have mutual prime factor relations in units of, for example, seconds, they are repetitively reproduced at an accuracy such that the mutual deviation is limited to $1/10$ seconds or less. Assuming that the first one has a duration of 3181 seconds and the second one has a duration of 3667 seconds, then it takes 11,164,727 seconds, i.e., 135 days until an identical combination recurs after simultaneous start from the beginning.

The original vibration signal and the plurality of vibration signals that can introduce the fundamental brain activation effect may be signals that are inputted from an external vibration source by wire or wirelessly or signals recorded in the storage device such as a hard disk or a solid memory. Moreover, by using this vibration complementing apparatus, it becomes possible to synthesize a vibration (hypersonic sound), that has the autocorrelation order capable and can most effectively introduce the fundamental brain activation effect in accordance with the kind of the original vibration signal.

Next, as a vibration generating apparatus and method according to the second preferred embodiment, a vibration signal having the predetermined autocorrelation order is generated by performing processing based on the feature of the autocorrelation order owned by a reference surface that can introduce the fundamental brain activation effect on a vibration signal that does not introduce the fundamental brain activation effect because it satisfies neither the first property nor the second property on the autocorrelation order while containing the super-high-frequency components exceeding the human audible range upper limit, and a vibration signal (hypersonic sound signal) that introduce the fundamental brain activation effect is generated by adding the super-high-frequency components to the original vibration signal that does not introduce the fundamental brain activation effect for complementing is described.

Figure 68:
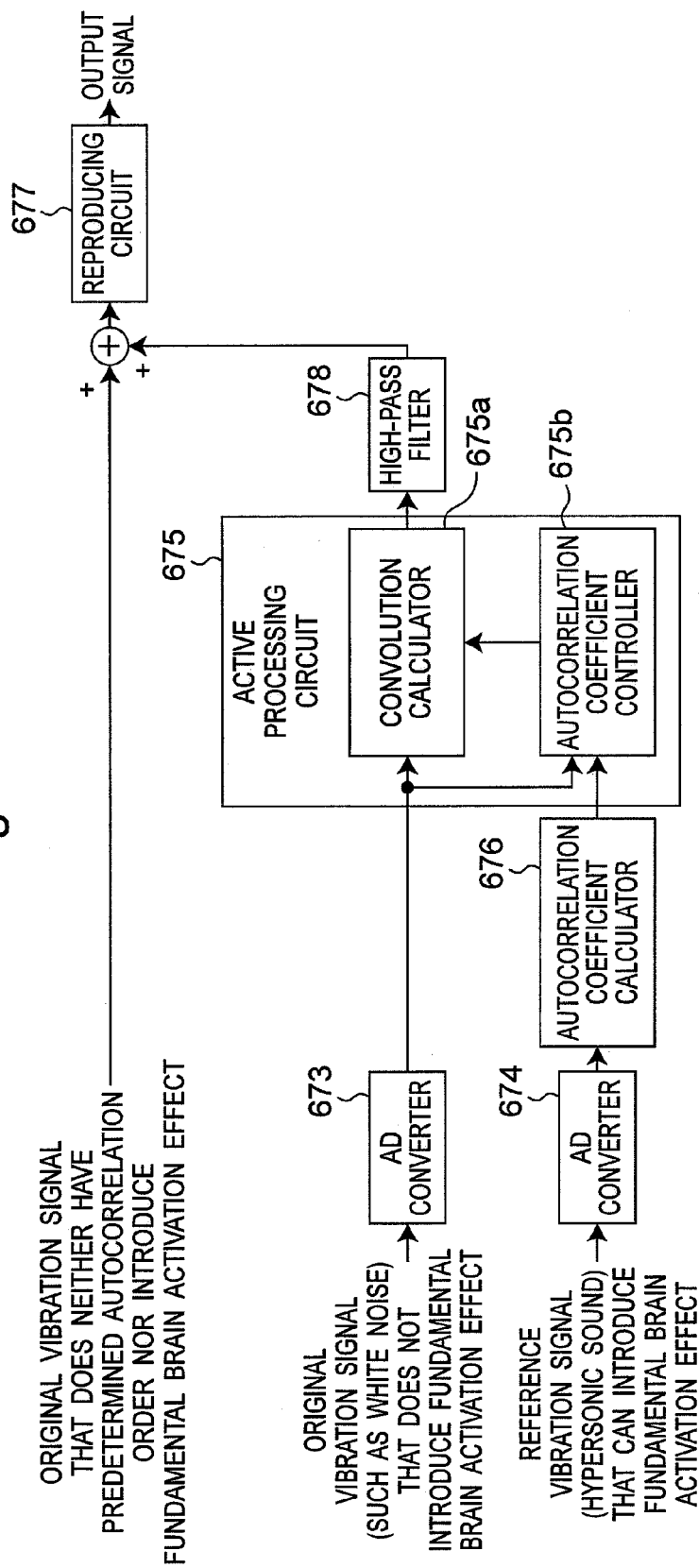
FIG. 68 is a block diagram showing a vibration signal generating apparatus that imparts the predetermined autocorrelation order of a vibration (hypersonic sound) capable of introducing the fundamental brain activation effect by performing processing based on an autocorrelation coefficient representing the property of the autocorrelation order owned by a reference vibration signal capable of introducing the fundamental brain activation effect to a vibration signal that does not introduce the fundamental brain activation effect according to the second preferred embodiment.

FIG. 68 shows a block diagram of a vibration signal generating apparatus that generates a vibration signal (hypersonic sound signal) that introduce the fundamental brain activation effect by analyzing the feature of the autocorrelation order owned by the reference vibration that can introduce the fundamental brain activation effect by using autocorrelation coefficients, generating a vibration signal that has the predetermined autocorrelation order by processing the signal of a vibration (e.g., a white noise) that does not introduce the fundamental brain activation effect, because it satisfies neither the first property nor the second property on the autocorrelation order while containing the super-high-frequency components exceeding the human audible range upper limit based on the result, and by adding the super-high-frequency components to the original vibration signal that does not introduce the fundamental brain activation effect for complementing. By thus generating the vibration (hypersonic sound) that contains the super-high-frequency components having the predetermined autocorrelation order, the effects of inducing activation of the fundamental brain network system including the reward system neural circuit responsible for the generation of reactions of pleasure, beauty and emotion, and the nerve center of the autonomic neural circuit, the endocrine system and the immune system responsible for the homeostatic maintenance and biophylaxis of the whole body in a human being, enhancing the aesthetic sensibility and ameliorating and improving the physical state are obtained.

The operation of the apparatus of FIG. 68 is described below.

Referring to FIG. 68, a reference vibration signal having definite time duration is inputted to an autocorrelation coefficient calculator, and an autocorrelation coefficient matrix of an autocorrelation model suited to a reference vibration signal is calculated by using, for example, the Yule-Walker method. A concrete calculation procedure of the autocorrelation coefficient calculator 676 is as follows.

(1) A reference vibration signal is first inputted to an AD converter 674, and sampled by a sampling frequency $2f_N$ ($f_N$ is the Nyquist frequency, or the highest frequency of the original signal). In this case, $f_N$ needs to sufficiently exceed 20 kHz at the audible range upper limit (e.g., $f_N$=96 kHz). When the reference vibration signal is a digital signal, the AD converter 674 may be eliminated.

(2) A signal having a total duration of T seconds outputted from the AD converter 674 is inputted to the autocorrelation coefficient calculator 676 and divided into "n" unit analysis intervals of duration of $T_E$ seconds (e.g., T=60 seconds, $T_E$=0.1 seconds, n=600).

(3) The time series data for an arbitrary interval is assumed to be x(t) (t=1, 2, ..., $2f_N \times T_E$), and the autocorrelation model of m dimensions representing the current value by using the values at past "m" points is applied. That is, assuming that a1, a2, ..., $a_m$ are autocorrelation coefficients in the autocorrelation model of m dimensions (e.g., m=10) and $\epsilon$(t) applied to it is a random noise, then time series data x(t) is expressed by the following equation:

$$x(t)=a_1x(t-1)+a_2x(t-2)+\ldots+a_mx(t-m)+\epsilon(t).$$

In this case, assuming that the autocorrelation function of the time series data x(t) is $C_k$ (k=1, 2, ..., m) (provided that k is lag time), then the simultaneous equations of the following equation (hereinafter referred to as Yule-Walker equation) holds:

$$\begin{bmatrix} C_0 & C_1 & \cdots & C_m \\ C_1 & C_0 & \cdots & C_{m-1} \\ \vdots & \vdots & \ddots & \vdots \\ C_m & C_{m-1} & \cdots & C_0 \end{bmatrix} \begin{bmatrix} 1 \\ -a_1 \\ \vdots \\ -a_m \end{bmatrix} = \begin{bmatrix} P_m \\ 0 \\ \vdots \\ 0 \end{bmatrix}$$

where $P_m$ is the variance of a difference between a predictive value obtained from the autocorrelation coefficient of:

$$x_p(t)=a_1x(t-1)+a_2x(t-2)+\ldots+a_mx(t-m),$$

and the actually measured value x(t), and generally called the variance of prediction errors.

(4) The Yule-Walker equation, which is a simultaneous equation including m+1 equations, can be solved if there are m+1 unknowns. According to the Yule-Walker method, it is assumed that the autocorrelation function $C_k$ is known, and m+1 variables consisting of $a_1, a_2, \ldots, a_m, P_m$ are unknowns. By using Levinson algorithm, the autocorrelation coefficients are calculated starting from m=1 by successively incrementing m by one (See, for example, the Non-Patent Document 7).

(5) For the divided unit analysis interval "i" (i=1, 2, ..., n), the autocorrelation coefficients calculated by the aforementioned method are assumed to be $a_{i1}, a_{i2}, \ldots, a_{im}$. The autocorrelation coefficients are calculated in all the "n" unit analysis intervals, and the autocorrelation coefficient matrix A of the following equation is formed:

$$A = \begin{bmatrix} a_{11} & a_{12} & \cdots & a_{1m} \\ a_{21} & a_{22} & \cdots & a_{2m} \\ \vdots & \vdots & \ddots & \vdots \\ a_{n1} & a_{n2} & \cdots & a_{nm} \end{bmatrix}$$

In this equation, the i-th row is a row vector having the autocorrelation coefficients $a_{i1}, a_{i2}, \ldots, a_{im}$ of the interval "i" as the elements of the matrix A. The number of rows of the matrix A is the number of intervals (n rows), and the number of columns becomes the number of dimensions of the autocorrelation coefficients (m columns).

Although the calculation example of the autocorrelation coefficient using the Yule-Walker method is described according to the above-mentioned calculation procedure, another method such as the Bergh method or the like. In the case of the Bergh method, unknowns are m+2 variables consisting of $a_1, a_2, \ldots, a_m, P_m, C_m$ in the above-mentioned case (4). In the case, no derivation can be achieved only by m+1 simultaneous equations, and therefore, a condition such that "a sum of variance $P_m$ of prediction errors of both of a case of prediction of the autocorrelation coefficients from the past to the future by forward convolution of time series data and a case of prediction from the future to the past by reverse convolution of time series data by reversing the order of the autocorrelation coefficients is minimized" is added as a new judgment criterion.

Assuming that $\Delta t=1/(2f_N)$ and j is an imaginary unit, then one-side power spectrum Q(f) of the time series data x(t) can be expressed by the following equation, and the information entropy density can also be obtained from it (See "supplementary explanation of the formula" described in detail later):

$$Q(f) = \frac{\Delta t P_m}{\left|1 - \sum_{k=1}^{m} a_k \exp(j2\pi f_k \Delta t)\right|^2}$$

Next, concrete processing of an active processing circuit 675 is described below. In this case, the active processing circuit 675 is constituted of a convolution calculator 675a and an autocorrelation coefficient controller 675b.

The autocorrelation coefficient matrix outputted from the autocorrelation coefficient calculator 676 is inputted to the active processing circuit 675 together with the signal of a vibration (e.g., white noise) that does not introduce the fundamental brain activation effect because it satisfies neither the first property nor the second property on the autocorrelation order while containing super-high-frequency components. In the active processing circuit 675, a convolution calculation between the vibration signal that does not introduce the fundamental brain activation effect and the autocorrelation coefficients that are the row vectors of the autocorrelation coefficient matrix A is performed to generate a vibration signal having the properties on the aforementioned autocorrelation order.

A concrete calculation procedure in the convolution calculator inside the active processing circuit 675 is as follows.

(1) The signal of a vibration (e.g., white noise) that does not introduce the fundamental brain activation effect is first inputted to an AD converter 673 (external circuit of the circuit 675) and sampled by the same sampling frequency $2f_N$ ($f_N$ is the Nyquist frequency, or the maximum frequency of the original signal) as that of the reference signal. The AD converter 675 may be eliminated when the reference vibration signal is a digital signal, whereas resampling is performed by the sampling frequency $2f_N$ when the sampling frequency is different from $2f_N$.

(2) The vibration signal that does not introduce the fundamental brain activation effect and is outputted from the AD converter 673 is subsequently inputted to the active processing circuit 675. The time series data of the signal is divided into unit intervals of duration of $T_E$ seconds, and the time series data for the i-th interval is assumed to be the following:

$$y_i(t) (i=1,2,\ldots,n; t=1,2,\ldots,2f_N \times T_E).$$

(3) The autocorrelation coefficients are inputted from the autocorrelation coefficient calculator 676 to the convolution calculator 675a via an autocorrelation coefficient controller 675b described in the following clause. The convolution calculation of the following equation between the inputted autocorrelation coefficients $a_{i1}, a_{i2}, \ldots, a_{im}$ and the input signal $y_i(t)$ is performed:

$$z_i(t) = a_{i1} y_i(t-1) + a_{i2} y_i(t-2) + \ldots + a_{im} y_i(t-m),$$

where $z_i(t)$ is an output signal, which is obtained by the convolution calculation and serves as a vibration signal, that has the property on the autocorrelation order and can introduce the fundamental brain activation effect.

When the time duration of the vibration signal that does not introduce the fundamental brain activation effect is longer than the time duration of the reference vibration signal, the number of autocorrelation coefficient vectors for performing the convolution calculation becomes insufficient. Accordingly, the autocorrelation coefficient controller 675b has a function to continuously send out autocorrelation coefficients by iterating or generating so that the convolution calculation can be continued how long the time duration of the vibration signal that does not introduce the fundamental brain activation effect is. With this function, it becomes possible to generate the vibration signal having the property on the autocorrelation order for arbitrary time duration, even when the time duration of the reference vibration signal is short. In concrete, it is performed according to the procedure described below.

(1) The autocorrelation coefficient matrix A calculated in the autocorrelation coefficient calculator 676 is inputted to the autocorrelation coefficient controller 675b. In the autocorrelation coefficient controller 675b, the autocorrelation coefficients are sequentially inputted from the first row of the autocorrelation coefficient matrix A to the convolution calculator.

(2) In a case where the inputting of the vibration signal that does not introduce the fundamental brain activation effect is still continued at the time point when the autocorrelation coefficient of the last row (n-th row) of the autocorrelation coefficient matrix A is inputted, any one of the following operations is carried out.

(2-1) Simple iteration: Returning to the first row of the autocorrelation coefficient matrix A, and the autocorrelation coefficients are inputted once again sequentially from the autocorrelation coefficient of the first row to the convolution calculator 675a. When the inputting of the vibration signal that does not introduce the fundamental brain activation effect is still continued at the time point of the last row (n-th row) of the autocorrelation coefficient matrix A, the same operation is performed again. The iteration is thus continued until the vibration signal that does not introduce the fundamental brain activation effect ends.

(2-2) A matrix in which the rows are replaced in a random order: A matrix B obtained by replacing the rows of the first row to the n-th row of the matrix A in a random order is generated. The autocorrelation coefficients of the generated matrix B are sequentially inputted from the autocorrelation coefficient of the first row to the convolution calculator. When the inputting of the vibration signal that does not introduce the fundamental brain activation effect is still continued at the time point of the last row (n-th row) of the autocorrelation coefficient matrix B, the rows of the first row to the n-th row of the matrix A are replaced in a random order to generate another matrix B'. The autocorrelation coefficients of the generated matrix B' are sequentially inputted from the autocorrelation coefficient of the first row to the convolution calculator 675a. As described above, similar operation is continued until the inputting of the vibration signal that does not introduce the fundamental brain activation effect ends. Although the example in which the rows are replaced in a random order is described according to the above-mentioned procedure example, it is acceptable to achieve the replacement in conformity to a certain rule by, for example, reversing the order of the rows, replacing the odd-number rows to the first half and replacing the even-number rows to the latter half.

(2-3) A return autocorrelation coefficient matrix in which the columns are reversed: By rearranging the m dimension autocorrelation coefficients $a_{i1}, a_{i2}, \ldots, a_{im}$ into a reverse order, i.e., $a_{im}, a_{im-1}, \ldots, a_{i1}$ regarding all the row vectors of the autocorrelation coefficient matrix A, the return autocorrelation coefficient matrix RevA of the following equation in which the columns are reversed in order is formed:

$$RevA(i,k)=A(i,m-k+1), (i=1, 2, \ldots, n; k=1,2, \ldots, m).$$

Inputting is sequentially performed from the first row of the generated matrix RevA to the convolution calculator 675b. When the vibration signal that does not introduce the fundamental brain activation effect is still continued at the time point of the last row (n-th row) of the autocorrelation coefficient matrix RevA, the autocorrelation coefficients are inputted from the autocorrelation coefficient matrix A and the return autocorrelation coefficient matrix RevA in a manner similar to that of the above-mentioned case. As described above, the same operation is continued until the vibration signal that does not introduce the fundamental brain activation effect ends.

A matrix in which the columns are reversed and the rows are replaced may be generated. Moreover, the operations of (2-1) to (2-3) may be carried out in combination.

Although the example in which the single reference vibration signal is inputted is described in the example of the above-mentioned procedure, a plurality of autocorrelation coefficient matrixes generated by inputting a plurality of reference vibration signals may be inputted from those arranged in an arbitrary order.

By adding the vibration signal that has the property on the autocorrelation order and can introduce the fundamental brain activation effect generated by this apparatus to the original vibration signal that does not introduce the fundamental brain activation effect, it becomes possible to generate a vibration signal that can introduce the fundamental brain activation effect. In the case where the output signal of this apparatus is added to the original vibration, it is acceptable to use together one or a plurality of circuits of the high-pass filter 663, the gate circuit having the comparator 670 and the switches 664a and 664b, the voltage-controlled amplifier 665 and so on in FIG. 66 as described above.

As described above, by using this apparatus, it becomes possible to generate a signal that has a variety of kinds of structures and does not exist in the nature while having the feature of the autocorrelation order capable of introducing the fundamental brain activation effect for a free time duration.

Figure 69:
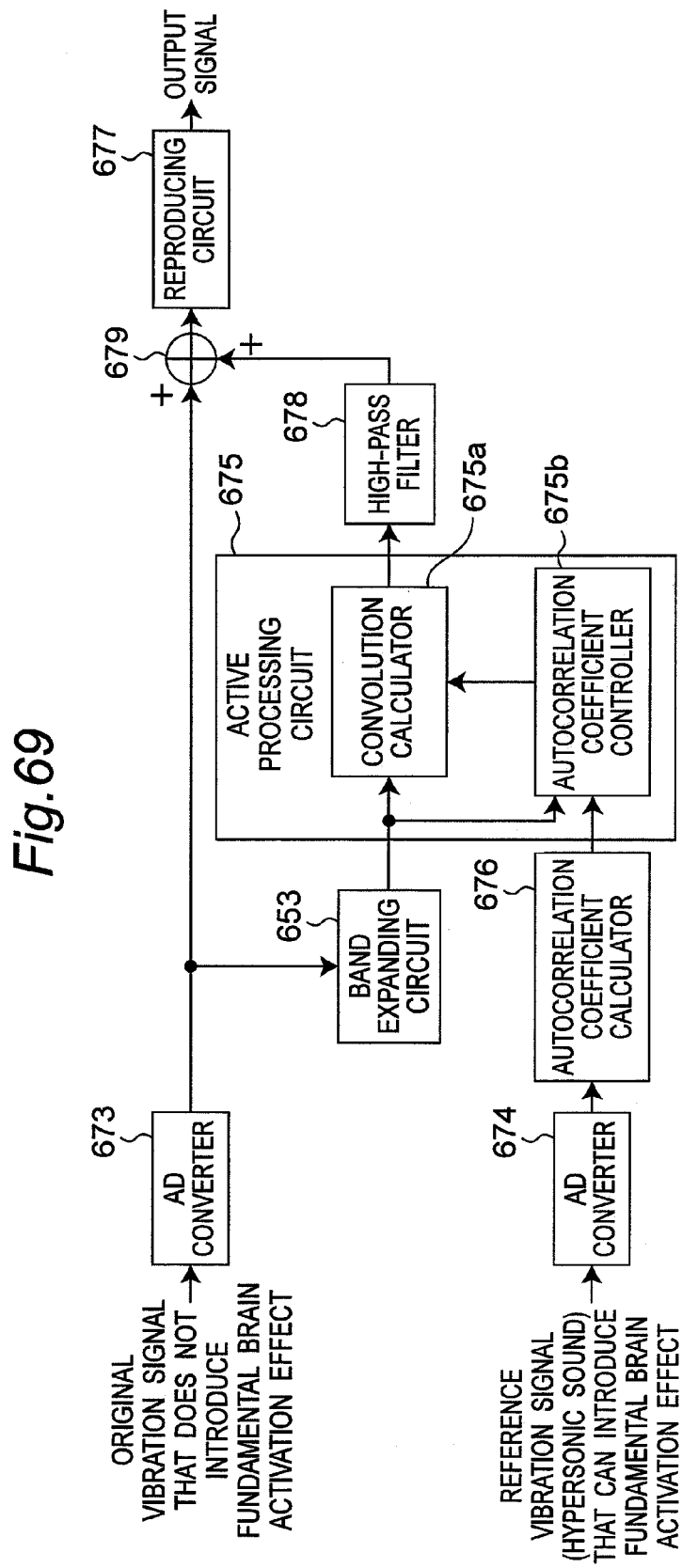
FIG. 69 is a block diagram showing a modified preferred embodiment of the vibration signal generating apparatus of FIG. 68.

FIG. 69 is a block diagram showing a modified preferred embodiment of the vibration signal generating apparatus of FIG. 68. FIG. 69 shows an example of an apparatus that generates a vibration (hypersonic sound) that can introduce the fundamental brain activation effect by enhancing or imparting the first property or the second property on the autocorrelation order and adding an output signal to an original vibration signal. In this case, the original vibration signal that cannot introduce the fundamental brain activation effect because it contains no super-high-frequency component is inputted to a band expanding circuit 653 and has its band expanded by using the existent band expanding means, and its output signal is inputted to the active processing circuit 675. On the other hand, an autocorrelation coefficient set generated by a method similar to that of FIG. 68 is inputted to the active processing circuit 675, a convolution calculation is performed between both of them, and the calculation result is outputted as a signal. The outputted signal is a vibration signal, that has the property of the autocorrelation order similar to that of a reference vibration and can introduce the fundamental brain activation effect. The outputted signal has its audible range removed by a high-pass filter 678, and thereafter added to the original vibration signal that cannot introduce the fundamental brain activation effect because it contains no super-high-frequency component in an adder 679. A signal of the addition result is outputted, subjected to DA conversion by a reproducing circuit 677 and outputted. The outputted vibration is a vibration (hypersonic sound) that can introduce the fundamental brain activation effect. In the addition stage, it is acceptable to adjust the timing of the two vibration signals added together by using a delay circuit, adjust the delay of time necessary for band expanding and convolution calculation or take other measures.

By using this apparatus, it becomes possible to generate a vibration (hypersonic sound signal) that can introduce the fundamental brain activation effect from the vibration signals that cannot introduce the fundamental brain activation effect, such as vibration signals recorded in the digital formats capable of recording super-high-frequency components in the storage media of the conventional CDs, MDs, memories, hard disks, media players by network transmission, portable telephones, DVD videos, DVD audios, Blu-ray Discs, and PC data files, and signals in the digital formats capable of recording super-high-frequency components transmitted and distributed by the current terrestrial digital broadcastings, BS digital broadcastings, communications of Internet and telephone lines. Moreover, even in the case of vibration signals recorded in the formats capable of recording super-high-frequency components in the storage media as described above or even in the case of vibration signals obtained by transducing the vibrations of a solid, a liquid, a gas or the like into electrical variations by using an apparatus capable of transducing and transmitting super-high-frequency components, when the vibration does not introduce the fundamental brain activation effect, it becomes possible to generate a vibration (hypersonic sound) that can introduce the fundamental brain activation effect from the vibration signal by this apparatus. By thus generating the vibration (hypersonic sound) that contains the super-high-frequency components having the predetermined autocorrelation order, the effects of inducing activation of the fundamental brain and the fundamental brain network (fundamental brain network system) including the reward system neural circuit responsible for the generation of reactions of pleasure, beauty and emotion, and the nerve center of the autonomic neural circuit, the endocrine system and the immune system responsible for the homeostatic maintenance and biophylaxis of the whole body in a human being, consequently enhancing the aesthetic sensibility and ameliorating and improving the physical state are obtained.

Figure 70:
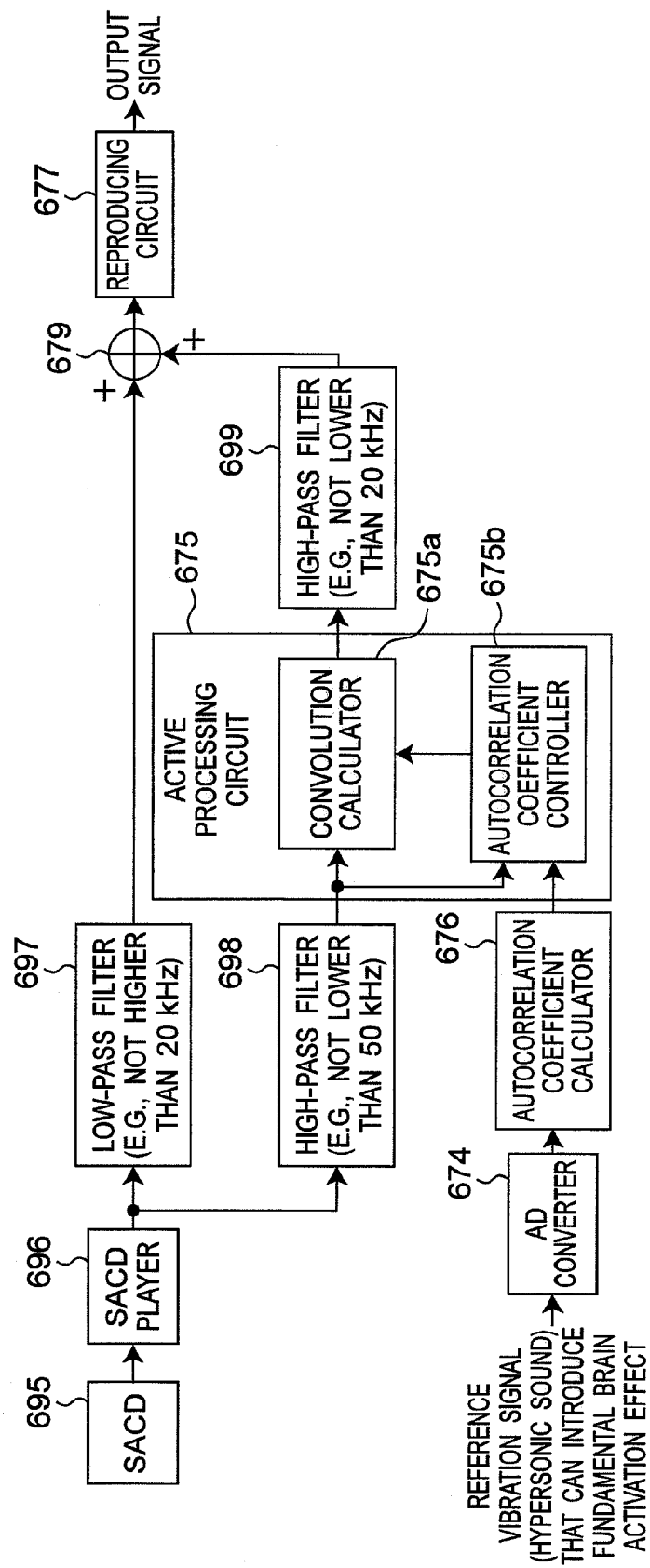
FIG. 70 is a block diagram showing an example of an apparatus that generates a vibration (hypersonic sound)

FIG. 70 is a block diagram showing an example of an apparatus that generates a vibration (hypersonic sound) that can introduce the fundamental brain activation effect by processing the 1-bit quantization noise owned by the high-speed sampling 1-bit quantization system according to the second preferred embodiment. FIG. 70 is a modified preferred embodiment of the apparatus of FIG. 68 and generates a vibration signal (hypersonic sound signal) that can introduce the fundamental brain activation effect by imparting the first property or the second property on the autocorrelation order to the 1-bit quantization noise owned by a vibration signal that is digitalized by the high-speed sampling 1-bit quantization system and recorded in the existent SACD (Super Audio CD), a hard disk, a solid memory or the like.

Referring to FIG. 70, an SACD 695 is inserted into the drive of an SACD player 696, and its output signal is outputted to an adder 679 via a low-pass filter 697 having a cutoff frequency of, for example, 20 kHz and outputted to an adder 679 via a high-pass filter 698 having a cutoff frequency of, for example, 30 kHz, an active processing circuit 675 and a high-pass filter 699 having a cutoff frequency of, for example, 20 kHz. The adder 679 adds together the inputted two digital signals, and outputs a digital signal of the addition result to a reproducing circuit 677. Then, the reproducing circuit 677 subjects the inputted digital signal to DA conversion, and outputs the resulting signal. It is noted that an AD converter 674 and an autocorrelation coefficient calculator 676 for processing a reference vibration signal are connected to the active processing circuit 675 in a manner similar to that of the apparatuses of FIGS. 68 and 69.

When a digital signal recorded by using the high-speed sampling 1-bit quantization system is reproduced, the 1-bit quantization noise theoretically accompanies with a definite dispersion about a specific frequency depending on the sampling frequency and the ΔΣ calculation order. The noise is generated in a frequency domain at and around 50 kHz in the current SACD contents or the like adopting a sampling frequency of 2.8 Mbps and, in addition, it does not introduce the fundamental brain activation effect because it has no appropriate autocorrelation order. Accordingly, currently in order to remove the noise, a low-pass filter is provided in the SACD player to remove the super-high-frequency components of not lower than about 50 kHz.

In the present implemental example, the 1-bit quantization noise is utilized as a super-high-frequency signal material. A 1-bit quantization noise extracted by a high-pass filter 698 without intervention of the low-pass filter described in the preceding paragraph from an analog signal obtained by converting the digital signal recorded in the SACD 695 is inputted to the active processing circuit 675, while the autocorrelation coefficient set obtained from the reference vibration signal is inputted to the active processing circuit 675 to perform a high-speed convolution calculation between both of them, and a signal of the calculation result is outputted. By adding this signal to the reproduction signal of the SACD contents that does not introduce the fundamental brain activation effect or audible range components obtained by filtering it by the low-pass filter 697, it becomes possible to generate a vibration signal (hypersonic sound signal) that can introduce the fundamental brain activation effect. By using this apparatus, a vibration (hypersonic sound) that can introduce the fundamental brain activation effect can be reproduced when the contents recorded by the high-speed sampling 1-bit quantization system inclusive of the conventional SACD contents are reproduced. By thus generating the vibration (hypersonic sound) that can introduce the fundamental brain activation effect because it contains super-high-frequency components having the predetermined autocorrelation order contained, the effects of inducing activation of the fundamental brain network system including the reward system neural circuit responsible for the generation of reactions of pleasure, beauty and emotion, and the nerve center of the autonomic neural circuit, the endocrine system and the immune system responsible for the homeostatic maintenance and biophylaxis of the whole body in a human being, enhancing the aesthetic sensibility and ameliorating and improving the physical state are obtained. In the addition stage, it is acceptable to adjust the timing of the two vibration signals added together by using a delay circuit, adjust the delay of time necessary for the convolution calculation or take similar measures. Although the reproduction signal from the SACD 695 is shown as the object in the figure, this may be a media reproduction signal of a hard disk, a solid memory or the like or a signal that is transmitted and distributed by a network or the like.

FIG. 71 is a block diagram showing a vibration signal generating apparatus that generates a vibration signal (hypersonic sound signal) that introduces the fundamental brain activation effect by analyzing the feature of the autocorrelation order owned by the reference vibration that can introduce the fundamental brain activation effect by using autocorrelation coefficients, generating a vibration signal having the predetermined autocorrelation order by processing the signal of a vibration (e.g., a white noise) that does not introduce the fundamental brain activation effect, because it satisfies neither the first property nor the second property on the autocorrelation order while containing the super-high-frequency components exceeding the human audible range upper limit based on the result, and by adding the super-high-frequency components to the original vibration signal that does not introduce the fundamental brain activation effect for complementing. By using the transfer function, it becomes possible to perform processing in the frequency domain, and provide a function to perform automatic equalizing in accordance with the changes in the reference vibration. By thus generating the vibration (hypersonic sound) that can introduce the fundamental brain activation because it contains super-high-frequency components having the predetermined autocorrelation order, the effects of inducing activation of the fundamental brain network (fundamental brain network system) including the reward system neural circuit responsible for the generation of reactions of pleasure, beauty and emotion, and the nerve center of the autonomic neural circuit, the endocrine system and the immune system responsible for the homeostatic maintenance and biophylaxis of the whole body in a human being, enhancing the aesthetic sensibility and ameliorating and improving the physical state are obtained.

The operation of the apparatus of FIG. 71 is described below.

Referring to FIG. 71, a transfer function is first calculated from a reference vibration signal having certain time duration. The concrete calculation procedure is as follows.

(1) A reference vibration signal (standard vibration signal) is first inputted to an AD converter 674, and sampled by a sampling frequency $2f_N$ ($f_N$ is the Nyquist frequency) by a quantization bit count of not less than 12 bits. In this case, $f_N$ needs to sufficiently exceed 20 kHz at the audible frequency range upper limit (e.g., $f_N$=96 kHz). When the reference vibration signal is a digital signal, the AD converter 674 may be eliminated.

(2) A signal having a total duration of T seconds outputted from the AD converter 674 is inputted to a transfer function calculator 676*a* and divided into "n" unit analysis intervals of duration of $T_E$ seconds (e.g., T=60 seconds, $T_E$=0.1 seconds, n=600).

(3) A system that outputs a reference signal when a white noise is inputted every divided unit analysis interval is assumed, and its transfer function is assumed to be H(jω) (j is imaginary unit, ω is angular frequency, ω=2πf, provided that f is frequency). Assuming that a function obtained by subjecting time series data of the white noise to Laplace transform and expressing it by a frequency domain is W(jω) and a function obtained by subjecting time series data of the reference signal to Laplace transform and expressing it by a frequency domain is X(jω), then the following equation of multiplication can be simply given:

$$X(j\omega)=H(j\omega)\cdot W(j\omega).$$

(4) The transfer function $H(j\omega)$ is expressed by the following equation by using coefficients $\{a_1, a_2, \ldots, a_m\}$, $\{b_1, b_2, \ldots, b_l\}$:

$$H(j\omega) = \frac{a_m(j\omega)^m + a_{m-1}(j\omega)^{m-1} + \ldots + a_1 j\omega + a_0}{b_l(j\omega)^l + b_{n-1}(j\omega)^{l-1} + \ldots + b_1 j\omega + b_0}$$

(5) The transfer function is calculated for all of the "n" unit analysis intervals in the divided unit analysis interval "i" (i=1, 2, ..., n) to form a transfer function matrix A. In the transfer function matrix A, the i-th row is a row vector constituted of the coefficients $\{a_{i1}, a_{i2}, \ldots, a_{im}, b_{i1}, b_{i2}, \ldots, b_{il}\}$ of the transfer function in the interval "i". The number of rows of the matrix A becomes the number of intervals (n rows), and the number of columns of the matrix A becomes a sum ((m+l) columns) of the dimensions of the coefficients of the transfer function.

On the other hand, the signal of a vibration (e.g., white noise) that does not introduce the fundamental brain activation effect is first inputted to the AD converter 673 and sampled by the same sampling frequency $2f_N$ ($f_N$ is the Nyquist frequency) as that of the reference signal. When the reference vibration signal is a digital signal, the AD converter 673 may be eliminated. However, when the sampling frequency is different from $2f_N$, resampling is performed by the sampling frequency $2f_N$. The vibration signal that does not introduce the fundamental brain activation effect and is outputted from the AD converter is subsequently inputted to a frequency converter 673a, and a signal $Y(j\omega)$ obtained by Fast Fourier Transform (FFT) from the time domain to the frequency domain is generated.

The transfer function matrix A outputted from the transfer function calculator 673a and the vibration signal $Y(j\omega)$ that does not introduce the fundamental brain activation effect and is converted into the frequency domain are both inputted to the active processing circuit 675A.

The active processing circuit 675A is constituted of a multiplier 675c and a transfer function controller 675d. The operation of the transfer function controller 675d is described in detail in the following clause. A transfer function $H(j\omega)$ is inputted from the transfer function calculator 676a to the multiplier 675c via the transfer function controller 675d. Multiplication is performed between the inputted transfer function $H(j\omega)$ and the vibration signals $Y(j\omega)$ that do not introduce the fundamental brain activation effect and is converted into the frequency domain, and a signal $Z(j\omega)$ of the following equation is generated:

$$Z(j\omega) = H(j\omega) \cdot Y(j\omega).$$

Subsequently, the signal $Z(j\omega)$ is converted into a time series signal, and a signal having a property on the autocorrelation order is generated.

When the time duration of the vibration signal that does not introduce the fundamental brain activation effect is longer than the time duration of the reference vibration signal, the number of transfer functions for performing the multiplication becomes insufficient. Accordingly, the transfer function controller 675d has a function to continuously send out the transfer functions by iterating or generating so that the multiplication can be continued how long the time duration of the vibration signal that does not introduce the fundamental brain activation effect is. With this function, it becomes possible to generate the vibration signal having the property on the autocorrelation order for an arbitrary time duration, even when the time duration of the reference vibration signal is short. In concrete, it is performed according to the procedure described below.

(1) The transfer function matrix A calculated in the transfer function calculator 676a is inputted to the transfer function controller 675d. In the transfer function controller 675d, the transfer function coefficients are sequentially read from the first row of the transfer function matrix A, and the transfer function is inputted to the multiplier 675c.

(2) when the inputting of the vibration signal that does not introduce the fundamental brain activation effect is still continued at the time point of read of the transfer function coefficients of the last row (n-th row) of the transfer function matrix A, either one of the following operations is carried out.

(2-1) Simple iteration: The transfer function controller 675d returns to the first row of the transfer function matrix A, reads once again the transfer function coefficients of the first row and sequentially inputs the transfer function to the multiplier 675c. When the inputting of the vibration signal that does not introduce the fundamental brain activation effect is still continued at the time point of the last row (n-th row) of the transfer function matrix A, the same operation is performed once again. The iteration is thus continued until the vibration signal that does not introduce the fundamental brain activation effect ends.

(2-2) Matrix in which the rows are replaced in a random order: The transfer function controller 675d generates a matrix B in which the rows of the first row to the n-th row of the matrix A are replaced in a random order. The transfer function coefficients are read from the first row of the generated matrix B, and the transfer functions are sequentially inputted to the multiplier 675c. When the vibration signal that does not introduce the fundamental brain activation effect is still continued at the time point of the last row (n-th row) of the transfer function matrix B, the rows of the first row to the n-th row of the matrix A are replaced once again in a random order to generate another matrix B'. The transfer function coefficients are sequentially read from the first row of the generated matrix B', and the transfer function is inputted to the multiplier 675c. Similar operation is thus continued until the inputting of the vibration signal that does not introduce the fundamental brain activation effect ends. Although the example in which the rows are replaced in a random order in described according to the above-mentioned procedure example, it is acceptable to achieve the replacement in conformity to a certain rule by, for example, reversing the order of the rows, replacing the odd-number rows to the first half and replacing the even-number rows to the latter half.

Although the example in which the single reference vibration signal is inputted is described according to the above-mentioned procedure example, it is also acceptable to read the transfer function coefficients from an arrangement such that a plurality of transfer function matrixes generated by inputting a plurality of reference vibration signals are arranged in an arbitrary order.

By adding the vibration signal that has the property on the autocorrelation order and can introduce the fundamental brain activation effect generated by this apparatus to the original vibration signal that does not introduce the fundamental brain activation effect, it becomes possible to generate a vibration signal that can introduce the fundamental brain activation effect. In the case where the output signal of this apparatus is added to the original vibration, it is acceptable to use together one or a plurality of circuits of the high-pass filter 663, the gate circuit having the comparator 670 and the switches 664a and 664b, the voltage-controlled amplifier 665 and so on in FIG. 66.

As described above, it becomes possible to generate a signal having a variety of kinds of structures that do not naturally exist while having the feature of the autocorrelation order that can introduce the fundamental brain activation effect for a free time duration.

Next, an implemental example corresponding to a vibration generating apparatus that performs enhancement and impartation of effective vibration components and attenuation and removal of unnecessary vibration components by using an elastic vibrating object is described below.

FIG. 72 is a block diagram showing a vibration generating apparatus (apparatus example using a moving magnet type fluctuation detector device) that can introduce the fundamental brain activation effect using an elastic vibrating object according to the second preferred embodiment. Referring to FIG. 72, by applying a vibration that contains super-high-frequency components exceeding the human audible range upper limit and has at least either one of the first property and the second property on the predetermined autocorrelation order, a vibration that does not contain super-high-frequency components themselves or a variation that contains neither the first property nor the second property on the predetermined autocorrelation order although it has super-high-frequency components to an elastic vibrating object of metal or the like, it is possible to enhance the super-high-frequency components owned by the vibration and enhance the predetermined property on the autocorrelation order by utilizing the physical characteristics of elasticity, natural vibration, stress strain and so on or to impart the super-high-frequency components that are not owned by the vibration and impart the predetermined property on the autocorrelation order. Furthermore, the vibration not having the aforementioned properties of the vibrations can be attenuated or removed. By thus generating the vibration (hypersonic sound) that can introduce the fundamental brain activation because it contains super-high-frequency components having the predetermined autocorrelation order, the effects of inducing activation of the fundamental brain and the fundamental brain network (fundamental brain network system) including the reward system neural circuit responsible for the generation of reactions of pleasure, beauty and emotion, and the nerve center of the autonomic neural circuit, the endocrine system and the immune system responsible for the homeostatic maintenance and biophylaxis of the whole body in a human being, consequently enhancing the aesthetic sensibility and ameliorating and improving the physical state are obtained.

Referring to FIG. 72, an electric signal of a vibration that can introduce the fundamental brain activation effect or a vibration that does not satisfy it is transduced into an elastic vibration by an actuator 701, and a vibration propagated to the other end of an elastic vibrating object 702 is retransduced into an electric signal by a moving magnet type fluctuation detector device 703. In the propagation process on this elastic vibrating object 702, the super-high-frequency components exceeding the human audible range upper limit and the first property or the second property on the autocorrelation order are enhanced or imparted by the physical vibration characteristics of elasticity, natural vibration, stress and strain and so on owned by the elastic vibrating object 702 and the vibration characteristics of a peripheral vibration transmission medium 706 or their interactions. Moreover, a vibration (e.g., rectangular wave) having a structure that can exist as a vibration signal in an electric signal but hardly or impossibly exists in the elastic vibration is transduced into a vibration that is attenuated while propagating through the elastic vibrating object or able to introduce the fundamental brain activation effect.

The kind of the actuator 701 can be provided by a dynamic coil type that drives a coil by an electromagnetic force generated in accordance with an inputted current, a piezoelectric device type that deforms in accordance with an inputted voltage, a supermagnetostrictive device type of which the size changes in accordance with an inputted current, or the like. Moreover, it is possible to use a variety of kinds of metals, alloys, resins, ceramics, glass, rocks, woods, bamboo, secretions from living things such as ivory, tortoiseshell, animal's bone and corals, hunks of meats, bodies of animals and plants and so on for the material of the elastic vibrating object 702. The elastic vibrating object 702 is peripherally filled with a vibration transmission medium (oil, aqueous solution, organic solvent, etc.) 706. Moreover, the shape of the vibration transmission medium filled container 700 for the filling of the vibration transmission medium 706 may be any one of shapes of high symmetric properties such as rectangular parallelepiped and oval or shapes of high asymmetric properties. In the implemental example of FIG. 72, the moving magnet type fluctuation detector device 703 that generates an electric signal in accordance with the displacement acceleration of the magnet is used as a functional device for detecting a vibration from the elastic vibrating object 702 and transducing it into an electric signal. In this case, the moving magnet type fluctuation detector device 703 is configured of a coil 705 wound around the outer periphery of a moving magnet 704, and an output electric signal is obtained from both ends of the coil 705.

In the present implemental example, by transducing the electric signal of a vibration that can introduce the fundamental brain activation effect or cannot introduce it into an elastic vibration by an actuator 701, applying it to the elastic vibrating object 702, and processing the applied vibration by using the vibration characteristic owned by the applied elastic vibrating object 702, the super-high-frequency components exceeding the human audible range upper limit and at least either one of the first property and the second property on the autocorrelation order in the signal are enhanced or imparted, and by attenuating or removing the vibration components that cannot exist in the natural elastic vibrating object although it can exist as an electric signal and do not introduce the fundamental brain activation effect or transducing it into a vibration that can introduce the fundamental brain activation effect, the effect of the vibration that can introduce the fundamental brain activation effect can be enhanced. The signal (hypersonic sound signal) of the vibration that contain the super-high-frequency components having the predetermined autocorrelation order and can introduce the fundamental brain activation effect generated as described above may be used as a complementing vibration signal in the vibration complementing apparatus according to the second preferred embodiment described in detail hereinabove with reference to FIGS. 59 to 67. That is, by using the generated vibration signal itself or extracting the super-high-frequency components from it and adding it to the original vibration signal that does not introduce the fundamental brain activation effect for the achievement of complementing, a vibration signal (hypersonic sound signal) that introduces the fundamental brain activation effect can be generated.

Although the elastic vibrating object 702 is supported so as to be positioned in the vibration transmission medium 706 inside the medium filled container 700 in the above-mentioned implemental example, the present invention is not limited to this, and the elastic vibrating object 702 may be vibrated in a free space without the vibration transmission medium 706.

FIG. 73 is a block diagram showing a vibration generating apparatus (apparatus example using a capacitor type fluctuation detector device 710) that can introduce the fundamental brain activation effect using an elastic vibrating object according to the second preferred embodiment. FIG. 73 shows a capacitor type fluctuation detector device 710 that generates an electric signal by a change in an electrostatic capacity in accordance with the displacement of a movable electrode. The capacitor type fluctuation detector device 710 is constituted by interposing a movable electrode 711 connected to one end of the elastic vibrating object 702 between one pair of stationary electrodes 712 and 713 to which a predetermined bias voltage is applied by a predetermined bias voltage source 714 and obtains an output electric signal from the movable electrode 711 and one stationary electrode 713.

Besides this, it is acceptable to use the systems of a moving coil type that generates an electric signal in accordance with the displacement acceleration of a coil, a piezoelectric device type that generates a voltage change in accordance with a change in an applied pressure, a supermagnetostrictive device type that generates an electric signal in accordance with a change in size, a laser Doppler type that transduces a positional displacement into an electric signal in a noncontact manner by utilizing optical reflection or the like. The thus generated vibration signal (hypersonic sound signal) that can introduce the fundamental brain activation effect or the super-high-frequency components extracted from it may be used as a complementing vibration signal in the vibration complementing apparatus described in detail hereinabove.

FIG. 74 is a block diagram showing a vibration generating apparatus that can introduce the fundamental brain activation effect using a spiral spring elastic vibrating object according to the second preferred embodiment. Although the elastic vibrating object 702 has the plate-like shape in FIGS. 72 to 73, an elastic vibrating object 720 having a spiral spring shape is used in FIG. 74. With this arrangement, by indirectly transmitting the vibration in a portion of the elastic vibrating object 720 to other portions via the infilling vibration transmission medium 706, the super-high-frequency components exceeding the human audible range upper limit and the property of their autocorrelation order are enhanced or imparted, and the vibration not having the property of the vibrations can be expected to be attenuated or removed. An actuator 701 is connected to one end of the elastic vibrating object 720, while a fluctuation detector device 710 is connected to other end. Then, an output signal is obtained from the coil-shaped other end of the elastic vibrating object 720. In this case, the shape of the elastic vibrating object 720 may be a coil-like shape of a spiral spring wound more densely, a wave-like shape or the like. These elastic vibrating bodies having the spiral spring shape, coil shape or wave shape may simply have the shapes unchanged or allowed to have their one end or both ends connected to a lever-like shape. In this case, the lever-shaped structure also functions as an elastic vibrating object and contributes to the generation of a vibration (hypersonic sound) that can introduce the fundamental brain activation effect. The thus generated vibration signal (hypersonic sound signal) that can introduce the fundamental brain activation effect or the super-high-frequency components extracted from it may be used as a complementing vibration signal in the vibration complementing apparatus described in detail hereinabove.

FIG. 75 is a block diagram showing a vibration (hypersonic sound) generating apparatus (apparatus example in which an elastic vibrating object is served as a fluctuation detecting coil) that can introduce the fundamental brain activation effect using an elastic vibrating object according to the second preferred embodiment. FIG. 75 is a modified preferred embodiment in which the elastic vibrating object itself of FIG. 72 is made to function as a coil for vibration signal detection. Referring to FIG. 75, a fluctuation detecting coil 730 with an elastic vibrating object is constituted by winding an elastic vibrating object using a conductor, and this is interposed between one pair of permanent magnets 731 and 732, constituting a movement generating structure similar to the fluctuation detector device. With this arrangement, it becomes possible to transduce the entire vibration of a propagation to the other end of a vibration given to one end of the fluctuation detecting coil 730 with an elastic vibrating object from the actuator 701 into an electric signal. Moreover, since the fluctuation detecting coil 730 with an elastic vibrating object has a coil-like shape, it is herein actualized that the super-high-frequency components exceeding the human audible range upper limit and the property of their autocorrelation order due to the interactions of vibrations by way of the vibration transmission medium 706 shown in FIG. 72 are enhanced or imparted, and the vibration not having the properties of the vibrations are attenuated or removed or transduced into a vibration that can introduce the fundamental brain activation effect. The conductor wound around the coil may be provided by one having a planar shape besides the linear one. The fluctuation detecting coil with an elastic vibrating object may simply have the shapes unchanged or allowed to have their one end or both ends connected to a lever-like shape. In this case, the lever-shaped structure also functions as an elastic vibrating object and contributes to the generation of a vibration (hypersonic sound) that can introduce the fundamental brain activation effect. The thus generated vibration signal (hypersonic sound signal) that can introduce the fundamental brain activation effect or the super-high-frequency components extracted from it may be used as a complementing vibration signal in the vibration complementing apparatus described in detail hereinabove.

FIG. 76 is a block diagram showing a vibration generating apparatus (apparatus example in which an elastic vibrating object is made to function as a fluctuation detecting coil) that can introduce the fundamental brain activation effect using an elastic vibrating object according to the second preferred embodiment. FIG. 76 is a modified preferred embodiment of a positional relation between the fluctuation detecting coil 730 with an elastic vibrating object and a stationary magnet. Referring to FIG. 76, the fluctuation detecting coil 730 with an elastic vibrating object is constituted by being wound around an N-pole magnet 731 and interposing them between one pair of S-pole magnets 732 and 732. Then, an output signal is obtained from both ends of the fluctuation detecting coil 730. The shape of the fluctuation detecting coil 730 and the positional relation among the stationary magnets 731, 732 and 732 may be other than the illustrated example. The fluctuation detecting coil with an elastic vibrating object may simply have the shape unchanged or allowed to have their one end or both ends connected to a lever-like shape. In this case, the lever-shaped structure also functions as an elastic vibrating object and contributes to the generation of a vibration (hypersonic sound) that can introduce the fundamental brain activation effect. The thus generated vibration signal (hypersonic sound signal) that can introduce the fundamental brain activation effect or the super-high-frequency components extracted from it may be used as a complementing vibration signal in the vibration complementing apparatus described in detail hereinabove.

FIG. 77 is a block diagram showing a vibration generating apparatus (apparatus example in which a plurality of vibration generating apparatuses are concurrently used by using an elastic vibrating object) that can introduce the fundamental brain activation effect using an elastic vibrating object according to the second preferred embodiment. FIG. 77 is an example in which a vibration generating apparatus that can introduce the fundamental brain activation effect and is shown in FIGS. 72 to 76 is used concurrently in a plurality of channels. Referring to FIG. 77, there is a configuration of a plurality of actuators 701, a plurality of elastic vibrating bodies 750 and a plurality of fluctuation detector devices 751, which are connected correspondingly. In this case, elastic vibrations are allowed to be transmitted mutually by filling spaces between the elastic vibration bodies 750 with a vibration transmission medium (oil, aqueous solution, organic solvent, etc.) 706, and this makes it possible to induce cross modulation due to the interactions among the individual channels to enhance or impart the super-high-frequency components exceeding the audible range upper limit and the property on the predetermined autocorrelation order, and to attenuate or remove the vibration not having the property of the vibrations. For example, a plurality of output signals may be added together by an adder. Although only the example of FIG. 72 has the multiple use arrangement for simplicity in the figures, it is acceptable to use another example or mix them together. The thus generated vibration signal (hypersonic sound signal) that can introduce the fundamental brain activation effect or the super-high-frequency components extracted from it may be used as a complementing vibration signal in the vibration complementing apparatus described in detail hereinabove.

Next, an implemental example corresponding to a vibration signal that is recorded in a recording medium and a vibration signal that is transmitted and distributed by telecommunications is described below.

An example of "Blu-ray Disc version AKIRA soundtrack" (composed by Shoji Yamashiro) is described as an example of a vibration signal obtained by recording a vibration signal (hypersonic sound signal) that can introduce the fundamental brain activation effect synthesized by using a vibration signal generating apparatus including a vibration complementing apparatus into a Blu-ray Disc. Moreover, experimental results indicating that the fundamental brain activation effect is introduced by electroencephalographic recording are described.

The synthetic vibration signal used for the experiment is the "Blu-ray Disc version AKIRA soundtrack" (composed by Shoji Yamashiro). The past AKIRA soundtrack of a DVD or the like can neither record nor reproduce the band components of not lower than 24 kHz because the vibration signal has been recorded by a digital format of a sampling frequency of 48 kHz and a quantization bit count of 16 bits, and therefore, it cannot introduce the fundamental brain activation effect by recording and reproducing a hypersonic sound. Accordingly, the vibration signal of the "Blu-ray Disc version AKIRA soundtrack" was formed by using the signal of the "DVD version AKIRA soundtrack" as an original vibration, expanding the band of the signal, synthesizing an output signal by adding the super-high-frequency components of the tropical rain forest environmental sound that could typically introduce the fundamental brain activation effect and the like by using a vibration signal generating apparatus including the vibration complementing apparatus shown in FIG. 66 and recording it in a Blu-ray Disc in the digital format of a sampling frequency of 192 kHz and a quantization bit count of 24 bits.

FIG. 78 is a spectral diagram showing a power spectrum of the vibration signal recorded in the soundtracks of the "DVD version AKIRA" and the "Blu-ray Disc version AKIRA" measured in the second preferred embodiment. Referring to FIG. 78, the average FFT power spectrums of the vibration signals of an identical part of the "DVD version AKIRA soundtrack" of the original vibration signal and the "Blu-ray Disc version AKIRA soundtrack" synthesized by the vibration signal generating apparatus including the vibration complementing apparatus are compared with each other. As is apparent from FIG. 78, the synthesized vibration signal of the "Blu-ray Disc version AKIRA soundtrack" contained abundant super-high-frequency components exceeding 90 kHz and sufficiently had the super-high-frequency components of the essential components capable of introducing the fundamental brain activation effect.

FIG. 79 is a graph showing a local exponent of fractal dimension of the vibration signal of the "Blu-ray Disc version AKIRA soundtrack" measured in the second preferred embodiment. FIG. 79 shows the result of examining the first property on the autocorrelation order of the "Blu-ray Disc version AKIRA soundtrack" synthesized by the aforementioned method. As is apparent from FIG. 79, the "local exponent of fractal dimension" of the vibration signal of the "Blu-ray Disc version AKIRA soundtrack" is consistently not smaller than 2.2 when the spectro-temporal index is between $2^{-1}$ and $2^{-5}$, and its fluctuation range has a value within 0.4. For the above-mentioned reasons, the vibration signal of the "Blu-ray Disc version AKIRA soundtrack" satisfies the first property on the autocorrelation order.

FIG. 80 is a graph showing an information entropy density of the vibration signal of the "Blu-ray Disc version AKIRA soundtrack" measured in the second preferred embodiment, and FIG. 81 is a graph showing an entropy variation index (EV-index) of the vibration signal of the "Blu-ray Disc version AKIRA soundtrack" measured in the second preferred embodiment. As is apparent from FIG. 80, the information entropy density of this vibration signal consistently has a value of not smaller than −5 and smaller than zero. As is apparent from FIG. 81, the entropy variation index (EV-index) of this vibration signal has a value of not smaller than 0.001. For the above-mentioned reasons, the vibration signal of the "Blu-ray Disc version AKIRA soundtrack" satisfies the second property on the autocorrelation order.

FIG. 82 is a graph showing a deep brain activity index (DBA-index) recorded from a listener under a high-cut sound condition and a full-range sound condition generated by using the "Blu-ray Disc version AKIRA soundtrack" measured in the second preferred embodiment. The present inventor and others recorded the brain wave during listening in order to examine whether the vibration generated by using the "Blu-ray Disc version AKIRA soundtrack" introduced the fundamental brain activation effect. The DBA-indexes were calculated and compared between the listening condition of the full-range sound obtained by reproducing the vibration signal of the "Blu-ray Disc version AKIRA soundtrack" unchanged in the state in which the super-high-frequency components were contained and the listening condition of the high-cut sound having a feature similar to that of the "DVD version AKIRA soundtrack" obtained by removing the frequency components of not lower than 24 kHz from it. FIG. 82 shows the results. In the measurement, the DBA-index was obtained from each of ten test human subjects under both the conditions, and a statistical examination was performed based on those data. It was clarified that the DBA-index indicated a statistically significantly high value and the fundamental brain was activated in the full-range sound condition in comparison with the high-cut sound condition.

FIG. 83 is a graph and a table showing an impression evaluation of sounds by the listeners on the high-cut sound condition and the full-range sound condition generated by using the "Blu-ray Disc version AKIRA soundtrack" measured in the second preferred embodiment. Fourteen evaluation words expressing the impression of the sound were shown on the questionnaire used for answers, and they were made to perform evaluations by five-rank evaluation. The answers of nine test human subjects in total were analyzed.

The left chart of FIG. 83 is one in which a difference is obtained by subtracting the impression grade of sound in the high-cut sound condition from the impression grade of the sound in the full-range sound condition regarding each test human subject, and averages are obtained regarding all the test human subjects and plotted. This numerical value indicated that the sound in the full-range sound condition was more positively evaluated as it was greater and defined as "favorability rating". The right chart of FIG. 83 shows the results of examination by the signed rank test of Wilcoxon (Wilcoxon) as to whether a significance exists in the bias of the "favorability rating".

As a result, the favorability of the sound impression was higher in the full-range sound condition than in the high-cut sound condition concerning all the evaluation words. In particular, the evaluation words of the six items: "impressed by sound", "sound quality is good", "sound volume is more plentiful", "deep bass is rich", "sound reverberates sweetly" and "sound separation is good and not collapsed even at full blast" are evaluated statistical significantly positively with $p<0.05$ (mark ** in the right figure of FIG. 83). Moreover, with regard to the evaluation words of the two items: "sound is smooth" and "loudspeaker sounds are heard to be interlinked", are positively evaluated with a high tendency of $p<0.10$ (mark * in the right figure of FIG. 83). This indicated that the full-range sound induced the activation of the fundamental brain and the fundamental brain network (fundamental brain network system) including the reward system neural circuit of the brain responsible for the generation of reactions of pleasure, beauty and emotion in a human being, consequently enhancing the aesthetic sensibility to sounds and further intensifying the impressions of pleasure, beauty and so on.

In using the vibration generating apparatuses as described above in various facilities, it is acceptable to control on/off and the level of the hypersonic sound signal in accordance with the existence and the number of people. That is, for example, when even a person enters a room, the event is automatically sensed by a sensor of infrared rays or the like to turn on the vibration signal or turn off the vibration signal when all of them leave the room. Otherwise, a method for turning on/off also the vibration signal in accordance with turning on/off the illumination interlockedly with the illumination power can be considered. Moreover, a method for interlocking it with a room entering/leaving control system of a card key or the like is possible. Further, a system for automatically counting the number of people who have entered a room and increasing or decreasing the level of the hypersonic sound signal in accordance with an increase and decrease in the number of people can be considered.

Moreover, by applying the vibration generating apparatus of the second preferred embodiment, the original vibration signal that does not introduce the fundamental brain activation effect and accompanies an unpleasant sensation because it contains no super-high-frequency component or has neither the first property nor the second property on the autocorrelation order while containing the super-high-frequency components is complemented with the vibration (hypersonic sound) that can introduce the fundamental brain activation effect, by which the effects of suppressing the deterioration in the fundamental brain activity and alleviating the unpleasant sensation can be developed.

In this case, it is acceptable to use an apparatus that absorbs and removes the vibration accompanied by unpleasant sensation in combination with the vibration complementing apparatus. For example, by combining it with a vibration absorbing apparatus that selectively absorbs the vibration in the audible range, a vibration removing apparatus that uses the existent active servo technology or the like, the unpleasant sensation can be effectively alleviated.

Moreover, in this case, it is acceptable to use the circuit of a vibration detector apparatus and a gate apparatus and (or) a voltage-controlled amplifier (VCA) together with the vibration complementing apparatus. This makes it possible to complement an unpleasant sound existing in an environment with a vibration (hypersonic sound) that can introduce the fundamental brain activation effect adjusted to an appropriate level in accordance with the state of existence and the level of the sound.

For example, by installing in a station a vibration complementing apparatus for a vibration accompanied by unpleasant sensation such as arrival sounds and departure sounds of trains in the station, premises announcement sounds, vending machine manipulation sounds and the like and adding a vibration (hypersonic sound) that contains super-high-frequency components having the predetermined autocorrelation order and can introduce the fundamental brain activation effect, the effects of suppressing the deterioration in the fundamental brain activity and alleviating the unpleasant sensation can be produced.

FIG. 89 is an external view showing an example of a vibration generating apparatus 962a mounted in a station yard according to a modified preferred embodiment of the second preferred embodiment. For example, by integrating the public-address system installed in a premises with a vibration complementing apparatus 961 for the recorded arrival and departure chimes and recorded announcement, a vibration (hypersonic sound) that can introduce the fundamental brain activation effect is generated for complementing, by which the effects of suppressing the deterioration in the fundamental brain activity and alleviating the unpleasant sensation can be developed.

Moreover, by using a detection generating apparatus 962 with a built-in premises sound detector apparatus 962b and a gate circuit or a voltage-controlled amplifier (VCA) for, for example, vibrations that do not introduce the fundamental brain activation effect and are generated on site and have impetuous sound volume variation, such as arrival sounds and departure sounds of trains, announcement voiced by station attendants, vending machine manipulation sounds and other environmental noises, the vibrations can be effectively complemented. The gate circuit has the operation of producing the effect of complementing with the vibration that can introduce the fundamental brain activation effect by opening the switch of the gate circuit when the vibration level detected by the premises sound detector apparatus 962b exceeds a definite value or not producing the effect of complementing by closing the switch of the gate circuit when the level does not exceed the definite value. The voltage-controlled amplifier (VCA) has the operation of producing the effect of complementing with the vibration that can introduce the fundamental brain activation effect at a level tightly correlated to the vibration level detected by the premises sound detector apparatus. As a result, by producing the effect of complementing with the vibration that can introduce the fundamental brain activation effect at a level appropriately adjusted to the state of the existence of vibrations in the premises, the effects of effectively suppressing the deterioration in the fundamental brain activity and alleviating the unpleasant sensation can be developed.

Besides these, by similarly installing a vibration complementing apparatus for vibrations accompanied by unpleasant sensation, such as automobile noises, motorbike noises, airplane noises, ocean vessel noises, mechanical noises in factories, traffic noises in cities, and configuration noises in configuration sites and adding a vibration that contains the super-high-frequency components having the predetermined autocorrelation order and can introduce the fundamental brain activation effect, the effects of suppressing the deterioration in the fundamental brain activity and alleviating the unpleasant sensation can be developed.

Besides these, by complementing stresses caused by presence in an unpleasant public space such as a packed train, a crowd home, a queue of a ticket machine, a theme park or the like, a people jam crush in an urban district or the like or irritative feelings that tend to occur in play facilities, racetracks and so on with a vibration (hypersonic sound) that can introduce the fundamental brain activation effect because it contains super-high-frequency components having the predetermined autocorrelation order in the space, the effects of suppressing the deterioration in the fundamental brain activity and alleviating the stresses can be developed. With this arrangement, it can be expected to alleviate the human irritative feelings and exert a pervasive effect for reducing violent behaviors and so on.

Moreover, by producing the effect of complementing with a vibration (hypersonic sound) that can introduce the fundamental brain activation effect because it contains super-high-frequency components having the predetermined autocorrelation order in operating rooms and treatment chambers in hospitals and clinics, nurse's offices and dispensaries in schools and companies, and the like, the effects of suppressing the deterioration in the fundamental brain activity of patients, visitors and the like in the room and alleviating the stresses caused by pains and sufferings can be expected.

Third Preferred Embodiment

In the third preferred embodiment according to the present invention, complex sensory information means for comprehensively working on a plurality of sensory systems is provided. The means is to solve such a problem that, as a result of the trade-off state in the information capacity usable between mutually different pieces of sensory information due to a tendency of the occurrence of restrictions in the capacity of recordable and transmittable information and the information transmission rate of various kinds of sensory information and consequent strain on the data saving of a part of sensory information, a possible deterioration in the expressive effect owned by the sensory information and double ruin due to an effort to make both of them effective are avoided. As a background of the means for solving this problem, the present inventor and others paid attention to the actual state in which the generation of reactions of pleasure, beauty, and emotion in a human being were unitarily comprehensively managed by the reward system neural circuit of the brain, the fact that the reward system neural circuit was included in the fundamental brain and the fundamental brain network and the activity was identified to the activity of the whole fundamental brain and the phenomenon that the fundamental brain and the fundamental brain network were activated by a hypersonic sound. By making examinations based on these, the present inventor and others discovered the phenomena that, when a hypersonic effect was introduced by making the sound information contained in the complex sensory information have an appropriate structure to activate the fundamental brain and the fundamental brain network (fundamental brain network system) including the reward system neural circuit of the brain unitarily comprehensively responsible for the generation of reactions of pleasure, beauty and emotion in a human being, the aesthetic sensibility to a variety of kinds of sensory information inputs other than the auditory sensation was also enhanced in parallel with an increase in the aesthetic sensibility to sounds, developing the effects of enhancing the reactions of pleasure, beauty and emotion, and obtained an idea to apply it.

The vibration generating apparatus and method according to the third preferred embodiment is characterized in that, by applying a hypersonic sound, i.e., a vibration containing audible range components and super-high-frequency components having the feature of the predetermined autocorrelation order while applying predetermined information to a person concerning at least one of visual sensation, gustatory sensation, somatic sensation and olfactory sensation other than the auditory sensation to the person, the fundamental brain and the fundamental brain network (fundamental brain network system) including the reward system neural circuit of the brain unitarily comprehensively responsible for the generation of reactions of pleasure, beauty and emotion in a human being are activated, thereby enhancing also the aesthetic sensibility to a variety of kinds of sensory information inputs other than the auditory sensation and improving the expressive effect of the sensory information other than the auditory sensation.

That is, in the third preferred embodiment, an example of an apparatus and method that enhances the aesthetic sensibility to the sensory inputs (meaning visual sensation, gustatory sensation, somatic sensation and olfactory sensation) other than the auditory sensation and can improve the expressive effect as the entire sensory system by complex sensory information generating means for comprehensively working on a plurality of sensory systems is described.

In recent years, regarding the contents that synthetically work on a plurality of sensory systems such as video and audio contents recorded in large-capacity package media that are recently rapidly popularized and videos and audios that are distributed and delivered by using Internet and the like, there is such a problem that the information capacity usable for videos and the information capacity usable for audios are in a trade-off state due to restrictions in the capacity of recordable and transmittable information and the information transmission rate, and the image quality and the sound quality of the contents are consequently in an antinomy state. Against the problems, the present inventor and others discovered the phenomena that, when a hypersonic effect was introduced by making the sound information contained in the complex sensory information have an appropriate structure to activate the fundamental brain and the fundamental brain network (fundamental brain network system) including the reward system neural circuit of the brain unitarily comprehensively responsible for the generation of pleasure, beauty and emotion in the recipient, the aesthetic sensibility to a variety of kinds of sensory information inputs other than the auditory sensation was also enhanced in parallel with an increase in the aesthetic sensibility to sound, and the effects of enhancing the reactions of pleasure, beauty and emotion were developed, and invented an apparatus and method for solving the problems by applying it.

The present preferred embodiment is the complex sensory information generating means of the so-called composite art and the like that include the generation of a sound, i.e., an elastic vibration in an expressive style for comprehensively working on the plurality of sensory systems, such as video package media, movies, television broadcastings, Internet distribution videos and theatrical arts. By containing sound information as an essential element that constitutes the complex sensory information and making it as a vibration that contains audible range components and super-high-frequency components having the predetermined autocorrelation order, the activation effect of the recipient's fundamental brain and fundamental brain network (fundamental brain network system) can be introduced. As a result, the reward system neural circuit of the brain, which is the essential element of the fundamental brain and fundamental brain network (fundamental brain network system) and unitarily comprehensively responsible for the generation of reactions of pleasure, beauty and emotion in a human being are activated, by which the aesthetic sensibility induced by not only the auditory sensation but also sensory information induced by sensations other than the auditory sensation are comprehensively enhanced. As a result, the expressive effects introduced by the sensory information other than the auditory sensation, such as screen images, pictorial images, and visual information of lives that constitute the complex sensory information generating means are enhanced, and sensuous artistic value such as moving impression are remarkably heightened.

FIG. 84 shows an example in which, an increase in the moving impression of screen image expression and an improvement in the image quality are induced by forming a sound to be put in a soundtrack in video-and-audio complex package media such as a Blu-ray Disc into a vibration, that has audible range components and the feature of the predetermined autocorrelation order and can introduce the fundamental brain activation effect, i.e., a hypersonic sound. The aesthetic sensibility to screen images of a viewer who is watching the screen images of a Blu-ray Disc is enhanced, and his or her pleasure, beauty and emotion can be heightened. The video and audio system of FIG. 84 is constituted of a display 852, a Blu-ray Disc player 854 in which a Blu-ray Disc 853 is mounted, an AV amplifier 855, and a 5.1-ch surround loudspeaker system 856. Moreover, when the vibration signal recorded in the soundtrack of the video-and-audio complex package media of the Blu-ray Disc or the like is a vibration that does neither contain super-high-frequency components nor introduce the fundamental brain activation effect, it is complemented with a vibration that can introduce the fundamental brain activation effect at terminal equipment by the various kinds of apparatuses and methods described in the second preferred embodiment or the like and then reproduced.

An example of an experiment to evaluate a difference in the impression of the screen image caused by a difference as to whether the sound has the fundamental brain activation effect by using the "Blu-ray Disc version AKIRA" as an example of the complex sensory information that comprehensively works on the plurality of sensory systems is described below.

The screen image of the "Blu-ray Disc version AKIRA" used for the experiment is obtained by recording the screen image of an animation movie presented in a theater into the image track of the Blu-ray Disc.

The sound is edited for the "Blu-ray Disc version AKIRA soundtrack". The past AKIRA soundtrack, of which the vibration signal has been recorded in DVDs in the digital format of a sampling frequency of 48 kHz and a quantization bit count of 16 bits, can neither record nor reproduce the band components of not lower than the Nyquist frequency of 24 kHz, or a half of the sampling frequency and is therefore unable to introduce the fundamental brain activation effect. Accordingly, the audio signal for the DVD version AKIRA soundtrack" was used as an original vibration, and the signal was subjected to band expansion. In addition, by synthesizing an output signal by adding a tropical rain forest environmental sound that is a typical vibration that could introduce the fundamental brain activation effect, and the super-high-frequency components exceeding the audible range upper limit extracted from it and so on to the sound by using the vibration signal generating apparatus including the vibration complementing apparatus shown in FIG. 66 and recording it into a Blu-ray Disc in the digital format of a sampling frequency of 192 kHz and a quantization bit count of 24 bits, the vibration signal of the "Blu-ray Disc version AKIRA soundtrack" was formed and recorded into a Blu-ray Disc. As shown in FIGS. 78 to 81, this sound is a sound that sufficiently contains the super-high-frequency components having the two properties on the autocorrelation order and can introduce the fundamental brain activation effect.

In the experiment, an identical screen image was consistently presented, while the sound was presented under the blindfold by switchover between two conditions. That is, one of them presented the vibration signal of the "Blu-ray Disc version AKIRA soundtrack" unchanged as the original in the state of a vibration signal (full-range sound) that contained super-high-frequency components having the property on the autocorrelation order and could introduce the fundamental brain activation effect, and the other presented a sound reproduced in the state of a vibration signal (high-cut signal) that could not introduce the fundamental brain activation effect obtained by removing the frequency components of not lower than 24 kHz from it by a low-pass filter. The experiment presented and compared two kinds of sounds with a screen image reproduced from an utterly identical image data under the blindfold.

The test human subjects were made to answer respective impressions by a questionnaire about the images under the full-range sound condition that could introduce the fundamental brain activation effect and the high-cut sound condition that could not introduce the fundamental brain activation effect. Twelve evaluation words expressing the impressions about the screen image were shown on the questionnaire, and the subjects were made to perform evaluations by five-rank evaluation. The answers of ten test human subjects in total were analyzed.

FIG. 85 shows the experimental results. The left chart is one in which a difference is obtained by subtracting the impression grade of the screen image in the high-cut sound condition from the impression grade of the screen image in the full-range sound condition regarding each test human subject, and averages are obtained regarding all the test human subjects and plotted. This numerical value indicates that the sound in the full-range sound condition is more positively evaluated as it is greater and defined hereinbefore as "favorability rating". The right chart shows the results of examination by the signed rank test of Wilcoxon (Wilcoxon) as to whether a significance exists in the bias of the "favorability rating".

As a result, it was clarified that the screen image that the viewer watched while receiving the full-range sound having the fundamental brain activation effect had a higher favorability rating and was received more beautifully and movingly than the screen image that the viewer watched while receiving the high-cut sound having no such an effect regardless of that the identical screen image reproduced from utterly identical image data under the completely identical condition was consistently prescribed in the experiment. In particular, the evaluation words: "impressed by screen image" and "image quality is good" are evaluated statistically significantly positively with p<0.05 (mark ** in the right figure of FIG. 85). Moreover, with regard to the evaluation words of the seven items of "motion picture movement is smooth", "depiction of picture is accurate", "background picture is realistic", "screen texture is fine", "nuance of picture is rich", "depth is felt on screen" and "color is vivid" are positively evaluated with a high tendency of p<0.10 (mark * in the right figure of FIG. 85). Besides these, the evaluation words: "image contrast is high and clearly viewed", "easy to view" and "coloration is complicated" are positively evaluated.

As described above, regarding the video-and-audio complex package media of "Blu-ray Disc version AKIRA", the screen image, which was reproduced from the identical image data under the identical conditions and had no difference as the image itself, was received as those having mutually different image qualities depending on whether the sound of the soundtrack that was concurrently reproduced and presented to the viewer introduced the fundamental brain activation effect, and it was statistically significantly indicated that the viewer received the screen image as one having higher image quality and more moving when the hypersonic sound capable of introducing the fundamental brain activation effect was presented than when the contrary sound was presented.

As described above, the effectiveness of the aforementioned idea of the inventor and others were proven. That is, the inventor and others paid attention to the actual state in which the generation of reactions of pleasure, beauty, and emotion in a human being were unitarily comprehensively managed by the reward system neural circuit of the brain, the fact that the reward system neural circuit was included in the fundamental brain and the fundamental brain network and the phenomenon that the fundamental brain and the fundamental brain network were activated by a hypersonic sound, and obtained an idea that, the aesthetic sensibility to a variety of kinds of sensory information inputs other than the auditory sensation was also enhanced in parallel with an increase in the aesthetic sensibility to sounds, developing the effects of enhancing the reactions of pleasure, beauty and emotion when a hypersonic effect was introduced by making the sound information contained in the complex sensory information have an appropriate structure to activate the fundamental brain and the fundamental brain network (fundamental brain network system) including the reward system neural circuit of the brain unitarily comprehensively responsible for the generation of reactions of pleasure, beauty and emotion in a human being, and obtained an idea to apply it. The above-mentioned experimental results proved that the idea hit the mark.

The evaluation words: "depiction of picture is accurate", "screen texture is fine" and "background picture is realistic" by which the favorability rating is raised by this experimental results surprisingly coincide with the evaluations that indicate an increase in the image quality characteristically appearing when the information capacity consumed for the image data is increased to densify the screen image. The evaluation results indicate the amazing fact that an effect equivalent to increasing the information capacity distributed to the image data can be introduced by giving the property of the autocorrelation order that introduces the fundamental brain activation effect to the sound information presented simultaneously with the image. That is, the contents, which comprehensively works on the plurality of sensory systems as described above, have such a serious problem that, due to restrictions in the recordable and transmittable information capacity and the information transmission rate, a trade-off relation results between different sorts of sensory information such as image quality and sound quality to give a strain to partial sensory information, consequently causing a deterioration in the expressive effect owned by the sensory information and double ruin as a result of trying to make use of each other. Regarding this fateful problem owned by the complex sensory information generating means, it is indicated that superb solution means can be provided by using the apparatus and method of the present invention. In general, it is necessary for improvements in the image quality to achieve technological development requiring a huge cost and system of the contents, such as, first of all, an increase in the recordable data capacity, further developments in the data compression technology and data transfer technology, and development of hardware for reproduction. However, by using the apparatus and method of the present invention, it becomes possible to solve the problems by inducing the image quality improvement effect by an extremely realistic acoustic technology and method without depending on the developments in advanced information processing related technologies as described above.

Next, application examples of the third preferred embodiment are described.

FIG. 86 is a perspective view showing an example of an apparatus that can enhance the aesthetic sensibility of the viewer, improve the television image quality, and let the viewer receive the vision more pleasantly, beautifully and movingly by applying a vibration that can introduce the fundamental brain activation effect from a loudspeaker that reproduces the television sound to the viewer by transmitting a vibration signal (hypersonic sound signal) that can introduce the fundamental brain activation effect in television broadcastings.

When the sound source itself to be broadcasted is a vibration (hypersonic sound signal) that contain super-high-frequency components having the property of the autocorrelation order and can introduce the fundamental brain activation effect, a television signal that has this effect by actualizing the broad-banded sound standard can be transmitted although the sound standard of the current television broadcastings can neither contain nor transmit the super-high-frequency components. Moreover, it may be transmitted by using high-speed large-capacity Internet communications or the like.

Moreover, when the sound source to be broadcasted is a vibration that cannot introduce the fundamental brain activation effect, by transmitting it after complementing it with a vibration signal (hypersonic sound signal) that can introduce the fundamental brain activation effect by various kinds of complementing apparatuses and complementing methods described in the second preferred embodiment at the time of editing it in the broadcasting station, it is also possible to activate the reward system neural circuit, enhance the recipient's aesthetic sensibility, heighten the pleasure, beauty and emotion and achieve an improvement in the received image quality. Also, in the case, it can be transmitted by actualizing the broadbanded sound standard although the sound standard of the current television broadcastings can neither contain nor transmit the super-high-frequency components. Moreover, it may be transmitted by using high-speed large-capacity Internet communications or the like.

Further, when the vibration signal transmitted to broadcasting peripheral equipment such as the current digital television and the like is a vibration signal that can neither contain super-high-frequency components nor introduce the fundamental brain activation effect, it is acceptable to complement it with a vibration (hypersonic sound) that can introduce the fundamental brain activation effect in the peripheral equipment by the various kinds of apparatuses and methods described in the second preferred embodiment and reproduce it. By so doing, it is also possible to activate the reward system neural circuit, enhance the recipient's aesthetic sensibility, achieve an improvement in the received image quality and enhance the pleasure, beauty and emotion.

The apparatus also includes the current terrestrial digital broadcastings (including one-segment broadcastings), BS digital broadcastings, analog TV broadcastings and video and audio contents that are transmitted and distributed by the communications of Internet or the like as the objects thereof.

Other application examples are described. The following includes more positive application examples paying attention not to a solution for such a problem that the qualities of different sorts of sensory information fall into the antinomy state due to the trade-off relation because of the technological constraints but to the fact that the hypersonic sound activates the fundamental brain by the complex sensory information generating means for working on the plurality of sensory systems and induces the effect of activating the reward system having the function unitarily comprehensively responsible for the generation of pleasure, beauty and emotion in a human being. For example, by constituting the vibration of the music to which the audiences listen as a hypersonic sound that can introduce the fundamental brain activation effect having the predetermined autocorrelation order in a case of, for example, a dance performance in a theater, the aesthetic sensibility of the audiences is enhanced to make them feel the dance more beautifully and pleasantly. This example can be applied also to other live performances, art museums, museums, art galleries, jewelry shops, boutiques, cosmetics departments and so on.

As application examples to other sensations, by constituting the music to which the guests listen as a hypersonic sound that can introduce the fundamental brain activation effect in, for example, a music restaurant, the guest's gustatory sensibility is enhanced, making him or her feel the dish more delicious. This example can be applied also to tea shops, dining rooms, bars and so on.

Moreover, by constituting the music received by the guest as a hypersonic sound that can introduce the fundamental brain activation effect in a case of bathing and massage and music in a music spa or the like, the sensibility of the guest's somatic sensation is enhanced, allowing him or her to physically feel the bathing or massage more pleasantly.

Further, by constituting the sound received by the passengers or trainmen as a hypersonic sound that can introduce the fundamental brain activation effect in vehicles of railways, cars, airplanes, ocean vessels, rockets and so on, the favorability rating of the somatic sensations of the passengers or trainmen are enhanced, allowing them to physically feel comfortable ride quality.

Moreover, by constituting the aroma and music received by the guest as a hypersonic sound that can introduce the fundamental brain activation effect in a case of music aroma therapy and the like, the sensibility of the guest's olfactory sensation is enhanced, allowing him or her to feel more pleasant aroma and inducing higher healing effects.

As described above, by applying a hypersonic sound, i.e., a vibration that contains audible range components and super-high-frequency components having the feature of the predetermined autocorrelation order to a human being while applying predetermined information to the person regarding at least one of visual sensation, gustatory sensation, somatic sensation and olfactory sensation other than the auditory sensation, the fundamental brain and the fundamental brain network (fundamental brain network system) including the reward system neural circuit, which is the brain function region unitarily comprehensively responsible for the generation of reactions of pleasure, beauty and emotion in the human being are activated, by which the aesthetic sensibility to sensory inputs other than the auditory sensation is also enhanced, allowing the expressive effect of the sensory information other than the auditory sensation to be heightened.

Fourth Preferred Embodiment

Next, in the fourth preferred embodiment, a vibration generating apparatus and method characterized in that two effects of sensitization and comforting of sensation are developed or intensified in a coexistent state by enhancing the activity of the entire fundamental brain network system by applying the vibration generating apparatuses described in the first through third preferred embodiments is described.

There is a problem of the occurrence of an antinomy phenomenon such that the "necessary information cannot be caught unless the sound volume is increased" and "it becomes noisy and unpleasant if the sound volume is increased" when a sound aimed for information transmission by, for example, public-address broadcasting coexists with other sounds, such as a remarkable background noise, which have properties of disturbing the transmission. Problems similar to this exist under various situations, and, for example, the sound effects of audio and video contents and the sound effects of a theatrical performance have the antinomy problem such that the "intended artistic effects cannot be obtained unless the sound volume is increased" and "it becomes unpleasant if the sound volume is increased".

In order to solve this problem without contradiction, it becomes possible to develop or enhance both of sensitization and comforting of the sound perception by enhancing the activity of the entire fundamental brain network system, activating the thalamus and the brain stem that are included in the system and have the operation of sensitizing the sensibility to the general sensory information inputs (excluding the olfactory sensation) and concurrently activating in parallel the reward system neural circuit that is included in the same system and has an operation to generate a pleasurable sensation and alleviate unpleasant sensation, with the complementing of a vibration (hypersonic sound) that contains super-high-frequency components having the feature of the autocorrelation order.

First of all, the two effects of a vibration that can introduce the hypersonic effect, i.e., a hypersonic sound is described with the grounds thereof.

The first effect is the effect of sensitizing the sensibility to the sensory information inputs by enhancing the activity of the thalamus and the brain stem included in the listener's fundamental brain network system and making him or her more clearly recognize the sensory information of the sound or the like. This is proven by the results of the following psychological experiments. That is, the three conditions of a condition that a vibration (hypersonic sound) that could introduce the fundamental brain activation effect because of the contained super-high-frequency components having the predetermined autocorrelation order was presented, a condition that a vibration (audible sound) that did neither contain the super-high-frequency components nor could introduce the fundamental brain activation effect was presented, and a condition that no particular sound was presented were daily set in a library. Questionnaire investigation was carried out on one hundred or more test human subjects who stayed for several minutes to several tens of minutes in the library when they left the room to inquire a difference in their conscious senses between before entering the room and at the time of leaving the room.

As a result, the answers that "the sound became clearly heard" and "things became clearly seen" at the time of leaving the room than before entering the room frequently occurred with an extremely high statistical significance on the days when the hypersonic sound was presented in the library in comparison with the days when the audible sound was presented and the days when no particular sound was presented (See FIG. 105). That is, it was proven that the sensibility to the sensory information inputs became sensitized by the fundamental brain activation effect, and the consciousness that the visual and auditory information was recognized more clearly was heightened.

The second effect is the effect of enhancing the aesthetic sensibility to the sensory information by similarly inducing the activation of the reward system neural circuit included in the listener's fundamental brain network system and making him or her feel comfortable a vibration input at full blast. This is proved from the results of the following behavioral experiments. That is, the test human subject is made to hear a sound at full blast and to select his or her favorite sound volume by freely adjusting the sound volume by using an adjuster for increasing and decreasing the sound volume. In this case, the test human subject cannot see the scale for the volume adjustment. As a result of this experiment, the finally adjusted sound volume becomes statistically significantly increased when the listener is made to hear the vibration (hypersonic sound) that can introduce the fundamental brain activation effect because it contains super-high-frequency components having the predetermined autocorrelation order than when the listener is made to hear the vibration (audible sound) that cannot introduce the fundamental brain activation effect (hypersonic effect) because it contains no super-high-frequency component (See FIG. 106). Moreover, a tendency of gradually turning up the volume is observed while repeating. For this reason, it can be understood that a larger sound volume is selected due to a high comfortable sensation in the case of the hypersonic sound, by contrast to which the sound volume is set smaller conversely due to a high unpleasant sensation in the case of the audible sound. The above indicates that the listener's comfortable sensation to the vibration input at full blast can be heightened by presenting the hypersonic sound.

Moreover, when the super-high-frequency components contained in the hypersonic sound were further enhanced by a similar experiment, the test human subjects adjusted the level so that the sound volume was further raised (See FIG. 107). In this case, it was indicated that the favorite volumes set by these test human subjects were increased with a high correlation to the DBA-index, or the index of the fundamental brain activity.

As described above, the hypersonic sound introduces the two effects of heightening the degree of awakening by sensitizing the sensibility to the sensory inputs including the auditory sensation by the activation of the thalamus and the brain stem and introducing a cognition improving effect, and introducing an improvement in the sense of comfort and alleviating the unpleasant sensation by the activation of the reward system in a state in a coexistent state.

An implemental example obtained by applying the feature of the coexistence of the two effects is described below. The first example is an example of public-address broadcasting for the purpose of transmitting information to the passengers in a station yard. Announcement sounds and broadcast sounds issued in a station yard need to be reliably transmitted to the users, and therefore, a sound volume required for the purpose must be secured. In particular, "the necessary information cannot be caught unless the sound volume is increased" in many cases where background noises are significant, and therefore, the users must be exposed to the public-address sounds at full blast in terms of achieving the purpose of information transmission, and this inevitably leads to such a problem that the unpleasant sensation of "noisy" and so on is caused.

In addition, also when the sound to be subjected to the public-address broadcasting is an audio signal that has been already recorded or artificially generated and when the response characteristics of the public-address broadcasting system are not sufficient in the frequency domain of not lower than the audible frequency range, the user is exposed to the public-address sound that lacks the super-high-frequency components at full blast even when a live sound is subjected to the public-address broadcasting, and this possibly causes a risk of deteriorating the fundamental brain activity (See FIGS. 90 and 17). The deterioration in the fundamental brain activity induces a stress reaction such as an increase in the adrenaline concentration, further intensifying the unpleasant sensation of "noisy" and the like and leads to irritative feelings. As described above, in addition to the disadvantage that the necessary information is not effectively transmitted, there is such a serious problem that the risk of triggering violent behaviors and abnormal behaviors rises.

Solution measures against such a problem is described below. In this case, the configuration of the sounds existing in the station yard are classified into "transmission sound (audible sound)=sounds of announcement and chime that transmit information necessary for user", "background noise (audible sound)=noises in station yard, train noises, BGM, and other sounds that disturb transmission", "hypersonic sound", and "super-high-frequency components of hypersonic sound" (expressed as "hypersonic sound or its super-high-frequency components" when either one of both is valid).

The transmission sound (audible sound) is complemented with a hypersonic sound or its super-high-frequency components by installing a vibration generating apparatus to which any one of the first to third preferred embodiments is applied. The vibration for complementing may be the hypersonic sound itself like, for example, a tropical rain forest environmental sound that does not disturb the transmission of the necessary information or only the super-high-frequency components of the hypersonic sound. With this arrangement, the regions of the thalamus and the brain stem belonging to the fundamental brain network system are activated to enhance the sensibility and the degree of awakening to sensory information inputs, and this induces the effects of improving the cognition of the sound and transmitting the transmission sound (audible sound) to be easily caught even if the user is in a space having significant background noises. In this case, in addition to the aforementioned effects, the reward system neural circuit of the brain that similarly belongs to the fundamental brain network system and is responsible for the generation of reactions of pleasure, beauty and emotion in a human being is activated in parallel, and the aesthetic sensibility to sensory information inputted to the user is enhanced. Therefore, the comfortable sensation even to the transmission sound (audible sound) at full blast is increased, and the unpleasant feelings and irritative feelings such as "noisy" can be alleviated. In this case, the comfortable sensation to the sound at full blast is further increased as the power ratio of the super-high-frequency components of the hypersonic sound is increased.

Concrete examples of vibration complementing apparatuses and methods for complementing with a hypersonic sound or its super-high-frequency components are described below.

(1) As shown in FIG. 108, the transmission sound (audible sound) and the hypersonic sound or its super-high-frequency components are recorded in mixture at a prescribed balance, and its signal is reproduced by using a public-address system 472 having a faithful response performance. In this case, the vibration complementing apparatus is constituted of a vibration signal reproducing apparatus 470 that reproduces a vibration signal by using a recording medium 470d in which the transmission sound (audible sound) and the hypersonic sound or its super-high-frequency components are recorded in mixture, a vibration signal amplifier 471, and the public-address system 472.

(2) As shown in FIG. 109, the transmission sound (audible sound) and the hypersonic sound or its super-high-frequency components are generated by using public-address systems 472 and 472 that are varied depending on different sound sources. In this case, the transmission sound (audible sound) and the hypersonic sound or its super-high-frequency components can be severally independently controlled in level. In this case, the vibration complementing apparatus is constituted of:

(a) a first apparatus that includes a microphone 473 that collects the transmission sound (audible sound), the vibration signal amplifier 471, and the public-address system 472; and (b) a second apparatus that includes a vibration signal reproducing apparatus 470 that reproduces the vibration signal by using the recording medium 470d in which the hypersonic sound or its super-high-frequency components are recorded, the vibration signal amplifier 471, and the public-address system 472.

(3) This is a modified preferred embodiment of the above-mentioned case (2), in which the transmission sound (audible sound) and the hypersonic sound or its super-high-frequency components are synthesized on the spot and generated from one public-address system 472 as shown in FIG. 110. The vibration complementing apparatus is constituted of the microphone 473 that collects the transmission sound (audible sound), the vibration signal reproducing apparatus 470 that reproduces the vibration signal by using the recording medium 470d in which the hypersonic sound or its super-high-frequency components are recorded, a vibration signal addition adjuster 474, the vibration signal amplifier 471, and the public-address system 472. The vibration signal addition adjuster 474 adjusts the levels of inputted two signals, adds them together, and outputs the resultant to the public-address system 472 via the vibration signal amplifier 471.

(4) This is an example in which an adjusting function is further incorporated into the above-mentioned case (3). As shown in FIG. 111, a background noise (audible sound) is collected by a microphone 475, the feature of the background noise (audible sound) is measured by a vibration measuring instrument 476 based on the collected vibration signal, and the measured data is inputted to the vibration signal addition adjuster 474. The other configurations include the configuration of the above-mentioned case (3). The vibration signal addition adjuster 474 has a function to adjust the transmission sound (audible sound) and the hypersonic sound or its super-high-frequency components in accordance with the feature of the background noise (audible sound). As examples of the adjustment function, there is, for example, a function to turn on the hypersonic sound or its super-high-frequency components when the noise level of the background noise (audible sound) exceeds a definite value or a function to amplify the level of the transmission sound (audible sound) and the hypersonic sound or its super-high-frequency components by an amplification factor correlated to the noise level of the background noise (audible sound) or a function to analyze the feature of the autocorrelation order of the background noise (audible sound) and emphasize or suppress the feature of the autocorrelation order of the hypersonic sound or its super-high-frequency components, or the like.

FIG. 112 shows an example in which the vibration generating apparatus is installed by various installation methods in a station yard 480. In FIG. 112, reference numeral 481 is a pillar mounted type vibration generating apparatus, 482 is a signal receiver of the transmission sound (audible sound) such as an announcement sound, 483 is a super-high-frequency vibration signal receiver, 484 is a loudspeaker (public-address system) that generates a transmission sound (audible sound), and 489 is a super-high-frequency vibration generating apparatus. Reference numeral 485 is a ceiling embedded type vibration generating apparatus with a built-in memory 485m that stores a super-high-frequency vibration signal, 486 is a hypersonic sound generating apparatus, 487 is a loudspeaker (public-address system) that generates a hypersonic sound or its super-high-frequency components together with the transmission sound (audible sound), and 488 is a person. This vibration generating apparatus may be newly installed or additionally incorporated into the existent premises public-address system. Moreover, the signal of the vibration may be externally inputted by wire or provided by receiving a signal externally transmitted wirelessly (electromagnetic wave, infrared rays, LAN, Bluetooth (registered trademark), etc.) Otherwise, it may be recorded in a memory and integrated into each vibration generating apparatus. Moreover, it may be artificially generated in the vibration generating apparatus. Moreover, it is acceptable to generate a vibration from the entire housing of the public-address system or generate a vibration from a cable and its sheath, a peripheral ceiling or wall, a pillar, an architectural material or the like.

Similar examples of this implemental example are described. Applications can also be provided for various kinds of announcements of departure and arrival guidance, boarding guidance, accident information, and schedule changes in airports and vehicles, evacuation guidance broadcastings at streets, underground shopping centers, event sites, amusement parks, and stadiums, cases where public-address broadcastings and the like intended for information transmission in spaces having significant background noises are performed such as indoor broadcastings in public institutions and factories.

Moreover, in the disaster sites of fire, earthquake and accident, it is important to appropriately guide the victims by an evacuation guidance with a broadcast sound or a public-address sound, and there is a risk that it cannot be caught due to masking by the background noises of a large sound volume, and this leads to such a problem that a group panic easily occurs. In contrast to this, by providing a complementing vibration that can introduce the fundamental brain activation effect in a space, the victims' sensibilities to the sensory information input are sensitized to allow them to easily catch the vocal information of the evacuation guidance for the victims, and the reward system neural circuit is activated to alleviate the insecurity feelings. It consequently becomes helpful for appropriately guiding the victims without causing the group panic.

Further, there is such a problem that the driver and fellow passengers in a car become irritated by congestion and getting sleepy on an expressway or an ordinary road. With regard to this, a hypersonic sound signal is transmitted together with traffic information transmitted to the car or independently. The vehicle running on the road generates a hypersonic sound by transducing the received signal into an aerial vibration by receiving this vibration signal together with traffic information or solely or using the vibration signal generating apparatus installed in the vehicle. With this arrangement, the degree of awakening of the driver and the fellow passengers is heightened, and this leads to an effect of improving cognition to the traffic information. In addition, the abilities of cognition and judgment to visual information inputs are heightened, inducing an accident preventing effect, and it is expected to alleviate the irritative feelings due to the congestion.

Likewise, it is sometimes the case where broadcast sounds intended for information transmission of guidance of users or the like are hardly caught due to masking by significant background noises in public institutions such as airports, outdoor and indoor event sites, hospitals, schools, and libraries, facilities such as concert halls, department stores, and amusement parks, and other public spaces having significant background noises, such as shopping streets, station squares and parks. With regard to this, by complementing with a hypersonic sound that can introduce the fundamental brain activation effect in a space, the users' sensibilities to sensory information inputs are sensitized to allow the broadcast sound to be easily caught, and the reward system neural circuit is activated to alleviate the unpleasant sensation and irritative feelings such as "noisy", allowing the comfort to be improved.

Next, coexistence of the two effects of the vibration that can introduce the hypersonic effect, i.e., the hypersonic sound is described below by taking the movie BD "AKIRA" as an example of the second implemental example utilized for enhancing the artistic expression effect.

For example, three factors of the movie sound are called DMS obtained from the capital letters of D (Dialogue), M (Music), and S (Sound effect). Among these, regarding S (sound effect), a sense of presence is increased and stage effects such as an increase in thrill are obtained as the sound volume is increased. However, if the sound volume is increased, there is such an inevitable problem that "unpleasant" and "noisy" reactions occurs.

With regard to this problem, in the BD "AKIRA", movie sounds were classified into "dialogue and music (audible sound), "sound effect (audible sound)=sound intended for stage effect dramatic impacts", "hypersonic sound", and "super-high-frequency component of hypersonic sound" (expressed as "hypersonic sound or its super-high-frequency components" when either one of both is valid). By complementing not only the "dialogue and music (audible sound)" but also the "sound effects (audible sound)" with a hypersonic sound or its super-high-frequency components, it is successful to remarkably boost the stage effects by compatibly heightening the comfortable sensation with a large sound volume without causing the noisy reaction. Asakura Reiji's says, "the range of sound is exceptionally wide, and the impression is "unnoisy" at a word. It was my first experience to see a movie where such unnoisy action scenes continued. There were many ordinary tiring DVD/BD action movies though having punches, but this "AKIRA" was ferment, exciting in the best sense, and attentive surround" (from the BD "AKIRA" liner notes).

As similar examples of this kind, there are movies, plays and musicals in theaters, television broadcastings, live performances and so on. Concrete examples of methods for complementing the audible sound with the hypersonic sound are described below.

(1) An audible sound and a hypersonic sound or its super-high-frequency components are elaborated in package media by previously deciding the balance.

(2) A case where an audible sound and a hypersonic sound or its super-high-frequency components are transmitted by previously deciding the balance in a manner similar to that of programs that are broadcasted and distributed.

(3) An audible sound and a hypersonic sound or its super-high-frequency components are controlled on the spot in a manner similar to that of lives.

(4) Also in the package media, broadcastings, and distributed programs, an audible sound and the super-high-frequency components of a hypersonic sound are put in another track or other package media, and the balance between both of them is made controllable at the time of reproducing.

Next, a third implemental example, in which the coexistence of the two effects of a vibration that can introduce the hypersonic effect, i.e., a hypersonic sound is utilized for attracting customers and enhancing the business effects, is described below. In play facilities such as video arcades and pachinko parlors, actions for enhancing the guests' excitability and the like are produced by exposing the guests to a BGM at full blast, explosive sounds of game machines, gushing pachinko ball sounds and the like, trying to link it to the attraction and business effects. However, the exposure to the sound at full blast inevitably causes the problem of the "unpleasant" and "noisy" reactions.

Further, when a sound containing no super-high-frequency component such as a CD is used for the in-store BGM or the like, there are the risks of causing deteriorations in the fundamental brain activities of guests and clerks, increasing irritative feelings, and this leads to stress reactions such as an increase in the adrenaline concentration, and triggering violent behaviors and abnormal behaviors. In particular, negative influences on the play facilities where youth tend to gather are serious problems.

Regarding the problems as described above, in play facilities such as video arcades and pachinko parlors, by complementing the audible sounds (in-store BGMs, conversational voices, game machine sounds, gushing pachinko ball sounds, etc.) with a hypersonic sound or its super-high-frequency components in the store, it becomes difficult to cause the "unpleasant" and "noisy" reactions in spite of the large sound volume that sufficiently achieves the purpose of enhancing the excitability of the guests. Moreover, it contributes to preventing deteriorations in the fundamental brain activities of guests and clerks, suppressing generation of irritative feelings and stresses, and preventing violent behaviors and abnormal behaviors. As similar examples of this kind, there are discotiques, music tearooms, and face-to-face demonstration sales (e.g., cattail oil sales, etc.)

The vibration generating apparatuses described in the first to third preferred embodiments of the present application can be applied to the vibration generating apparatus for achieving this. This vibration generating apparatus may be incorporated into the in-store walls, ceilings, internal trim parts, individual game machines, pachinko machines and the like or externally attached. The sound source may be previously recorded in a recording medium or transmitted by broadcastings and telecommunications.

Concrete examples of the complementing method are described below.

(1) An audible sound and a hypersonic sound or is super-high-frequency components are recorded at a previously decided balance, and the signal is reproduced by using a public-address system having a faithful response performance.

(2) A case where an audible sound and a hypersonic sound or is super-high-frequency components are generated by a vibration generating apparatus varied depending on different sound sources. They can be independently controlled in level.

(3) A modified preferred embodiment of the case (2), in which an audible sound and a hypersonic sound or its super-high-frequency components are synthesized on the spot and generated from one vibration generating apparatus.

Next, a fourth implemental example, in which the coexistence of the two effects of a vibration that can introduce the hypersonic effect, i.e., a hypersonic sound is utilized for safety measures, is described below. The following is an implemental example applied to an electric vehicle.

Recently, in place of the gasoline powered vehicles, development of electric vehicles (including hybrid cars, fuel cell powered cars, solar powered cars, etc.) has been rapidly promoted, and they have many advantages that the exhaust is clean and environment friendly, they have no engine noise, and so on. However, there is such an emerging serious problem that the electric vehicles, which use motors producing small noises in place of internal combustion engines that generate blast sounds, have quiet running noises, and therefore, the pedestrians, bicycle riders, car drivers and the like tend to fail in perceiving approaching electric vehicles, increasing the risks of traffic accidents, and urgent countermeasures need to be devised.

Accordingly, measures to generate a sort of sound from the electric vehicles are considered for easy perception of approaching electric vehicles. However, generating a sound at a level perceivable by the pedestrians and the like in the significant background noises on roads inevitably causes the problem of the "unpleasant" and "noisy" reactions.

This problem can be solved by utilizing the coexistence of the two effects of a hypersonic sound that introduce the hypersonic effect and enhances the fundamental brain activity. By generating a hypersonic sound from an electric vehicle 490 or complementing with the super-high-frequency components of the hypersonic sound, the pedestrians' sensibilities to sounds are sensitized, thereby inducing an effect that the sounds generated from electric vehicles can be easily caught even in an environment having significant traffic noises. On the other hand, the reward system of the brain is activated to improve the comfort of the sounds, and the level of the sound generated from the electric vehicle 490 can be raised up to a height sufficient for making a person 488 of the pedestrian or the like recognize the existence and approach of the vehicle and assure his or her safety without causing his or her "unpleasant" and "noisy" reactions. By the coexistence of the two effects, the comfort and safety can be remarkably improved (See FIG. 113). In FIG. 113, reference numeral 490 is an electric vehicle, in which a vibration generating apparatus 491 is installed.

A vibration generating apparatus and a sound source for achieving this can be provided by applying the vibration generating apparatuses described in the first to third preferred embodiments of the present application. Moreover, this vibration generating apparatus may be previously incorporated into the vehicle body, tires, window panes and the like or externally attached. Moreover, it is acceptable to generate a hypersonic sound having the predetermined autocorrelation order and contains an audible sound and a super-high-frequency vibration from a single vibration generating apparatus or to generate an audible sound and a super-high-frequency vibration from separate vibration generating apparatuses and make the levels and balances of them freely adjustable. Further, the sound source may be recorded in a recording medium or transmitted by broadcasting or a telecommunication system.

Further, the following advantages are also obtained in this implemental example. By radiating the hypersonic sound generated from the electric vehicle into a space of footways and motorways, the effects of inducing activation of the fundamental brain and the fundamental brain network of the pedestrians, bicycle riders, and the like existing in the space, leading the autonomic neural system, the endocrine system and the immune system responsible for the homeostatic maintenance and biophylaxis of the body to satisfactory states and enhancing comfort can be expected.

Further, by applying this vibration generating apparatus, an individual vehicle discrimination system can be made as follows. That is, in manufacturing an electric vehicle into which the vibration generating apparatus is incorporated, a signal structure having an individual frequency and time structure for each car is added into a vibration signal in the super-high-frequency range that exceeds the audible range upper limit and is not perceivable as a sound generated from it. This becomes a super-high-frequency unperceivable "vibration fingerprint", and it becomes possible to make it bear an individual vehicle identification function.

Then, a "vehicle super-high-frequency vibration fingerprint automatic reading apparatus" that automatically reads the "super-high-frequency vibration fingerprint" of each vehicle passing on a road is installed at each strategic spot on the road. It can be expected to utilize this system as a clue of criminal investigations such as pursuit of wanted vehicles and the like, making good use of it for crime prevention.

Other applications of this effect are shown. By complementing with a hypersonic sound or its super-high-frequency components in an office, the effects of enhancing the sensibility and the degree of awakening to sensory information inputs and improving the comfort, thereby improving the labor effectiveness of work.

By complementing with a hypersonic sound or its super-high-frequency components in houses and facilities where senior citizens reside, there are the effects of enhancing the senior citizens' sensibilities to sensory information inputs. As a result, the effect of preventing dementia is consequently expected, and the effect of heightening the comfort and maintaining and promoting psychosomatic health is provided.

By complementing with a hypersonic sound or its super-high-frequency components in classrooms in classrooms of schools, there are effects of improving the learning effect by enhancing the learners' sensibility to sensory information inputs, alleviating the irritative feelings of students and teachers, reducing school violence, and supporting the healthy growth of children and comfortable school lives.

By complementing with a hypersonic sound or its super-high-frequency components in the working environments of doctors and nurses who work in hospitals and clinics, there are the effects of enhancing the sensibilities to sensory information inputs and alleviating the tiredness and stress, thereby reducing medical errors.

By complementing with a hypersonic sound or its super-high-frequency components in the National Diet Building and other spaces that hold conferences, there are the effects of enhancing the conference attendees' sensibilities to sensory information inputs and alleviating angry feelings and irritative feelings due to conflicts of opinions, thereby reducing futile antagonisms and promoting smooth parliamentary proceedings.

Fifth Preferred Embodiment

A vibration discriminating apparatus and method according to the present invention is characterized by discriminating whether or not a given vibration signal is a vibration, that has components (audible range components) within the range of 20 Hz to 15 kHz or 20 kHz, or the audible frequency range perceivable as a sound by human beings and contains super-high-frequency components within the range exceeding the audible range up to, for example, 1 MHz, discriminating whether or not the given vibration signal has the autocorrelation order represented by the first property, discriminating whether or not the given vibration signal has the autocorrelation order represented by the second property, and discriminating whether or not the given vibration signal has the feature of the vibration signal by colligating the discrimination results by the above-mentioned three means.

An implemental example of the vibration discriminating apparatus and method is described below.

FIG. 87 is a flow chart showing derivation control processing of the fundamental brain activation effect according to the fifth preferred embodiment. That is, FIG. 87 shows the flow chart of a method for discriminating whether or not a given vibration signal is a variation that contains audible range components and super-high-frequency components having the predetermined autocorrelation order and can introduce the fundamental brain activation effect.

Referring to FIG. 87, a vibration signal is first inputted in step S1, and the power spectrum of the given vibration signal is calculated in step S2 by using the FFT method or a power spectrum estimation method using an autocorrelation model such as the maximum entropy method and the Yule-Walker method. Next, it is discriminated in step S3 whether or not the given vibration signal contains components (hereinafter referred to as audible range components) within the human audible frequency range of not lower than 20 Hz and not higher than 20 kHz based on the obtained power spectrum, and it is judged that it is a vibration signal that cannot solely introduce the fundamental brain activation effect when no audible range components are contained (step S19). When the audible range components are contained, it is judged in step S4 whether or not the vibration signal contains frequency components (hereinafter referred to as super-high-frequency components) that exceeds 20 kHz, or the human audible range upper limit and ranges up to a maximum frequency of, for example, 1 MHz. When no super-high-frequency component is contained, it is judged that it is a vibration that cannot solely introduce the fundamental brain activation effect. When super-high-frequency components are contained, the program flow proceeds to a first property discriminating process (steps S5 to S10) and a second property discriminating process (steps S11 to S16) on the autocorrelation order.

Regarding the first property evaluation on the autocorrelation order, a three-dimensional power spectrum array of the vibration signal is first drawn in step S5 by using the aforementioned method. Next, the local exponent of fractal dimension of the obtained three-dimensional power spectrum array is obtained in step S6 by using the aforementioned method, and it is discriminated in step S7 whether or not the minimum value of the local exponent of fractal dimension is not smaller than 2.2 within a range in which the spectro-temporal index ranges from $2^{-1}$ to $2^{-5}$. When the minimum value of the local exponent of fractal dimension is smaller than 2.2, it is judged that the first property is not satisfied (step S10). When the minimum value of the local exponent of fractal dimension is not smaller than 2.2, the program flow proceeds to evaluation of the fluctuation range of the local exponent of fractal dimension. It is judged that the first property is satisfied (step S9) when the fluctuation range (absolute value) of the local exponent of fractal dimension is not greater than 0.4 when the spectro-temporal index is within the range of $2^{-1}$ to $2^{-5}$ in step S8, or it is judged that the first property is not satisfied (step S10) when the fluctuation range (absolute value) similarly exceeds 0.4 (step S10). Then, the program flow proceeds to step S17.

On the other hand, regarding evaluation of the second property on the autocorrelation order, an information entropy density is calculated in step S11 by using the aforementioned method. Next, when the information entropy density obtained in step S12 is zero or not greater than −5, it is judged that the second property is not satisfied (step S16). When the information entropy density is smaller than zero and not smaller than −5, the program flow proceeds to evaluation of the entropy variation index (EV-index) that is the time variance of the information entropy density. It is judged that the second property is satisfied when the entropy variation index (EV-index) calculated in step S13 by the aforementioned method is greater than 0.001 (step S15), and it is judged that the second property is not satisfied when it is not greater than 0.001 (step S16). Then, the program flow proceeds to step S17.

In step S17, by colligating the above-mentioned results, it is judged that a vibration that satisfies either one of the first property and the second property on the autocorrelation order among vibrations that contain both the audible range components and the super-high-frequency components is the vibration that can introduce the fundamental brain activation effect (step S18). In contrast to this, it is judged that a vibration that satisfies neither the first property nor the second property, a vibration that contains no audible range components and a vibration that contains no super-high-frequency component among the vibrations that contain both the audible range components and the super-high-frequency components are each the vibration that cannot introduce the fundamental brain activation effect (step S19). Then, the present processing ends. It is acceptable to replace the order of execution of "step S3" with "step 4 to the step just before step S17". Moreover, it is acceptable to replace the order of execution of "step S7" with "step S8".

It is also acceptable to constitute the processing step of FIG. 87 of a computer program that can be executed by a computer, record it into a recording medium such as an optical disk that can be read by a computer and reproduce it by a drive apparatus. Moreover, it is acceptable to transmit the program of the processing by using a communication apparatus or a communication system.

FIG. 88 is a block diagram showing a structural example of a hardware circuit that carries out derivation control processing of the fundamental brain activation effect according to the fifth preferred embodiment. That is, FIG. 88 shows an example of an apparatus that discriminates whether a vibration signal satisfies the conditions as a vibration that contains audible range components and super-high-frequency components having the predetermined autocorrelation order and can introduce the fundamental brain activation effect. This apparatus is constituted mainly of the three constituents of a power spectrum judgment circuit 880, a first property judgment circuit 884 of the autocorrelation order, and a second property judgment circuit 890 of the autocorrelation order described below, and these processes are constituted in correspondence with the processing of FIG. 87.

The power spectrum judgment circuit 880 is constituted of an AD converter circuit 881 that digitizes an inputted vibration signal, a fast Fourier transform circuit 882 that carries out fast Fourier transform by using the output result thereof, and outputs a power spectrum, and a level judgment circuit 883 that judges whether or not the outputted power spectrum has a predetermined level in the audible range and the super-high-frequency range.

The first property judgment circuit 884 of the autocorrelation order is constituted of an AD converter circuit 885 that digitizes an inputted vibration signal, a high-pass filter 886 that has a cutoff frequency of, for example, 20 kHz, a three-dimensional power spectrum array calculating circuit 887 that carries out power spectrum estimation of the vibration signal by using an autocorrelation model and draws a three-dimensional power spectrum array based on it, a local exponent of fractal dimension calculating circuit 888 that calculates the fractal dimension of a three-dimensional power spectrum array curved surface, and a numerical value judgment circuit 889 that judges whether the obtained local exponent of fractal dimension and its fluctuation range have a predetermined property.

The second property judgment circuit 890 of the autocorrelation order is constituted of an AD converter circuit 891 that digitizes an inputted vibration signal, an information entropy calculating circuit 892 that calculates the information entropy density of the vibration signal and the entropy variation index (EV-index) that is its time variance by using the autocorrelation model, a numerical value judgment circuit 893 that judges whether the obtained information entropy density has a value within a predetermined range, an EV-index calculating circuit 894 that calculates the variance of the information entropy density and obtains the entropy variation index (EV-index), and a numerical value judgment circuit 895 that judges whether the value of the obtained entropy variation index (EV-index) is not smaller than a predetermined value.

Upon receiving inputs of the judgment results from these three circuits 880, 884 and 890, a logic judgment circuit 896 in the final stage judges whether the inputted vibration signal (1) has the audible range components and the super-high-frequency components, which are the essential conditions to be owned by the vibration signal that can introduce the fundamental brain activation effect, (2) has the first property on the autocorrelation order, or (3) satisfies the second property on the autocorrelation order, and judges whether or not the conditions of the vibration signal that can introduce the fundamental brain activation effect are satisfied based on the result.

The vibration discriminating apparatus of FIG. 88 may be configured of, for example, a DSP (digital signal processor), a digital calculator or computer.

Moreover, the vibration signal inputted to the vibration discriminating apparatus of FIG. 88 may be inputted by transducing the signal recorded in a storage medium such as a magnetic tape, a solid memory, an optical disk, a magnetooptical disk, and a hard disk into an electric signal or an electric vibration that is transduced and inputted from a receiver of an electromagnetic wave, light, an electric signal, or the like. Further, the inputted vibration signal may be an electric vibration transduced from an aerial vibration by a microphone or an electric signal transduced from a vibration of a solid or a liquid by a transducer.

Although FIG. 88 shows the example in which the vibration signal is inputted in parallel to the power spectrum judgment circuit 880, the first property judgment circuit 884 and the second property judgment circuit 890, these three circuits 880, 884 and 890 may be connected in series or only two the three circuits 880, 884 and 890 may be connected in parallel.

By using the discriminating apparatus of FIG. 88, it becomes possible to judge whether or not the vibration signal outputted from the vibration generating apparatus or the individual mechanisms constituting it satisfies the conditions of the vibration signal that contains the audible range components and the super-high-frequency components having the predetermined autocorrelation order and can introduce the fundamental brain activation effect. Moreover, the characteristics of the vibration generating apparatus or the individual mechanisms constituting it can also be adjusted by feeding the judgment result back to the vibration generating apparatus or the individual mechanisms constituting it. Furthermore, by discriminating the vibration signal outputted from a given equipment, it becomes possible to evaluate whether or not the equipment has a function to appropriately process the vibration signal that can introduce the fundamental brain activation effect.

Next, an apparatus having a function to discriminate whether or not the conditions of the vibration that can introduce the fundamental brain activation effect by monitoring the actual vibration, and feeds it back to the vibration generating apparatus as a practical application of the aforementioned vibration discriminating apparatus is described below.

When it is judged that the vibration signal served as an object to be discriminated does not satisfy the conditions that it "contains the audible range components and the super-high-frequency components having the predetermined autocorrelation order" in a vibration discriminating apparatus, an actual vibration generated from the vibration signal has a high risk of deteriorating the fundamental brain activity in comparison with that in an ordinary background noise state in addition to the fact that it cannot introduce the fundamental brain activation effect. In such a case, it is effective to generate an alarm or the like as a reminder by feeding the discrimination result back to the vibration generating apparatus or to generate a vibration that can introduce the fundamental brain activation effect by adding a signal of a hypersonic sound or its super-high-frequency components.

FIG. 114 is a perspective view showing an implemental example of a vibration monitoring system 500 for adjusting the vibration generating setting by feedback to the vibration generating apparatus by using the judgment result on the autocorrelation order owned by the vibration according to the fifth preferred embodiment, and FIG. 115 is a block diagram showing a detailed configuration of the vibration monitoring system 500 of FIG. 114.

The vibration monitoring system 500 shown in FIG. 114 is constituted of a vibration generating apparatus 501, a vibration signal input apparatus 502 configured of a microphone 911 and a microphone amplifier 912, a vibration discriminating apparatus 503, a discrimination result-based control signal generating apparatus 504, an alarm generator 506, a vibration complementing apparatus 507, and a discrimination result monitor apparatus 505. Referring to FIG. 114, an actual vibration generated from the vibration generating apparatus 501 is transduced into an electric signal by the vibration signal input apparatus 502 and thereafter inputted to the vibration discriminating apparatus 503. The vibration discriminating apparatus 503, which is configured similarly to the vibration discriminating apparatus of FIG. 88, discriminates whether the inputted vibration signal has the conditions of the vibration that can introduce the fundamental brain activation effect, and outputs the discrimination result to the discrimination result-based control signal generating apparatus 504 and the discrimination result monitor apparatus 505. When it is discriminated that "the inputted vibration signal does not have the conditions of the vibration that can introduce the fundamental brain activation effect, i.e., the inputted vibration signal cannot introduce the fundamental brain activation effect", the discrimination result-based control signal generating apparatus 504 outputs a control signal to the alarm generator 506 to generate an alarm, and/or outputs a control signal to the vibration complementing apparatus 507 to generate a hypersonic sound or its super-high-frequency component signal, and adds the generated signal to the signal of the vibration generating apparatus 501 to generate an addition signal. The discrimination result monitor apparatus 505 displays the discrimination result.

By the vibration monitoring system 500 as described above, the listener becomes able to confirm whether the vibration to which he or she is currently listening has the conditions of the vibration that can introduce the fundamental brain activation effect and becomes able to receive the hypersonic sound when the conditions are not satisfied, and this produces the positive effects of ameliorating and improving the psychosomatic state through the activation of the fundamental brain network system in addition to preventing the deterioration in his or her fundamental brain activity and assuring safety.

Supplementary Explanation of Formula

Hereinafter, the calculating formulas that derive the first property and the second property on the autocorrelation order are described. First of all, the local exponent of the fractal dimension of the temporospatial structure is described below. In this case, with regard to the three-dimensional power spectrum array of vibration signal data, the local exponent of the fractal dimension (box count dimension) of its shape was obtained according to the following procedure.

(1) It is assumed that unit analysis interval time series data obtained by dividing the time series data X of a vibration having a total duration of T seconds sampled by a sampling frequency $2f_N$ ($f_N$ is the Nyquist frequency, or the maximum frequency of the object signal) into intervals having a duration of $T_E$ seconds are $X_i(t)$ ($i=1, 2, \ldots, n; t=1, 2, \ldots, 2f_N \times T_E$). In this case, it is assumed that $X_i(t)$ and $X_{i+1}(t)$ have an overlap interval of $T_E/2$ seconds corresponding to a half of the unit analysis interval duration. That is as follows:

$$X_{i+1}(t)=X_i(t+f_N \times T_E) \quad (1).$$

It is noted that $i=1, 2, \ldots, n-1; t=1, 2, \ldots, f_N \times T_E$. In this case, one-side power spectrum $Q_i(f)$ of the time series data $X_i(t)$ for each unit analysis interval is obtained by using the Yule-Walker (Yule-Walker) method of a 10-dimension autoregression model.

(2) From the one-side power spectrums $Q_i(f)$, components exceeding 20 kHz at the human audible range upper limit is extracted, and the same expressed in dB is assumed to be a power $P_i(f)$. That is as follows:

$$P_i(f)=10 \times \log_{10} Q_i(f) \quad (2).$$

It is noted that $20 \text{ kHz} \leq f \leq f_N$.

(3) Next, a plot in a three-dimensional space, of which the transverse axis represents the frequency f ($20 \text{ kHz} \leq f \leq f_N$), the anteroposterior axis represents the interval "i" ($i=1, 2, \ldots, n$), and the vertical axis represents the power $P_i(f)$, is called a three-dimensional power spectrum array. It is noted that the vertical axis is a logarithmic representation of the power spectrum $Q_i(f)$.

(4) In general, it is assumed that the number of cubes necessary when a curved surface S is covered with cubes each having one side length of r is N(r). When D such that N(r) is proportional to $r^{-D}$ exists, D is called a fractal dimension (box count dimension) of the curved surface S. That is, when the curved surface S has the fractal structure, $$N(r) \propto rD \quad (3)$$

that is the following equation holds:

$$N(r)=C \times r^{-D} \text{ (where } C \text{ is a constant)} \quad (4).$$

If the logarithms of both members are taken in this case, the following equation is obtained:

$$\log N(r)=-D \times \log(r)+\log(C) \quad (5).$$

The Equation (5) indicates that the fractal dimension is formed by multiplying −1 by the inclination of a straight line when the number N(r) of cubes with respect to various lengths r is obtained in the curved surface S, and r and N(r) are plotted by double logarithm. However, it is infrequent that the actually given curved surface S takes a complete fractal structure. Accordingly, a sign-inverted inclination of a regression line obtained when the number N(r) with respect to various lengths r is plotted by double logarithm in the given curved surface S is regarded as a statistical fractal dimension.

(5) On the above basis, the three-dimensional power spectrum array obtained by the Equation (4) is considered to be a three-dimensional curved surface SA, and the transverse axis and the anteroposterior axis are first severally scaled so that the maximum width along each axes of the curved surface SA each becomes one. In the vertical axis direction, the amplitude is scaled by the geometric mean of the scales of contraction/enlargement on the transverse axis and the anteroposterior axis.

(6) Next, a cube $B_k$ obtained by equally dividing each side of a cube, which has a side length of one and a bottom surface defined by the orthogonal projection of the curved surface SA on a flat plane constituted of the transverse axis and the anteroposterior axis, by $q^k$ is considered. In this case, q is a real number satisfying $q>1$, and k is an integer satisfying $k \geq 0$. The length of one side of the cube $B_k$ is $q^{-k}$. Moreover, assuming that the number of cubes $B_k$ necessary for covering the curved surface SA with the cubes $B_k$ is M(k), then $N(r)=M(k)$, and $r=q^{-k}$ in the Equation (5). When these are substituted into the Equation (5) paying attention to the fact that D is an inclination obtained from the regression line, the following equation is obtained:

$$\log M(k) \approx D \times \log(q^k)+\log(C) \quad (6).$$

Likewise, the following equation is obtained.

$$\log M(k+1) \approx D \times \log(q^{k+1})+\log(C) \quad (7).$$

(7) In this case, assuming that the value of local D between k and k+1 is L(k), then the following equation is obtained.

$$\begin{aligned} L(k) &= (\log M(k+1) - \log M(k)) / (\log(q^{k+1}) - \log(q^k)) \\ &= (\log M(k+1) - \log M(k)) / \log(q). \end{aligned} \quad (8)$$

It is herein defined that $q^{-k}$ is the spectro-temporal index of the curved surface SA, and L(k) is the local exponent of fractal dimension of the curved surface SA at the spectro-temporal index $q^{-k}$.

(8) The local exponent L(k) of the fractal dimension corresponds to the derivative value of the graph in the Equation (5) obtained by a difference and can be calculated in a curved surface of which the fractal dimension cannot be strictly defined. When the curved surface SA takes a fractal structure within a definite range of the spectro-temporal index, L(k) has a value close to a constant value that is not an integer (two in the case of a flat surface) corresponding to the topological dimension. Accordingly, the fractal structure of the curved surface SA was analyzed by examining the behavior of this local exponent.

In the preferred embodiments and the implemental examples of the present invention, calculations are performed by using the above-mentioned method on the conditions: $f_N$=96 kHz, T=51.2 seconds, $T_E$=0.2 seconds, q=2, and k=1, 2, 3, 4, 5.

Next, the calculation method of the information entropy density of the vibration signal is described below. In this case, the information entropy density of the time series data of a vibration signal was obtained according to the following procedures.

(1) It is assumed that the time series data X of a vibration having a total duration of T seconds sampled by a sampling frequency $2f_N$ ($f_N$ is the Nyquist frequency, or the maximum frequency of the object signal) into intervals having a duration of $T_E$ seconds are $X_i(t)$ (i=1, 2, ..., n; t=1, 2, ..., $2f_N \times T_E$).

(2) Assuming that the two-side and one-side power spectrums of $X_i(t)$ are $S_i(f)$ and $Q_i(f)$, when the probability density function of $X_i(t)$ has a Gaussian distribution, the information entropy density $h_i$ is expressed by the following equation (See, for example, the Non-Patent Document 7):

$$h_i = \frac{1}{4f_N} \int_{-f_N}^{f_N} \log S_i(f) \, df + \frac{1}{2}\log 2f_N$$

$$= \frac{1}{2f_N} \int_0^{f_N} \log\{f_N \times Q_i(f)\} \, df$$

(3) If the one-side power spectrum $Q_i(f)$ is obtained from the time series data $X_i(t)$ for each unit analysis interval by using the Yule-Walker method of a 10-dimension autocorrelation model and substituted into the Equation (2), then the information entropy density $h_i$ for an interval "i" is obtained.

(4) With regard to the information entropy density $h_i$, it is assumed that a variance var($h_i$) from an interval 1 to an interval n is the entropy variation index (EV-index). In the present preferred embodiment, calculations are performed under the conditions: $f_N$=96 kHz, T=51.2 seconds, and $T_E$=0.2 seconds.

INDUSTRIAL APPLICABILITY

As described in detail above, according to the present invention, the detailed properties of the hypersonic sound are clarified, and the apparatuses and methods that can introduce the hypersonic sound and the apparatuses and methods for discriminating the vibration can be provided. With the above-mentioned arrangement, it becomes possible to induce the activation of the fundamental brain and the fundamental brain network (fundamental brain network system) including the reward system neural circuit of the brain unitarily comprehensively responsible for the generation of reactions of pleasure, beauty and emotion in a human being, consequently boost the aesthetic sensibility to various general sensory inputs inclusive of sounds, and enhance the pleasure, beauty and emotion. Moreover, it becomes possible to not only induce the effects of invigorating the physical activation such as homeostatic maintenance and biophylaxis of the whole body managed by the fundamental brain but also comprehensively remedying lifestyle-related diseases of metabolic syndromes such as hypertension, hyperlipemia and diabetes, cancer, cerebrovascular disorder and cardiopathy, immune abnormalities including pollinosis and atopic dermatitis, various mental disorders such as depression, schizophrenia, dementia, chronic fatigue syndrome and attention-deficit hyperactivity disorder, behavioral abnormalities such as suicide and self-injurious behaviors, abnormal exaltation of aggressiveness and so on, which are caused by the abnormality of the fundamental brain activity and pose serious problems in the modern society, also making it possible to induce the effect of maintaining healthy and comfortable life. These effects owned by the present invention are expected to be used in the following various industries.

First of all, the present invention directly provides technological innovations for various industries relevant to the information and communication technology.

In the audio equipment industry, many of the existent audio apparatuses and audio and video (AV) apparatuses used in home theaters and the like, which have been rapidly popularized in recent years, can neither record nor reproduce super-high-frequency components essential for introducing the fundamental brain activation effect due to the signal formats and limitations in the performance of the reproducing apparatuses and therefore unable to introduce the fundamental brain activation effect. The present invention makes it possible to generate a vibration that introduce the fundamental brain activation effect even when these existent apparatuses are used and provide the listeners with beauty, emotion, health and comfort. By the present technological innovation, it is expected to open a new market in the audio equipment industry.

In the contents industry, the majority of huge amount of contents, which have been audio recorded or audio and video recorded in the field after the 1980's, have recordable and reproducible band upper limits limited to 22 kHz to 24 kHz in conformity to digital contents standard used in the contemporary studios coping with the changeover in the mainstream of the package media to the digital media of CDs and the like, and unable to introduce the fundamental brain activation effect. The present invention makes it possible to generate a vibration that can introduce the fundamental brain activation effect from such contents. This makes it possible to heighten the artistic values of the huge amount of existent contents properties and safety. In addition, by making it possible to generate the fundamental brain activation effect even in the video and audio contents such that an image and a sound are simultaneously presented, the present invention overcomes such a conventional technological problem that image quality and sound quality are in a trade-off relation due to restrictions in the recordable and transmissible information capacity and the information transmission rate, thereby enhancing the listeners' aesthetic sensibilities to images and sounds in parallel to introduce an effect substantially equivalent to an increase in the information capacity and making it possible to produce contents of which the sensuous artistic values are comprehensively heightened.

In the broadcasting and distribution industries, most of the audio signals that are transmitted and distributed via the current television broadcastings and Internet communications cannot activate the fundamental brain since they use formats that can neither record nor reproduce super-high-frequency components essential for introducing the fundamental brain activation effect. The present invention makes it possible to generate a vibration that can introduce the fundamental brain activation effect from these vibration signals that are broadcasted and distributed. Moreover, if a format capable of transmitting super-high-frequency components will be adopted in the future, the present invention makes it possible to produce and transmit contents containing vibration signals that can introduce the fundamental brain activation effect. Further, similar to the effects expected in the contents industry, means for transmitting a plurality of different kinds of sensory information such as videos and images in a manner similar to that of the television broadcasting and moving picture distribution overcomes such a conventional technological problem that image quality and sound quality are in a trade-off relation due to restrictions in the information transmission rate of the communication lines, thereby enhancing the viewers' aesthetic sensibilities to videos and sounds in parallel to introduce an effect substantially equivalent to an increase in the information capacity transmittable per hour and making it possible to distribute contents of which the sensuous artistic values are comprehensively heightened.

In addition to the uses in various industries relevant to the information and communication technologies described above, the present invention makes it possible to improve vibration information of the environment that surrounds human beings to make it able to introduce the fundamental brain activation effect. This new information environment creating technique is expected to be used in various industries.

First of all, in the medical industry field, by improving the vibration information in the spaces where modern people live to make it able to introduce the fundamental brain activation effect, it becomes possible to conduct the prevention and remedy of various disorders, which are generally called the modern diseases such as various lifestyle-related diseases and mental and behavioral disorders considered to be largely influenced by the deterioration in the fundamental brain activity on the onset and transition of the diseases and cause serious problems in the modern society. Further, it becomes possible to heighten the immunity, reduce stresses, and establish and maintain a healthy comfortable lives by improving the fundamental brain activity.

Next, in the city planning and building industry field, by improving vibration information in urban districts and public spaces and the like in the current cities to make it able to introduce the fundamental brain activation effect, it becomes possible to conduct improvements and prevention of various lifestyle-related diseases and mental and behavioral disorder symptoms due to the deterioration in the fundamental brain activity, which causes serious problems under the modern urban environments, and maintain healthy lives of people who reside or commute to work or study in cities. Further, by actualizing towns that people want to visit again, moles that make shopping happier, prosperous paths, and plazas that somehow attract people, it becomes possible to improve the comfort and ability to pull in more customers and conduct the activation of districts.

In the child care and educational industrial field, improving vibration information in domestic spaces and school spaces to make it able to introduce the fundamental brain activation effect conducts prevention of autism that is caused by the malfunction of the fundamental brain activity and is rapidly increasing in recent years, conducts improvement and prevention of various mental and behavioral disorder symptoms such as bullying, truancy, suicidal and self-injurious behaviors, eating disorders and classroom disruption and has large industrial applicability in achieving child's psychosomatic healthy growth.

In the public transportation and automobile industry field, by improving vibration information at driver's seats and cockpit seats of railways, airplanes, automobiles and the like to make it able to introduce the fundamental brain activation effect, it is expected to heighten the attention arousal level, which is one of the important functions that the fundamental brain bears and prevent the occurrence of accidents caused by human errors, doze and the like of pilots and drivers. In addition, by improving vibration information in stations and airports or vehicles and airplanes to make it able to introduce the fundamental brain activation effect, it becomes possible to remarkably improve comfort in customer gathering and prevent the violent behaviors of passengers and suicidal cases, which have increased particularly in the railroad industry in recent years causing serious problems. Further, it is expected to prevent or remedy the onset of passengers' modern diseases by utilizing the public transportation system and achieve a public transportation that can maintain healthier lives.

By being linked to not only the aforementioned industries but also any and all environment creation industries of individual spaces and public spaces, such as living spaces, duty spaces, public institution spaces, and urban district spaces, the present invention is expected to be linked to the rise of a new industry, which should be called an "information environment creation industry" that creates a vibration information environment to heighten the comfort and safety of people who use those spaces.

The present invention leads to full-fledged restructuring of the contents and vibration generating apparatuses of vibration information that has conventionally been accumulated and used in all the aforementioned industries and the environmental creation techniques that utilize them.

The industrial economical effects, which are produced by the practical applications of the present invention that can be developed to expansive domains as described above, are immeasurable.

REFERENCE NUMERALS

1: gamelan
2: microphone
3: preamplifier
4: AD converter
5: DA converter
6: reproducing amplifier
7a: high-pass filter (HPF)
7b: low-pass filter (LPF)
8a, 8b: power amplifier
9aa, 9ba: right loudspeaker
9ab, 9bb: left loudspeaker
10: magnetic recording and reproducing device
11: magnetic recording part
12: magnetic recording head
13: magnetic tape
14: magnetic reproducing head
15: magnetic reproducing part
16: magnetic tape running direction
20: room
30: human being (listener)
31: brain wave data receiving and recording apparatus
32: brain wave detecting and transmitting device
33, 34: antenna
41: tomographic apparatus
42: tomographic detecting device
70: vibration signal amplifier
71, 71A: loudspeaker
72: vibration signal recording and reproducing apparatus
74: microphone
75: audible range sound characteristic measuring instrument
76: reproduction vibration characteristic adjuster
77: BGM reproducing apparatus
81, 82, 83: Listener
81p: portable music player
90: human being (listener)
91: chair
92: vibration generating device
101: brainstem
102: thalamus 110: head portion
110a: external auditory meatus
111: headphone
111a, 111b: headphone housing
112: headband
115: signal band dividing circuit
116, 117: signal amplifier
118: signal input plug
120: super-high-frequency vibration generating device
121: audible range loudspeaker
124: ear pad
125: small battery
160: broach type signal generating apparatus
161: battery socket cover
162: memory socket cover
163: clasp fastening portion
164: clasp
170: flat plate
171, 171a: liquid current generating apparatus
172, 172a-172i: protrusion
173, 174, 175: transducer
176: actuator
177: depth variable circular dimple
178: height variable circular protrusion
179: protrusion
180: vibration signal generating apparatus
181: vibration signal preamplifier
182: high-pass filter
183: super-high-frequency component vibration signal amplifier
184: super-high-frequency component vibration generating device
185: low-pass filter
186: audible range component vibration signal amplifier
187: audible range component vibration generating device
200: signal reproducing apparatus
201: memory
202: micro amplifier
203: battery
210: shirt
230: horizontal waterway
231: floor surface
240: apparatus housing
241: water droplet generator
242: liquid
243, 244: transducer
245: microphone
246: mixer
250: apparatus housing
251-255: partition plate
256: compressed air generator
257, 258, 259: partition plate position variable direction
260: metal piece
260a: metal piece vibration direction
261: cylindrical member
262: protrusion
300: signal source disc
301: player
302: preamplifier
310: left channel circuit
311: high-pass filter (HPF)
312: low-pass filter (LPF)
313, 313a, 313b: earphone amplifier
314, 314a, 314b: power amplifier
320: right channel circuit
330: loudspeaker system
331: tweeter
332: full-range loudspeaker
333: woofer
334, 334a, 334b: earphone
335: power distribution network
340: listener
341: listener's head
350: full face helmet
360: sound insulation full body coat
370: vibration generating apparatus
371: connection type super-high-frequency vibration generating device
372, 373: super-high-frequency vibration generating device
374: super-high-frequency vibration generating device integrated cable
375: signal source memory
376: amplifier unit
377: power supply unit
380: signal transmitter
381: transducer
382: signal reconstruction circuit
383: signal transmission circuit
390: distribution network
391: signal reconstruction circuit
400: portable signal receiver
401: signal receiving circuit
402: signal reconstruction circuit
403: vibration generating apparatus
410: Portable telephone
411: loudspeaker
412: housing
413: sheet
414: super-high-frequency vibration generating device
415: headset
416: cable
417: super-high-frequency vibration generating device
418: piezoplastic sheath
420: portable music player
421: earphone
422: cable
423: vibration generating apparatus
424: super-high-frequency vibration generating device
425: memory
426: micro amplifier
427: battery
430: concert hall
431: stage
432: wireless vibration signal transmitter
433: wireless vibration signal receiver and vibration generating apparatus
434: pendant type vibration generating apparatus
435: ceiling hanged type vibration generating apparatus
436: chair mounted type vibration generating apparatus
437: chair embedded type vibration generating apparatus
440: electronic musical instrument apparatus
441: electronic musical instrument
442: complementing vibration source
443: adder
444: digital synthesizer
450: space
451: vibration generating apparatus
460: vibrating wall
461: listener
470: vibration signal reproducing apparatus
470d: recording medium
471: vibration signal amplifier
472: public-address system
473: microphone 474: vibration signal addition adjuster
475: microphone
476: vibration measuring instrument
480: Station yard
481: pillar mounted type vibration generating apparatus
482: signal receiver
483: super-high-frequency vibration signal receiver
484: loudspeaker (public-address system)
485: vibration generating apparatus
485m: memory
486: hypersonic sound generating apparatus
487: loudspeaker (public-address system)
488: person
489: super-high-frequency vibration generating apparatus
490: electric vehicle
491: vibration generating apparatus
500: vibration monitoring system
501: vibration generating apparatus
502: vibration signal input apparatus
503: vibration discriminating apparatus
504: discrimination result-based control signal generating apparatus
505: discrimination result monitor apparatus
506: alarm generator
507: vibration complementing apparatus
511: vibration signal analyzing apparatus
512: risk judgment apparatus
513: vibration complementing apparatus
540: vibration generating space
541: vibration signal storage device
542: vibration generating apparatus
560: vibration generating space
561: sound source
562: chair
563: listener
570: vibration generating space
571, 572: vibration generating apparatus
581, 582, 584: amplifier
583: adder
610: CD player
611: signal complementing apparatus
612: amplifier
613: loudspeaker
620: portable player
621: signal complementing apparatus
622: earphone
623: super-high-frequency vibrating object
624: listener
630: television receiver
631: signal complementing apparatus
632: loudspeaker
641, 643: reproducing circuit
642: band expanding circuit
644: adder
645: high-pass filter
651, 661, 661-1-661-4: original vibration signal storage device
652, 662, 662-1-662-4: reproducing circuit
653: band expanding circuit
654: adder
663: high-pass filter
664a, 664b, 667a, 667b: switch
665: voltage-controlled amplifier (VCA)
666: attenuator
670: comparator
671: absolute value signal detector circuit
672: control signal generator circuit
673, 674: AD converter
673a: frequency converter
675, 675A: active processing circuit
675a: convolution calculator
675b: autocorrelation coefficient controller
675c: multipliers
675d: transfer function controller
675e: time series converter
676: autocorrelation coefficient calculator
676a: transfer function calculator
677: reproducing circuit
678: high-pass filter
679: adder
680: controller
680m: memory
681-688: switch
691, 692: adder
693,694: filter
695: Super Audio CD (SACD)
696: SACD player
697: low-pass filter
698, 699: high-pass filter
700: vibration transmission medium filled container
701: actuator
702: elastic vibrating object
703: moving magnet type fluctuation detector device
704: moving magnet
705: coil
706: vibration transmission medium
710: capacitor type fluctuation detector device
711: movable electrode
712, 713: fixed electrode
714: bias voltage source
720: elastic vibrating object
730: fluctuation detecting coil with elastic vibrating object
731, 732: permanent magnet
750: elastic vibrating object
751: vibration detector device
800, 800a, 800b, 800c: super-high-frequency vibration generating apparatus
812: listener
812a: head portion
812b: body surface
830p: pendant type vibration generating apparatus
832: transducer
832A: super-high-frequency vibration reproducing apparatus
832a: super-high-frequency transducer
833: micro amplifier
834: memory
835: battery
850: portable music player
851: headphone
852: display
853: Blu-ray Disc
854: Blu-ray disc player
855: AV amplifier
856: 5.1 ch surround loudspeaker system
860: super-high-frequency vibration presenting apparatus
860S: signal generating apparatus
860C: bathtub
860L: liquid
870: loudspeaker
870A: full-range loudspeaker
881: AD converter circuit
882: Fast Fourier transform circuit
883: level judgment circuit
884: first property judgment circuit 885: AD converter circuit
886: high-pass filter
887: three-dimensional power spectrum array calculating circuit
888: local exponent of fractal dimension calculating circuit
889: numerical value judgment circuit
890: second property judgment circuit
891: AD converter circuit
892: information entropy density calculating circuit
893: numerical value judgment circuit
894: EV-index calculating circuit
895: numerical value judgment circuit
896: logic judgment circuit
900: audible range vibration generating apparatus
900a: headphone
910: vibration signal input apparatus
911: microphone
912: microphone amplifier
915: analysis result monitor
916: alarm generator
950: vibration generating apparatus
952: sauna type super-high-frequency vibration presenting apparatus
952a: super-high-frequency transducer
954: cockpit of airplane etc.
954a to 954d: super-high-frequency vibration presenting apparatus
955: super-high-frequency vibration shower room
955a: shower type super-high-frequency vibration presenting apparatus
961: vibration complementing apparatus
962: detection generating apparatus
962a: vibration generating apparatus
962b: premises sound detector apparatus
SW1, SW2, SW3, SW4: switch

The invention claimed is:

1. A vibration generating apparatus comprising:
a device for generating one of a vibration and a vibration signal, the one of the vibration and the vibration signal containing (i) audible range components that are vibration components in an audible frequency range and (ii) super-high-frequency components within a range exceeding the audible frequency range up to a predetermined maximum frequency,
wherein the one of the vibration and the vibration signal has an autocorrelation order represented by at least one of a first property and a second property,
wherein the vibration generating apparatus introduces a fundamental brain activation effect into (i) a fundamental brain of a human including a brain stem, a thalamus and a hypothalamus, the brain stem, the thalamus and the hypothalamus being regions performing fundamental functions of the fundamental brain of the human and (ii) a fundamental brain network of neuronal projection from the fundamental brain to various brain regions, the fundamental brain activation effect being introduced by applying one of the vibration and an actual vibration generated from the vibration signal to the human,
wherein the first property has a fractal nature, such that (i) a shape of a three-dimensional power spectrum array of time, frequency and power of components of the one of the vibration and the vibration signal exceeding the audible frequency range is a complexity having a self-similarity, (ii) a local exponent of fractal dimension represents the self-similarity of the shape, (iii) the local exponent of fractal dimension is obtained by calculating a fractal dimension of a curved surface of the three-dimensional power spectrum array using a box-counting method and by inverting a sign of an inclination of a straight line that interconnects two mutually adjacent points when logarithms of a necessary minimum number of reference boxes for covering the curved surface are plotted with respect to a logarithm of a size of each one side of the reference boxes, (iv) the local exponent of fractal dimension is not smaller than 2.2 and not greater than 2.8 in a range in which a spectro-temporal index defined by normalizing one side of a reference box of the reference boxes is $2^{-1}$ to $2^{-5}$ and (v) a fluctuation range of the local exponent of fractal dimension is within 0.4 when the spectro-temporal index changes in the range of $2^{-1}$ to $2^{-5}$, and
wherein the second property is defined, such that (i) a degree of one of predictability and irregularity of a time series of the vibration signal changes with time, except for the time series of the vibration signal that is completely predictable and regular and except for the time series of the vibration signal that is completely unpredictable and random, (ii) an information entropy density representing an irregularity of time series data has a value in a range of not smaller than −5 and smaller than zero and (iii) an entropy variation index (EV-index), which is a variance of the information entropy density and represents a degree of time variance, has a value of not smaller than 0.001 for 51.2 seconds.

2. A vibration generating space apparatus for generating a vibration having an autocorrelation order by radiating the vibration generated by one of (i) at least one vibration generating apparatus installed in the vibration generating space apparatus for forming a vibration generating space, into the vibration generating space apparatus, (ii) applying one of addition and mutual interference to vibrations in the vibration generating space apparatus, and (iii) making elements constituting the vibration generating space apparatus resonate with the vibrations, the vibration generating space apparatus comprising:
a device for generating one of a vibration and a vibration signal, the one of the vibration and the vibration signal containing (i) audible range components that are vibration components in an audible frequency range and (ii) super-high-frequency components within a range exceeding the audible frequency range up to a predetermined maximum frequency,
wherein the one of the vibration and the vibration signal has the autocorrelation order represented by at least one of a first property and a second property,
wherein the vibration generating space apparatus introduces a fundamental brain activation effect into (i) a fundamental brain of a human including a brain stem, a thalamus and a hypothalamus, the brain stem, the thalamus and the hypothalamus being regions performing fundamental functions of the fundamental brain of the human and (ii) a fundamental brain network of neuronal projection from the fundamental brain to various brain regions, the fundamental brain activation effect being introduced by applying one of the vibration and an actual vibration generated from the vibration signal to the human,
wherein the first property has a fractal nature, such that (i) a shape of a three-dimensional power spectrum array of time, frequency and power of components of the one of the vibration and the vibration signal exceeding the audible frequency range is a complexity having a self-similarity, (ii) a local exponent of fractal dimension represents the self-similarity of the shape, (iii) the local exponent of fractal dimension is obtained by calculating a fractal dimension of a curved surface of the three-dimensional power spectrum array using a box-counting method and by inverting a sign of an inclination of a straight line that interconnects two mutually adjacent points when logarithms of a necessary minimum number of reference boxes for covering the curved surface are plotted with respect to a logarithm of a size of each one side of the reference boxes, (iv) the local exponent of fractal dimension has a value of not smaller than 2.2 and not greater than 2.8 in a range in which a spectro-temporal index defined by normalizing one side of a reference box of the reference boxes is $2^{-1}$ to $2^{-5}$ and (v) a fluctuation range of the local exponent of fractal dimension is within 0.4 when the spectro-temporal index changes in the range of $2^{-1}$ to $2^{-5}$, and wherein the second property is defined, such that (i) a degree of one of predictability and irregularity of a time series of the vibration signal changes with time, except for the time series of the vibration signal that is completely predictable and regular and except for the time series of the vibration signal that is completely unpredictable and random, (ii) an information entropy density representing an irregularity of time series data has a value in a range of not smaller than −5 and smaller than zero and (iii) an entropy variation index (EV-index), which is a variance of the information entropy density and represents a degree of time variance, has a value of not smaller than 0.001 for 51.2 seconds.

3. A vibration generating method comprising:

a step of generating one of a vibration and a vibration signal, the one of the vibration and the vibration signal containing (i) audible range components that are vibration components in an audible frequency range and (ii) super-high-frequency components within a range exceeding the audible frequency range up to a predetermined maximum frequency, wherein the one of the vibration and the vibration signal has an autocorrelation order represented by at least one of a first property and a second property, wherein the vibration generating method introduces a fundamental brain activation effect into (i) a fundamental brain of a human including a brain stem, a thalamus and a hypothalamus, the brain stem, the thalamus and the hypothalamus being regions performing fundamental functions of the fundamental brain of the human and (ii) a fundamental brain network of neuronal projection from the fundamental brain to various brain regions, the fundamental brain activation effect being introduced by applying one of the vibration and an actual vibration generated from the vibration signal to the human, wherein the first property has a fractal nature, such that (i) a shape of a three-dimensional power spectrum array of time, frequency and power of components of the one of the vibration and the vibration signal exceeding the audible frequency range is a complexity having a self-similarity, (ii) a local exponent of fractal dimension represents the self-similarity of the shape, (iii) the local exponent of fractal dimension is obtained by calculating a fractal dimension of a curved surface of the three-dimensional power spectrum array using a box-counting method and by inverting a sign of an inclination of a straight line that interconnects two mutually adjacent points when logarithms of a necessary minimum number of reference boxes for covering the curved surface are plotted with respect to a logarithm of a size of each one side of the reference boxes (iv) the local exponent of fractal dimension is not smaller than 2.2 and not greater than 2.8 in a range in which a spectro-temporal index defined by normalizing one side of a reference box of the reference boxes is $2^{-1}$ to $2^{-5}$ and (v) a fluctuation range of the local exponent of fractal dimension is within 0.4 when the spectro-temporal index changes in the range of $2^{-1}$ to $2^{-5}$, and wherein the second property is defined, such that (i) a degree of one of predictability and irregularity of a time series of the vibration signal changes with time, except for the time series of the vibration signal that is completely predictable and regular and except for the time series of the vibration signal that is completely unpredictable and random, (ii) an information entropy density representing an irregularity of time series data has a value in a range of not smaller than −5 and smaller than zero and (iii) an entropy variation index (EV-index), which is a variance of the information entropy density and represents a degree of time variance, has a value of not smaller than 0.001 for 51.2 seconds.

4. The vibration generating apparatus as claimed in claim 1, further comprising an adder for adding a complementing vibration signal that has the autocorrelation order and is generated by the vibration generating apparatus to an original vibration signal not having the autocorrelation order, and for outputting a vibration signal of a result of the adding.

5. The vibration generating apparatus as claimed in claim 1, further comprising:

a band expanding device for performing band expanding so that a band of an original signal exceeds the audible frequency range with respect to an original vibration signal not having the autocorrelation order, and for outputting a band-expanded vibration signal that contains the band exceeding the audible frequency range and the band of the original vibration signal; and an adder for adding a complementing vibration signal that has the autocorrelation order and is generated by the vibration generating apparatus to the band-expanded vibration signal, and for outputting a vibration signal of a result of the adding.

6. The vibration generating apparatus as claimed in claim 4, further comprising a high-pass filter device, which is located between the vibration generating apparatus and the adder, for performing high-pass filtering of the complementing vibration signal having the autocorrelation order.

7. The vibration generating apparatus as claimed in claim 5, further comprising an attenuator for comparing a signal level of one of the original vibration signal and the band-expanded vibration signal with a predetermined threshold value, and attenuating, by a predetermined attenuation amount, one of the complementing vibration signal that has the autocorrelation order and is inputted to the adder, and a high-pass filtered signal thereof when a signal level is smaller than the predetermined threshold value.

8. The vibration generating apparatus as claimed in claim 5, further comprising a level changing device for detecting an absolute value of a signal level of one of the original vibration signal and the band-expanded vibration signal and performing one of amplification and attenuation of a signal level of one of the complementing vibration signal that has the autocorrelation order and is inputted to the adder, and a high-pass filtered signal thereof in accordance with a magnitude of the absolute value of the signal level.

9. The vibration generating apparatus as claimed in claim 5,
wherein the complementing vibration signal that has the autocorrelation order and is inputted to the adder contains a plurality of kinds of vibration signals each having the autocorrelation order, and
wherein the vibration generating apparatus further comprises a controller for selecting at least one kind of complementing vibration signal from among the plurality of kinds of complementing vibration signals in correspondence with at least one of the original vibration signal and the band-expanded vibration signal, and outputting the selected signal to the adder.

10. The vibration generating apparatus as claimed in claim 1, further comprising a first processor for calculating an autocorrelation coefficient of a reference vibration signal having the autocorrelation order, and performing a convolution calculation of an original vibration signal not having the autocorrelation order with the calculated autocorrelation coefficient, so as to generate the vibration signal having the autocorrelation order.

11. The vibration generating apparatus as claimed in claim 1, further comprising a second processor for calculating a transfer function of a reference vibration signal having the autocorrelation order, and multiplying an original vibration signal not having the autocorrelation order by the calculated transfer function, so as to generate the vibration signal having the autocorrelation order.

12. The vibration generating apparatus as claimed in claim 1, comprising:
an elastic vibrating object which elastically vibrates by utilizing physical characteristics including elasticity, natural vibration, and stress strain;
a first transducer for transducing one of the vibration signal having the autocorrelation order, and a vibration signal not having the autocorrelation order into a vibration, and applying the transduced vibration to the elastic vibrating object; and
a second transducer for transducing the vibration of the elastic vibrating object into an electric signal,
wherein one of enhancement and imparting is performed on at least one of the first property and the second property on the autocorrelation order in the vibration signal by application of the vibration signal to the elastic vibrating object by the first transducer, and
wherein one of attenuation and removal is performed on vibration components not introducing the fundamental brain activation effect and existing as an electric signal but not existing in the elastic vibrating object, so as to perform one of emphasizing and imparting an effect of a vibration that can introduce the fundamental brain activation effect.

13. The vibration generating apparatus as claimed in claim 12, wherein the elastic vibrating object is installed in a container filled with a predetermined vibration transmission medium.

14. The vibration generating apparatus as claimed in claim 1, wherein the vibration generating apparatus introduces the fundamental brain activation effect into (i) a fundamental brain of the human including a reward system neural circuit, which is a brain function region being unitarily comprehensively responsible for a generation of all reactions of pleasure, beauty and emotion and (ii) the fundamental brain network, the fundamental brain activation effect being introduced by applying a vibration generated by the vibration generating apparatus to the human while applying predetermined information to the human through at least one of visual sensation, gustatory sensation, somatic sensation and olfactory sensation other than auditory sensation, so as to enhance aesthetic sensibility to at least one piece of information, which is applied to the human at a same time as the vibration and is selected from visual sensation, gustatory sensation, somatic sensation and olfactory sensation other than auditory sensation, and enhancing reactions of pleasure, beauty and emotion.

15. The vibration generating method as claimed in claim 3, wherein the vibration generating method includes:
introducing the fundamental brain activation effect into (i) a fundamental brain of the human including a reward system neural circuit, which is a brain function region being unitarily comprehensively responsible for a generation of all reactions of pleasure, beauty and emotion and (ii) the fundamental brain network, the fundamental brain activation effect being introduced by applying a vibration generated by the vibration generating apparatus to the human while applying predetermined information to the human through at least one of visual sensation, gustatory sensation, somatic sensation and olfactory sensation other than auditory sensation, so as to enhance aesthetic sensibility to at least one piece of information, which is applied to the human at a same time as the vibration and is selected from visual sensation, gustatory sensation, somatic sensation and olfactory sensation other than auditory sensation, and enhancing reactions of pleasure, beauty and emotion.

16. A non-transitory computer-readable recording medium for recording a vibration signal generated by a vibration generating apparatus, the vibration signal being recorded onto the non-transitory computer-readable recording medium by a computer,
wherein the vibration generating apparatus comprises a device for generating one of a vibration and a vibration signal, the one of the vibration and the vibration signal containing (i) audible range components that are vibration components in an audible frequency range and (ii) super-high-frequency components within a range exceeding the audible frequency range up to a predetermined maximum frequency,
wherein the one of the vibration and the vibration signal has an autocorrelation order represented by at least one of a first property and a second property,
wherein the vibration generating introduces a fundamental brain activation effect into (i) a fundamental brain of a human including a brain stem, a thalamus and a hypothalamus, the brain stem, the thalamus and the hypothalamus being regions performing fundamental functions of the fundamental brain of the human and (ii) a fundamental brain network of neuronal projection from the fundamental brain to various brain regions, the fundamental brain activation effect being introduced by applying one of the vibration and an actual vibration generated from the vibration signal to the human,
wherein the first property has a fractal nature, such that (i) a shape of a three-dimensional power spectrum array of time, frequency and power of components of the one of the vibration and the vibration signal exceeding the audible frequency range is a complexity having a self-similarity, (ii) a local exponent of fractal dimension represents the self-similarity of the shape, (iii) the local exponent of fractal dimension is obtained by calculating a fractal dimension of a curved surface of the three-dimensional power spectrum array using a box-counting method and by inverting a sign of an inclination of a straight line that interconnects two mutually adjacent points when logarithms of a necessary minimum number of reference boxes for covering the curved surface are plotted with respect to a logarithm of a size of each one side of the reference boxes, (iv) the local exponent of fractal dimension is not smaller than 2.2 and not greater than 2.8 in a range in which a spectro-temporal index defined by normalizing one side of a reference box of the reference boxes is $2^{-1}$ to $2^{-5}$ and (v) a fluctuation range of the local exponent of fractal dimension is within 0.4 when the spectro-temporal index changes in the range of $2^{-1}$ to $2^{-5}$, and wherein the second property is defined, such that (i) a degree of one of predictability and irregularity of a time series of the vibration signal changes with time, except for the time series of the vibration signal that is completely predictable and regular and except for the time series of the vibration signal that is completely unpredictable and random, (ii) an information entropy density representing an irregularity of time series data has a value in a range of not smaller than −5 and smaller than zero and (iii) an entropy variation index (EV-index), which is a variance of the information entropy density and represents a degree of time variance, has a value of not smaller than 0.001 for 51.2 seconds.

17. A communication apparatus comprising:
a communication device for transmitting a vibration signal generated by a vibration generating apparatus via a communication medium,
wherein the vibration generating apparatus comprises a device for generating one of a vibration and a vibration signal, the one of the vibration and the vibration signal containing (i) audible range components that are vibration components in an audible frequency range and (ii) super-high-frequency components within a range exceeding the audible frequency range up to a predetermined maximum frequency,
wherein the one of the vibration and the vibration signal has an autocorrelation order represented by at least one of a first property and a second property,
wherein the vibration generating apparatus introduces a fundamental brain activation effect into (i) a fundamental brain of a human including a brain stem, a thalamus and a hypothalamus, the brain stem, the thalamus and the hypothalamus being regions performing fundamental functions of the fundamental brain of the human and (ii) a fundamental brain network of neuronal projection from the fundamental brain to various brain regions, the fundamental brain activation effect being introduced by applying one of the vibration and an actual vibration generated from the vibration signal to the human,
wherein the first property has a fractal nature, such that (i) a shape of a three-dimensional power spectrum array of time, frequency and power of components of the one of the vibration and the vibration signal exceeding the audible frequency range is a complexity having a self-similarity, (ii) a local exponent of fractal dimension represents the self-similarity of the shape, (iii) the local exponent of fractal dimension is obtained by calculating a fractal dimension of a curved surface of the three-dimensional power spectrum array using a box-counting method and by inverting a sign of an inclination of a straight line that interconnects two mutually adjacent points when logarithms of a necessary minimum number of reference boxes for covering the curved surface are plotted with respect to a logarithm of a size of each one side of the reference boxes, and, (iv) the local exponent of fractal dimension is not smaller than 2.2 and not greater than 2.8 in a range in which a spectro-temporal index defined by normalizing one side of a reference box of the reference boxes is $2^{-1}$ to $2^{-5}$ and (v) a fluctuation range of the local exponent of fractal dimension is within 0.4 when the spectro-temporal index changes in the range of $2^{-1}$ to $2^{-5}$, and wherein the second property is defined, such that (i) a degree of one of predictability and irregularity of a time series of the vibration signal changes with time, except for the time series of the vibration signal that is completely predictable and regular and except for the time series of the vibration signal that is completely unpredictable and random, (ii) an information entropy density representing an irregularity of time series data has a value in a range of not smaller than −5 and smaller than zero and (iii) an entropy variation index (EV-index), which is a variance of the information entropy density and represents a degree of time variance, has a value of not smaller than 0.001 for 51.2 seconds.

18. A vibration discriminating apparatus comprising:
a discriminator for discriminating whether or not an inputted vibration signal (i) contains audible range components that are vibration components in an audible frequency range (ii) contains super-high-frequency components within a range exceeding the audible frequency range up to a predetermined maximum frequency and (iii) has an autocorrelation order represented by at least one of a first property and a second property,
wherein the discriminator further discriminates whether or not a fundamental brain activation effect can be introduced into (i) a fundamental brain of a human including a brain stem, a thalamus and a hypothalamus, the brain stem, the thalamus and the hypothalamus being regions performing fundamental functions of the fundamental brain of the human and (ii) a fundamental brain network of neuronal projection from the fundamental brain to various brain regions, by applying an actual vibration generated from the vibration signal to the human,
wherein the first property has a fractal nature, such that (i) a shape of a three-dimensional power spectrum array of time, frequency and power of components of the one of the vibration and the vibration signal exceeding the audible frequency range is a complexity having a self-similarity, (ii) a local exponent of fractal dimension represents the self-similarity of the shape, (iii) the local exponent of fractal dimension is obtained by calculating a fractal dimension of a curved surface of the three-dimensional power spectrum array using a box-counting method and by inverting a sign of an inclination of a straight line that interconnects two mutually adjacent points when logarithms of a necessary minimum number of reference boxes for covering the curved surface are plotted with respect to a logarithm of a size of each one side of the reference boxes, (iv) the local exponent of fractal dimension is not smaller than 2.2 and not greater than 2.8 in a range in which a spectro-temporal index defined by normalizing one side of a reference box of the reference boxes is $2^{-1}$ to $2^{-5}$ and (v) a fluctuation range of the local exponent of fractal dimension is within 0.4 when the spectro-temporal index changes in the range of $2^{-1}$ to $2^{-5}$, and wherein the second property is defined, such that (i) a degree of one of predictability and irregularity of a time series of the vibration signal changes with time, except for the time series of the vibration signal that is completely predictable and regular and except for the time series of the vibration signal that is completely unpredictable and random, (ii) an information entropy density representing an irregularity of time series data has a value in a range of not smaller than −5 and smaller than zero and (iii) an entropy variation index (EV-index), which is a variance of the information entropy density and represents a degree of time variance, has a value of not smaller than 0.001 for 51.2 seconds.

19. The vibration discriminating apparatus as claimed in claim 8, wherein the discriminator comprises:
a first partial discriminator for discriminating whether or not the inputted vibration signal contains (i) components in the audible frequency range and (ii) the super-high-frequency components within the range exceeding the audible frequency range up to the predetermined maximum frequency;
a second partial discriminator for discriminating whether or not the inputted vibration signal has the autocorrelation order represented by the first property;
a third partial discriminator for discriminating whether or not the inputted vibration signal has the autocorrelation order represented by the second property; and
a final discriminator for discriminating whether or not the inputted vibration signal has the autocorrelation order based on discrimination results of the first partial discriminator, the second partial discriminator and the third partial discriminator.

20. A vibration monitoring system comprising a vibration discriminating apparatus,
wherein the vibration discriminating apparatus comprises a discriminator for discriminating whether or not an inputted vibration signal (i) contains audible range components that are vibration components in an audible frequency range (ii) contains super-high-frequency components within a range exceeding the audible frequency range up to a predetermined maximum frequency and (iii) has an autocorrelation order represented by at least one of a first property and a second property,
wherein the discriminator further discriminates whether or not a fundamental brain activation effect can be introduced into (i) a fundamental brain of a human including a brain stem, a thalamus and a hypothalamus, the brain stem, the thalamus and the hypothalamus being regions performing fundamental functions of the fundamental brain of the human and (ii) a fundamental brain network of neuronal projection from the fundamental brain to various brain regions, applying an actual vibration generated from the vibration signal to the human,
wherein the first property has a fractal nature, such that (i) a shape of a three-dimensional power spectrum array of time, frequency and power of components of the one of the vibration and the vibration signal exceeding the audible frequency range is a complexity having a self-similarity, (ii) a local exponent of fractal dimension represents the self-similarity of the shape, (iii) the local exponent of fractal dimension is obtained by calculating a fractal dimension of a curved surface of the three-dimensional power spectrum array using a box-counting method and by inverting a sign of an inclination of a straight line that interconnects two mutually adjacent points when logarithms of a necessary minimum number of reference boxes for covering the curved surface are plotted with respect to a logarithm of a size of each one side of the reference boxes, (iv) the local exponent of fractal dimension is not smaller than 2.2 and not greater than 2.8 in a range in which a spectro-temporal index defined by normalizing one side of a reference box of the reference boxes is $2^{-1}$ to $2^{-5}$ and (v) a fluctuation range of the local exponent of fractal dimension is within 0.4 when the spectro-temporal index changes in the range of $2^{-1}$ to $2^{-5}$, and
wherein the second property is defined, such that (i) a degree of one of predictability and irregularity of a time series of the vibration signal changes with time, except for the time series of the vibration signal that is completely predictable and regular and except for the time series of the vibration signal that is completely unpredictable and random, (ii) an information entropy density representing an irregularity of time series data has a value in a range of not smaller than −5 and smaller than zero and (iii) an entropy variation index (EV-index), which is a variance of the information entropy density and represents a degree of time variance, has a value of not smaller than 0.001 for 51.2 seconds, and
wherein the vibration monitoring system comprises at least one of the following:
an alarm generator for outputting an alarm when a discrimination result of the discriminator indicates that the inputted vibration signal cannot introduce the fundamental brain activation effect; and
an adder for adding a complementing vibration signal that has the autocorrelation order and is generated by the vibration generating apparatus claimed in claim 1 to the inputted vibration signal when the discrimination result of the discriminator indicates that the inputted vibration signal cannot introduce the fundamental brain activation effect.

21. A vibration discriminating method comprising:
a discrimination step of discriminating whether or not an inputted vibration signal (i) contains audible range components that are vibration components in an audible frequency range, ii) contains super-high-frequency components within a range exceeding the audible frequency range up to a predetermined maximum frequency and (iii) has an autocorrelation order represented by at least one of a first property and a second property,
wherein the discrimination step further includes discriminating whether or not a fundamental brain activation effect can be introduced into (i) a fundamental brain of a human including a brain stem, a thalamus and a hypothalamus, the brain stem, the thalamus and the hypothalamus being regions performing fundamental functions of the fundamental brain of the human and (ii) a fundamental brain network of neuronal projection from the fundamental brain to various brain regions, by applying an actual vibration generated from the vibration signal to the human,
wherein the first property has a fractal nature, such that (i) a shape of a three-dimensional power spectrum array of time, frequency and power of components of the one of the vibration and the vibration signal exceeding the audible frequency range is a complexity having a self-similarity, (ii) a local exponent of fractal dimension represents the self-similarity of the shape, (iii) the local exponent of fractal dimension is obtained by calculating a fractal dimension of a curved surface of the three-dimensional power spectrum array using a box-counting method and by inverting a sign of an inclination of a straight line that interconnects two mutually adjacent points when logarithms of a necessary minimum number of reference boxes for covering the curved surface are plotted with respect to a logarithm of a size of each one side of the reference boxes, (iv) the local exponent of fractal dimension is not smaller than 2.2 and not greater than 2.8 in a range in which a spectro-temporal index defined by normalizing one side of a reference box of the reference boxes is $2^{-1}$ to $2^{-5}$ and (v) a fluctuation range of the local exponent of fractal dimension is within 0.4 when the spectro-temporal index changes in the range of $2^{-1}$ to $2^{-5}$, and wherein the second property is defined, such that (i) a degree of one of predictability and irregularity of a time series of the vibration signal changes with time, except for the time series of the vibration signal that is completely predictable and regular and except for the time series of the vibration signal that is completely unpredictable and random, (ii) an information entropy density representing an irregularity of time series data has a value in a range of not smaller than −5 and smaller than zero and (iii) an entropy variation index (EV-index), which is a variance of the information entropy density and represents a degree of time variance, has a value of not smaller than 0.001 for 51.2 seconds.

22. The vibration discriminating method as claimed in claim 21, wherein the discrimination step further comprises:
a first partial discrimination step of discriminating whether or not the inputted vibration signal contains (i) components in the audible frequency range and (ii) the super-high-frequency components within the range exceeding the audible frequency range up to the predetermined maximum frequency;
a second partial discrimination step of discriminating whether or not the inputted vibration signal has the autocorrelation order represented by the first property;
a third partial discrimination step of discriminating whether or not the inputted vibration signal has the autocorrelation order represented by the second property; and
a final discrimination step of discriminating whether or not the inputted vibration signal has the autocorrelation order based on discrimination results of the first partial discrimination step, the second partial discrimination step and the third partial discrimination step.

23. A computer-executable program product, the program product causing a computer to execute a vibration discriminating method comprising:
a discrimination step of discriminating whether or not an inputted vibration signal (i) contains audible range components that are vibration components in an audible frequency range, (ii) contains super-high-frequency components within a range exceeding the audible frequency range up to a predetermined maximum frequency and (iii) has an autocorrelation order represented by at least one of a first property and a second property,
wherein the discrimination step further includes discriminating whether or not a fundamental brain activation effect can be introduced into (i) a fundamental brain of a human including a brain stem, a thalamus and a hypothalamus, the brain stem, the thalamus and the hypothalamus being regions performing fundamental functions of the fundamental brain of the human and (ii) a fundamental brain network of neuronal projection from the fundamental brain to various brain regions, by applying an actual vibration generated from the vibration signal to the human,
wherein the first property has a fractal nature, such that (i) a shape of a three-dimensional power spectrum array of time, frequency and power of components of the one of the vibration and the vibration signal exceeding the audible frequency range is a complexity having a self-similarity, (ii) a local exponent of fractal dimension represents the self-similarity of the shape, (iii) the local exponent of fractal dimension is obtained by calculating a fractal dimension of a curved surface of the three-dimensional power spectrum array using a box-counting method and by inverting a sign of an inclination of a straight line that interconnects two mutually adjacent points when logarithms of a necessary minimum number of reference boxes for covering the curved surface are plotted with respect to a logarithm of a size of each one side of the reference boxes, (iv) the local exponent of fractal dimension is not smaller than 2.2 and not greater than 2.8 in a range in which a spectro-temporal index defined by normalizing one side of a reference box of the reference boxes is $2^{-1}$ to $2^{-5}$ and (v) a fluctuation range of the local exponent of fractal dimension is within 0.4 when the spectro-temporal index changes in the range of $2^{-1}$ to $2^{-5}$, and wherein the second property is defined, such that (i) a degree of one of predictability and irregularity of a time series of the vibration signal changes with time, except for the time series of the vibration signal that is completely predictable and regular and except for the time series of the vibration signal that is completely unpredictable and random, (ii) an information entropy density representing an irregularity of time series data has a value in a range of not smaller than −5 and smaller than zero and (iii) an entropy variation index (EV-index), which is a variance of the information entropy density and represents a degree of time variance, has a value of not smaller than 0.001 for 51.2 seconds.

24. A non-transitory computer-readable recording medium having a program product recorded thereon, the program product being executed by a computer and causing the computer to execute a vibration discriminating method comprising:
a discrimination step of discriminating whether or not an inputted vibration signal (i) contains audible range components that are vibration components in an audible frequency range, (ii) contains super-high-frequency components within a range exceeding the audible frequency range up to a predetermined maximum frequency and (iii) has an autocorrelation order represented by at least one of a first property and a second property,
wherein the discrimination step further includes discriminating whether or not a fundamental brain activation effect can be introduced into (i) a fundamental brain of a human including a brain stem, a thalamus and a hypothalamus, the brain stem, the thalamus and the hypothalamus being regions performing fundamental functions of the fundamental brain of the human and (ii) a fundamental brain network of neuronal projection from the fundamental brain to various brain regions, by applying an actual vibration generated from the vibration signal to the human,
wherein the first property has a fractal nature, such that (i) a shape of a three-dimensional power spectrum array of time, frequency and power of components of the one of the vibration and the vibration signal exceeding the audible frequency range is a complexity having a self-similarity, (ii) a local exponent of fractal dimension represents the self-similarity of the shape, (iii) the local exponent of fractal dimension is obtained by calculating a fractal dimension of a curved surface of the three-dimensional power spectrum array using a box-counting method and by inverting a sign of an inclination of a straight line that interconnects two mutually adjacent points when logarithms of a necessary minimum number of reference boxes for covering the curved surface are plotted with respect to a logarithm of a size of each one side of the reference boxes, (iv) the local exponent of fractal dimension is not smaller than 2.2 and not greater than 2.8 in a range in which a spectro-temporal index defined by normalizing one side of a reference box of the reference boxes is $2^{-1}$ to $2^{-5}$ and (v) a fluctuation range of the local exponent of fractal dimension is within 0.4 when the spectro-temporal index changes in the range of $2^{-1}$ to $2^{-5}$, and wherein the second property is defined, such that (i) a degree of one of predictability and irregularity of a time series of the vibration signal changes with time, except for the time series of the vibration signal that is completely predictable and regular and except for the time series of the vibration signal that is completely unpredictable and random, (ii) an information entropy density representing an irregularity of time series data has a value in a range of not smaller than −5 and smaller than zero and (iii) an entropy variation index (EV-index), which is a variance of the information entropy density and represents a degree of time variance, has a value of not smaller than 0.001 for 51.2 seconds.

* * * * *